United States Patent
Bhamra et al.

(10) Patent No.: US 10,047,079 B2
(45) Date of Patent: Aug. 14, 2018

(54) N-PYRIDINYL ACETAMIDE DERIVATIVES AS INHIBITORS OF THE WNT SIGNALING PATHWAY

(71) Applicant: Redx Pharma PLC, Macclesfield (GB)

(72) Inventors: Inder Bhamra, Macclesfield (GB);
Matilda Bingham, Macclesfield (GB);
Richard Testar, Macclesfield (GB);
Louise Sargent, Macclesfield (GB);
Craig Donoghue, Macclesfield (GB)

(73) Assignee: Redx Pharma PLC, Macclesfield (GB)

( * ) Notice: Subject to any disclaimer, the term of this patent is extended or adjusted under 35 U.S.C. 154(b) by 0 days.

(21) Appl. No.: 15/514,046

(22) PCT Filed: Oct. 8, 2015

(86) PCT No.: PCT/GB2015/052939
§ 371 (c)(1),
(2) Date: Mar. 24, 2017

(87) PCT Pub. No.: WO2016/055786
PCT Pub. Date: Apr. 14, 2016

(65) Prior Publication Data
US 2017/0275276 A1    Sep. 28, 2017

(30) Foreign Application Priority Data

Oct. 8, 2014  (GB) .................................. 1417829.7
Jun. 29, 2015 (GB) .................................. 1511387.1

(51) Int. Cl.
| | | |
|---|---|---|
| *C07D 401/14* | (2006.01) | |
| *C07D 403/14* | (2006.01) | |
| *A61K 31/444* | (2006.01) | |
| *A61K 31/4439* | (2006.01) | |
| *A61K 31/496* | (2006.01) | |
| *C07D 417/14* | (2006.01) | |
| *A61K 31/506* | (2006.01) | |
| *A61K 31/497* | (2006.01) | |
| *C07D 405/14* | (2006.01) | |
| *C07D 413/14* | (2006.01) | |
| *A61K 31/501* | (2006.01) | |
| *C07D 409/14* | (2006.01) | |

(52) U.S. Cl.
CPC .......... *C07D 417/14* (2013.01); *A61K 31/444* (2013.01); *A61K 31/496* (2013.01); *A61K 31/497* (2013.01); *A61K 31/501* (2013.01); *A61K 31/506* (2013.01); *C07D 401/14* (2013.01); *C07D 405/14* (2013.01); *C07D 409/14* (2013.01); *C07D 413/14* (2013.01)

(58) Field of Classification Search
CPC ............................. C07D 401/14; C07D 403/14
See application file for complete search history.

(56) References Cited

FOREIGN PATENT DOCUMENTS

| GB | 2513403 A | 10/2014 |
|---|---|---|
| WO | WO-2006/040526 | 4/2006 |
| WO | WO-2009075874 A1 | 6/2009 |
| WO | WO-2010/101849 | 9/2010 |
| WO | WO-2012/003189 | 1/2012 |

OTHER PUBLICATIONS

CAS Reg No. 1444682-40-9, entered into STN on Jul. 16, 2013 (Year: 2013).*
CAS Reg No. 1581941-95-8, entered into STN on Apr. 8, 2014 (Year: 2014).*
Database Registry Chemical Abstracts, Database Accession No. 1288841-31-5, CAS Registry No. 1288841-31-5, May 1, 2011.
Database Registry Chemical Abstracts, Database Accession No. 1295247-32-3, CAS Registry No. 1295247-32-3, May 15, 2011.
Database Registry Chemical Abstracts, Database Accession No. 1299655-90-5, CAS Registry No. 1299555-90-5, May 24, 2011.
Database Registry Chemical Abstracts, Database Accession No. 1301556-14-8, CAS Registry No. 1301556-14-8, May 27, 2011.
Database Registry Chemical Abstracts, Database Accession No. 1302708-04-8, CAS Registry No. 1302708-04-8, May 30, 2011.
Database Registry Chemical Abstracts, Database Accession No. 1316737-77-5, CAS Registry No. 1316737-77-5, Aug. 12, 2011.
Database Registry Chemical Abstracts, Database Accession No. 1317719-23-5, CAS Registry No. 1317719-23-5, Aug. 15, 2011.
Database Registry Chemical Abstracts, Database Accession No. 1386181-57-2, CAS Registry No. 1386181-57-2, Aug. 3, 2012.
Database Registry Chemical Abstracts, Database Accession No. 1388490-10-5, CAS Registry No. 1388490-10-5, Aug. 9, 2012.
Database Registry Chemical Abstracts, Database Accession No. 1424389-59-2, CAS Registry No. 1424389-59-2, Mar. 15, 2013.
Database Registry Chemical Abstracts, Database Accession No. 1568738-00-0, CAS Registry No. 1568738-00-0, Mar. 14, 2014.
Database Registry Chemical Abstracts, Database Accession No. 1570651-85-2, CAS Registry No. 1570651-85-2, Mar. 20, 2014.
Database Registry Chemical Abstracts, Database Accession No. 1576185-33-5, CAS Registry No. 1576185-33-5, Mar. 30, 2014.
Database Registry Chemical Abstracts, Database Accession No. 1576375-50-2, CAS Registry No. 1576375-50-2, Mar. 31, 2014.
Database Registry Chemical Abstracts, Database Accession No. 1578215-59-4, CAS Registry No. 1578215-59-4, Apr. 1, 2014.

(Continued)

*Primary Examiner* — Rebecca L Anderson
*Assistant Examiner* — Karen Cheng
(74) *Attorney, Agent, or Firm* — Foley Hoag LLP

(57) ABSTRACT

Disclosed are compounds useful as inhibitors of the Wnt signalling pathway. Specifically, inhibitors of Porcupine (Porcn) are contemplated by the invention. In addition, the invention contemplates processes to prepare the compounds and uses of the compounds. The compounds of the invention may therefore be used in treating conditions mediated by the Wnt signalling pathway, for example, in treating cancer, sarcoma, melanoma, skin cancer, haematological tumors, lymphoma, carcinoma, and leukemia; or enhancing the effectiveness of an anti-cancer treatment.

16 Claims, No Drawings

(56) References Cited

OTHER PUBLICATIONS

Database Registry Chemical Abstracts, Database Accession No. 1578467-95-4, CAS Registry No. 1578467-95-4, Apr. 2, 2014.
Database Registry Chemical Abstracts, Database Accession No. 1580113-36-5, CAS Registry No. 1580113-36-5, Apr. 3, 2014.
Database Registry Chemical Abstracts, Database Accession No. 1580615-34-4, CAS Registry No. 1580615-34-4, Apr. 4, 2014.
Database Registry Chemical Abstracts, Database Accession No. 1582521-35-4, CAS Registry No. 1582521-35-4, Apr. 9, 2014.
Database Registry Chemical Abstracts, Database Accession No. 1584968-83-1, CAS Registry No. 1584968-83-1, Apr. 15, 2014.
Database Registry Chemical Abstracts, Database Accession No. 1589273-90-4, CAS Registry No. 1589273-90-4, Apr. 23, 2014.
Database Registry Chemical Abstracts, Database Accession No. 1601652-07-6, CAS Registry No. 1601652-07-6, May 9, 2014.
International Preliminary Report on Patentability for International Application No. PCT/GB2015/052939 dated Sep. 26, 2016.
International Search Report and Written Opinion for International Application No. PCT/GB2015/052939 dated Jan. 22, 2016.
CHEMCATS Accession No. 0332943537, publication Sep. 15, 2014, CAS Registry No. 1241300-12-8.
CHEMCATS Accession No. 0920130802, publication Sep. 15, 2014, CAS Registry No. 1252119-72-4.
CHEMCATS Accession No. 1478503327, publication Sep. 15, 2014, CAS Registry No. 949247-57-8.
CHEMCATS Accession No. 1764757946, publication Sep. 15, 2014, CAS Registry No. 1042862-31-6.
Liu et al., "Targeting Wnt-driven cancer through the inhibition of Porcupine by LGK974," Proc Natl Acad Sci U S A, 110(50):20224-20229 (2014).
Search Report issued by Intellectual Property Office in corresponding Application No. GB1417829.7, dated Jun. 12, 2015.

\* cited by examiner

N-PYRIDINYL ACETAMIDE DERIVATIVES AS INHIBITORS OF THE WNT SIGNALING PATHWAY

RELATED APPLICATIONS

This application is a § 371 national stage application based on Patent Cooperation Treaty Application serial number PCT/GB2015/052939, filed Oct. 8, 2015; which claims the benefit of priority to GB 1417829.7, filed Oct. 8, 2014; and GB 1511387.1, filed Jun. 29, 2015.

This invention relates to compounds. More specifically, the invention relates to compounds useful as inhibitors of the Wnt signalling pathway. Specifically, inhibitors of Porcupine (Porcn) are contemplated by the invention. In addition the invention contemplates processes to prepare the compounds and uses of the compounds.

The compounds of the invention may therefore be used in treating conditions mediated by the Wnt signalling pathway, for example secreted Wnt ligand mediated diseases which may be treated by inhibition of porcupine; treating cancer, sarcoma, melanoma, skin cancer, haematological tumors, lymphoma, carcinoma, and leukemia; or enhancing the effectiveness of an anti-cancer treatment.

BACKGROUND

The Wnt genes encode a large and highly conserved family of secreted growth factors. During normal development, transcription of Wnt family genes is tightly regulated both temporally and spatially. To date, 19 Wnt proteins have been discovered in humans. All of the Wnt proteins are 38- to 43-kDa cysteine-rich glycoproteins. Wnts have a range of roles during development, governing cell fate, migration, proliferation and death. These include body axis formation in zebrafish and xenopus, wing and eye development in drosophila and brain development in mice (Parr, et al. (1994) Curr. Opinion Genetics & Devel. 4:523-528, McMahon A P, Bradley A (1990) Cell 62: 1073-1085). In adults the role of Wnts is thought to be linked to maintaining tissue homeostasis with aberrant signalling implicated in a variety of cancers.

Wnt-mediated signalling occurs through binding of Wnt ligand to frizzled (Fzd) proteins, seven-transmembrane receptors. These receptors contain an N-terminal cysteine rich domain (CRD) which serves as the Wnt binding domain. Binding is stabilised by low-density-lipoprotein receptor-related proteins 5 and 6 (Lrp5 and Lrp6) (He, et al. (2004) Dev Apr; 131(8):1663-77). Fizzled ligation by Wnt is known to activate at least three different signalling pathways including the "canonical" β-catenin pathway, "non-canonical" planar cell polarity (PCP) and calcium pathways. Wnt signalling is further regulated by alternative receptors, including Ror2, secreted antagonists, such as WIF-1 (Hsieh, et al. (1999) Nature Apr. 1; 398(6726):431-6) and alternative Wnt receptors, such as Dickkopf (DKK) (Niehrs C (2006) Oncogene December 4; 25(57):7469-81).

When inactive, β-Catenin is rapidly turned over by a conglomeration of several proteins known as the "destruction complex". The complex consists of Axin, adenomatous polyposis coli (APC), casein kinase (CK)-1a and glycogen synthasekinase (GSK)-3β (Hamada, et al. (1999) Science 12; 283(5408):1739-42). In this state, β-catenin is phosphorylated on serine-threonine on the amino terminus leading to ubiquitination (Behrens, et al. (1998) Science 280: 596-599). In the canonical pathway of Wnt activation, Wnt-ligated Fzd binds to and activates cytoplasmic Dishevelled (Dvi) (Chen, et al. (2003) Science 301:1391-94). Wnt-ligated Lrp5 and Lrp6 directly bind to cytoplasmic Axin, inhibiting its function as a destruction complex stabiliser (Zeng, et al. (2008) Dev. 135, 367-375). These associations lead to a destabilisation of the destruction complex and cytosolic accumulation of β-catenin. Stabilisation and accumulation of β-catenin leads to nuclear translocation where it complexes with T cell factor/lymphoid enhancer factor (TCF/LEF) high mobility group transcription factors and promotes transcription of target genes such as Cyclin D1, p21 and cMyc.

Oncogenic mutations in the β-catenin gene CTNNb1 exclusively affect specific serine and threonine and surrounding residues vital for targeted degradation by APC (Hart, et al. (1999) Curr. Biol. 9:207-210). This interaction is especially apparent in colorectal cancer, where the majority of tumours present with APC mutations and an increased proportion of the remainder express CTNNb1 mutations (Iwao, et al. (1998) Cancer Res Mar. 1, 1998 58; 1021).

Many recent studies have investigated compounds targeting β-catenin or other downstream Wnt pathway proteins. Recent research suggests that modulating Wnt-Wnt receptor interaction at the cell surface is effective in reducing cell oncogenicity. This has been shown in systems with tumourgenicity driven by Wnt ligand overexpression (Liu, et al. (2013) PNAS 10; 110(50):20224-9) and where Wnt expression is driven by downstream pathway activation (Vincan et al., Differentiation 2005; 73: 142-153). Vincan et al transfected non-functional Frd7 receptor into a SK-CO-1 cell line with a homozygous APC mutation driving Wnt pathway activation. These cells demonstrated modulated morphology and reduced tumour-forming efficiency compared to parental cells in a xenograft model. This data suggests that modulating Wnt ligand-mediated signalling may have a beneficial effect even in malignancies with downstream Wnt pathway mutations.

The described invention is proposed to inhibit Wnt-mediated signalling. This includes paracrine signalling in the tissues surrounding tumours and autocrine and paracrine signalling in cancer cells.

Wnt proteins undergo post-translational modification, shown in several mutation experiments to be vital for effective protein trafficking and secretion (Tang, et al. (2012) Dev. Biol 364, 32-41, Takada, R. et al (2006) Dev. Cell 11, 791-801). Palmitoylation of Wnt proteins occurs at several conserved amino acids (C77, S209) and is performed by porcupine, an O-acetyltransferase, in the endoplasmic reticulum. Mutations in porcupine have been shown to be the cause of developmental disorders, including focal dermal hypoplasia, through impaired Wnt pathway signalling (Grzeschik, et al. (2007) Nat. Genet, 39 pp. 833-835). The dependence of Wnt ligand signalling on porcupine and the body of evidence linking Wnt pathway signalling to cancer has led to porcupine being identified as a potential anti-cancer target.

US 2014/0038922 discloses compounds that inhibit the Wnt signalling pathway and the use of these compounds in the treatment of Wnt signalling-related diseases. Similarly, WO 2012/003189 and WO 2010/101849 disclose compounds and methods for modulating Wnt signalling pathway.

An aim of the present invention is to provide alternative or improved Wnt signalling modulators. For example, an aim of the present invention is to provide alternative or improved Wnt signalling inhibitors, optionally inhibitors of porcupine.

Furthermore, it is an aim of certain embodiments of this invention to provide new compounds for use in: Wnt mediated diseases, such as secreted Wnt ligand mediated diseases which may be treated by inhibition of porcupine; treating cancer, sarcoma, melanoma, skin cancer, haematological tumors, lymphoma, carcinoma, and leukemia; or enhancing the effectiveness of an anti-cancer treatment.

It is an aim of certain embodiments of this invention to provide new cancer treatments. In particular, it is an aim of certain embodiments of this invention to provide compounds which have comparable activity to existing treatments, ideally they should have better activity. Certain embodiments of the invention also aim to provide improved solubility compared to prior art compounds and existing therapies. It is particularly attractive for certain compounds of the invention to provide better activity and better solubility over known compounds.

It is an aim of certain embodiments of this invention to provide compounds which exhibit reduced cytotoxicity relative to prior art compounds and existing therapies.

Another aim of certain embodiments of this invention is to provide compounds having a convenient pharmacokinetic profile and a suitable duration of action following dosing. A further aim of certain embodiments of this invention is to provide compounds in which the metabolised fragment or fragments of the drug after absorption are GRAS (Generally Regarded As Safe).

Certain embodiments of the present invention satisfy some or all of the above aims.

BRIEF SUMMARY OF THE DISCLOSURE

In accordance with the present invention there is provided a compound of formula (I):

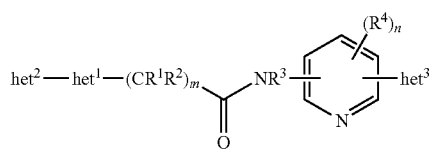

(I)

wherein
het$^1$ represents a 5 membered heterocyclic ring system comprising 1, 2 or 3 heteroatoms selected from N, O or S and being unsubstituted or substituted, and when substituted the ring system is substituted with 1, 2, or 3 groups independently selected at each occurrence from: halo, $C_{1-4}$ alkyl, $C_{1-4}$ haoalkyl, —OR$^{A2}$, —NR$^{A2}$R$^{B2}$, —CN, —SO$_2$R$^{A2}$, and $C_{3-6}$ cycloalkyl;
het$^1$ has a bond to het$^2$ and to —(CR$^1$R$^2$)$_m$C(O)NR$^3$—, wherein het$^2$ and —(CR$^1$R$^2$)$_m$C(O)NR$^3$— are bonded to non-adjacent atoms of het$^1$;
het$^2$ is a 5 or 6 membered heterocyclic ring which may be unsubstituted or substituted, and when substituted the ring is substituted with 1, 2 or 3 groups independently selected at each occurrence from: halo, $C_{1-4}$ alkyl, $C_{1-4}$ haloalkyl, —OR$^{A1}$, —NR$^{A1}$R$^{B1}$, —CN, —NO$_2$, —NR$^{A1}$C(O)R$^{B1}$, —C(O)NR$^{A1}$R$^{B1}$, —NR$^{A1}$SO$_2$R$^{B1}$, —SO$_2$NR$^{A1}$R$^{B1}$, —SO$_2$R$^{A1}$, —C(O)R$^{A1}$, —C(O)OR$^{A1}$ and $C_{3-6}$ cycloalkyl;
het$^3$ is a 5 or 6 membered heterocyclic ring or a phenyl ring which may be unsubstituted or substituted, and when substituted the ring is substituted with 1, 2 or 3 groups independently selected at each occurrence from: halo, $C_{1-4}$ alkyl, $C_{1-4}$ haloalkyl, —OR$^{A1}$, —NR$^{A1}$R$^{B1}$, —CN, —NO$_2$, —NR$^{A1}$C(O)R$^{B1}$, —C(O)NR$^{A1}$R$^{B1}$, —NR$^{A1}$SO$_2$R$^{B1}$, —SO$_2$NR$^{A1}$R$^{B1}$, —SO$_2$R$^{A1}$, —C(O)R$^{A1}$, —C(O)OR$^{A1}$ and $C_{3-6}$ cycloalkyl;
R$^1$ and R$^2$ are independently selected at each occurrence from: H, halo, $C_{1-4}$ alkyl, $C_{1-4}$ haloalkyl, —OR$^{A3}$, —NR$^{A3}$R$^{B3}$ and $C_{3-6}$ cycloalkyl;
R$^3$ is selected from: H, $C_{1-4}$ alkyl, $C_{1-4}$ haloalkyl, and $C_{3-6}$ cycloalkyl;
R$^4$ is independently selected at each occurrence from: halo, $C_{1-4}$ alkyl, $C_{1-4}$ haloalkyl, —CN, —OR$^{A4}$, —NR$^{A4}$R$^{B4}$, —SO$_2$R$^{A4}$, $C_{3-6}$ cycloalkyl and $C_{3-6}$ halocycloalkyl;
m is selected from, 1, 2 or 3;
n is selected from 0, 1 or 2; and
R$^{A1}$, R$^{B1}$, R$^{A2}$, R$^{B2}$, R$^{A3}$, R$^{B3}$, R$^{A4}$ and R$^{B4}$ are at each occurrence independently selected from: H, $C_{1-4}$ alkyl, $C_{1-4}$ haloalkyl.

In an embodiment the compound according to formula (I) is a compound according to formulae (IIa) or (IIb):

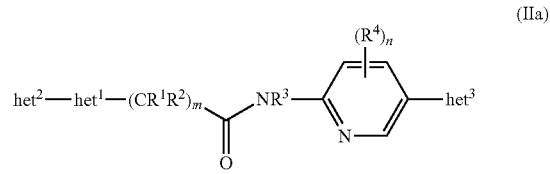

(IIa)

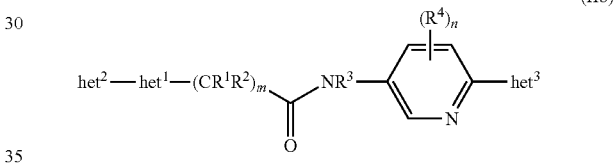

(IIb)

Het$^2$ may represent a 5 or 6 membered heterocycloalkyl, heterocycloalkenyl or heteroaryl ring which may be unsubstituted or substituted. Preferably, het$^2$ may represent a 5 or 6 membered heterocycloalkenyl or heteroaryl ring which may be unsubstituted or substituted. Most preferably, het$^2$ may represent a 5 or 6 membered heteroaryl ring which may be unsubstituted or substituted.

Het$^2$ may be represented by an aromatic, saturated or unsaturated 5 or 6 membered heterocyclic ring which is unsubstituted or substituted. Het$^2$ may be represented by an aromatic, saturated or unsaturated 5 or 6 membered heterocyclic ring which is unsubstituted or substituted wherein the heterocyclic ring contains 1, 2 or 3 N heteroatoms, optionally with no additional heteroatoms (other than N).

Het$^2$ may be represented by a ring selected from unsubstituted or substituted: pyrazole, imidazole, pyridine, pyrazine, pyrimidine, pyridazine, thiazole, isothiazole, triazole, oxazole, isoxazole, dihydropyridine, tetrahydropyridine, pyran, tetrahydropyran, dihydropyran, piperidine, piperazine, morpholine, thiomorpholine, oxazine, dioxine, dioxane, thiazine, oxathiane and dithiane.

Het$^2$ may be represented by a ring selected from unsubstituted or substituted: pyrazole, imidazole, pyridine, pyrazine, pyrimidine, pyridazine, pyran, tetrahydropyran, dihydropyran, piperidine, piperazine, morpholine, thiomorpholine, oxazine, dioxine, dioxane, thiazine, oxathiane and dithiane.

Preferably, het$^2$ may be represented by unsubstituted or substituted: pyrazole, imidazole, pyridine, pyridazine, pyrimidine, thiazole, isothiazole, triazole, isoxazole, tetrahydropyridine, tetrahydropyran and dihydropyran.

Particularly preferred, het² may be represented by unsubstituted or substituted: pyridine, pyrazole, tetrahydropyran and dihydropyran.

Preferably, het² may be represented by unsubstituted or substituted: pyrazole, imidazole, pyridine, tetrahydropyran, dihydropyran, piperidine, piperazine and morpholine.

Het² may be represented by a ring selected from unsubstituted or substituted: pyrazole, imidazole, pyrazine, pyrimidine, pyridazine, pyran, tetrahydropyran, dihydropyran, piperidine, piperazine, morpholine, thiomorpholine, oxazine, dioxine, dioxane, thiazine, oxathiane and dithiane.

Het² may be represented by unsubstituted or substituted: pyrazole, imidazole, tetrahydropyran, dihydropyran, piperidine, piperazine and morpholine.

Het² may be represented by a ring selected from unsubstituted or substituted: pyrazole, imidazole, pyran, tetrahydropyran, dihydropyran, piperazine, morpholine, thiomorpholine, oxazine, dioxine, dioxane, thiazine, oxathiane and dithiane.

Het² may be represented by unsubstituted or substituted: pyrazole, imidazole, tetrahydropyran, dihydropyran, piperazine and morpholine.

Optionally, het² is represented by an unsubstituted or substituted pyridine.

Het² may be unsubstituted or substituted with 1, 2 or 3 groups selected from: halo, $C_{1-4}$ alkyl, $C_{1-4}$ haloalkyl, $-OR^{A1}$, $-NO_2$, $-NR^{A1}C(O)R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl Het² may be unsubstituted or substituted with 1, 2, or 3 groups selected from: halo, $C_{1-4}$ alkyl, $C_{1-4}$ haloalkyl, $-OR^{A1}$, $-NR^{A1}R^{B1}$, $-CN$, $-C(O)OR^{A1}$ and $C_{3-6}$ cycloalkyl. Preferably, het² may be unsubstituted or substituted with 1, 2, or 3 groups selected from: halo, $C_{1-4}$ alkyl, $-OR^{A1}$, and $C_{1-4}$ haloalkyl, wherein $R^{A1}$ is H, methyl, or trifluoromethyl.

Het² may be unsubstituted or substituted with 1, 2, or 3 groups selected from: halo, $C_{1-4}$ alkyl, $C_{1-4}$ haloalkyl, $-OR^{A1}$, $-NR^{A1}R^{B1}$, $-CN$ and $C_{3-6}$ cycloalkyl. Preferably, het² may be unsubstituted or substituted with 1, 2, or 3 groups selected from: halo, $C_{1-4}$ alkyl, $-OR^{A1}$, and $C_{1-4}$ haloalkyl, wherein $R^{A1}$ is H, methyl, or trifluoromethyl.

In a preferred embodiment het² is unsubstituted or substituted with 1 or 2 groups selected from: fluoro, chloro, methyl, ethyl, isopropyl, difluoromethyl, trifluoromethyl, trifluoroethyl, cyclopentyl, cyclopropyl, $-NH_2$, $-NMe_2$, $-CN$, $-C(O)O^tBu$, $-OMe$ and $-OCF_3$.

In a particularly preferred embodiment het² is unsubstituted or substituted with 1 or 2 groups selected from: fluoro, methyl, trifluoromethyl and $-CN$.

In a particular preferred embodiment het² is unsubstituted or substituted with 1 or 2 groups selected from: fluoro, chloro, methyl, ethyl, trifluoromethyl, trifluoroethyl, and $-OCF_3$.

Preferably, het² is unsubstituted or substituted with 1 or 2 groups. More preferably, het² is unsubstituted or substituted with 1 group.

Het² may be unsubstituted pyridine, unsubstituted thiazole, unsubstituted triazole, unsubstituted pyrazole, unsubstituted isothiazole, unsubstituted pyrimidine, unsubstituted isoxazole, unsubstituted pyridazine, unsubstituted tetrahydropyridine, unsubstituted tetrahydropyran, unsubstituted dihydropyran, methylpyridine, dimethylpyridine, ethylpyridine, iso-propylpyridine, tert-butylpyridine, difluoromethylpyridine, trifluoromethylpyridine, fluoropyridine, chloropyridine, methoxypyridine, ethyoxypyridine, aminopyridine, N-methyl-aminopyridine, N,N-dimethyl-aminopyridine, nitropyridine, cyanopyridine, cyclopropylpyridine, cyclopentylpyridine, methylthiazole, dimethylthiazole, ethylthiazole, iso-propylthiazole, tert-butylthiazole, difluoromethylthiazole, trifluoromethylthiazole, fluorothiazole, chlorothiazole, methoxythiazole, ethyoxythiazole, aminothiazole, N-methyl-aminothiazole, N,N-dimethyl-aminothiazole, nitrothiazole, cyanothiazole, cyclopropylthiazole, cyclopentylthiazole, methyltriazole, dimethyltriazole, ethyltriazole, iso-propyltriazole, tert-butyltriazole, difluoromethyltriazole, trifluoromethyltriazole, fluorotriazole, chlorotriazole, methoxytriazole, ethyoxytriazole, aminotriazole, N-methyl-aminotriazole, N,N-dimethyl-aminotriazole, nitrotriazole, cyanotriazole, cyclopropyltriazole, cyclopentyltriazole, methylpyrazole, dimethylpyrazole, ethylpyrazole, iso-propylpyrazole, tert-butylpyrazole, difluoromethylpyrazole, methyl(trifluoromethyl)pyrazole, trifluoromethylpyrazole, fluoropyrazole, chloropyrazole, methoxypyrazole, ethyoxypyrazole, aminopyrazole, N-methyl-aminopyrazole, N,N-dimethyl-aminopyrazole, nitropyrazole, cyanopyrazole, cyclopropylpyrazole, cyclopentylpyrazole, methylisothiazole, dimethylisothiazole, ethylisothiazole, iso-propylisothiazole, tert-butylisothiazole, difluoromethylisothiazole, trifluoromethylisothiazole, fluoroisothiazole, chloroisothiazole, methoxyisothiazole, ethyoxyisothiazole, aminoisothiazole, N-methyl-aminoisothiazole, N,N-dimethyl-aminoisothiazole, nitroisothiazole, cyanoisothiazole, cyclopropylisothiazole, cyclopentylisothiazole, methylpyrimidine, dimethylpyrimidine, ethylpyrimidine, iso-propylpyrimidine, tert-butylpyrimidine, difluoromethylpyrimidine, trifluoromethylpyrimidine, fluoropyrimidine, chloropyrimidine, methoxypyrimidine, ethyoxypyrimidine, aminopyrimidine, N-methyl-aminopyrimidine, N,N-dimethyl-aminopyrimidine, N,N-dimethyl-amino(trifluoromethyl)pyrimidine, nitropyrimidine, cyanopyrimidine, cyclopropylpyrimidine, cyclopentylpyrimidine, methylisoxazole, dimethylisoxazole, ethylisoxazole, iso-propylisoxazole, tert-butylisoxazole, difluoromethylisoxazole, trifluoromethylisoxazole, fluoroisoxazole, chloroisoxazole, methoxyisoxazole, ethyoxyisoxazole, aminoisoxazole, N-methyl-aminoisoxazole, N,N-dimethyl-aminoisoxazole, nitroisoxazole, cyanoisoxazole, cyclopropylisoxazole, cyclopentylisoxazole, methylpyridazine, dimethylpyridazine, ethylpyridazine, iso-propylpyridazine, tert-butylpyridazine, difluoromethylpyridazine, trifluoromethylpyridazine, fluoropyridazine, chloropyridazine, methoxypyridazine, ethyoxypyridazine, aminopyridazine, N-methyl-aminopyridazine, N,N-dimethyl-aminopyridazine, nitropyridazine, cyanopyridazine, cyclopropylpyridazine, cyclopentylpyridazine, methyltetrahydropyridine, dimethyltetrahydropyridine, ethyltetrahydropyridine, iso-propyltetrahydropyridine, tert-butyltetrahydropyridine, difluoromethyltetrahydropyridine, trifluoromethyltetrahydropyridine, fluorotetrahydropyridine, chlorotetrahydropyridine, methoxytetrahydropyridine, ethyoxytetrahydropyridine, aminotetrahydropyridine, N-methyl-aminotetrahydropyridine, N,N-dimethyl-aminotetrahydropyridine, nitrotetrahydropyridine, cyanotetrahydropyridine, cyclopropyltetrahydropyridine, cyclopentyltetrahydropyridine, methyltetrahydropyran, dimethyltetrahydropyran, ethyltetrahydropyran, iso-propyltetrahydropyran, tert-butyltetrahydropyran, difluoromethyltetrahydropyran, trifluoromethyltetrahydropyran, fluorotetrahydropyran, chlorotetrahydropyran, methoxytetrahydropyran, ethyoxytetrahydropyran, aminotetrahydropyran, N-methyl-aminotetrahydropyran, N,N-dimethyl-aminotetrahydropyran, nitrotetrahydropyran, cyanotetrahydropyran, cyclopropyltetrahydropyran, cyclopentyltetrahydropyran, methyldihydropyran, dimethyldihydropyran ethyldihydropyran, iso-propyldihydropyran, tert-butyldihydropyran, difluoromethyldihydropyran, trifluoromethyldihydropyran, fluorodihydropyran, chlorodihydropyran, methoxydihydropyran, ethyoxydihydropyran, aminodihydropyran, N-methyl-aminodihydropyran, N,N-dimethyl-aminodihydropyran, nitrodihydropyran, cyanodihydropyran cyclopropyldihydropyran, and cyclopentyldihydropyran.

Het$^2$ may be unsubstituted pyridine, unsubstituted tetrahydropyran, unsubstituted dihydropyran, unsubstituted piperidine, unsubstituted piperazine and unsubstituted morpholine, methylpyridine, ethylpyridine, iso-propylpyridine, tert-butylpyridine, trifluoromethylpyridine, methoxypyridine, ethyoxypyridine, aminopyridine, N-methyl-aminopyridine, N,N-dimethyl-aminopyridine, nitropyridine, cyanopyridine, methyltetrahydropyran, ethyltetrahydropyran, iso-propyltetrahydropyran, tert-butyltetrahydropyran, trifluoromethyltetrahydropyran, methoxytetrahydropyran, ethyoxytetrahydropyran, aminotetrahydropyran, N-methyl-aminotetrahydropyran, N,N-dimethyl-aminotetrahydropyran, nitrotetrahydropyran, cyanotetrahydropyran, methyldihydropyran, ethyldihydropyran, iso-propyldihydropyran, tert-butyldihydropyran, trifluoromethyldihydropyran, methoxydihydropyran, ethyoxydihydropyran, aminodihydropyran, N-methyl-aminodihydropyran, N,N-dimethyl-aminodihydropyran, nitrodihydropyran, cyanodihydropyran, methylpiperidine, ethylpiperidine, iso-propylpiperidine, tert-butylpiperidine, trifluoromethylpiperidine, methoxypiperidine, ethyoxypiperidine, aminopiperidine, N-methyl-aminopiperidine, N,N-dimethyl-aminopiperidine, nitropiperidine, cyanopiperidine, methylpiperazine, ethylpiperazine, iso-propylpiperazine, tert-butylpiperazine, trifluoromethylpiperazine, methoxypiperazine, ethyoxypiperazine, aminopiperazine, N-methyl-aminopiperazine, N,N-dimethyl-aminopiperazine, nitropiperazine, cyanopiperazine, methylmorpholine, ethylmorpholine, iso-propylmorpholine, tert-butylmorpholine, trifluoromethylmorpholine, methoxymorpholine, ethyoxymorpholine, aminomorpholine, N-methyl-aminomorpholine, N,N-dimethyl-aminomorpholine, nitromorpholine or cyanomorpholine.

Het$^2$ may be unsubstituted pyridine, unsubstituted thiazole, unsubstituted triazole, unsubstituted pyrazole, unsubstituted isothiazole, unsubstituted pyrimidine, unsubstituted isoxazole, unsubstituted pyridazine, unsubstituted tetrahydropyridine, unsubstituted tetrahydropyran, unsubstituted dihydropyran, methylpyridine, difluoromethylpyridine, trifluoromethylpyridine, fluoropyridine, chloropyridine, methoxypyridine, aminopyridine, N,N-dimethyl-aminopyridine, cyanopyridine, methylthiazole, methyltriazole, methylpyrazole, iso-propylpyrazole, cyclopropylpyrazole, cyclopentylpyrazole, methyl(trifluoromethyl)pyrazole, methylisothiazole, methylpyrimidine, trifluoromethylpyrimidine, chloropyrimidine, N,N-dimethyl-amino(trifluoromethyl)pyrimidine, dimethylisoxazole, methylpyridazine, chloropyridazine, tert-butyloxycarbonyl-tetrahydropyridine, dimethyltetrahydropyran, or dimethyldihydropyran. Preferably, het$^2$ is trifluoropyridine.

Het$^2$ may be pyridyl. Het$^2$ may be substituted or unsubstituted pyridyl. Preferably, Het$^2$ is substituted or unsubstituted 4-pyridyl. 4-Pyridyl refers to a pyridine group which is attached to Het$^1$ at the four position of pyridine. The 1-position of pyridine is the nitrogen atom as would be readily understood by the skilled person. For example, 4-pyridyl, which may be substituted, is:

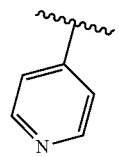 [SMILES: *c1ccncc1]

Optionally, het$^2$ is pyridyl, pyrimidyl, pyrazinyl, pyridazinyl or piperidinyl substituted with 1 group selected from: —NR$^{A1}$R$^{B1}$, —CN and —C(O)NR$^{A1}$R$^{B1}$. Optionally, het$^2$ is substituted meta or para to het$^1$.

Optionally, het$^2$ is not pyridyl.

In an embodiment the compound is a compound of the invention with the proviso that het$^2$ is not pyridyl.

In an embodiment the compound is a compound of the invention with the proviso that het$^2$ is not pyridyl, pyrimidyl, pyrazinyl, pyridazinyl or piperidinyl substituted to het$^1$ with 1 group selected from: —NR$^{A1}$R$^{B1}$, —CN, —C(O)NR$^{A1}$R$^{B1}$. Optionally, het$^2$ is not pyridyl, pyrimidyl, pyrazinyl, pyridazinyl or piperidinyl substituted meta or para to het$^1$ with 1 group selected from: —NR$^{A1}$R$^{B1}$, —CN, —C(O)NR$^{A1}$R$^{B1}$.

In an embodiment het$^2$ is a 5 or 6 membered heterocyclic ring which may be unsubstituted or substituted, and when substituted the ring is substituted with 1, 2 or 3 groups selected from: halo, C$_{1-4}$ alkyl, C$_{1-4}$ haloalkyl, —OR$^{A1}$, —NO$_2$, —NR$^{A1}$C(O)R$^{B1}$, —NR$^{A1}$SO$_2$R$^{B1}$, —SO$_2$NR$^{A1}$R$^{B1}$, —SO$_2$R$^{A1}$, —C(O)R$^{A1}$, —C(O)OR$^{A1}$ and C$_{3-6}$ cycloalkyl;
provided that het$^2$ is not pyridyl.

Het$^3$ may be a 6 membered heterocyclic ring which is unsubstituted or substituted, and when substituted the ring is substituted with 1, 2 or 3 groups independently selected at each occurrence from: halo, C$_{1-4}$ alkyl, C$_{1-4}$ haloalkyl, —OR$^{A1}$, —NR$^{A1}$R$^{B1}$, —CN, —NO$_2$, —NR$^{A1}$C(O)R$^{B1}$, —C(O)NR$^{A1}$R$^{B1}$, —NR$^{A1}$SO$_2$R$^{B1}$, —SO$_2$NR$^{A1}$R$^{B1}$, —SO$_2$R$^{A1}$, —C(O)R$^{A1}$, —C(O)OR$^{A1}$ and C$_{3-6}$ cycloalkyl.

Het$^3$ may be a 5 or 6 membered heterocyclic ring or a phenyl ring which are unsubstituted or substituted, and when substituted the ring is substituted with 1, 2 or 3 groups independently selected at each occurrence from: halo, C$_{1-4}$ haloalkyl, —OR$^{A1}$, —NR$^{A1}$R$^{B1}$, —CN, —NO$_2$, —NR$^{A1}$C(O)R$^{B1}$, —C(O)NR$^{A1}$R$^{B1}$, —NR$^{A1}$SO$_2$R$^{B1}$, —SO$_2$NR$^{A1}$R$^{B1}$, —SO$_2$R$^{A1}$, —C(O)R$^{A1}$, —C(O)OR$^{A1}$ and C$_{3-6}$ cycloalkyl;

Het$^3$ may be represented by an aromatic, saturated or unsaturated 6 membered heterocyclic ring which is unsubstituted or substituted and comprises at least one nitrogen atom, preferably the ring is aromatic or saturated.

Het$^3$ may be represented by an aromatic, saturated or unsaturated 5 or 6 membered heterocyclic ring or a phenyl ring which are unsubstituted or substituted and comprises at least one nitrogen atom. The heterocyclic ring may optionally be an aromatic or saturated ring. The heterocyclic ring may optionally be an aromatic or unsaturated ring. Preferably, the heterocyclic ring is an aromatic ring.

Het$^3$ may be represented by an aromatic, saturated or unsaturated 6 membered heterocyclic ring which is unsubstituted or substituted and comprises 2 heteroatoms, preferably the ring is aromatic or saturated. In a preferred embodiment het$^3$ is represented by an aromatic, saturated or unsaturated 6 membered heterocyclic ring which is unsubstituted or substituted and comprises 2 nitrogen atoms, preferably the ring is aromatic or saturated.

Het³ may be represented by a ring selected from unsubstituted or substituted: an aromatic, saturated or unsaturated 6 membered heterocyclic ring which comprises 1 or 2 heteroatoms (optionally N atoms), preferably the ring is aromatic or saturated; a 5 membered heteroaryl ring; and a phenyl ring. Preferably Het³ is an unsubstituted or substituted aromatic 6 membered heterocyclic ring.

Het³ may be represented by a ring selected from unsubstituted or substituted: pyrimidine, pyrazine, pyridazine, piperazine, dioxine, dioxane, morpholine and thiomorpholine. Alternatively, het³ may be represented by a ring selected from unsubstituted or substituted: phenyl, pyrazole, pyridine, pyrimidine, pyrazine, dihydropyran, and piperazine. Optionally, het³ may be represented by a ring selected from unsubstituted or substituted: pyridine, pyrimidine, pyrazine, dihydropyran, and piperazine.

Preferably, het³ may be represented by a ring selected from pyrimidine, pyrazine, pyridazine or piperazine. Preferably, het³ may be represented by a ring selected from phenyl, pyrazole, pyridine, pyrimidine, pyrazine, pyridazine or piperazine.

Preferably, het³ may be represented by a ring selected from pyrimidine, pyrazine or pyridazine.

Optionally, het³ is represented by a ring selected from unsubstituted or substituted: pyrimidine and pyrazine. Particularly preferred is for het³ to be pyrazine.

Optionally, het³ is as disclosed elsewhere herein with the proviso that het³ is not a ring selected from: alkyl substituted pyridine, unsubstituted imidazole, alkyl substituted imidazole, unsubstituted oxadiazole, alkyl substituted oxazole, unsubstituted oxazole, Optionally, het³ is as disclosed elsewhere herein with the proviso that het³ is not a ring selected from: unsubstituted oxazole, unsubstituted morpholine or methyl piperazine. Optionally, het³ is as disclosed elsewhere herein with the proviso that het³ is not a ring selected from: alkyl substituted pyridine, unsubstituted imidazole, alkyl substituted imidazole, unsubstituted oxadiazole, alkyl substituted oxazole, unsubstituted oxazole, unsubstituted morpholine or methyl piperazine.

Het³ may be unsubstituted or substituted with 1, 2, or 3 groups selected from: halo, $C_{1-4}$ alkyl, $C_{1-4}$ haloalkyl, —OR$^{A1}$, —NR$^{A1}$R$^{B1}$, —CN, —C(O)R$^{A1}$, —C(O)OR$^{A1}$, —NR$^{A1}$C(O)R$^{B2}$, and $C_{3-6}$ cycloalkyl. Het³ may be unsubstituted or substituted with 1, 2 or 3 groups selected from: halo, $C_{1-4}$ alkyl, $C_{1-4}$ haloalkyl, —OR$^{A1}$, —C(O)R$^{A1}$ and —C(O)OR$^{A1}$, wherein R$^{A1}$ is H, methyl, tert-butyl or trifluoromethyl. Preferably, het³ may be unsubstituted or substituted with 1, 2, or 3 groups selected from: $C_{1-4}$ alkyl, —OR$^{A1}$, —NR$^{A1}$R$^{B1}$, —CN, or —NR$^{A1}$C(O)R$^{B1}$, wherein R$^{A1}$ is H, methyl, tert-butyl or trifluoromethyl (preferably methyl) and R$^{B1}$ is H, methyl, tert-butyl or trifluoromethyl (preferably H or methyl).

In a particular preferred embodiment het³ is unsubstituted or substituted with 1 or 2 groups selected from: fluoro, chloro, methyl, ethyl, trifluoromethyl, trifluoroethyl, —OCF₃, —C(O)Me, —C(O)OMe, —C(O)Et and —C(O)O$^t$Bu.

In a particular preferred embodiment het³ is unsubstituted or substituted with 1 or 2 groups selected from: methyl, —OMe, —CN, —NMe₂, or —NHC(O)Me.

Preferably, het³ is unsubstituted or substituted with 1 or 2 groups. More preferably, het³ is unsubstituted or substituted with 1 group.

In an embodiment het² is represented by an aromatic, saturated or unsaturated 6 membered heterocyclic ring which is unsubstituted or substituted, (optionally wherein het² is not represented by pyridine) and het³ is represented by an aromatic, saturated or unsaturated 6 membered heterocyclic ring which is unsubstituted or substituted and comprises 2 heteroatoms.

In an embodiment het² is represented by a 5 or 6 membered heterocycloalkenyl or heteroaryl ring which is unsubstituted or substituted, (optionally wherein het² is not represented by pyridine) and het³ is represented by an aromatic, saturated or unsaturated 5 or 6 membered heterocyclic ring comprising 1 or 2 heteroatoms or a phenyl ring which are unsubstituted or substituted.

In an embodiment het² is represented by a ring selected from unsubstituted or substituted: pyridine, pyrazole, imidazole, pyrazine, pyrimidine, pyridazine, pyran, tetrahydropyran, dihydropyran, piperidine, piperazine, morpholine, thiomorpholine, oxazine, dioxine, dioxane, thiazine, oxathiane and dithiane (optionally pyrazole, imidazole, pyrazine, pyrimidine, pyridazine, pyran, tetrahydropyran, dihydropyran, piperidine, piperazine, morpholine, thiomorpholine, oxazine, dioxine, dioxane, thiazine, oxathiane and dithiane); and het³ is represented by a ring selected from unsubstituted or substituted: pyrimidine, pyrazine, pyridazine, piperazine, dioxine, dioxane, morpholine and thiomorpholine.

In an embodiment het² is represented by a ring selected from unsubstituted or substituted: pyridine, pyrazole, imidazole, pyrazine, pyrimidine, pyridazine, thiazole, isothiazole, triazole, oxazole, isoxazole, dihydropyridine, tetrahydropyridine, pyran, tetrahydropyran, dihydropyran, piperidine, piperazine, morpholine, thiomorpholine, oxazine, dioxine, dioxane, thiazine, oxathiane and dithiane (optionally pyrazole, imidazole, pyridine, pyridazine, pyrimidine, thiazole, isothiazole, triazole, isoxazole, tetrahydropyridine, tetrahydropyran and dihydropyran); and het³ is represented by a ring selected from unsubstituted or substituted: phenyl, pyrazole, pyridine, pyrimidine, pyrazine, dihydropyran, and piperazine.

Preferably, het² is represented by a ring selected from unsubstituted or substituted: pyridine, pyrazole, imidazole, tetrahydropyran, dihydropyran, piperidine, piperazine and morpholine (optionally pyrazole, imidazole, tetrahydropyran, dihydropyran, piperidine, piperazine and morpholine); and het³ is represented by a ring selected from unsubstituted or substituted: pyrimidine, pyrazine, pyridazine and piperazine.

Preferably, het² is represented by a ring selected from unsubstituted or substituted: pyrazole, imidazole, pyridine, pyridazine, pyrimidine, thiazole, isothiazole, triazole, isoxazole, tetrahydropyridine, tetrahydropyran and dihydropyran (optionally pyridine, pyrazole, tetrahydropyran and dihydropyran); and het³ is represented by a ring selected from unsubstituted or substituted: phenyl, pyrazole, pyridine, pyrimidine, pyrazine, dihydropyran, and piperazine.

Het¹ may represent a 5 membered heterocyclic ring system comprising 1, 2 or 3 (optionally 1 or 2) N or S atoms and being unsubstituted or substituted, and when substituted the ring system is substituted with 1, 2, or 3 groups independently selected at each occurrence from: halo, $C_{1-4}$ alkyl, $C_{1-4}$ haloalkyl, —OR$^{A2}$, —NR$^{A2}$R$^{B2}$, —CN, —SO₂R$^{A2}$, and $C_{3-6}$ cycloalkyl.

Het¹ may represent a 5 membered heterocyclic ring system comprising 1, 2 or 3 (optionally 1 or 2) N atoms and being unsubstituted or substituted, and when substituted the ring system is substituted with 1, 2, or 3 groups independently selected at each occurrence from: halo, $C_{1-4}$ alkyl, $C_{1-4}$ haloalkyl, —OR$^{A2}$, —NR$^{A2}$R$^{B2}$, —CN, —SO₂R$^{A2}$, and $C_{3-6}$ cycloalkyl.

Het¹ may represent a 5 membered heterocyclic ring system comprising 1, 2 or 3 (optionally 1 or 2) heteroatoms selected from N, O or S and being unsubstituted or substituted, and when substituted the ring system is substituted with 1, 2, or 3 groups independently selected at each occurrence from: halo, $C_{1-4}$ alkyl, $C_{1-4}$ haloalkyl, —$OR^{A2}$, —$NR^{A2}R^{B2}$, —CN, —$SO_2R^{A2}$, and $C_{3-6}$ cycloalkyl;

provided that the 5 membered heterocyclic ring system of $het^1$ does not represent pyrrole, pyrazole, imidazole and triazole.

$Het^1$ may represent a 5 membered heterocyclic ring system comprising 1, 2 or 3 heteroatoms (optionally 1 or 2) selected from N, O or S, wherein when the 5 membered heterocyclic ring comprises 1 or 2 N atoms it also comprises at least one atom selected from O or S.

In an embodiment the compound is a compound of the invention with the proviso that $het^2$ is not pyridyl; and $het^1$ is represented by a 5 membered heterocyclic ring system comprising 1, 2 or 3 (optionally 1 or 2) N atoms and being unsubstituted or substituted, and when substituted the ring system is substituted with 1, 2, or 3 groups independently selected at each occurrence from: halo, $C_{1-4}$ alkyl, $C_{1-4}$ haloalkyl, —$OR^{A2}$, —$NR^{A2}R^{B2}$, —CN, —$SO_2R^{A2}$, and $C_{3-6}$ cycloalkyl.

In an embodiment the compound is a compound of the invention with the proviso that $het^2$ is not pyridyl; and $het^1$ may represent a 5 membered heterocyclic ring system comprising 1, 2 or 3 (optionally 1 or 2) heteroatoms selected from N, O or S and being unsubstituted or substituted, and when substituted the ring system is substituted with 1, 2, or 3 groups independently selected at each occurrence from: halo, $C_{1-4}$ alkyl, $C_{1-4}$ haloalkyl, —$OR^{A2}$, —$NR^{A2}R^{B2}$, —CN, —$SO_2R^{A2}$, and $C_{3-6}$ cycloalkyl;

provided that the 5 membered heterocyclic ring system of $het^1$ does not represent pyrrole, pyrazole, imidazole and triazole.

In an embodiment $het^1$ represents a 5 membered heterocyclic ring system comprising 1, 2 or 3 (optionally 1 or 2) N atoms and being unsubstituted or substituted, and when substituted the ring system is substituted with 1, 2, or 3 groups independently selected at each occurrence from: halo, $C_{1-4}$ alkyl, $C_{1-4}$ haloalkyl, —$OR^{A2}$, —$NR^{A2}R^{B2}$, —CN, —$SO_2R^{A2}$, and $C_{3-6}$ cycloalkyl; and $het^2$ is a 5 or 6 membered heterocyclic ring which may be unsubstituted or substituted, and when substituted the ring is substituted with 1, 2 or 3 groups selected from: halo, $C_{1-4}$ alkyl, $C_{1-4}$ haloalkyl, —$OR^{A1}$, —$NO_2$, —$NR^{A1}C(O)R^{B1}$, —$NR^{A1}SO_2R^{B1}$, —$SO_2NR^{A1}R^{B1}$, —$SO_2R^{A1}$, —$C(O)R^{A1}$, —$C(O)OR^{A1}$ and $C_{3-6}$ cycloalkyl; provided that $het^2$ is not pyridyl.

In an embodiment $het^1$ represents a 5 membered heterocyclic ring system comprising 1, 2 or 3 (optionally 1 or 2) heteroatoms selected from N, O or S and being unsubstituted or substituted, and when substituted the ring system is substituted with 1, 2, or 3 groups independently selected at each occurrence from: halo, $C_{1-4}$ alkyl, $C_{1-4}$ haloalkyl, —$OR^{A2}$, —$NR^{A2}R^{B2}$, —CN, —$SO_2R^{A2}$, and $C_{3-6}$ cycloalkyl;

provided that the 5 membered heterocyclic ring system of $het^1$ does not represent pyrrole, pyrazole, imidazole and triazole; and $het^2$ is a 5 or 6 membered heterocyclic ring which may be unsubstituted or substituted, and when substituted the ring is substituted with 1, 2 or 3 groups selected from: halo, $C_{1-4}$ alkyl, $C_{1-4}$ haloalkyl, —$OR^{A1}$, —$NO_2$, —$NR^{A1}C(O)R^{B1}$, —$NR^{A1}SO_2R^{B1}$, —$SO_2NR^{A1}R^{B1}$, —$SO_2R^{A1}$, —$C(O)R^{A1}$, —$C(O)OR^{A1}$ and $C_{3-6}$ cycloalkyl; provided that $het^2$ is not pyridyl.

$Het^1$ may represent a substituted or unsubstituted: 5-membered heteroaryl group comprising 1, 2 or 3 (optionally 1 or 2) heteroatoms selected from N, O or S.

$Het^1$ may represent a group selected from unsubstituted or substituted: pyrazole, imidazole, oxazole, thiazole, isoxazole, isothiazole, thiophene, furan, triazole, oxadiazole and thiadiazole.

$Het^1$ may represent a group selected from unsubstituted or substituted: pyrazole, imidazole, and triazole.

$Het^1$ may represent a group selected from unsubstituted or substituted: oxazole, thiazole, isoxazole, isothiazole, thiophene, furan, oxadiazole and thiadiazole.

Optionally, $het^1$ represents an unsubstituted or substituted: imidazole, pyrazole or thiophene.

$Het^1$ has a bond to $het^2$ and to —$(CR^1R^2)_mC(O)NR^3$— and $het^2$ and —$(CR^1R^2)_mC(O)NR^3$— are bonded to non-adjacent atoms of $het^1$. In an embodiment $het^2$ and —$(CR^1R^2)_mC(O)NR^3$— are bonded to atoms of $het^1$ and the atoms have at least one atom between them. For example in an embodiment $het^2$ and —$(CR^1R^2)_mC(O)NR^3$— have a 1,3 relationship on $het^1$. $Het^2$ and —$(CR^1R^2)_mC(O)NR^3$— may not have a 1,2 relationship on $het^1$.

In an embodiment $het^2$ and —$(CR^1R^2)_mC(O)NR^3$— may be substituted on $het^1$ at ring positions selected from: 1,3; 2,4; 3,5; 1,4; and 2,5.

In an embodiment the compound according to formula (I) is a compound according to formula (III):

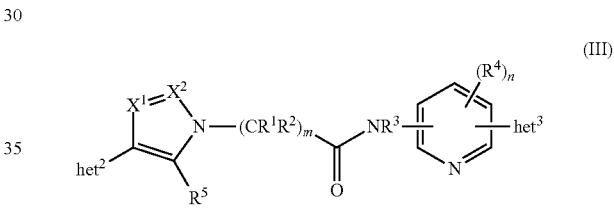

(III)

wherein
$X^1$ and $X^2$ are selected from $CR^6$ and N; and
$R^5$ and $R^6$ are, at each occurrence, independently selected from: H, halo, $C_{1-4}$ alkyl, $C_{1-4}$ haloalkyl, —$OR^{A2}$, —$NR^{A2}R^{B2}$, —CN, —$SO_2R^{A2}$, and $C_{3-6}$ cycloalkyl.

Preferably, one of $X^1$ and $X^2$ is $CR^6$ and the other is N. In an embodiment, $X^1$ is $CR^6$ and $X^2$ is N. Preferably, $X^1$ is N and $X^2$ is $CR^6$.

In an embodiment $R^5$ and $R^6$ are, at each occurrence, independently selected from: H or $C_{1-4}$ alkyl (preferably methyl). Therefore, $X^1$ may be CH or CMe and $X^2$ is N, or $X^1$ is N and $X^2$ is CH or CMe. In embodiments, $X^1$ is CH, $X^2$ is N, and $R^5$ is H; or $X^1$ is CMe, $X^2$ is N, and $R^5$ is H; $X^1$ is CH, $X^2$ is N, and $R^5$ is Me; or $X^1$ is CMe, $X^2$ is N, and $R^5$ is Me; or $X^1$ is N and $X^2$ is CH, and $R^5$ is H; or $X^1$ is N and $X^2$ is CMe, and $R^5$ is H; or $X^1$ is N and $X^2$ is CH, and $R^5$ is Me; or $X^1$ is N and $X^2$ is CMe, and $R^5$ is Me.

Preferably, $X^1$ is N and $X^2$ is CH, and $R^5$ is Me.

$Het^1$ may be unsubstituted or substituted with 1, 2, or 3 groups (preferably 1 or 2) selected from: halo, $C_{1-4}$ alkyl, $C_{1-4}$ haloalkyl, —$OR^{A2}$, —$NR^{A2}R^{B2}$ and —CN. $Het^1$ may be unsubstituted or substituted with 1 or 2 groups selected from: chloro, fluoro, methyl, ethyl, trifluoromethyl, trifluoroethyl, —$OCF_3$, —OH, —OMe, —OEt, —$NH_2$, —NHMe, —$NMe_2$ and —CN. Preferably, $Het^1$ may be unsubstituted or substituted with 1 or 2 methyl groups.

In an embodiment the compound according to formula (I) is a compound according to formula (IIIa):

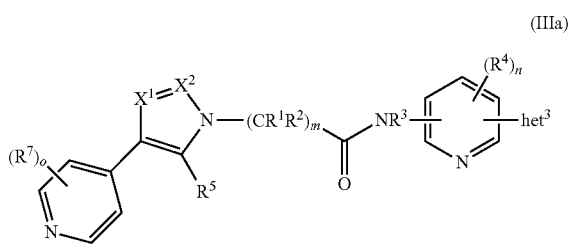

(IIIa)

wherein
R⁷ is, at each occurrence, independently selected from: halo, $C_{1-4}$ alkyl, $C_{1-4}$ haloalkyl, —$OR^{A1}$, —$NR^{A1}R^{B1}$, —CN, —$NO_2$, —$NR^{A1}C(O)R^{B1}$, —$C(O)NR^{A1}R^{B1}$, —$NR^{A1}SO_2R^{B1}$, —$SO_2NR^{A1}R^{B1}$, —$SO_2R^{A1}$, —$C(O)R^{A1}$, —$C(O)OR^{A1}$ and $C_{3-6}$ cycloalkyl, and
o is 0, 1, 2 or 3 (optionally 0, 1 or 2, preferably 0 or 1).

In an embodiment the compound according to formula (I) is a compound according to formula (IIIb):

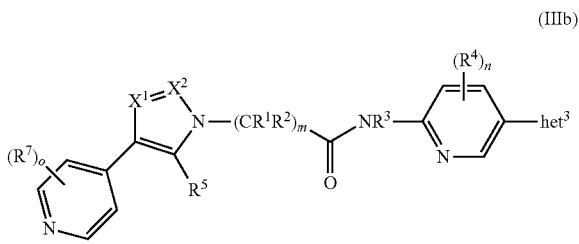

(IIIb)

R⁷ may be independently selected from: halo, $C_{1-4}$ alkyl, $C_{1-4}$ haloalkyl, —$OR^{A1}$, —$NO_2$, —$NR^{A1}C(O)R^{B1}$, —$NR^{A1}SO_2R^{B1}$, —$SO_2NR^{A1}R^{B1}$, —$SO_2R^{A1}$, —$C(O)R^{A1}$, —$C(O)OR^{A1}$ and $C_{3-6}$ cycloalkyl R⁷ may be independently selected from: halo, $C_{1-4}$ alkyl, $C_{1-4}$ haloalkyl, —$OR^{A1}$, —$NR^{A1}R^{B1}$, —CN, —$C(O)OR^{A1}$ and $C_{3-6}$ cycloalkyl. Preferably, R⁷ may be independently selected from: halo, $C_{1-4}$ alkyl, —$OR^{A1}$, and $C_{1-4}$ haloalkyl, wherein $R^{A1}$ is H, methyl, or trifluoromethyl.

R⁷ may be independently selected from: halo, $C_{1-4}$ alkyl, $C_{1-4}$ haloalkyl, —$OR^{A1}$, —$NR^{A1}R^{B1}$, —CN and $C_{3-6}$ cycloalkyl. Preferably, R⁷ may be independently selected from: halo, $C_{1-4}$ alkyl, —$OR^{A1}$, and $C_{1-4}$ haloalkyl, wherein $R^{A1}$ is H, methyl, or trifluoromethyl.

In a preferred embodiment R⁷ may be independently selected from: fluoro, chloro, methyl, ethyl, isopropyl, difluormethyl, trifluoromethyl, trifluoroethyl, cyclopentyl, cyclopropyl, —$NH_2$, —$NMe_2$, —CN, —$C(O)O^tBu$, —OMe and —$OCF_3$.

In a particularly preferred embodiment R⁷ may be independently selected from: fluoro, methyl, trifluoromethyl and —CN.

In a particular preferred embodiment R⁷ may be independently selected from: fluoro, chloro, methyl, ethyl, trifluoromethyl, trifluoroethyl, and —$OCF_3$.

In an embodiment het¹ represents a group selected from unsubstituted or substituted: pyrazole, imidazole, oxazole, thiazole, isoxazole, isothiazole, triazole, oxadiazole, and thiadiazole; het² is represented by an aromatic, saturated or unsaturated 6 membered heterocyclic ring which is unsubstituted or substituted; and het³ is represented by an aromatic, saturated or unsaturated 6 membered heterocyclic ring which is unsubstituted or substituted and comprises 2 heteroatoms.

In an embodiment het¹ represents a group selected from unsubstituted or substituted: pyrazole, imidazole, oxazole, thiazole, isoxazole, isothiazole, triazole, oxadiazole, and thiadiazole; het² is represented by a 5 or 6 membered heterocycloalkenyl or heteroaryl ring which is unsubstituted or substituted, (optionally wherein het² is not represented by pyridine) and het³ is represented by an aromatic, saturated or unsaturated 5 or 6 membered heterocyclic ring comprising 1 or 2 heteroatoms or a phenyl ring which are unsubstituted or substituted.

In an embodiment het¹ represents a group selected from unsubstituted or substituted: pyrazole, imidazole, oxazole, thiazole, isoxazole, isothiazole, triazole, oxadiazole, and thiadiazole; het² is represented by a ring selected from unsubstituted or substituted: pyrazole, imidazole, pyridine, pyrazine, pyrimidine, pyridazine, pyran, tetrahydropyran, dihydropyran, piperidine, piperazine, morpholine, thiomorpholine, oxazine, dioxine, dioxane, thiazine, oxathiane and dithiane; het² is represented by unsubstituted or substituted pyridine; and het³ is represented by a ring selected from unsubstituted or substituted: pyrimidine, pyrazine, pyridazine, piperazine, dioxine, dioxane, morpholine and thiomorpholine.

In an embodiment het¹ represents a group selected from unsubstituted or substituted: pyrazole, imidazole, oxazole, thiazole, isoxazole, isothiazole, triazole, oxadiazole, and thiadiazole; het² is represented by a ring selected from unsubstituted or substituted: pyridine, pyrazole, imidazole, pyrazine, pyrimidine, pyridazine, thiazole, isothiazole, triazole, oxazole, isoxazole, dihydropyridine, tetrahydropyridine, pyran, tetrahydropyran, dihydropyran, piperidine, piperazine, morpholine, thiomorpholine, oxazine, dioxine, dioxane, thiazine, oxathiane and dithiane (optionally pyrazole, imidazole, pyridine, pyridazine, pyrimidine, thiazole, isothiazole, triazole, isoxazole, tetrahydropyridine, tetrahydropyran and dihydropyran); and het³ is represented by a ring selected from unsubstituted or substituted: phenyl, pyrazole, pyridine, pyrimidine, pyrazine, dihydropyran, and piperazine.

Optionally, het¹ represents a group selected from unsubstituted or substituted: pyrazole, imidazole, oxazole, thiazole, isoxazole, isothiazole, triazole, oxadiazole, and thiadiazole; het² is represented by a ring selected from unsubstituted or substituted: pyrazole, imidazole, pyridine, tetrahydropyran, dihydropyran, piperidine, piperazine and morpholine; and het³ is represented by a ring selected from unsubstituted or substituted: pyrimidine, pyrazine, pyridazine and piperazine.

Optionally, het¹ represents a group selected from unsubstituted or substituted: pyrazole, imidazole, oxazole, thiazole, isoxazole, isothiazole, triazole, oxadiazole, and thiadiazole; het² is represented by a ring selected from unsubstituted or substituted: pyrazole, imidazole, pyridine, pyridazine, pyrimidine, thiazole, isothiazole, triazole, isoxazole, tetrahydropyridine, tetrahydropyran and dihydropyran (optionally pyridine, pyrazole, tetrahydropyran and dihydropyran); and het³ is represented by a ring selected from unsubstituted or substituted: phenyl, pyrazole, pyridine, pyrimidine, pyrazine, dihydropyran, and piperazine.

In an embodiment m is 1 or 2. In a preferred embodiment m is 1.

In an embodiment the compound according to formula (I) is a compound according to formula (IV):

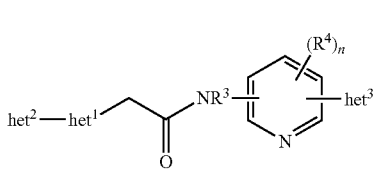
(IV)

In an embodiment the compound according to formula (I) is a compound according to formulae (IVa) or (IVb):

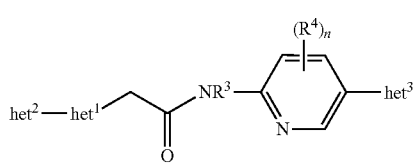
(IVa)

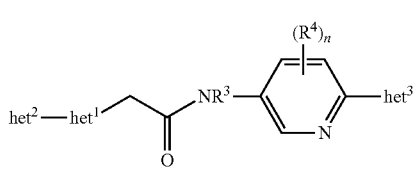
(IVb)

In an embodiment the compound according to formula (I) is a compound according to formula (V):

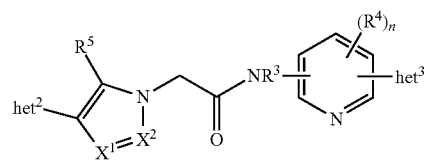
(V)

In an embodiment the compound according to formula (I) is a compound according to formulae (Va) and (Vb):

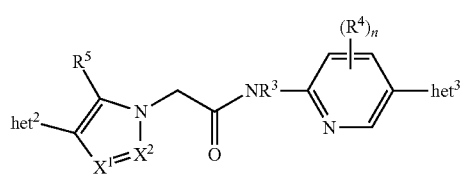
(Va)

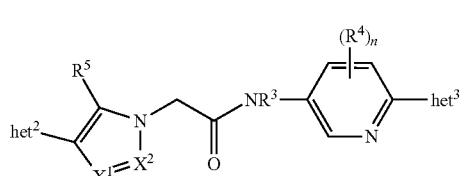
(Vb)

In an embodiment the compound according to formula (I) is a compound according to formula (Vc):

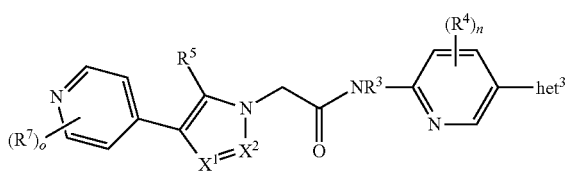
(Vc)

In an embodiment $het^1$ represents an unsubstituted or substituted pyrazole or $X^1$ is $CR^6$ and $X^2$ is N; $het^2$ is represented by an aromatic, saturated or unsaturated 6 membered heterocyclic ring which is unsubstituted or substituted, and $het^3$ is represented by an aromatic, saturated or unsaturated 6 membered heterocyclic ring which is unsubstituted or substituted and comprises 2 heteroatoms.

In an embodiment $het^1$ represents an unsubstituted or substituted pyrazole or $X^1$ is $CR^6$ and $X^2$ is N; $het^2$ is represented by a 5 or 6 membered heterocycloalkenyl or heteroaryl ring which is unsubstituted or substituted, (optionally wherein $het^2$ is not represented by pyridine) and $het^3$ is represented by an aromatic, saturated or unsaturated 6 membered heterocyclic ring which is unsubstituted or substituted and comprises 2 heteroatoms.

In an embodiment $het^1$ represents an unsubstituted or substituted pyrazole or $X^1$ is $CR^6$ and $X^2$ is N; $het^2$ is represented by a ring selected from unsubstituted or substituted: pyrazole, imidazole, pyridine, pyrazine, pyrimidine, pyridazine, pyran, tetrahydropyran, dihydropyran, piperidine, piperazine, morpholine, thiomorpholine, oxazine, dioxine, dioxane, thiazine, oxathiane and dithiane; and $het^3$ is represented by a ring selected from unsubstituted or substituted: pyrimidine, pyrazine, pyridazine, piperazine, dioxine, dioxane, morpholine and thiomorpholine.

In an embodiment $het^1$ represents an unsubstituted or substituted pyrazole or $X^1$ is $CR^6$ and $X^2$ is N; $het^2$ is represented by a ring selected from unsubstituted or substituted: pyrazole, imidazole, pyridine, pyridazine, pyrimidine, thiazole, isothiazole, triazole, isoxazole, tetrahydropyridine, tetrahydropyran and dihydropyran (optionally pyridine, pyrazole, tetrahydropyran and dihydropyran); and $het^3$ is represented by a ring selected from unsubstituted or substituted: pyrimidine, pyrazine, pyridazine, piperazine, dioxane, morpholine and thiomorpholine.

Optionally, $het^1$ represents an unsubstituted or substituted pyrazole or $X^1$ is $CR^6$ and $X^2$ is N; $het^2$ is represented by a ring selected from unsubstituted or substituted: pyrazole, imidazole, pyridine, tetrahydropyran, dihydropyran, piperidine, piperazine and morpholine; and $het^3$ is represented by a ring selected from unsubstituted or substituted: pyrimidine, pyrazine, pyridazine and piperazine.

Optionally, $het^1$ represents an unsubstituted or substituted pyrazole or $X^1$ is $CR^6$ and $X^2$ is N; $het^2$ is represented by a ring selected from unsubstituted or substituted: pyrazole, imidazole, pyridine, pyridazine, pyrimidine, thiazole, isothiazole, triazole, isoxazole, tetrahydropyridine, tetrahydropyran and dihydropyran (optionally pyridine, pyrazole, tetrahydropyran and dihydropyran); and $het^3$ is represented by a ring selected from unsubstituted or substituted: phenyl, pyrazole, pyridine, pyrimidine, pyrazine, dihydropyran, and piperazine.

In an embodiment $het^1$ represents an unsubstituted or substituted imidazole or $X^1$ is N and $X^2$ is $CR^6$; $het^2$ is represented by an aromatic, saturated or unsaturated 6 membered heterocyclic ring which is unsubstituted or substituted, and het³ is represented by an aromatic, saturated or unsubstituted 6 membered heterocyclic ring which is unsubstituted or substituted and comprises 2 heteroatoms.

In an embodiment het¹ represents an unsubstituted or substituted imidazole or $X^1$ is N and $X^2$ is $CR^6$; het² is represented by a 5 or 6 membered heterocycloalkenyl or heteroaryl ring which is unsubstituted or substituted, (optionally wherein het² is not represented by pyridine) and het³ is represented by an aromatic, saturated or unsaturated 6 membered heterocyclic ring which is unsubstituted or substituted and comprises 2 heteroatoms.

In an embodiment het¹ represents an unsubstituted or substituted imidazole or $X^1$ is N and $X^2$ is $CR^6$; het² is represented by a ring selected from unsubstituted or substituted: pyrazole, imidazole, pyridine, pyrazine, pyrimidine, pyridazine, pyran, tetrahydropyran, dihydropyran, piperidine, piperazine, morpholine, thiomorpholine, oxazine, dioxine, dioxane, thiazine, oxathiane and dithiane; and het³ is represented by a ring selected from unsubstituted or substituted: pyrimidine, pyrazine, pyridazine, piperazine, dioxine, dioxane, morpholine and thiomorpholine.

In an embodiment het¹ represents an unsubstituted or substituted imidazole or $X^1$ is N and $X^2$ is $CR^6$; het² is represented by a ring selected from unsubstituted or substituted: pyrazole, imidazole, pyridine, pyridazine, pyrimidine, thiazole, isothiazole, triazole, isoxazole, tetrahydropyridine, tetrahydropyran and dihydropyran (optionally pyridine, pyrazole, tetrahydropyran and dihydropyran); and het³ is represented by a ring selected from unsubstituted or substituted: pyrimidine, pyrazine, pyridazine, piperazine, dioxine, dioxane, morpholine and thiomorpholine.

Optionally, het¹ represents an unsubstituted or substituted imidazole; het² is represented by a ring selected from unsubstituted or substituted: pyrazole, imidazole, pyridine, tetrahydropyran, dihydropyran, piperidine, piperazine and morpholine; and het³ is represented by a ring selected from unsubstituted or substituted: pyrimidine, pyrazine, pyridazine and piperazine.

Optionally, het¹ represents an unsubstituted or substituted imidazole or $X^1$ is $CR^6$ and $X^2$ is N; het² is represented by a ring selected from unsubstituted or substituted: pyrazole, imidazole, pyridine, pyridazine, pyrimidine, thiazole, isothiazole, triazole, isoxazole, tetrahydropyridine, tetrahydropyran and dihydropyran (optionally pyridine, pyrazole, tetrahydropyran and dihydropyran); and het³ is represented by a ring selected from unsubstituted or substituted: phenyl, pyrazole, pyridine, pyrimidine, pyrazine, dihydropyran, and piperazine.

In an embodiment het¹ represents an unsubstituted or substituted thiophene; het² is represented by an aromatic, saturated or unsaturated 6 membered heterocyclic ring which is unsubstituted or substituted, and het³ is represented by an aromatic, saturated or unsaturated 6 membered heterocyclic ring which is unsubstituted or substituted and comprises 2 heteroatoms.

In an embodiment het¹ represents an unsubstituted or substituted thiophene; het² is represented by a 5 or 6 membered heterocycloalkenyl or heteroaryl ring which is unsubstituted or substituted, (optionally wherein het² is not represented by pyridine) and het³ is represented by an aromatic, saturated or unsaturated 6 membered heterocyclic ring which is unsubstituted or substituted and comprises 2 heteroatoms.

In an embodiment het¹ represents an unsubstituted or substituted thiophene; het² is represented by a ring selected from unsubstituted or substituted: pyrazole, imidazole, pyridine, pyrazine, pyrimidine, pyridazine, pyran, tetrahydropyran, dihydropyran, piperidine, piperazine, morpholine, thiomorpholine, oxazine, dioxine, dioxane, thiazine, oxathiane and dithiane; and het³ is represented by a ring selected from unsubstituted or substituted: pyrimidine, pyrazine, pyridazine, piperazine, dioxine, dioxane, morpholine and thiomorpholine.

In an embodiment het¹ represents an unsubstituted or substituted thiophene; represented by a ring selected from unsubstituted or substituted: pyrazole, imidazole, pyridine, pyridazine, pyrimidine, thiazole, isothiazole, triazole, isoxazole, tetrahydropyridine, tetrahydropyran and dihydropyran (optionally pyridine, pyrazole, tetrahydropyran and dihydropyran); and het³ is represented by a ring selected from unsubstituted or substituted: pyrimidine, pyrazine, pyridazine, piperazine, dioxine, dioxane, morpholine and thiomorpholine.

Optionally, het¹ represents an unsubstituted or substituted thiophene; het² is represented by a ring selected from unsubstituted or substituted: pyrazole, imidazole, pyridine, tetrahydropyran, dihydropyran, piperidine, piperazine and morpholine; and het³ is represented by a ring selected from unsubstituted or substituted: pyrimidine, pyrazine, pyridazine and piperazine.

Optionally, het¹ represents an unsubstituted or substituted thiophene; het² is represented by a ring selected from unsubstituted or substituted: pyrazole, imidazole, pyridine, pyridazine, pyrimidine, thiazole, isothiazole, triazole, isoxazole, tetrahydropyridine, tetrahydropyran and dihydropyran (optionally pyridine, pyrazole, tetrahydropyran and dihydropyran); and het³ is represented by a ring selected from unsubstituted or substituted: phenyl, pyrazole, pyridine, pyrimidine, pyrazine, dihydropyran, and piperazine.

In a preferred embodiment het¹ represents an unsubstituted or substituted: imidazole, pyrazole or thiophene; het² is represented by an unsubstituted or substituted pyridine; and het³ is represented by a ring selected from unsubstituted or substituted: pyrimidine, and pyrazine.

$R^1$ and $R^2$ may be independently selected at each occurrence from: H, halo, $C_{1-4}$ alkyl, $C_{1-4}$ haloalkyl, $-OR^{A3}$ and $-NR^{A3}R^{B3}$. $R^1$ and $R^2$ may be independently selected at each occurrence from: H, chloro, fluoro, methyl, ethyl, trifluoromethyl, trifluoroethyl, $-OCF_3$, $-OH$, $-OMe$, $-OEt$, $-NH_2$, $-NHMe$, and $-NMe_2$. Preferably, $R^1$ and $R^2$ are H.

In an embodiment m is 1 and $R^1$ and $R^2$ are H. In an alternative embodiment m is 2 and $R^1$ and $R^2$ are H. In an alternative embodiment m is 1 and $R^1$ is Me $R^2$ are H.

$R^3$ is optionally H or methyl.

$R^4$ is optionally selected at each occurrence from: halo, $C_{1-4}$ alkyl, $C_{1-4}$ haloalkyl, $-CN$, $-OR^{A4}$ and $-NR^{A4}R^{B4}$. $R^{A4}$ may be independently selected at each occurrence from: H, chloro, fluoro, methyl, ethyl, trifluoromethyl, trifluoroethyl, $-OCF_3$, $-OH$, $-OMe$, $-OEt$, $-NH_2$, $-NHMe$, and $-NMe_2$.

$R^{A1}$, $R^{B1}$, $R^{A2}$, $R^{B2}$, $R^{A3}$, $R^{B3}$, $R^{A4}$ and $R^{B4}$ are at each occurrence independently selected from: H, methyl, ethyl and $-OCF_3$.

In a preferred embodiment n is 0.

In a preferred embodiment the compounds of the invention are selected from compounds of formulae (IIa), (IIIb), (IVa), (Va) or (Vc).

The invention also provides pharmaceutically acceptable salts of compounds of the invention. Accordingly, there are provided compounds of formula (I) and pharmaceutically acceptable salts thereof.

The compound according to the invention may be selected from a group consisting of:

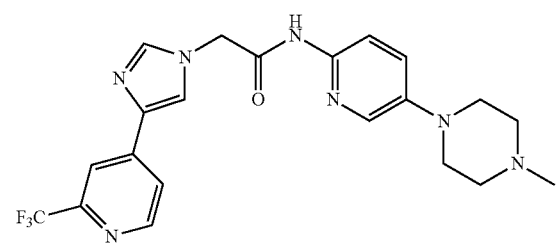
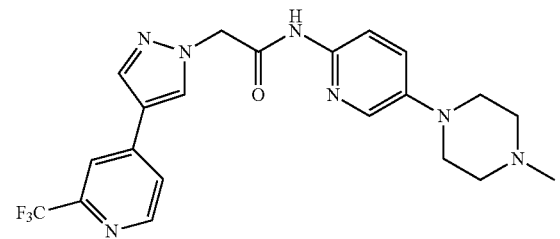
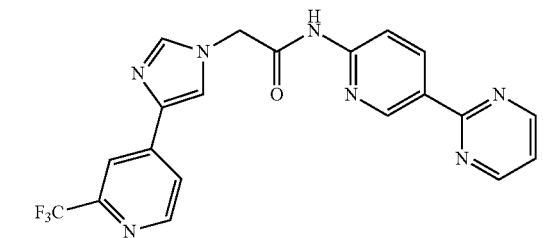
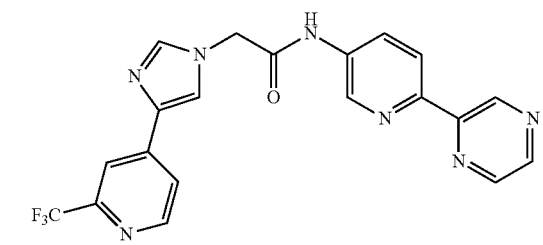
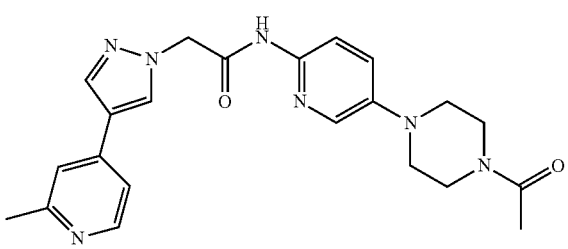
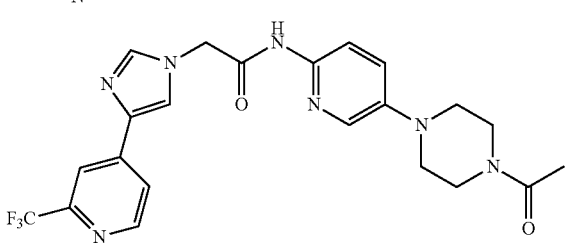
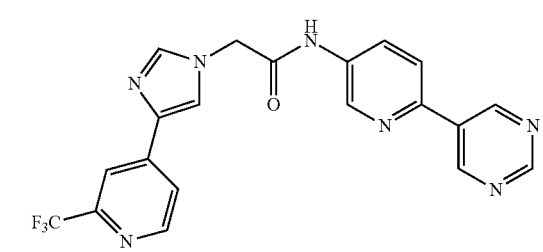
-continued
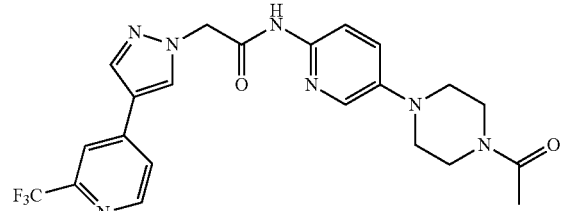
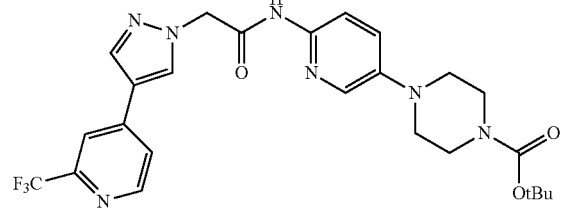
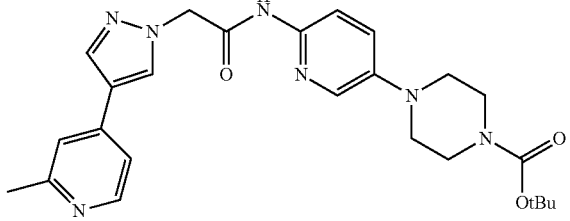
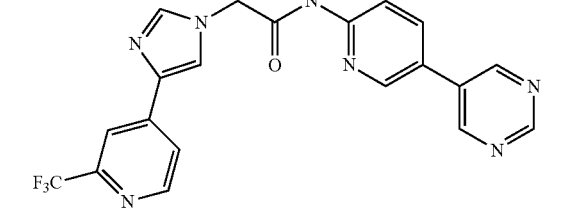
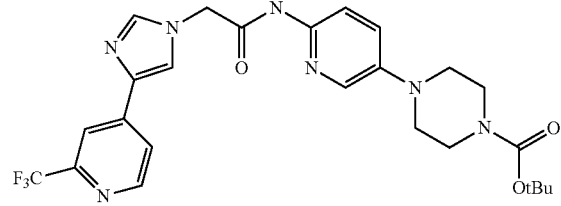
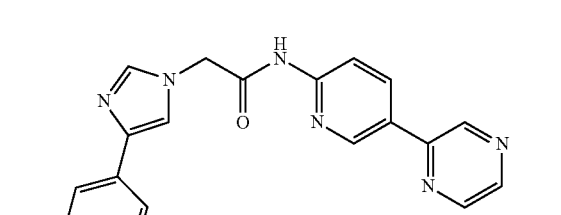
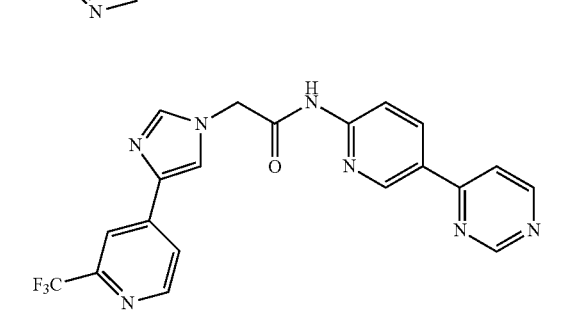

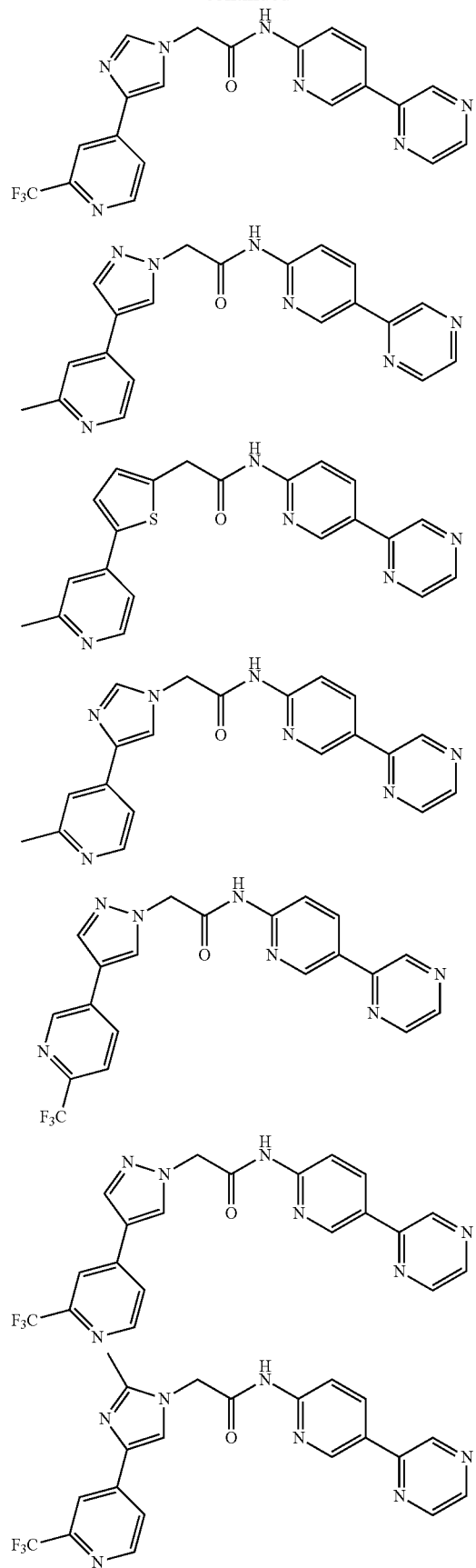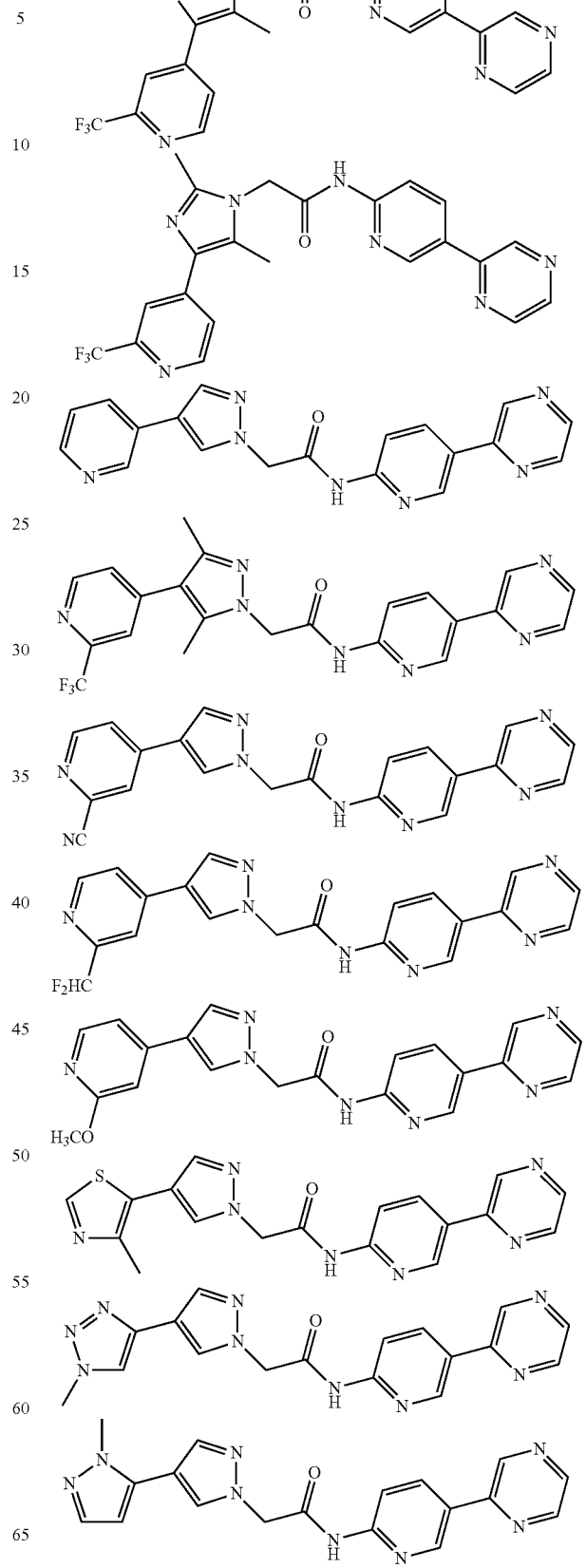

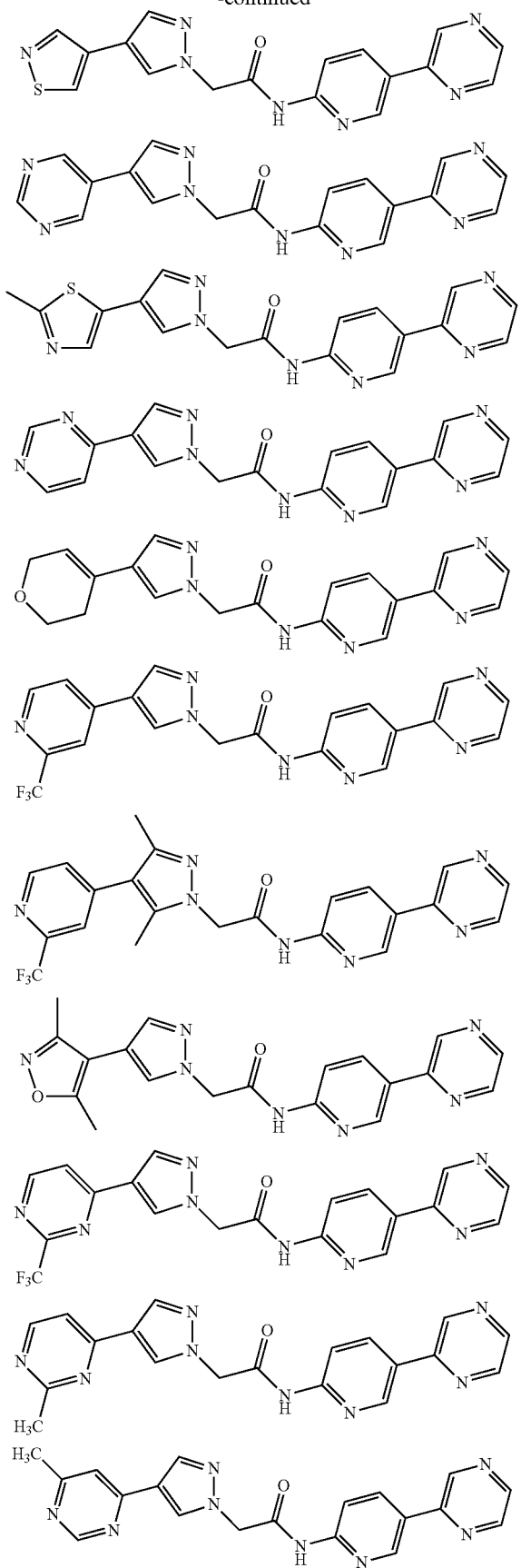
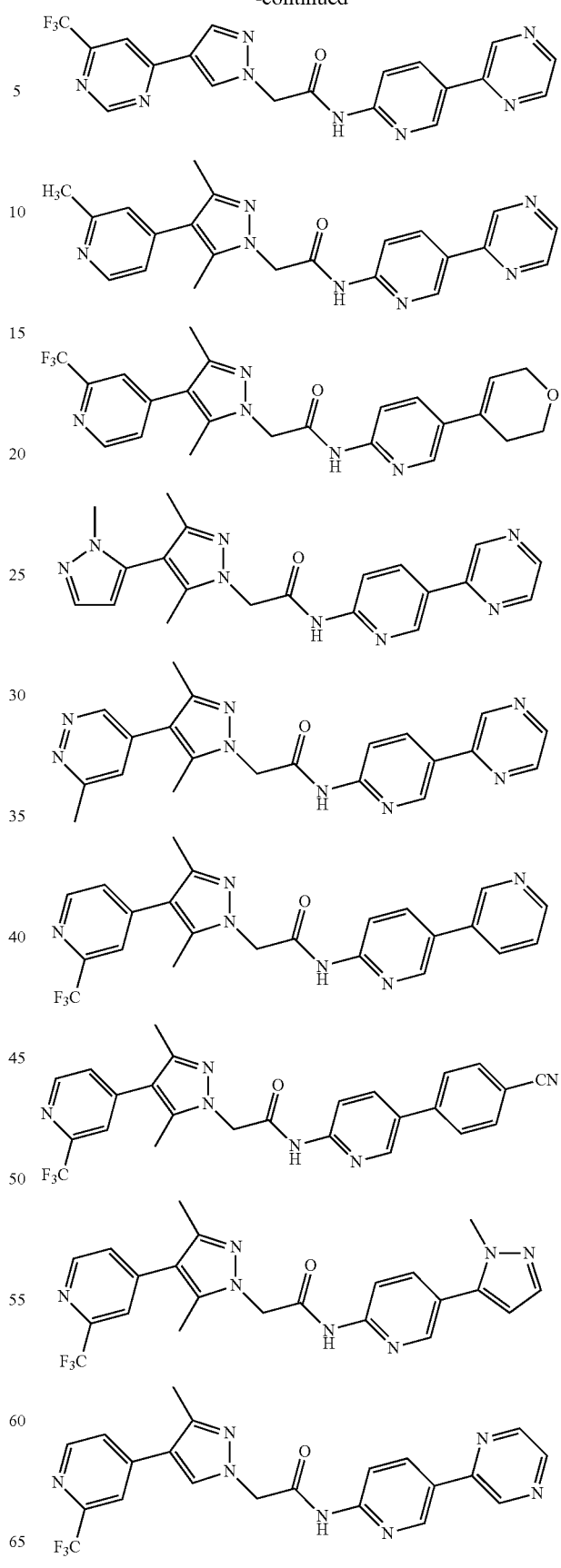

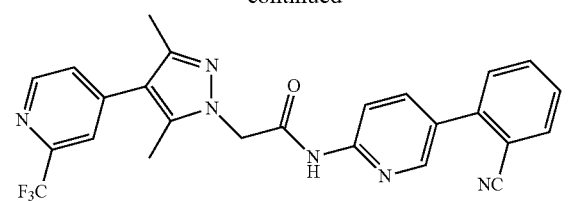
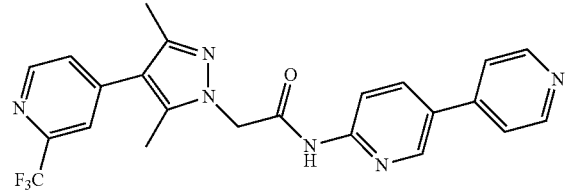
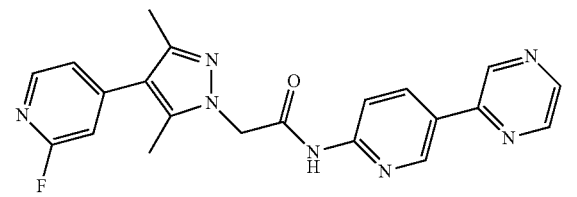
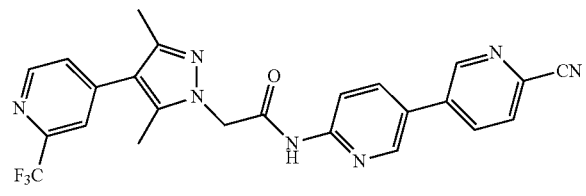
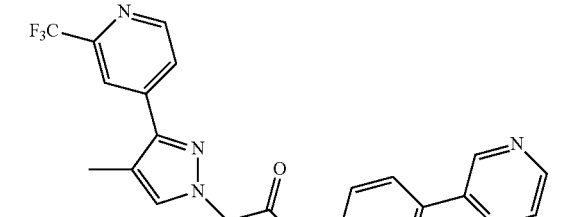
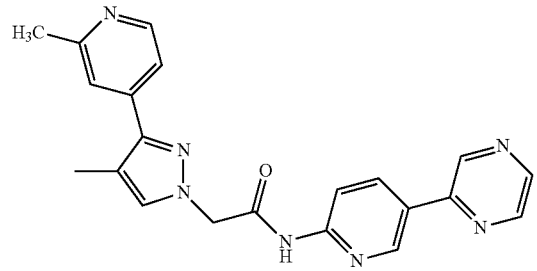
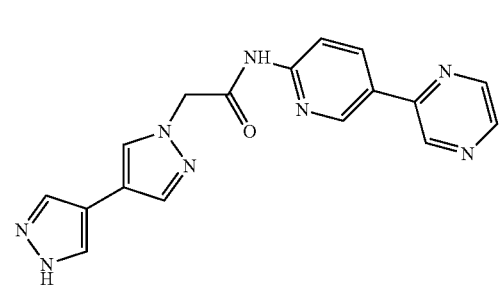
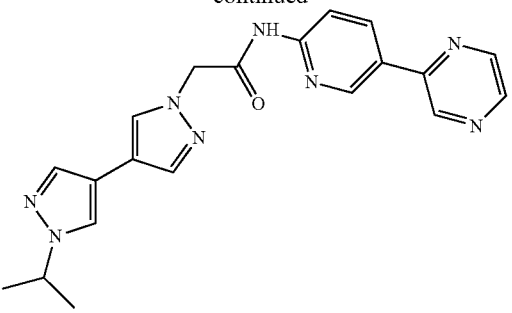
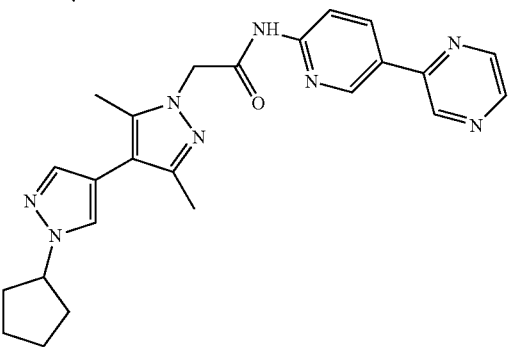
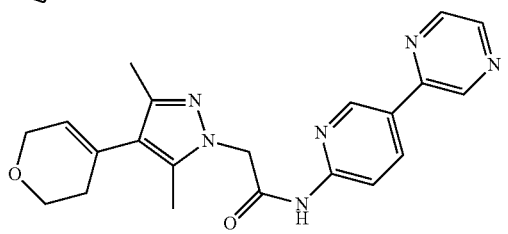
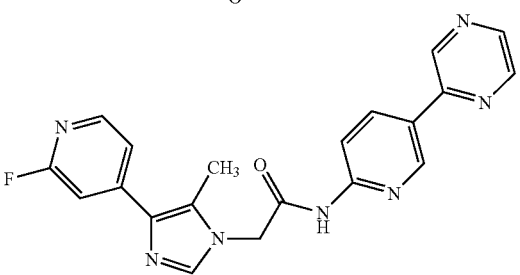
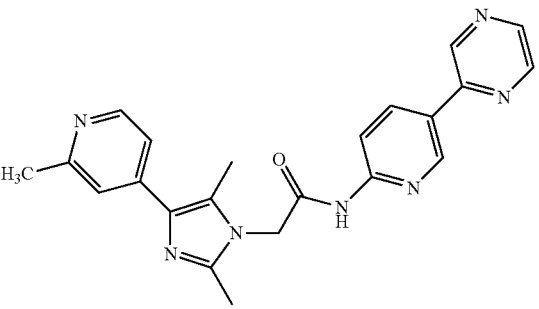
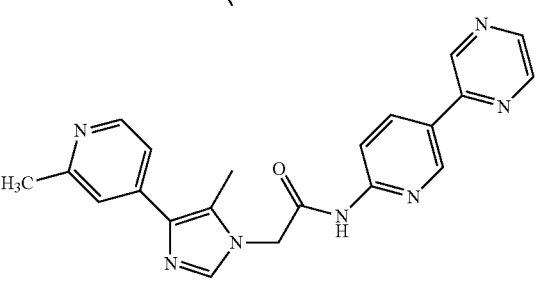

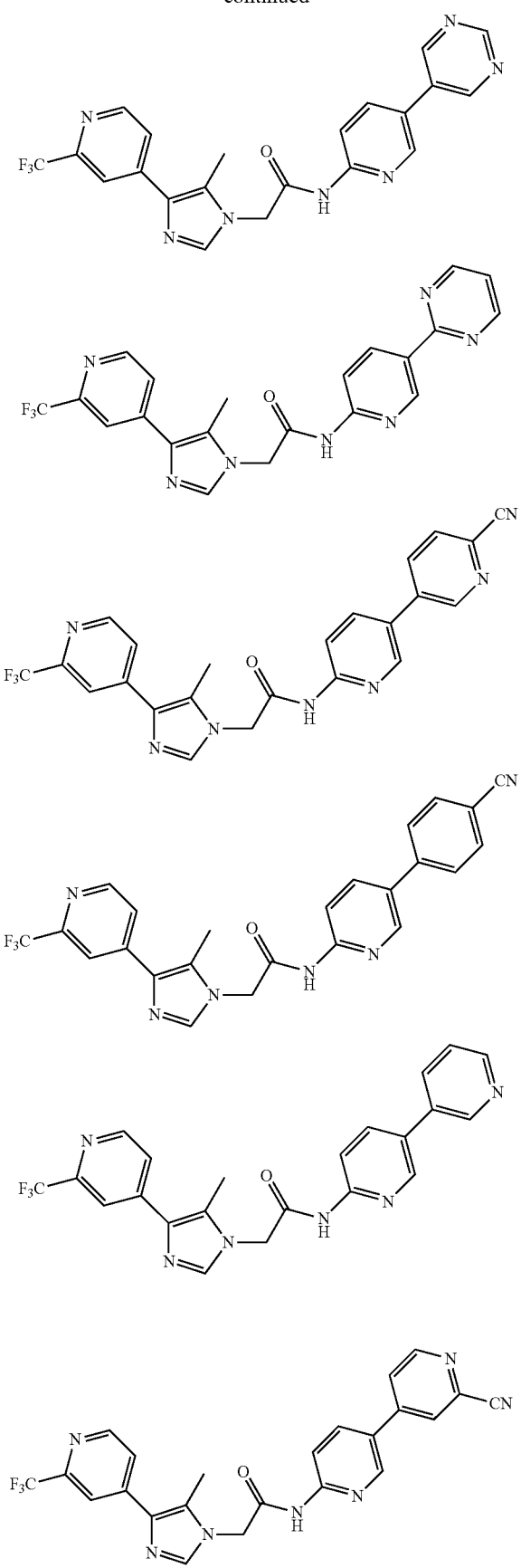
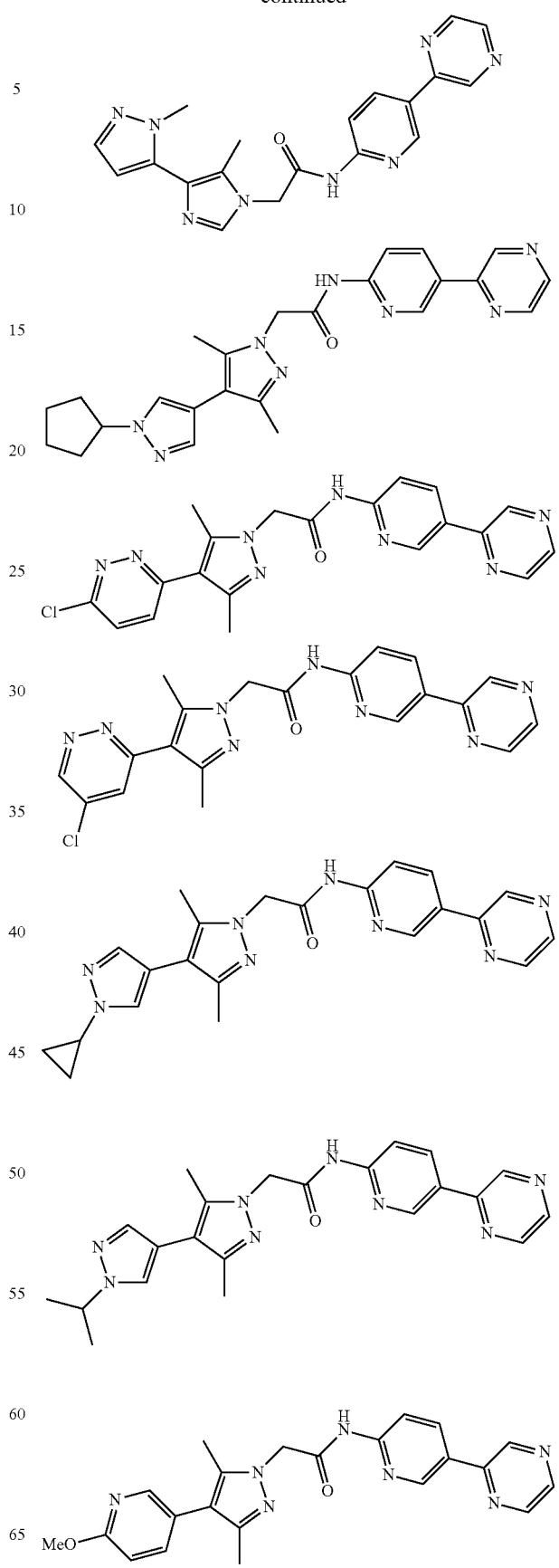

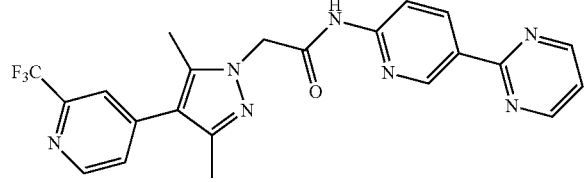
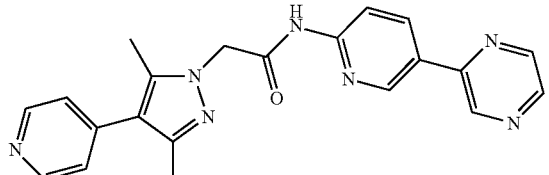
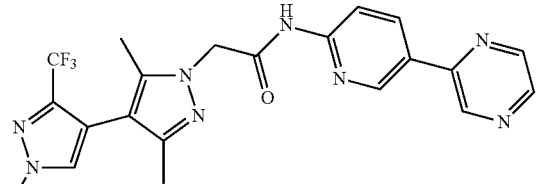
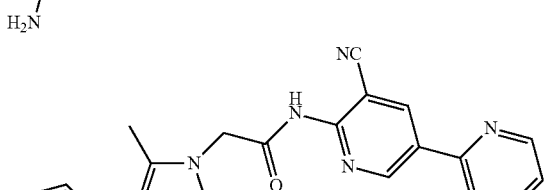
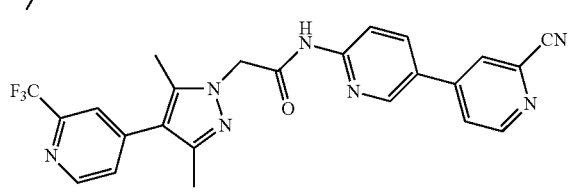
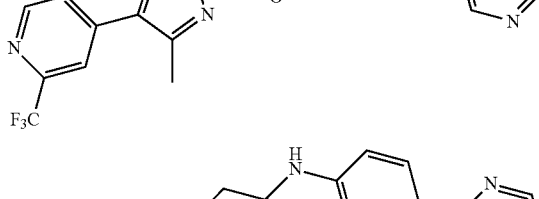
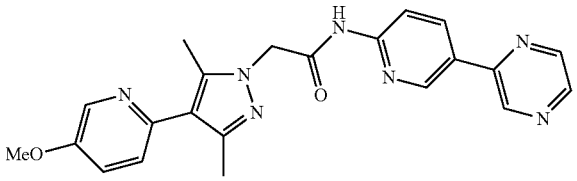
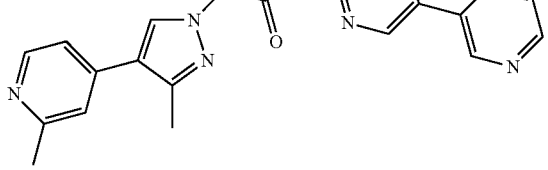
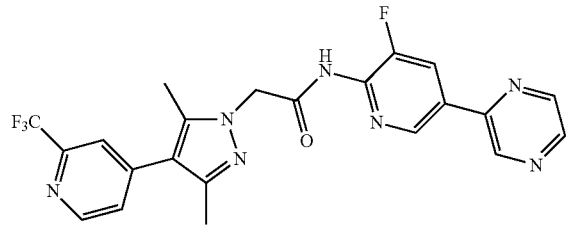
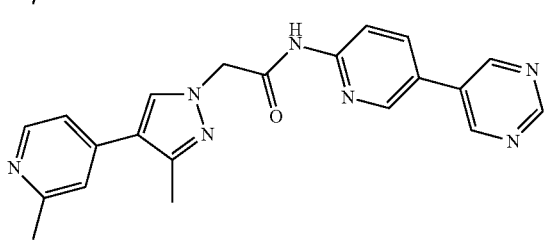
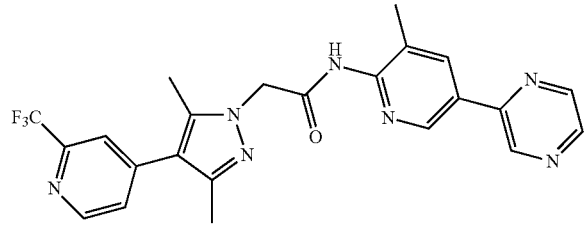
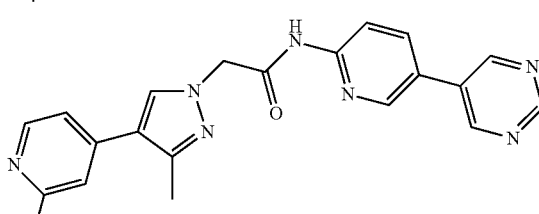
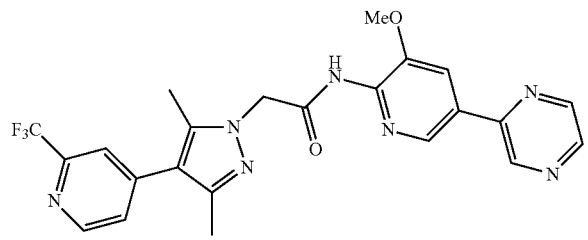
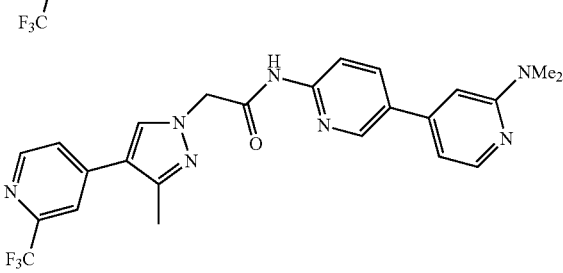
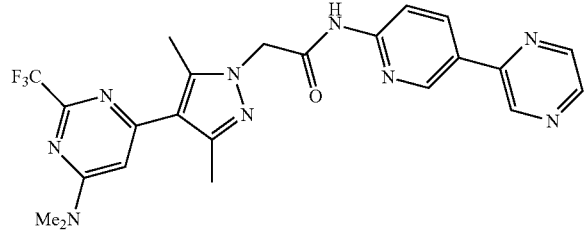
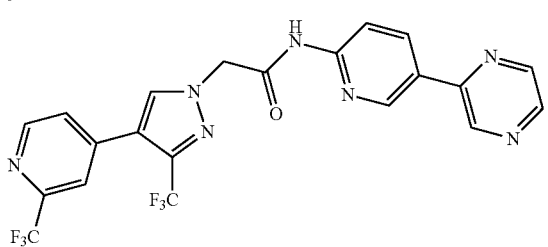

-continued

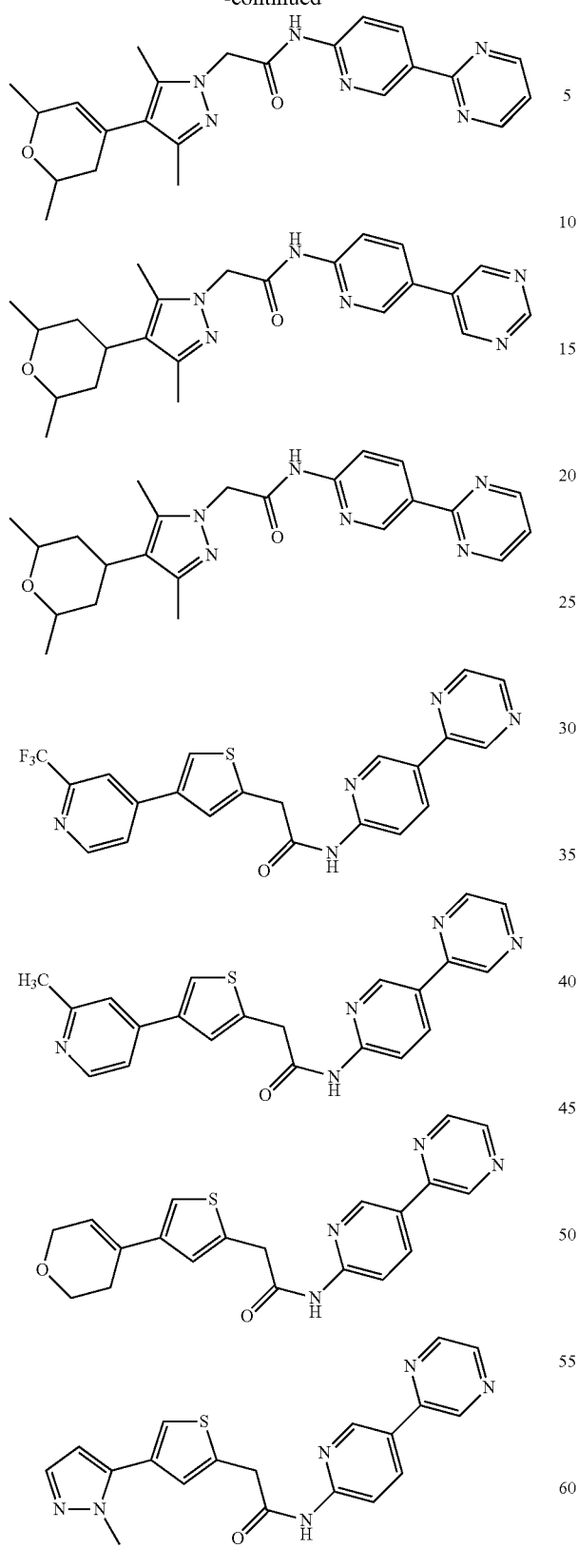
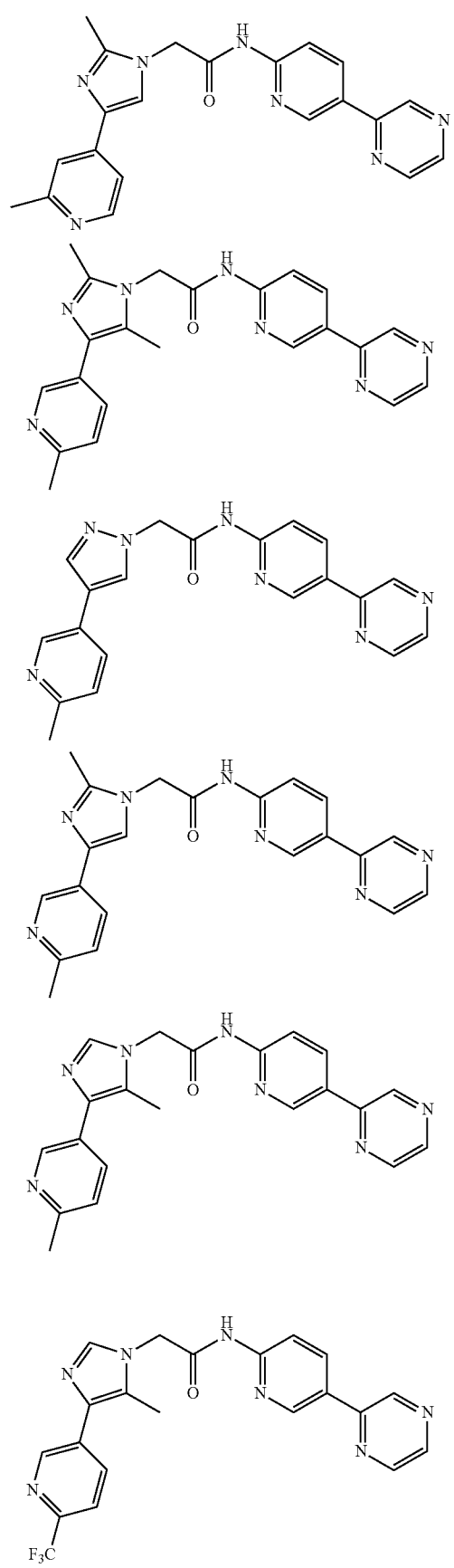
The compound according to the invention may also be selected from a group consisting of:

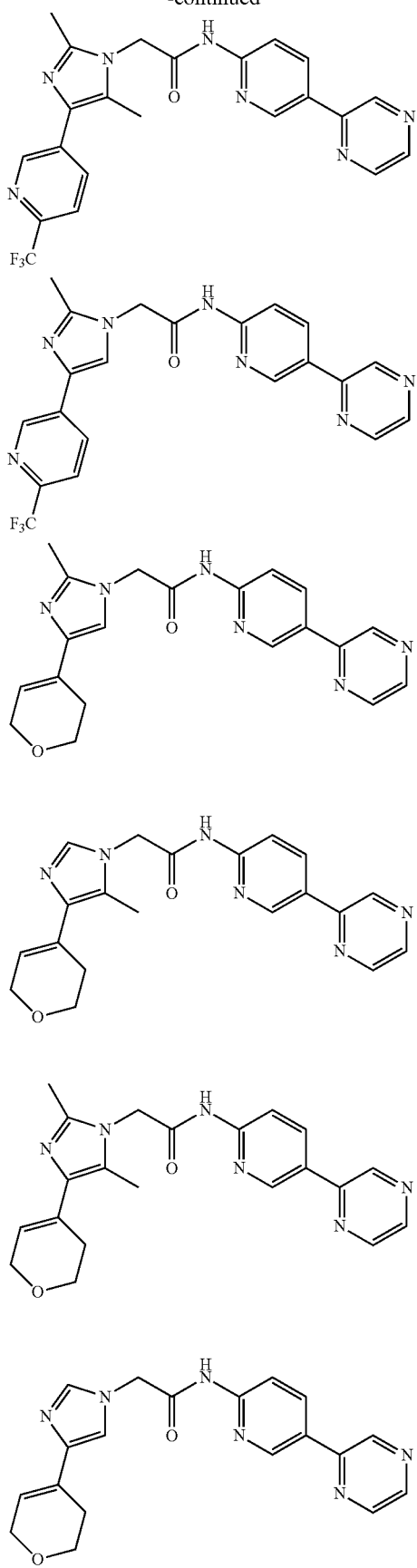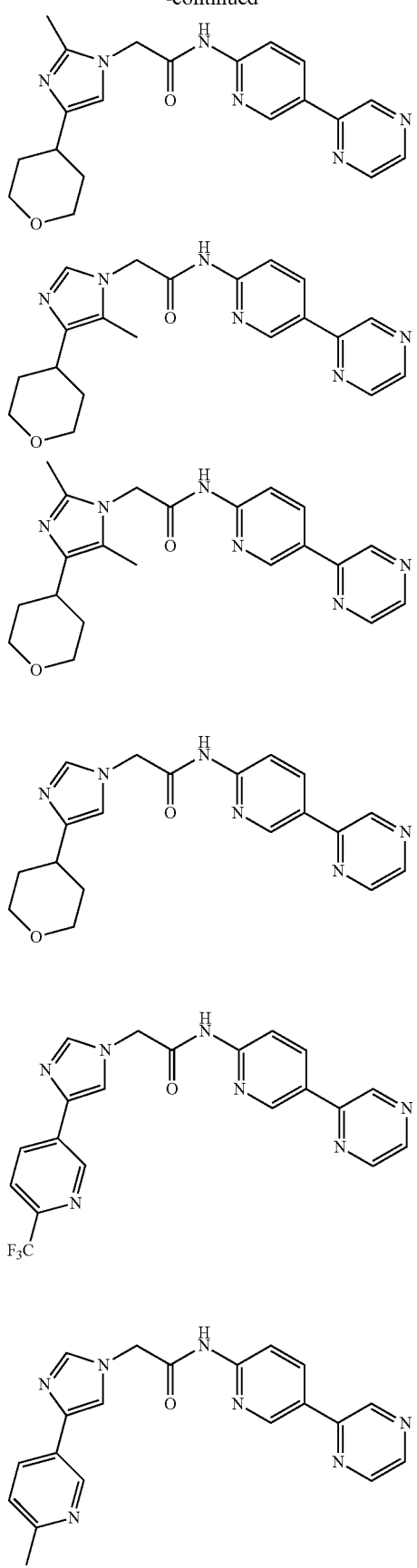

-continued
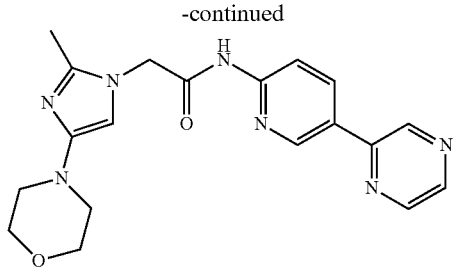
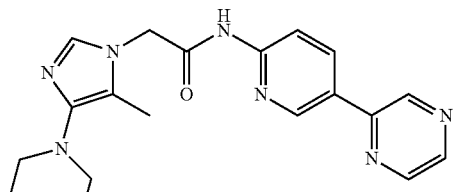
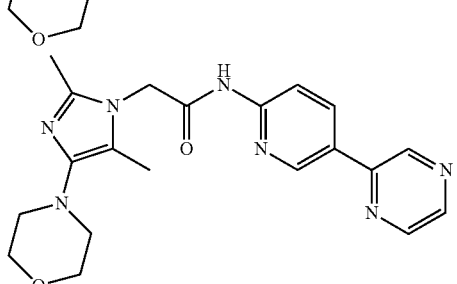
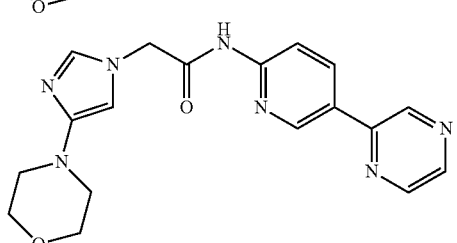
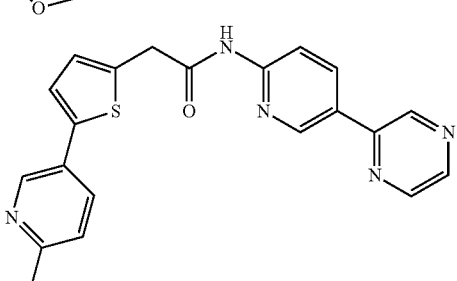
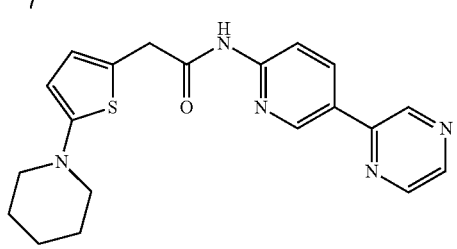
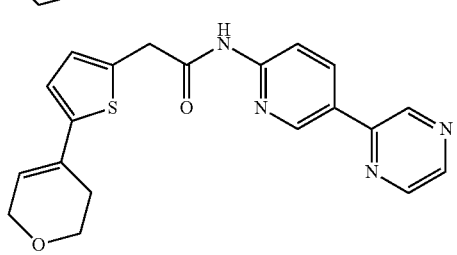
-continued
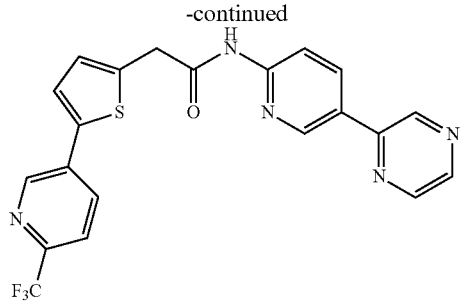
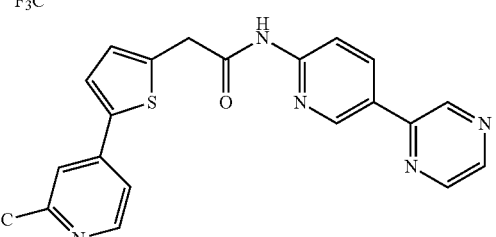
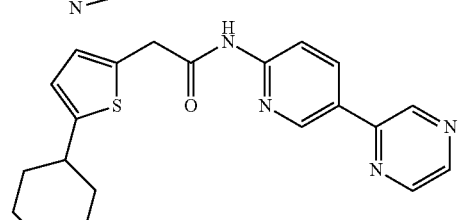
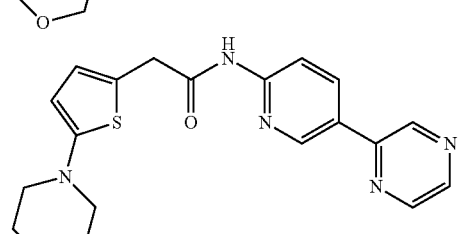
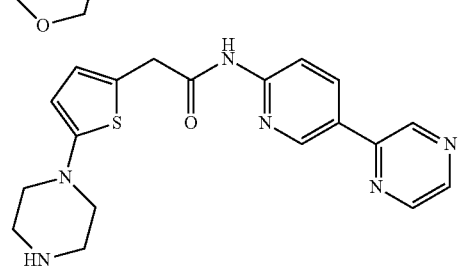
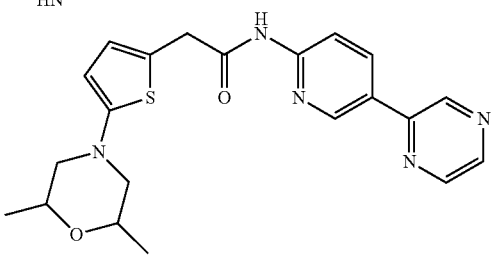
In an embodiment the compounds of the invention are not
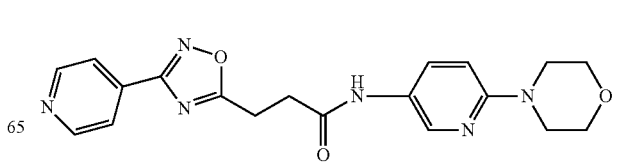

-continued

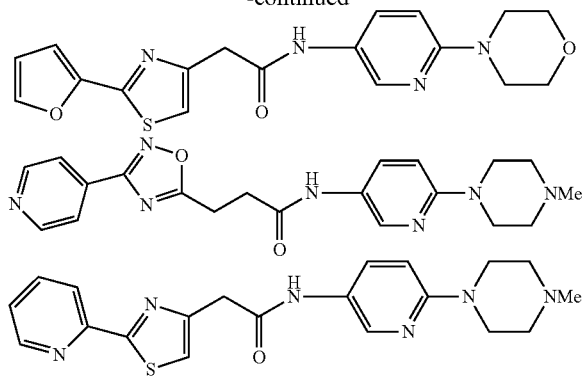

In accordance with another aspect, the present invention provides a compound of the present invention for use as a medicament.

In accordance with another aspect, the present invention provides a pharmaceutical formulation comprising a compound of the present invention and a pharmaceutically acceptable excipient.

In an embodiment the pharmaceutical composition may be a combination product comprising an additional pharmaceutically active agent. The additional pharmaceutically active agent may be an anti-tumor agent described below.

In accordance with another aspect, there is provided a compound of the present invention for use in the modulation of Wnt signalling. Optionally, the Wnt signalling is modulated by the inhibition of porcupine (Porcn). Modulation of Wnt signalling may include inhibition of paracrine signalling in the tissues surrounding tumours and autocrine and paracrine signalling in cancer cells In accordance with another aspect, there is provided a compound of the present invention for use in the treatment of a condition which can be modulated by inhibition of Porcn using a compound of the present invention. A compound of formula (I) may be for use in the treatment of a condition treatable by the inhibition of Porcn.

Porcn inhibition is relevant for the treatment of many different diseases associated with increased Wnt signalling. In embodiments the condition treatable by the inhibition of Porcn may be selected from: cancer, sarcoma, melanoma, skin cancer, haematological tumors, lymphoma, carcinoma, and leukemia. Specific cancers, sarcomas, melanomas, skin cancers, haematological tumors, lymphoma, carcinoma and leukemia treatable by the modulation of Wnt signalling or the inhibition of Porcn may be selected from: esophageal squamous cell carcinoma, gastric cancer, glioblastomas, astrocytomas; retinoblastoma, osteosarcoma, chondosarcoma, Ewing's sarcoma, rabdomysarcoma, Wilm's tumor, basal cell carcinoma, non-small cell lung cancer, brain tumour, hormone refractory prostate cancer, prostate cancer, metastatic breast cancer, breast cancer, metastatic pancreatic cancer, pancreatic cancer, colorectal cancer, cervical cancer, head and neck squamous cell carcinoma and cancer of the head and neck.

Porcn inhibition is also relevant for the treatment of a condition treatable by the inhibition of Wnt ligand secretion selected from: skin fibrosis, idiopathic pulmonary fibrosis, renal interstitial fibrosis, liver fibrosis, proteinuria, kidney graft rejection, osteoarthritis, Parkinsons's disease, cystoid macular edema, uveitis associated cystoid macular edema, retinopathy, diabetic retinopathy and retinopathy of prematurity.

The invention contemplates methods of treating the above mentioned conditions and contemplates compounds of the invention for use in a method of treatment of the above mentioned conditions.

In an aspect of the invention, a compound of the invention may be for use in the treatment of a condition selected from: cancer, sarcoma, melanoma, skin cancer, haematological tumors, lymphoma, carcinoma, and leukemia. Specific cancer, sarcoma, melanoma, skin cancer, haematological tumors, lymphoma, carcinoma, and leukemia that may be treated by the compound of the invention may be selected from: esophageal squamous cell carcinoma, gastric cancer, glioblastomas, astrocytomas; retinoblastoma, osteosarcoma, chondosarcoma, Ewing's sarcoma, rabdomysarcoma, Wilm's tumor, basal cell carcinoma, non-small cell lung cancer, brain tumour, hormone refractory prostate cancer, prostate cancer, metastatic breast cancer, breast cancer, metastatic pancreatic cancer, pancreatic cancer, colorectal cancer, cervical cancer, head and neck squamous cell carcinoma and cancer of the head and neck.

The compound of the invention also may be for use in the treatment of a condition selected from: skin fibrosis, idiopathic pulmonary fibrosis, renal interstitial fibrosis, liver fibrosis, proteinuria, kidney graft rejection, osteoarthritis, Parkinsons's disease, cystoid macular edema, uveitis associated cystoid macular edema, retinopathy, diabetic retinopathy and retinopathy of prematurity.

In an aspect of the invention there is provided a method of treatment of a condition which is modulated by Wnt signalling, wherein the method comprises administering a therapeutic amount of a compound of the invention, to a patient in need thereof. In an embodiment of the invention there is provided a method of treatment of a condition which is modulated by Porcn.

The method of treatment may be a method of treating a condition treatable by the modulation of Wnt signalling or Porcn. These conditions are described above in relation to conditions treatable by the inhibition of Porcn.

In an aspect of the invention there is provided a method of treatment of a condition selected from: cancer, sarcoma, melanoma, skin cancer, haematological tumors, lymphoma, carcinoma, and leukemia, wherein the method comprises administering a therapeutic amount of a compound of the invention, to a patient in need thereof. Specific cancer, sarcoma, melanoma, skin cancer, haematological tumors, lymphoma, carcinoma, and leukemia that may be treated by the method of treatment may be selected from: esophageal squamous cell carcinoma, gastric cancer, glioblastomas, astrocytomas; retinoblastoma, osteosarcoma, chondosarcoma, Ewing's sarcoma, rabdomysarcoma, Wilm's tumor, basal cell carcinoma, non-small cell lung cancer, brain tumour, hormone refractory prostate cancer, prostate cancer, metastatic breast cancer, breast cancer, metastatic pancreatic cancer, pancreatic cancer, colorectal cancer, cervical cancer, head and neck squamous cell carcinoma and cancer of the head and neck.

The method of treatment also may be the treatment of a condition selected from: skin fibrosis, idiopathic pulmonary fibrosis, renal interstitial fibrosis, liver fibrosis, proteinuria, kidney graft rejection, osteoarthritis, Parkinsons's disease, cystoid macular edema, uveitis associated cystoid macular edema, retinopathy, diabetic retinopathy and retinopathy of prematurity In an aspect of the invention there is provided a use of a compound of the invention in the manufacture of a medicament for the treatment of a condition which is modulated by Porcn. The condition may be any of the conditions mentioned above.

Aberrant Wnt signalling may be associated with a condition selected from: non small cell lung cancer (NSCLC); chronic lymphocytic leukemia (CLL); gastric cancer; head and neck squamous cell carcinoma (HNSCC); colorectal cancer; ovarian cancer; basal cell carcinoma (BCC); breast cancer bladder cancer; mesothelioma colorectal; prostate cancer; non-small cell lung cancer; lung cancer; osteosarcoma; Frz overexpression; has been associated with cancers such as prostate; colorectal; ovarian cancer; gastric; overexpression of Wnt signaling pathway components such as dishevelled; prostate cancer; breast cancer; mesothelioma; cervical; Frat-1 overexpression; pancreatic cancer; esophageal cancer; cervical cancer; breast cancer; and gastric cancer; Axin loss of function (LOF); hepatocellular cancer; medulloblastoma; gastric cancer; colorectal cancer; intestinal carcinoid; ovarian cancer; pulmonary adenocarcinoma; endometrial cancer; hepatocellular; hepatoblastoma; medulloblastoma; pancreatic cancer; thyroid cancer; prostate cancer; melanoma; pilomatricoma; Wilms' tumor; pancreatoblastomas; liposarcomas; juvenile nasopharyngeal angiofibromas; desmoid; synovial sarcoma; melanoma; leukemia; multiple myeloma; brain tumors, such as gliomas, astrocytomas, meningiomas, schwannomas, pituitary tumors, primitive neuroectodermal tumors (PNET), medulloblastomas, craniopharyngioma, pineal region tumors, and non-cancerous neurofibromatoses;

Inhibition of Wnt signaling with the Wnt antagonists of the present invention may be therapeutic in the treatment of disorders resulting from dysfunctional hematopoieses, such as leukemias and various blood related cancers, such as acute, chronic, lymphoid and myelogenous leukemias, myelodysplastic syndrome and myeloproliferative disorders. These include myeloma, lymphoma (e.g., Hodgkin's and non-Hodgkin's) chronic and nonprogressive anemia, progressive and symptomatic blood cell deficiencies, polycythemia vera, essential or primary thrombocythemia, idiopathic myelofibrosis, chronic myelomonocytic leukemia (CMML), mantle cell lymphoma, cutaneous T-cell lymphoma, and Waldenstrom macro globinemia.

Other disorders associated with aberrant Wnt signaling, include but are not limited to osteoporosis, osteoarthritis, polycystic kidney disease, diabetes, schizophrenia, vascular disease, cardiac disease, non-oncogenic proliferative diseases, and neurodegenerative diseases such as Alzheimers disease.

Aberrant Wnt signalling may be associated with a cancer selected from: brain; lung; colon; epidermoid; squamous cell; bladder; gastric; pancreatic; breast; head and neck; renal; kidney; liver; ovarian; prostate; uterine; oesophageal; testicular; gynaecological; thyroid; melanoma; acute myeloid leukemia; chronic myelogenous leukemia; MCL Kaposi's sarcoma;

Aberrant Wnt signalling may be associated with an inflammatory disease selected from: multiple sclerosis; rheumatoid arthritis; systemic lupus; inflammatory bowel disease; osteoarthritis; Alzheimer's.

DETAILED DESCRIPTION

Given below are definitions of terms used in this application. Any term not defined herein takes the normal meaning as the skilled person would understand the term.

The term "halo" refers to one of the halogens, group 17 of the periodic table. In particular the term refers to fluorine, chlorine, bromine and iodine. Preferably, the term refers to fluorine or chlorine.

The term "$C_{1-4}$ alkyl" refers to a linear or branched hydrocarbon chain containing 1, 2, 3, 4, 5 or 6 carbon atoms, for example methyl, ethyl, n-propyl, iso-propyl, n-butyl, sec-butyl, tert-butyl, n-pentyl and n-hexyl. Alkylene groups may likewise be linear or branched and may have two places of attachment to the remainder of the molecule. Furthermore, an alkylene group may, for example, correspond to one of those alkyl groups listed in this paragraph. The alkyl and alkylene groups may be unsubstituted or substituted by one or more substituents. Possible substituents are described below. Substituents for the alkyl group may be halogen, e.g. fluorine, chlorine, bromine and iodine, OH, $C_{1-6}$ alkoxy.

The term "$C_{1-4}$ alkoxy" refers to an alkyl group which is attached to a molecule via oxygen. This includes moieties where the alkyl part may be linear or branched and may contain 1, 2, 3, 4, 5 or 6 carbon atoms, for example methyl, ethyl, n-propyl, iso-propyl, n-butyl, sec-butyl, tert-butyl, n-pentyl and n-hexyl. Therefore, the alkoxy group may be methoxy, ethoxy, n-propoxy, iso-propoxy, n-butoxy, sec-butoxy, tert-butoxy, n-pentoxy and n-hexoxy. The alkyl part of the alkoxy group may be unsubstituted or substituted by one or more substituents. Possible substituents are described below. Substituents for the alkyl group may be halogen, e.g. fluorine, chlorine, bromine and iodine, OH, $C_{1-6}$ alkoxy.

The term "$C_{1-4}$ haloalkyl" refers to a hydrocarbon chain substituted with at least one halogen atom independently chosen at each occurrence, for example fluorine, chlorine, bromine and iodine. The halogen atom may be present at any position on the hydrocarbon chain. For example, $C_{1-4}$ haloalkyl may refer to chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl.

The term "$C_{2-6}$ alkenyl" refers to a branched or linear hydrocarbon chain containing at least one double bond and having 2, 3, 4, 5 or 6 carbon atoms. The double bond(s) may be present as the E or Z isomer. The double bond may be at any possible position of the hydrocarbon chain. For example, the "$C_{2-6}$ alkenyl" may be ethenyl, propenyl, butenyl, butadienyl, pentenyl, pentadienyl, hexenyl and hexadienyl.

The term "$C_{2-6}$ alkynyl" refers to a branched or linear hydrocarbon chain containing at least one triple bond and having 2, 3, 4, 5 or 6 carbon atoms. The triple bond may be at any possible position of the hydrocarbon chain. For example, the "$C_{2-6}$ alkynyl" may be ethynyl, propynyl, butynyl, pentynyl and hexynyl.

The term "$C_{1-6}$ heteroalkyl" refers to a branched or linear hydrocarbon chain containing 1, 2, 3, 4, 5, or 6 carbon atoms and at least one heteroatom selected from N, O and S positioned between any carbon in the chain or at an end of the chain. For example, the hydrocarbon chain may contain one or two heteroatoms. The $C_{1-6}$ heteroalkyl may be bonded to the rest of the molecule through a carbon or a heteroatom. For example, the "$C_{1-6}$ heteroalkyl" may be $C_{1-6}$ N-alkyl, $C_{1-6}$ N,N-alkyl, or $C_{1-6}$ O-alkyl.

The term "carbocyclic" refers to a saturated or unsaturated carbon containing ring system. A "carbocyclic" system may be monocyclic or a fused polycyclic ring system, for example, bicyclic or tricyclic. A "carbocyclic" moiety may contain from 3 to 14 carbon atoms, for example, 3 to 8 carbon atoms in a monocyclic system and 7 to 14 carbon atoms in a polycyclic system. "Carbocyclic" encompasses cycloalkyl moieties, cycloalkenyl moieties, aryl ring systems and fused ring systems including an aromatic portion.

The term "heterocyclic" refers to a saturated or unsaturated ring system containing at least one heteroatom selected from N, O or S. A "heterocyclic" system may contain 1, 2, 3 or 4 heteroatoms, for example 1 or 2. A "heterocyclic" system may be monocyclic or a fused polycyclic ring system, for example, bicyclic or tricyclic. A "heterocyclic" moiety may contain from 3 to 14 carbon atoms, for example, 3 to 8 carbon atoms in a monocyclic system and 7 to 14 carbon atoms in a polycyclic system. "Heterocyclic" encompasses heterocycloalkyl moieties, heterocycloalkenyl moieties and heteroaromatic moieties. For example, the heterocyclic group may be: oxirane, aziridine, azetidine, oxetane, tetrahydrofuran, pyrrolidine, imidazolidine, succinimide, pyrazolidine, oxazolidine, isoxazolidine, thiazolidine, isothiazolidine, piperidine, morpholine, thiomorpholine, piperazine, and tetrahydropyran.

The term "$C_{3-6}$ cycloalkyl" refers to a saturated hydrocarbon ring system containing 3, 4, 5, 6, 7 or 8 carbon atoms. For example, the "$C_{3-8}$ cycloalkyl" may be cyclopropyl, cyclobutyl, cyclopentyl, cyclohexyl, cycloheptyl and cyclooctyl.

The term "$C_{3-8}$ cycloalkenyl" refers to an unsaturated hydrocarbon ring system containing 3, 4, 5, 6, 7 or 8 carbon atoms that is not aromatic. The ring may contain more than one double bond provided that the ring system is not aromatic. For example, the "$C_{3-8}$ cycloalkyl" may be cyclopropenyl, cyclobutenyl, cyclopentenyl, cyclopentadienyl, cyclohexenyl, cyclohexadienly, cycloheptenyl, cycloheptadiene, cycloodenyl and cycloatadienyl.

The term "$C_{3-8}$ heterocycloalkyl" refers to a saturated hydrocarbon ring system containing 3, 4, 5, 6, 7 or 8 carbon atoms and at least one heteroatom within the ring selected from N, O and S. For example there may be 1, 2 or 3 heteroatoms, optionally 1 or 2. The "$C_{3-8}$ heterocycloalkyl" may be bonded to the rest of the molecule through any carbon atom or heteroatom. The "$C_{3-8}$ heterocycloalkyl" may have one or more, e.g. one or two, bonds to the rest of the molecule: these bonds may be through any of the atoms in the ring. For example, the "$C_{3-8}$ heterocycloalkyl" may be oxirane, aziridine, azetidine, oxetane, tetrahydrofuran, pyrrolidine, imidazolidine, succinimide, pyrazolidine, oxazolidine, isoxazolidine, thiazolidine, isothiazolidine, piperidine, morpholine, thiomorpholine, piperazine, and tetrahydropyran.

The term "$C_{3-8}$ heterocycloalkenyl" refers to an unsaturated hydrocarbon ring system, that is not aromatic, containing 3, 4, 5, 6, 7 or 8 carbon atoms and at least one heteroatom within the ring selected from N, O and S. For example there may be 1, 2 or 3 heteroatoms, optionally 1 or 2. The "$C_{3-8}$ heterocycloalkenyl" may be bonded to the rest of the molecule through any carbon atom or heteroatom. The "$C_{3-8}$ heterocycloalkenyl" may have one or more, e.g. one or two, bonds to the rest of the molecule: these bonds may be through any of the atoms in the ring. For example, the "$C_{3-8}$ heterocycloalkyl" may be tetrahydropyridine, dihydropyran, dihydrofuran, pyrroline.

The term "aromatic" when applied to a substituent as a whole means a single ring or polycyclic ring system with 4n+2 electrons in a conjugated π system within the ring or ring system where all atoms contributing to the conjugated π system are in the same plane.

The term "aryl" refers to an aromatic hydrocarbon ring system. The ring system has 4n+2 electrons in a conjugated π system within a ring where all atoms contributing to the conjugated π system are in the same plane. For example, the "aryl" may be phenyl and naphthyl. The aryl system itself may be substituted with other groups.

The term "heteroaryl" refers to an aromatic hydrocarbon ring system with at least one heteroatom within a single ring or within a fused ring system, selected from O, N and S. The ring or ring system has 4n+2 electrons in a conjugated π system where all atoms contributing to the conjugated π system are in the same plane. For example, the "heteroaryl" may be imidazole, thiene, furane, thianthrene, pyrrol, benzimidazole, pyrazole, pyrazine, pyridine, pyrimidine and indole.

The term "alkaryl" refers to an aryl group, as defined above, bonded to a $C_{1-4}$ alkyl, where the $C_{1-4}$ alkyl group provides attachment to the remainder of the molecule.

The term "alkheteroaryl" refers to a heteroaryl group, as defined above, bonded to a $C_{1-4}$ alkyl, where the alkyl group provides attachment to the remainder of the molecule.

The term "halogen" herein includes reference to F, Cl, Br and I. Halogen may be Cl. Halogen may be F.

A bond terminating in a "⌇" represents that the bond is connected to another atom that is not shown in the structure. A bond terminating inside a cyclic structure and not terminating at an atom of the ring structure represents that the bond may be connected to any of the atoms in the ring structure where allowed by valency.

Where a moiety is substituted, it may be substituted at any point on the moiety where chemically possible and consistent with atomic valency requirements. The moiety may be substituted by one or more substituents, e.g. 1, 2, 3 or 4 substituents; optionally there are 1 or 2 substituents on a group. Where there are two or more substituents, the substituents may be the same or different. The substituent(s) may be selected from: OH, NHR, amidino, guanidino, hydroxyguanidino, formamidino, isothioureido, ureido, mercapto, C(O)H, acyl, acyloxy, carboxy, sulfo, sulfamoyl, carbamoyl, cyano, azo, nitro, halo, $C_{1-6}$ alkyl, $C_{1-6}$ alkoxy, $C_{1-6}$ haloalkyl, $C_{3-8}$ cycloalkyl, $C_{2-6}$ alkenyl, $C_{2-6}$ alkynyl, aryl, heteroaryl or alkaryl. Where the group to be substituted is an alkyl group the substituent may be =O. R may be selected from H, $C_{1-6}$ alkyl, $C_{3-8}$ cycloalkyl, phenyl, benzyl or phenethyl group, e.g. R is H or $C_{1-3}$ alkyl. Where the moiety is substituted with two or more substituents and two of the substituents are adjacent the adjacent substituents may form a $C_{4-8}$ ring along with the atoms of the moiety on which the substituents are substituted, wherein the $C_{4-8}$ ring is a saturated or unsaturated hydrocarbon ring with 4, 5, 6, 7, or 8 carbon atoms or a saturated or unsaturated hydrocarbon ring with 4, 5, 6, 7, or 8 carbon atoms and 1, 2 or 3 heteroatoms.

Substituents are only present at positions where they are chemically possible, the person skilled in the art being able to decide (either experimentally or theoretically) without inappropriate effort which substitutions are chemically possible and which are not.

Ortho, meta and para substitution are well understood terms in the art. For the absence of doubt, "ortho" substitution is a substitution pattern where adjacent carbons possess a substituent, whether a simple group, for example the fluoro group in the example below, or other portions of the molecule, as indicated by the bond ending in "⌇".

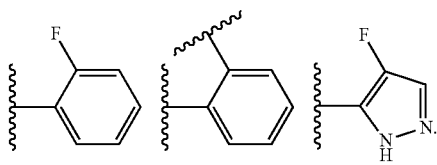

"Meta" substitution is a substitution pattern where two substituents are on carbons one carbon removed from each other, i.e with a single carbon atom between the substituted carbons. In other words there is a substituent on the second atom away from the atom with another substituent. For example the groups below are meta substituted.

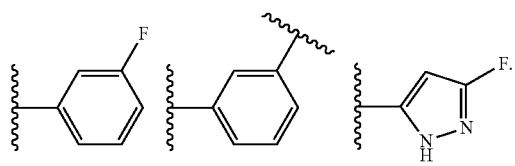

"Para" substitution is a substitution pattern where two substituents are on carbons two carbons removed from each other, i.e with two carbon atoms between the substituted carbons. In other words there is a substituent on the third atom away from the atom with another substituent. For example the groups below are para substituted.

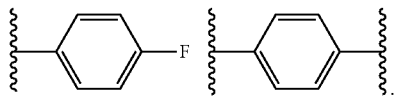

Where two groups are substituted on non-adjacent atoms, it will be understood by the skilled person that the two groups are not substituted on the same atom or on two atoms that are bonded to each other. For example, the pyrazole ring shown below is shown with two substituents which are bonded to non-adjacent atoms. Non-adjacent atoms have at least one atom in between them.

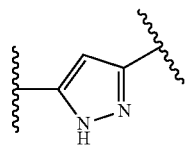 [SMILES: *c1cc(*)[nH]n1]

By "acyl" is meant an organic radical derived from, for example, an organic acid by the removal of the hydroxyl group, e.g. a radical having the formula R—C(O)—, where R may be selected from H, $C_{1-6}$ alkyl, $C_{3-8}$ cycloalkyl, phenyl, benzyl or phenethyl group, eg R is H or $C_{1-3}$ alkyl. In one embodiment acyl is alkyl-carbonyl. Examples of acyl groups include, but are not limited to, formyl, acetyl, propionyl and butyryl. A particular acyl group is acetyl.

Throughout the description the disclosure of a compound also encompasses pharmaceutically acceptable salts, solvates and stereoisomers thereof. Where a compound has a stereocentre, both (R) and (S) stereoisomers are contemplated by the invention, equally mixtures of stereoisomers or a racemic mixture are completed by the present application.

Where a compound of the invention has two or more stereocentres any combination of (R) and (S) stereoisomers is contemplated. The combination of (R) and (S) stereoisomers may result in a diastereomeric mixture or a single diastereoisomer. The compounds of the invention may be present as a single stereoisomer or may be mixtures of stereoisomers, for example racemic mixtures and other enantiomeric mixtures, and diasteroemeric mixtures. Where the mixture is a mixture of enantiomers the enantiomeric excess may be any of those disclosed above. Where the compound is a single stereoisomer the compounds may still contain other diastereoisomers or enantiomers as impurities. Hence a single stereoisomer does not necessarily have an enantiomeric excess (e.e.) or diastereomeric excess (d.e.) of 100% but could have an e.e. or d.e. of about at least 85%

The invention contemplates pharmaceutically acceptable salts of the compounds of the invention. These may include the acid addition and base salts of the compounds. These may be acid addition and base salts of the compounds. In addition the invention contemplates solvates of the compounds. These may be hydrates or other solvated forms of the compound.

Suitable acid addition salts are formed from acids which form non-toxic salts. Examples include the acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate and hemicalcium salts. For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:
(i) by reacting the compound of the invention with the desired acid or base;
(ii) by removing an acid- or base-labile protecting group from a suitable precursor of the compound of the invention or by ring-opening a suitable cyclic precursor, for example, a lactone or lactam, using the desired acid or base; or
(iii) by converting one salt of the compound of the invention to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of any formula include references to salts, solvates and complexes thereof and to solvates and complexes of salts thereof.

The compounds of the invention include compounds of a number of formula as herein defined, including all polymorphs and crystal habits thereof, prodrugs and isomers thereof (including optical, geometric and tautomeric isomers) as hereinafter defined and isotopically-labelled compounds of the invention.

The present invention also includes all pharmaceutically acceptable isotopically-labelled compounds of the invention wherein one or more atoms are replaced by atoms having the same atomic number, but an atomic mass or mass number different from the atomic mass or mass number most commonly found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Before purification, the compounds of the present invention may exist as a mixture of enantiomers depending on the synthetic procedure used. The enantiomers can be separated by conventional techniques known in the art. Thus the invention covers individual enantiomers as well as mixtures thereof.

For some of the steps of the process of preparation of the compounds of the invention, it may be necessary to protect potential reactive functions that are not wished to read, and to cleave said protecting groups in consequence. In such a case, any compatible protecting radical can be used. In particular methods of protection and deprotection such as those described by T. W. GREENE (Protective Groups in Organic Synthesis, A. Wiley-Interscience Publication, 1981) or by P. J. Kocienski (Protecting groups, Georg Thieme Verlag, 1994), can be used. All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

Also, the compounds of the present invention as well as intermediates for the preparation thereof can be purified according to various well-known methods, such as for example crystallization or chromatography.

One or more compounds of the invention may be combined with one or more pharmaceutical agents, for example anti-viral agents, chemotherapeutics, anti-cancer agents, immune enhancers, immunosuppressants, anti-tumour vaccines, anti-viral vaccines, cytokine therapy, or tyrosine kinase inhibitors, for the treatment of conditions modulated by the inhibition of Porcn, for example cancer, sarcoma, melanoma, skin cancer, haematological tumors, lymphoma, carcinoma, leukemia, central nervous system disorders, inflammation and immunological diseases The method of treatment or the compound for use in the treatment of cancer, sarcoma, melanoma, skin cancer, haematological tumors, lymphoma, carcinoma, leukemia, central nervous system disorders, inflammation and immunological diseases as defined hereinbefore may be applied as a sole therapy or be a combination therapy with an additional active agent.

The method of treatment or the compound for use in the treatment of cancer, sarcoma, melanoma, skin cancer, haematological tumors, lymphoma, carcinoma, leukemia, and central nervous system disorders may involve, in addition to the compound of the invention, conventional surgery or radiotherapy or chemotherapy. Such chemotherapy may include one or more of the following categories of anti-tumor agents:

(i) antiproliferative/antineoplastic drugs and combinations thereof, such as alkylating agents (for example cis-platin, oxaliplatin, carboplatin, cyclophosphamide, nitrogen mustard, uracil mustard, bendamustin, melphalan, chlorambucil, chlormethine, busulphan, temozolamide, nitrosoureas, ifosamide, melphalan, pipobroman, triethylene-melamine, triethylenethiophoporamine, carmustine, omustine, stroptozocin and dacarbazine); antimetabolites (for example gemcitabine and antifolates such as fluoropyrimidines like 5-fluorouracil and tegafur, raltitrexed, methotrexate, pemetrexed, cytosine arabinoside, floxuridine, cytarabine, 6-mercaptopurine, 6-thioguanine, fludarabine phosphate, pentostatine, and gemcitabine and hydroxyurea); antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); proteasome inhibitors, for example carfilzomib and bortezomib; interferon therapy; and topoisomerase inhibitors (for example epipodophyllotoxins like etoposide and teniposide, amsacrine, topotecan, mitoxantrone and camptothecin); bieomcin, dactinomycin, daunorubicin, doxorubicin, epirubicin, idarubicin, ara-C, paclitaxel (Taxol™), nabpaclitaxel, docetaxel, mithramycin, deoxyco-formycin, mitomycin-C, L-asparaginase, interferons (especially IFN-a), etoposide, and teniposide;

(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride; and navelbene, CPT-II, anastrazole, letrazole, capecitabine, reloxafme, cyclophosphamide, ifosamide, and droloxafine;

(iii) anti-invasion agents, for example dasatinib and bosutinib (SKI-606), and metalloproteinase inhibitors, inhibitors of urokinase plasminogen activator receptor function or antibodies to Heparanase;

(iv) inhibitors of growth factor function: for example such inhibitors include growth factor antibodies and growth factor receptor antibodies, for example the anti-erbB2 antibody trastuzumab [Herceptin™], the anti-EGFR antibody panitumumab, the anti-erbB1 antibody cetuximab, tyrosine kinase inhibitors, for example inhibitors of the epidermal growth factor family (for example EGFR family tyrosine kinase inhibitors such as gefitinib, erlotinib, 6-acrylamido-N-(3-chloro-4-fluorophenyl)-7-(3-morpholinopropoxy)-quinazolin-4-amine (CI 1033), erbB2 tyrosine kinase inhibitors such as lapatinib) and antibodies to costimulatory molecules such as CTLA-4, 4-1BB and PD-I, or antibodies to cytokines (IL-I0, TGF-beta); inhibitors of the hepatocyte growth factor family; inhibitors of the insulin growth factor family; modulators of protein regulators of cell apoptosis (for example Bcl-2 inhibitors); inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib, tipifarnib and lonafarnib), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor, kinase inhibitors; aurora kinase inhibitors and cyclin dependent kinase inhibitors such as CDK2 and/or CDK4 inhibitors; and CCR2, CCR4 or CCR6 modulator;

(v) antiangiogenic agents such as those which inhibit the effects of vascular endothelial growth factor, [for example the anti-vascular endothelial cell growth factor antibody bevacizumab (Avastin™); thalidomide; lenalidomide; and for example, a VEGF receptor tyrosine kinase inhibitor such as vandetanib, vatalanib, sunitinib, axitinib and pazopanib;

(vi) gene therapy approaches, including for example approaches to replace aberrant genes such as aberrant p53 or aberrant BRCA1 or BRCA2;

(vii) immunotherapy approaches, including for example antibody therapy such as alemtuzumab, rituximab, ibritumomab tiuxetan (Zevalin®) and ofatumumab; interferons such as interferon α; interleukins such as IL-2 (aldesleukin); interleukin inhibitors for example IRAK4 inhibitors; cancer vaccines including prophylactic and treatment vaccines such as HPV vaccines, for example Gardasil, Cervarix, Oncophage and Sipuleucel-T (Provenge); gp100; dendritic cell-based vaccines (such as Ad.p53 DC); and toll-like receptor modulators for example TLR-7 or TLR-9 agonists; and (viii) cytotoxic agents for example fludaribine (fludara), cladribine, pentostatin (Nipent™);

(ix) steroids such as corticosteroids, including glucocorticoids and mineralocorticoids, for example aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives. A combination of steroids may be used, for example a combination of two or more steroids mentioned in this paragraph;

(x) targeted therapies, for example PI3Kd inhibitors, for example idelalisib and perifosine; PD-1, PD-L1, PD-L2 and CTL4-A modulators, antibodies and vaccines; IDO inhibitors (such as indoximod); anti-PD-1 monoclonal antibodies (such as MK-3475 and nivolumab); anti-PDL1 monoclonal antibodies (such as MEDI-4736 and RG-7446); anti-PDL2 monoclonal antibodies; and anti-CTLA-4 antibodies (such as ipilimumab);

(xi) anti-viral agents such as nucleotide reverse transcriptase inhibitors (for example, zidovudine, didanosine, zalcitabine, stavudine, lamivudine, abacavir, adefovir diprovoxil, lobucavir, BCH-10652, emitricitabine, beta-L-FD4 (also called 3'-dicleoxy-5-fluoro-cytidine), (–)-beta-D-2, 6-diamino-purine dioxolane, and lodenasine), non-nucleoside reverse transcriptase inhibitors (for example, nevirapine, delaviradine, efavirenz, PNU-142721, AG-1549, MKC-442 (1-ethoxy-methyl)-5-(1-methyl-ethy)-6-(phenylmehtyl)-(2,4(1H,3H)pyrimidineone), and (+)-alanolide A and B) and protease inhibitors (for example, saquinavir, ritonavir, indinavir, nelfinavir, amprenavir, lasinavir, DMP-450, BMS-2322623, ABT-378 and AG-1 549);

(xii) chimeric antigen receptors, anticancer vaccines and arginase inhibitors.

The method of treatment or the compound for use in the treatment of inflammation and immunological diseases may involve, in addition to the compound of the invention, additional active agents. The additional active agents may be one or more active agents used to treat the condition being treated by the compound of the invention and additional active agent. The additional active agents may include one or more of the following active agents:—

(i) steroids such as corticosteroids, including glucocorticoids and mineralocorticoids, for example aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives. A combination of steroids may be used, for example a combination of two or more steroids mentioned in this paragraph;

(ii) TNF inhibitors for example etanercept; monoclonal antibodies (e.g. infliximab (Remicade), adalimumab (Humira), certolizumab pegol (Cimzia), golimumab (Simponi)); fusion proteins (e.g. etanercept (Enbrel)); and 5-$HT_{2A}$ agonists (e.g. 2,5-dimethoxy-4-iodoamphetamine, TCB-2, lysergic acid diethylamide (LSD), lysergic acid dimethylazetidide);

(iii) anti-inflammatory drugs, for example non-steroidal anti-inflammatory drugs;

(iv) dihydrofolate reductase inhibitors/antifolates, for example methotrexate, trimethoprim, brodimoprim, tetroxoprim, iclaprim, pemetrexed, ralitrexed and pralatrexate; and (v) immunosuppressants for example cyclosporins, tacrolimus, sirolimus pimecrolimus, angiotensin II inhibitors (e.g. Valsartan, Telmisartan, Losartan, Irbesatan, Azilsartan, Olmesartan, Candesartan, Eprosartan) and ACE inhibitors e.g. sulfhydryl-containing agents (e.g. Captopril, Zofenopril), dicarboxylate-containing agents (e.g. Enalapril, Ramipril, Quinapril, Perindopril, Lisinopril, Benazepril, Imidapril, Zofenopril, Trandolapril), phosphate-containing agents (e.g. Fosinopril), casokinins, lactokinins and lactotripeptides.

Such combination treatment may be achieved by way of the simultaneous, sequential or separate dosing of the individual components of the treatment. Such combination products employ the compounds of this invention within a therapeutically effective dosage range described hereinbefore and the other pharmaceutically-active agent within its approved dosage range.

Compounds of the invention may exist in a single crystal form or in a mixture of crystal forms or they may be amorphous. Thus, compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

For the above-mentioned compounds of the invention the dosage administered will, of course, vary with the compound employed, the mode of administration, the treatment desired and the disorder indicated. For example, if the compound of the invention is administered orally, then the daily dosage of the compound of the invention may be in the range from 0.01 micrograms per kilogram body weight (μg/kg) to 100 milligrams per kilogram body weight (mg/kg).

A compound of the invention, or pharmaceutically acceptable salt thereof, may be used on their own but will generally be administered in the form of a pharmaceutical composition in which the compounds of the invention, or pharmaceutically acceptable salt thereof, is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration of the compounds of the invention, the pharmaceutical composition which is used to administer the compounds of the invention will preferably comprise from 0.05 to 99% w (percent by weight) compounds of the invention, more preferably from 0.05 to 80% w compounds of the invention, still more preferably from 0.10 to 70% w compounds of the invention, and even more preferably from 0.10 to 50% w compounds of the invention, all percentages by weight being based on total composition.

The pharmaceutical compositions may be administered topically (e.g. to the skin) in the form, e.g., of creams, gels, lotions, solutions, suspensions, or systemically, e.g. by oral administration in the form of tablets, capsules, syrups, powders or granules; or by parenteral administration in the form of a sterile solution, suspension or emulsion for injection (including intravenous, subcutaneous, intramuscular, intravascular or infusion); by rectal administration in the form of suppositories; or by inhalation in the form of an aerosol.

For oral administration the compounds of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compounds of the invention may be admixed with, for example, a vegetable oil or polyethylene glycol. Hard gelatine capsules may contain granules of the compound using either the above-mentioned excipients for tablets. Also liquid or semi-solid formulations of the compound of the invention may be filled into hard gelatine capsules. Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, sweetening agents (such as saccharine), preservative agents and/or carboxymethylcellulose as a thickening agent or other excipients known to those skilled in art.

For intravenous (parenteral) administration the compounds of the invention may be administered as a sterile aqueous or oily solution.

The size of the dose for therapeutic purposes of compounds of the invention will naturally vary according to the nature and severity of the conditions, the age and sex of the animal or patient and the route of administration, according to well-known principles of medicine.

Dosage levels, dose frequency, and treatment durations of compounds of the invention are expected to differ depending on the formulation and clinical indication, age, and co-morbid medical conditions of the patient. The standard duration of treatment with compounds of the invention is expected to vary between one and seven days for most clinical indications. It may be necessary to extend the duration of treatment beyond seven days in instances of recurrent infections or infections associated with tissues or implanted materials to which there is poor blood supply including bones/joints, respiratory tract, endocardium, and dental tissues.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

EXAMPLES AND SYNTHESIS

Solvents, reagents and starting materials were purchased from commercial vendors and used as received unless otherwise described. All reactions were performed at room temperature unless otherwise stated. Compound identity and purity confirmations were performed by LCMS UV using a Waters Acquity SQ Detector 2 (ACQ-SQD2#LCA081). The diode array detector wavelength was 254 nM and the MS was in positive and negative electrospray mode (m/z: 150-800). A 2 μL aliquot was injected onto a guard column (0.2 μm×2 mm filters) and UPLC column (C18, 50×2.1 mm, <2 μm) in sequence maintained at 40° C. The samples were eluted at a flow rate of 0.6 mL/min with a mobile phase system composed of A (0.1% (v/v) Formic Acid in Water) and B (0.1% (v/v) Formic Acid in Acetonitrile) according to the gradients outlined in Table 1 below. Retention times RT are reported in minutes.

TABLE 1

| Time (min) | % A | % B |
|---|---|---|
| Method 1 | | |
| 0 | 95 | 5 |
| 1.1 | 95 | 5 |

TABLE 1-continued

| Time (min) | % A | % B |
|---|---|---|
| 6.1 | 5 | 95 |
| 7 | 5 | 95 |
| 7.5 | 95 | 5 |
| 8 | 95 | 5 |
| Method 2 | | |
| 0 | 95 | 5 |
| 0.3 | 95 | 5 |
| 2 | 5 | 95 |
| 2.6 | 95 | 5 |
| 3 | 95 | 5 |

NMR was also used to characterise final compounds. NMR spectra were obtained on a Bruker AVIII 400 Nanobay with 5 mm BBFO probe. Optionally, compound Rf values on silica thin layer chromatography (TLC) plates were measured.

Compound purification was performed by flash column chromatography on silica or by preparative LCMS. LCMS purification was performed using a Waters 3100 Mass detector in positive and negative electrospray mode (m/z: 150-800) with a Waters 2489 UV/Vis detector. Samples were eluted at a flow rate of 20 mL/min on a XBridge™ prep C18 5 μM OBD 19×100 mm column with a mobile phase system composed of A (0.1% (v/v) Formic Acid in Water) and B (0.1% (v/v) Formic Acid in Acetonitrile) according to the gradient outlined in Table 2 below.

TABLE 2

| Time (min) | % A | % B |
|---|---|---|
| 0 | 90 | 10 |
| 1.5 | 90 | 10 |
| 11.7 | 5 | 95 |
| 13.7 | 5 | 95 |
| 14 | 90 | 90 |
| 15 | 90 | 90 |

Chemical names in this document were generated using Elemental Structure to Name Conversion by Dotmatics Scientific Software. Starting materials were purchased from commercial sources or synthesised according to literature procedures.

The compounds of the invention may be synthesised by analogy with the following reaction routes:

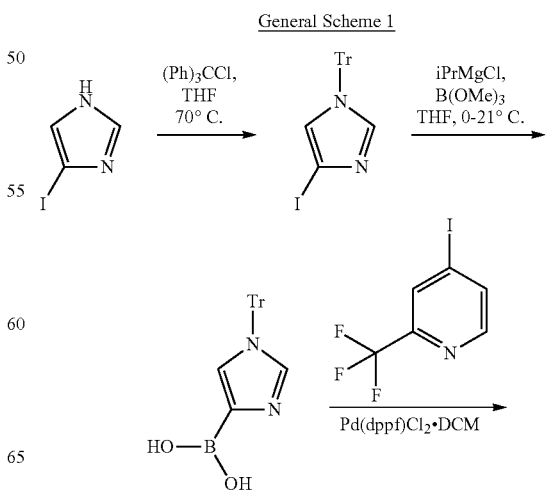

General Scheme 1

Biaryl Alpha-Chloroacetamide: Synthesis B

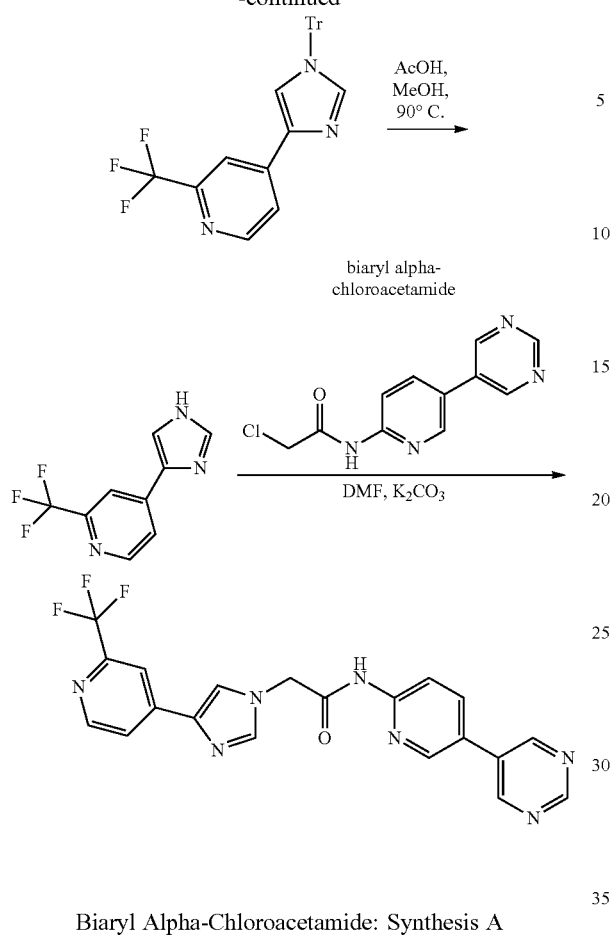

Biaryl Alpha-Chloroacetamide: Synthesis A

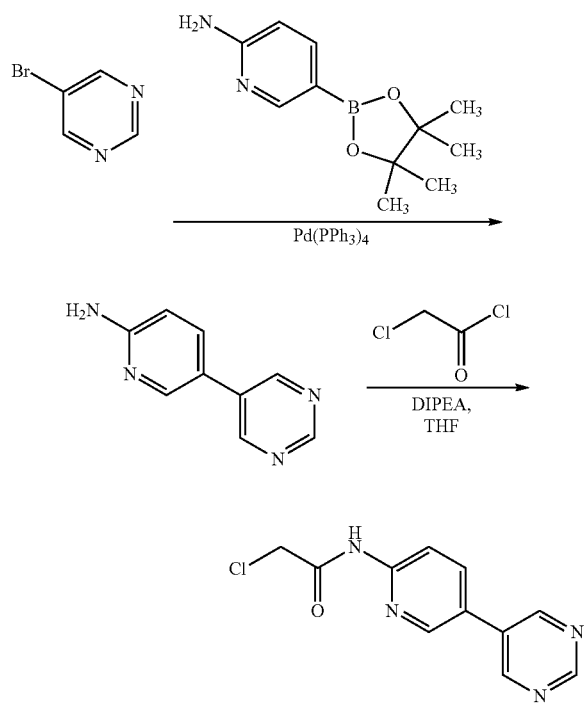

The steps within General Scheme 1 shown above may be performed in the order shown above or in a different order. For example, as the skilled person would appreciate, the Suzuki coupling could be carried out after coupling with the biaryl alpha-chloroacetamide etc. Protecting groups may be present or absent as necessary. For example a nitrogen atom may be protected or unprotected.

Intermediate 1

4-odo-1-trityl-imidazole

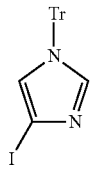

4-iodoimidazole (5.38 g, 27.72 mmol) was dissolved in THF (86 mL). Trityl chloride, (8.5 g, 30.49 mmol) and triethylamine (7.73 mL, 55.44 mmol) were added and the reaction was heated at 70° C. After 3 h, TLC showed that the reaction had gone to completion. Therefore, the reaction mixture was allowed to cool to 45° C. and filtered to remove the suspended white solid. The filtrate was concentrated, redissolved in DCM (300 mL) and washed with 5 wt % aq. sodium thiosulfate solution (300 mL), which was back-extracted with DCM (150 mL). The organics were combined, dried over sodium sulfate, filtered and concentrated to yield the crude product. The white solid was taken up in EtOAc (300 ml) and heated to reflux for 30 minutes. The mixture was cooled and the solid was obtained by vacuum filtration. The white solid was dried in the vacuum oven for 3 hours affording 4-iodo-1-trityl-imidazole (6.721 g, 15.40 mmol, 55.57% yield).

MS Method 2: RT 2.08 min, ES$^+$ m/z 459 [M+Na]$^+$ $^1$H NMR (400 MHz, DMSO) δ/ppm: 7.35-7.40 (m, 10H), 7.06-7.11 (m, 7H).

Intermediate 2

(1-tritylimidazol-4-yl)boronic acid

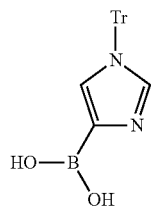

To a suspension of 4-iodo-1-trityl-imidazole (3.00 g, 6.88 mmol) in THF (55 mL) at 0° C. was slowly added isopropylmagnesium chloride (8.6 mL, 17.19 mmol), the clear solution was then left to stir for 10 minutes. Trimethyl borate (3.83 mL, 34.38 mmol) was added portion wise and the reaction mixture was left to stir for 10 minutes at 0° C. before being allowed to reach room temperature and stir for a further 10 minutes. 1M HCl (30 mL) was then added and the reaction was stirred for 10 minutes. The reaction was quenched by pouring it slowly in to a saturated solution of NaHCO$_3$ solution (100 mL) which was then extracted with EtOAc (3×50 mL). The combined organic phases were then dired over Na$_2$SO$_4$ and concentrated in vacuo to give the crude product (1-tritylimidazol-4-yl)boronic acid (2.53 g, 7.15 mmol, 103.92% yield) as an off white solid.

MS Method 2: RT 1.47 min, ES$^+$ m/z 355 [M+H]$^+$ $^1$H NMR (400 MHz, DMSO) δ/ppm: 7.20-7.45 (m, 10H), 6.95-7.10 (m, 7H).

Intermediate 3

4-(1-trityl-1H-imidazol-4-yl)-2-(trifluoromethyl)pyridine

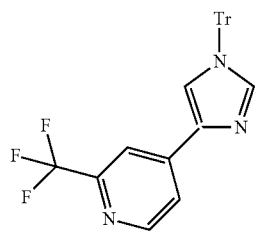

4-iodo-2-(trifluoromethyl)pyridine (0.03 mL, 3.27 mmol), (1-tritylimidazol-4-yl)boronic acid (1.01 g, 2.98 mmol), potassium carbonate (822.53 mg, 5.95 mmol) were added to a microwave vial with 1,4-dioxane (12 mL) and water (4 mL) (all reactants were split equally between two microwave vials), and the flask was flushed with nitrogen for 10 mins [1,1-Bis(diphenylphosphino)ferrocene]Palladium (II) chloride dichloromethane complex (121.50 mg, 0.15 mmol) was added, then the flask was flushed again with nitrogen for a further 5 mins. The reaction was heated under microwave irradiation at 100° C. for 1 hour. Product was seen however starting material also remained. The reaction was heated to 100° C. for a further hour thermally however the reaction did not progress any further. The reaction was concentrated and then partitioned between water and EtOAc. The organic layer was washed with water and brine, the organic layer was then dried over sodium sulphate, filtered and concentrated. Flash column chromatography (SiO$_2$, 0-50% EtOAc in heptane) gave 4-(1-trityl-1H-imidazol-4-yl)-2-(trifluoromethyl)pyridine (512 mg, 1.12 mmol, 37.7% yield).

MS Method 2: RT 2.16 min, ES$^+$ m/z 456 [M+H]$^+$ $^1$H NMR (400 MHz, CDCl$_3$) δ/ppm: 8.64-8.68 (d, J=7.9 Hz, 1H), 8.00 (s, 1H), 7.79-7.81 (d, J=7.9 Hz, 1H), 7.59 (s, 1H), 7.38-7.42 (m, 10H), 7.18-7.28 (m, 6H).

Biaryl Alpha-Chloroacetamide: Synthesis A—Step 1

Intermediate 4

5-pyrimidin-5-ylpyridin-2-amine

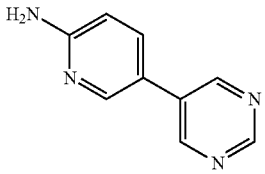 [SMILES: Nc1ccc(-c2cncnc2)cn1]

A microwave vial with stirrer bar was charged with 2-aminopyridine-5-boronic acid pinacol ester (0.95 g, 4.3 mmol) 5-bromopyrimidine (600 mg, 3.77 mmol), sodium carbonate (1.20 g, 11.32 mmol) Toluene (5 mL) Water (5 mL) Ethanol (5 mL) and degassed for 10 mins.

Tetrakis(triphenylphosphine)palladium(0) (436 mg, 0.38 mmol) was then added and the vial sealed then irradiated at 100° C. for 1 hr. Analysis showed completion so the reaction mixture was concentrated to dryness, then the residue was suspended in DCM and 1M aqueous HCl was then added. The phases were separated and the aqueous phase was basified with 10% aqueous NaOH until pH-12. The aqueous layer was re-extracted with EtOAc several times, dried over sodium sulphate, filtered and concentrated. The resulting solid was triturated with diethyl ether and then filtered giving 5-pyrimidin-5-ylpyridin-2-amine (355 mg, 1.65 mmol, 43.702% yield) as a pink powder.

MS Method 2: RT 0.36 min, ES$^+$ m/z 173 [M+H]$^+$ $^1$H NMR (400 MHz, MeOD) δ/ppm: 9.07-9.09 (s, 1H), 9.00-9.02 (s, 2H), 8.28-8.38 (dd, J=2.5, 0.7 Hz, 1H), 7.84-7.87 (dd, J=8.8, 2.5 Hz, 1H), 6.72-6.75 ((dd, J=8.8, 0.7 Hz, 1H).

Biaryl Alpha-Chloroacetamide: Synthesis A—Step 2

Intermediate 5

2-chloro-N-(5-pyrimidin-5-yl-2-pyridyl)acetamide

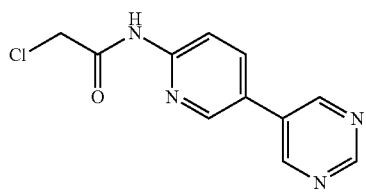 [SMILES: O=C(CCl)Nc1ccc(-c2cncnc2)cn1]

To a pink suspension of 5-pyrimidin-5-ylpyridin-2-amine (355 mg, 2.06 mmol), THF (1.5 mL) and N,N-diisopropylethylamine (0.72 mL, 4.12 mmol) was added drop-wise chloroacetyl chloride (0.16 mL, 2.06 mmol) at room temperature. The suspension turned black and a large exotherm was given off. Analysis of the reaction after 30 mins showed that it was complete. The reaction was diluted with methanol and then concentrated. The resulting residue was purified by flash column chromatography (12 g SiO$_2$, 30-100% EtOAc in heptane, then 0-20% MeOH in EtOAc) affording an off white/brown solid 2-chloro-N-(5-pyrimidin-5-yl-2-pyridyl)acetamide (194 mg, 0.78 mmol, 37.84% yield).

MS Method 2: RT 1.10 min, ES$^+$ m/z 249 [M+H]$^+$ $^1$H NMR (400 MHz, CDCl$_3$) δ/ppm: 9.29 (s, 1H), 8.98 (s, 1H), 8.93-8.97 (bs, 1H), 8.58-8.60 (dd, J=2.4, 0.7 Hz, 1H), 8.39-8.42 (d, J=8.7 Hz, 1H), 7.97-8.01 (dd, J=8.7, 2.4 Hz, 1H), 4.27 (s, 2H).

Example 1

N-(5-pyrimidin-yl-5-pyridyl)-2-[4-[2-(trifluoromethyl)-4-pyridyl]imidazol-1-yl]acetamide

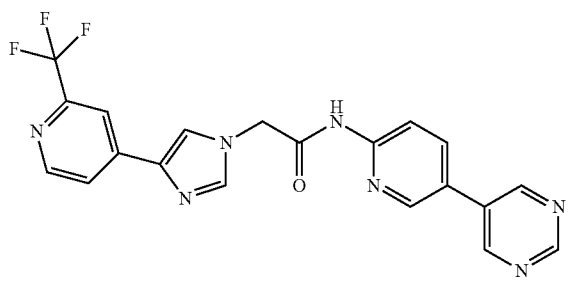 [SMILES: O=C(Cn1cnc(-c2ccnc(C(F)(F)F)c2)c1)Nc1ccc(-c2cncnc2)cn1]

To a round bottomed flask was added 2-chloro-N-(5-pyrimidin-5-yl-2-pyridyl)acetamide (64 mg, 0.26 mmol), DMF (2 mL) and potassium carbonate (71.14 mg, 0.5100 mmol), to the brown suspension was added 4-(1H-imidazol-4-yl)-2-(trifluoromethyl)pyridine (60.35 mg, 0.2800 mmol) and stirred at RT for 1 hour, a small amount of product was seen, the reaction was heated to 50° C. overnight. Analysis by LCMS showed the reaction was complete. The reaction was partitioned between water and EtOAc. The organic layer was then washed with brine, concentrated and then dissolved into a 8:1:1 DMSO: water MeCN mixture (15 mg/0.75 ml) and purified by preparatory LCMS.

The resulting fraction were combined, concentrated and dried overnight in the vacuum oven affording N-(5-pyrimidin-5-yl-2-pyridyl)-2-[4-[2-(trifluoromethyl)-4-pyridyl]imidazol-1-yl]acetamide (29.9 mg, 0.07 mmol, 27.31% yield).

MS Method 1: RT: 2.85 min, ES$^+$ m/z 426.1 [M+H]$^+$ $^1$H NMR (400 MHz, DMSO) δ/ppm: 11.20 (s, 1H), 9.22 (s, 2H), 9.21 (s, 1H), 8.85-8.87 (dd, J=2.4, 0.6 Hz, 1H), 8.69-8.71 (d, J=5.1, 1H), 8.29-8.33 (dd, J=8.7, 2.4, 1H), 8.16-8.19 (m, 3H), 7.99-8.22 (dd, J=5.1, 1.0 Hz, 1H), 7.88-7.90 (d, J=1.0 Hz, 1H), 5.14 (s, 2H).

Biaryl Alpha-Chloroacetamide: Synthesis B—Step 1

Intermediate 6

2-(5-nitro-2-pyridyl)pyrazine

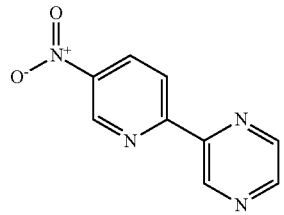 [SMILES: O=[N+]([O-])c1ccc(-c2cnccn2)nc1]

To a microwave vial was added 2-bromo-5-nitropyridine (800 mg, 3.94 mmol), triphenylphosphine (103.37 mg, 0.39 mmol), (tributylstannyl)-pyrazine (1.00 mL, 3.17 mmol) and toluene (8 mL), the reaction mixture was degassed with nitrogen for 10 minutes before the addition of Palladium(II) acetate (88.48 mg, 0.39 mmol). The reaction was degassed again and then heated in the microwave for 2 hours at 130° C. The reaction was partitioned between water and EtOAc, the organic layer was washed several times with water, and brine. The organic layer was dried over sodium sulphate, filtered and concentrated. The resulting residue was taken up in DCM and filtered to remove solids. The resulting residue from concentration of the filtrate was purified by flash column chromatography (40 g SiO$_2$, eluted with 0-70% EtOAc in heptane). Fractions 23-33 were combined and concentrated. The orange solid was then triturated with EtOH affording 2-(5-nitro-2-pyridyl)pyrazine (114 mg, 0.5639 mmol, 17.79% yield)

MS Method 2: RT: 1.38 min, ES$^-$ m/z 202.9 [M–H]$^-$ $^1$H NMR (400 MHz, DMSO) δ/ppm: 9.61-9.63 (d, J=1.4 Hz, 1H), 9.51-9.56 (m, 1H), 8.76-8.89 (m, 3H), 8.58-8.62 (dd, J=8.8, 0.7 Hz, 1H).

Biaryl Alpha-Chloroacetamide: Synthesis B—Step 2

Intermediate 7

6-pyrazin-2-ylpyridin-3-amine

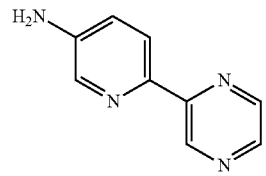 [SMILES: Nc1ccc(-c2cnccn2)nc1]

A round bottomed flask was charged with 2-(5-nitro-2-pyridyl)pyrazine (114 mg, 0.56 mmol) and methanol (5.64 mL). The mixture was purged and evacuated with nitrogen, to the reaction was added palladium, 10 wt. % on carbon powder, wet (60.02 mg) and the system was purged and evacuated again. A hydrogen balloon was then added and the reaction was stirred overnight at room temperature. Analysis by LCMS showed partial hydrogenation, the above procedure was repeated and further palladium, 10 wt. % on carbon powder, wet (60.02 mg) was added along with more hydrogen and stirred overnight at room temperature. Analysis by LCMS showed the reaction was complete. The mixture was filtered through celite and the filtrate was loaded directly onto a methanol primed SCX cartridge. The cartridge was eluted with methanol (3CV) and 1M ammonia in methanol (3CV). The ammonia flush was then concentrated, an ethanol trituration was attempted on the product however this failed to clean up the product, 6-pyrazin-2-ylpyridin-3-amine (113 mg, 0.66 mmol, 116% yield) taken on crude.

MS Method 2: RT: 0.45 min, ES+ m/z 173.2 [M+H]+

Biaryl Alpha-Chloroacetamide: Synthesis B—Step 3

Intermediate 8

2-chloro-N-(6-pyrazin-2-yl-3-pyridyl)acetamide

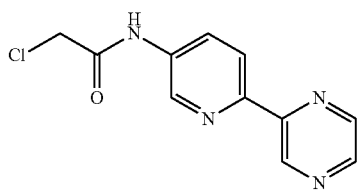 [SMILES: O=C(CCl)Nc1ccc(-c2cnccn2)nc1]

To an orange suspension of 6-pyrazin-2-ylpyridin-3-amine (113 mg, 0.66 mmol), THF (2.19 mL) and N,N-diisopropylethylamine (0.23 mL, 1.31 mmol) was added dropwise chloroacetyl chloride (0.05 mL, 0.66 mmol) at 0° C. and then allowed to reach room temperature. The suspension turned black and a large exotherm was given off. The reaction was then concentrated. The resulting residue was purified by flash column chromatography (12 g SiO$_2$, 0-100% EtOAc then 0-20% MeOH in EtOAc). Fractions 23-28 were combined and concentrated to give a brown solid 2-chloro-N-(6-pyrazin-2-yl-3-pyridyl)acetamide (60 mg, 0.24 mmol, 36.76% yield)

MS Method 2: RT: 1.19 min, ES+ m/z 249.0 [M+H]+

$^1$H NMR (400 MHz, MeOD) δ/ppm: 9.50-9.51 (d, J=1.5 Hz, 1H), 8.91-8.92 (m, 1H), 8.68-8.70 (dd, J=2.6, 1.5 Hz, 1H), 8.59-8.61 (d, J=2.6 Hz, 1H), 8.38-8.42 (m, 1H), 8.27-8.31 (dd, J=8.7, 2.7 Hz, 1H), 4.88 (s, 2H).

Example 2

N-(6-pyrazin-2-yl-3-pyridyl)-2-[4-[2-(trifluoromethyl)-4-pyridyl]imidazol-1-yl]acetamide

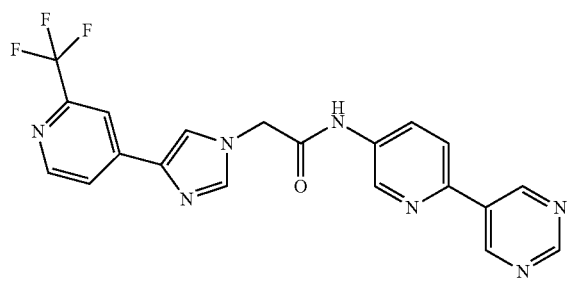 [SMILES: O=C(Cn1cnc(-c2ccnc(C(F)(F)F)c2)c1)Nc1ccc(-c2cncnc2)nc1]

To a round bottomed flask was added 2-chloro-N-(6-pyrazin-2-yl-3-pyridyl)acetamide (60 mg, 0.24 mmol), DMF (2 mL) and potassium carbonate (66.7 mg, 0.48 mmol), to the brown suspension was added 4-(1H-imidazol-4-yl)-2-(trifluoromethyl)pyridine (56.58 mg, 0.27 mmol) and the reaction was heated to 50° C. for 3 hours. Analysis by TLC showed a small amount of starting material present and mainly product. The reaction was cooled and diluted with EtOAc and water. The organic layer was washed several times with water. The organic layer was then dried over sodium sulphate, filtered and concentrated. The resulting yellow residue was purified by preparatory LCMS. The resulting fractions were loaded onto a MeOH primed SCX cartridge which was eluted with methanol (3CV) and then 1M Ammonia in Methanol, the ammonia flush was then concentrated and analysed however the product was still not clean enough. The resulting solid was recrystallized from EtOH. The resulting solid was dried in a vacuum oven at 40° C. overnight yielding N-(6-pyrazin-2-yl-3-pyridyl)-2-[4-[2-(trifluoromethyl)-4-pyridyl]imidazol-1-yl]acetamide (19.7 mg, 0.046 mmol, 19.19% yield).

MS Method 1: RT: 3.05 min, ES+ m/z 426.2 [M+H]+

$^1$H NMR (400 MHz, DMSO) δ/ppm: 108.86-10.91 (bs, 1H), 9.49-9.50 (d, J=1.5 Hz, 1H), 8.92-8.94 (m, 1H), 8.67-8.73 (m, 3H), 8.35-8.38 (d, J=8.6 Hz, 1H), 8.25-8.28 (dd, J=8.7, 2.6 Hz, 1H), 8.16-8.19 (m, 2H), 7.99-8.02 (m, 1H), 7.89-7.90 (d, J=1.0 Hz, 1H), 5.11 (s, 2H).

Example 3

The following compounds were prepared using biaryl alpha-chloroacetamide synthesis A in an analogous manner, varying the arylhalide and/or arylboronate used.

| Structure | STRUCTURE NAME | LCMS RT (min) | m/z MIM |
|---|---|---|---|
| 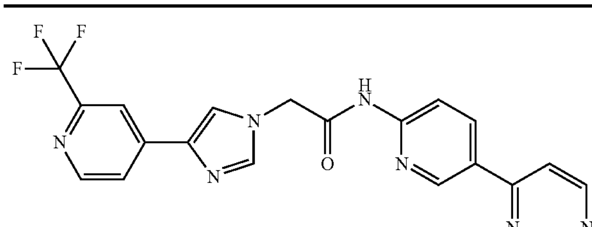 | N-(5-pyrimidin-4-yl-2-pyridyl)-2-[4-[2-(trifluoromethyl)-4-pyridyl]imidazol-1-yl]acetamide | 3.00 (Method 1) | 426.2 |

-continued

| Structure | STRUCTURE NAME | LCMS RT (min) | m/z MIM |
|---|---|---|---|
| 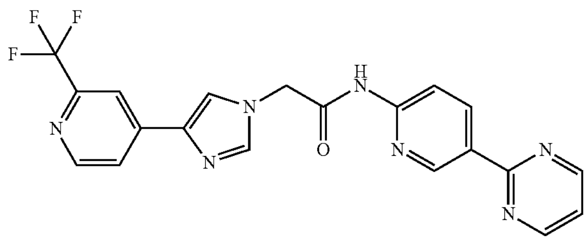 [SMILES: O=C(Cn1cnc(-c2ccnc(C(F)(F)F)c2)c1)Nc1ccc(-c2ncccn2)cn1] | N-(5-pyrimidin-2-yl-2-pyridyl)-2-[4-[2-(trifluoromethyl)-4-pyridyl]imidazol-1-yl]acetamide | 3.19 (Method 1) | 426.4 |
| 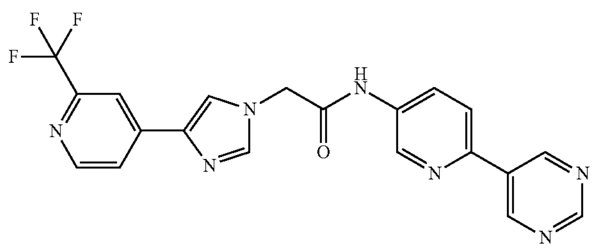 [SMILES: O=C(Cn1cnc(-c2ccnc(C(F)(F)F)c2)c1)Nc1ccc(-c2cncnc2)nc1] | N-(6-pyrimidin-5-yl-3-pyridyl)-2-[4-[2-(trifluoromethyl)-4-pyridyl]imidazol-1-yl]acetamide | 2.84 (Method 1) | 426.1 |
| 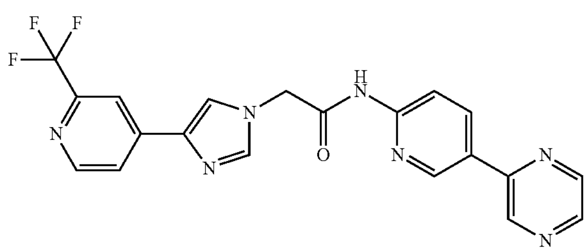 [SMILES: O=C(Cn1cnc(-c2ccnc(C(F)(F)F)c2)c1)Nc1ccc(-c2cnccn2)cn1] | N-(5-pyrazin-2-yl-2-pyridyl)-2-[4-[2-(trifluoromethyl)-4-pyridyl]imidazol-1-yl]acetamide | 3.03 (Method 1) | 426.3 |
| 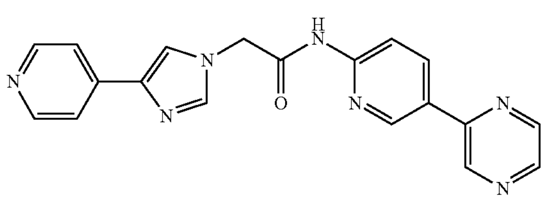 [SMILES: O=C(Cn1cnc(-c2ccncc2)c1)Nc1ccc(-c2cnccn2)cn1] | N-(5-pyrazin-2-yl-2-pyridyl)-2[4-(4-pyridyl)imidazol-1-yl]acetamide | 1.96 (Method 1) | 358.1 |
| 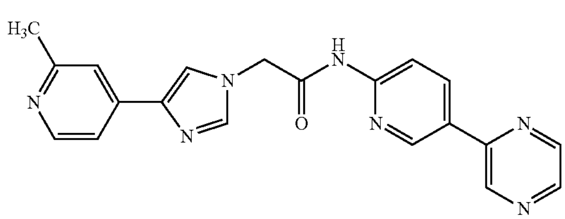 [SMILES: Cc1cc(-c2cn(CC(=O)Nc3ccc(-c4cnccn4)cn3)cn2)ccn1] | 2-[4-(2-methyl-4-pyridyl)imidazol-1-yl]-N-(5-pyrazin-2-yl-2-pyridyl)acetamide | 0.97 (Method 2) | 372.3 |

General Scheme 2
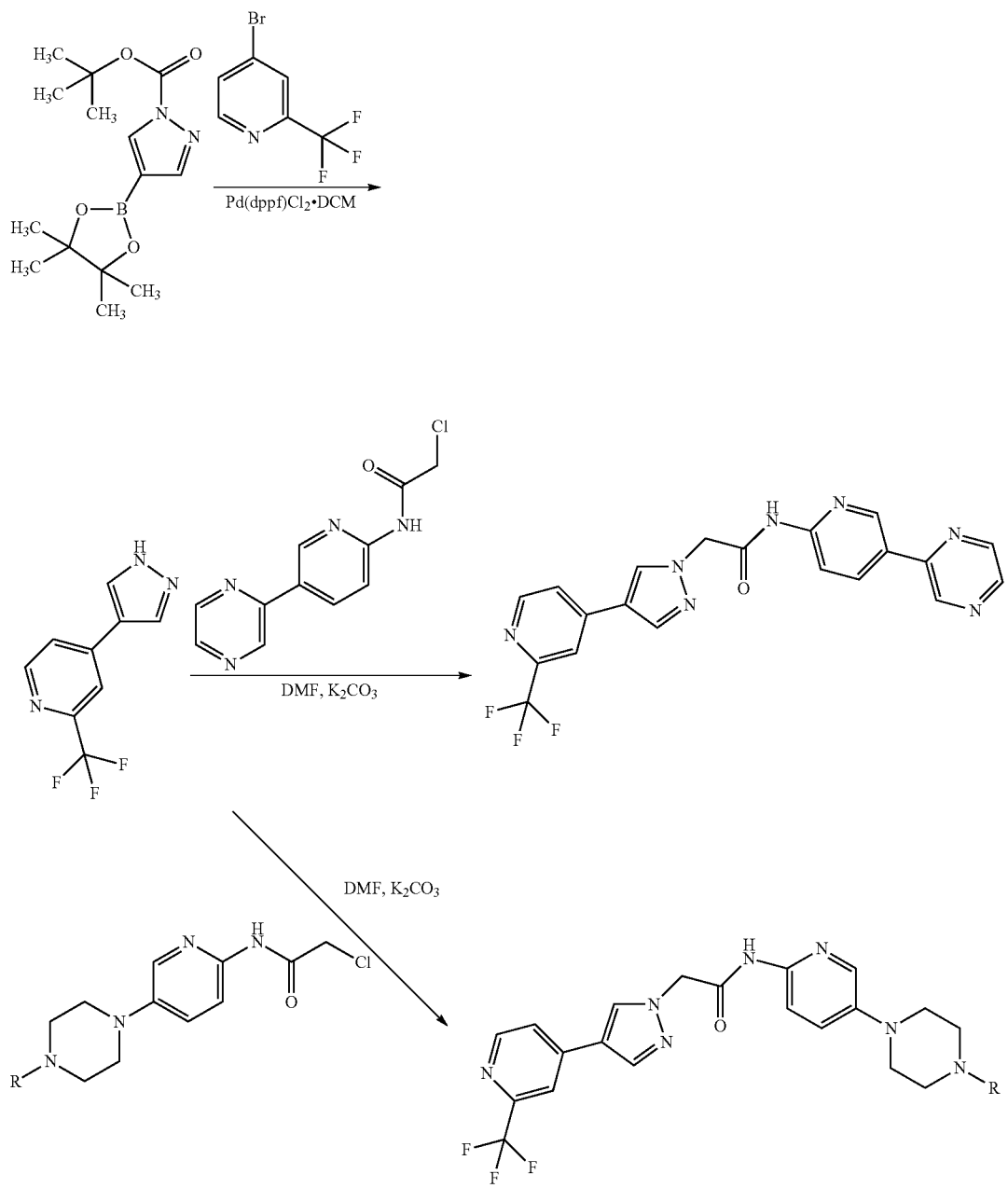
Monoaryl Alpha-Chloroacetamide: Synthesis A
-continued
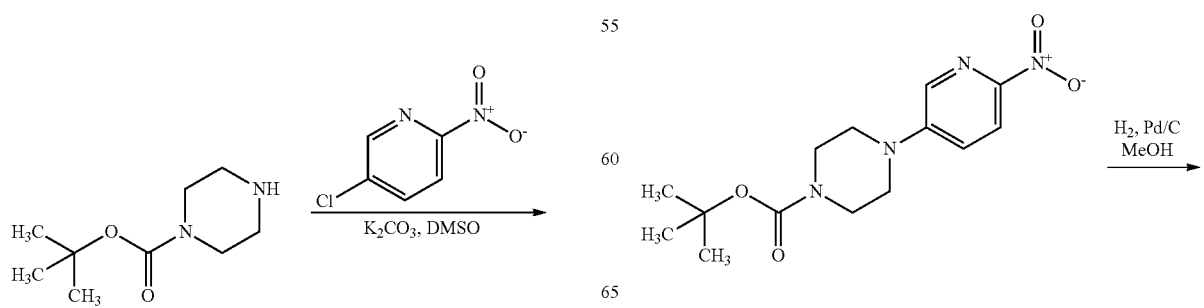

-continued

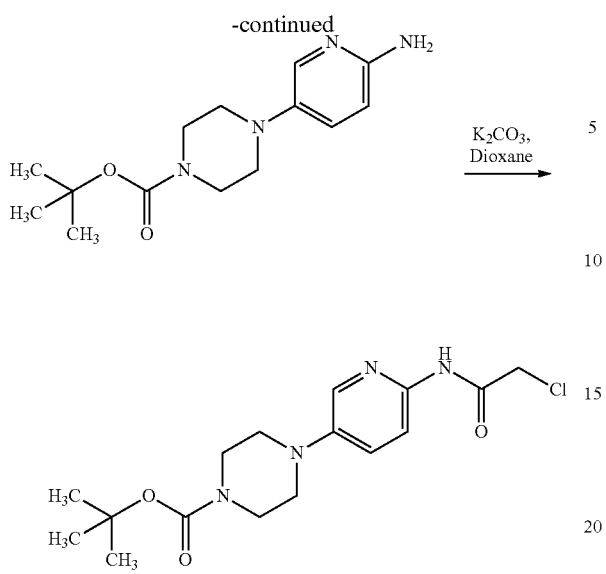

The steps within General Scheme 2 shown above may be performed in the order shown above or in a different order. For example, as the skilled person would appreciate, the Suzuki coupling could be carried out after coupling with the monoaryl alpha-chloroacetamide. Protecting groups may be present or absent as necessary. For example a nitrogen atom may be protected or unprotected.

Intermediate 9

4-(1H-pyrazol-4-yl)-2-(trifluoromethyl)pyridine

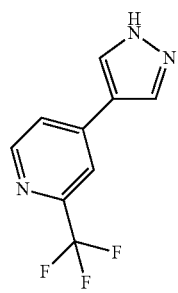 [SMILES: FC(F)(F)c1cc(-c2cn[nH]c2)ccn1]

A microwave vial was charged with 1,4-Dioxane (10 mL) and Water (3 mL) which was degassed with nitrogen for ~10 mins. To this was added 4-Iodo-2-(trifluoromethyl)pyridine (500 mg, 1.83 mmol), tert-butyl 4-(4,4,5,5-tetramethyl-1,3,2-dioxaborolan-2-yl)-1H-pyrazole-1-carboxylate (808 mg, 2.75 mmol) and potassium carbonate (506 mg, 3.66 mmol) followed by [1,1'-bis(diphenylphosphino)ferrocene]Palladium(II) chloride dichloromethane complex (149 mg, 0.1800 mmol). The vessel was then sealed, flushed with nitrogen and irradiated for 1 hour at 110° C. LC-MS after this time showed conversion to the deprotected product and no starting material remaining, so reaction was worked up.

The reaction mixture was concentrated to dryness then taken up in MeOH. This was loaded on to a 5 g SCX cartridge and washed through with ~10CV of MeOH. The product was then eluted with 1M ammonia in MeOH (~5CV). The ammonia wash was then concentrated to dryness, but did not yield the desired product. The MeOH washes were then concentrated to dryness and the remaining residue was triturated with chloroform. The resulting suspension was sonicated and then filtered, washing with a little chloroform, affording 4-(1H-pyrazol-4-yl)-2-(trifluoromethyl)pyridine (384 mg, 1.80 mmol, 98.35% yield) as a beige solid.

MS Method 2: RT: 1.30 min, ES+ m/z 214.0 [M+H]+

$^1$H NMR (400 MHz, MeOD) δ/ppm: 8.66 (s, 1H), 8.34-8.38 (m, 2H), 8.08 (s, 1H), 7.89-7.92 (m, 1H).

Example 4

N-(5-pyrazin-2-yl-2-pyridyl)-2-[4-[2-(trifluoromethyl)-4-pyridyl]pyrazol-1-yl]acetamide

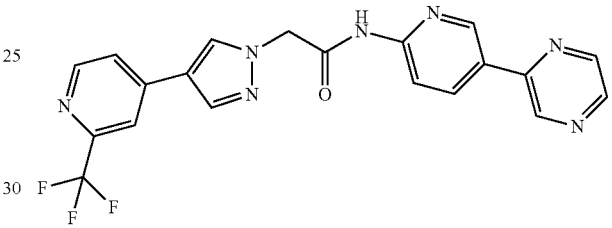

A vial was charged with 2-chloro-N-(5-pyrazin-2-yl-2-pyridyl)acetamide (50 mg, 0.20 mmol), 4-(1H-pyrazol-4-yl)-2-(trifluoromethyl)pyridine (64 mg, 0.30 mmol) and potassium carbonate (55 mg, 0.40 mmol) which was suspended in DMF (1 mL). The vessel was then sealed, flushed with nitrogen, and left to stir at room temp overnight. LC-MS after this time showed complete consumption of starting material and a new peak corresponding to the desired product.

The reaction mixture was diluted with EtOAc and washed with water. The aqueous layer was then extracted with EtOAc (×2). The organics were then combined, washed with brine, dried over sodium sulfate, filtered and concentrated to dryness, affording an off-white solid. Purification by flash column chromatography was performed, (12 g SiO$_2$, eluting with 50-100% EtOAc in heptane). The fractions containing product were combined and concentrated to dryness, affording a white solid. LC-MS showed desired product, the solid was further purified by prep-LCMS, the fractions combined and concentrated to dryness and dried further in the vac oven over night, giving N-(5-pyrazin-2-yl-2-pyridyl)-2-[4-[2-(trifluoromethyl)-4-pyridyl]pyrazol-1-yl]acetamide (10 mg, 0.024 mmol, 11.69% yield) as a white solid.

MS Method 1: RT: 3.27 min, ES+ m/z 426.2 [M+H]+

$^1$H NMR (400 MHz, DMSO) δ/ppm: 11.16-11.22 (bs, 1H), 9.31-9.33 (d, J=1.4 Hz, 1H), 9.14-9.16 (d, J=2.4 Hz, 1H), 8.64-8.74 (m, 4H), 8.54-8.58 (dd, J=8.6, 2.4 Hz, 1H), 8.31 (s, 1H), 8.17-8.21 (d, J=8.7 Hz, 1H), 8.14 (s, 1H), 7.92-7.95 (d, J=5.2 Hz, 1H), 5.24 (s, 2H).

Example 5

N-(5-Pyrazin-2-yl-2-pyridyl)-2-[4-[2-(methyl)-4-pyridyl]pyrazol-1-yl]acetamide was prepared in an analogous fashion

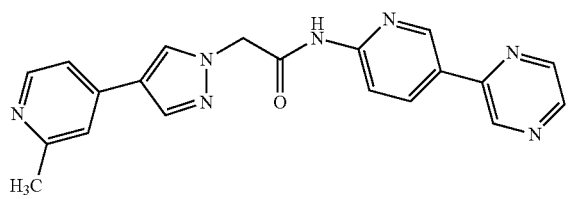 [SMILES: Cc1cc(-c2cnn(CC(=O)Nc3ccc(-c4cnccn4)cn3)c2)ccn1]

MS Method 1: RT: 2.09 min, ES+ m/z 372.2 [M+H]+
$^1$H NMR (400 MHz, DMSO) δ/ppm: 9.31-9.33 (d, J=1.5 Hz, 1H), 9.13-9.15 (dd, J=2.5, 1.7 Hz, 1H), 8.72-8.74 (m, 1H), 8.64-8.65 (d, J=2.5 Hz, 1H), 8.54-8.57 (dd, J—8.7, 2.4 Hz, 1H), 8.42-8.43 (d, J=0.7 Hz, 1H), 8.37-8.39 (d, J=5.2 Hz, 1H), 8.17-8.2 (d, J=8.7 Hz, 1H), 8.10-8.11 (d, J=0.7 Hz, 1H), 7.47-7.51 (bs, 1H), 7.38-7.41 (dd, J=5.1, 1.2 Hz, 1H), 5.25 (s, 2H). 2.5 (s, 3H).

Example 6

The following compounds were prepared using general scheme 2 varying the substitution on the pyrazole boronate ester and the aryl halide. The method of biaryl alpha-chloroacetamide synthesis A was used to prepare the coupling partner for the final step in an analogous manner, varying the arylhalide and/or aryl/vinylboronate used.

| Structure | STRUCTURE NAME | LCMS RT (min) | m/z MIM |
|---|---|---|---|
| 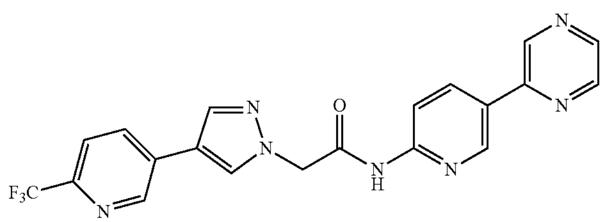 [SMILES: O=C(Cn1cc(-c2ccc(C(F)(F)F)nc2)cn1)Nc1ccc(-c2cnccn2)cn1] | N-(5-pyrazin-2-yl-2-pyridyl)-2-[4-[6-(trifluoromethyl)-3-pyridyl]pyrazol-1-yl]acetamide | 3.38 (Method 1) | 426.2 |
| 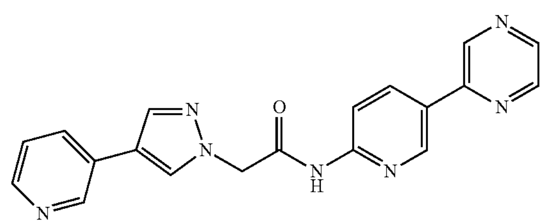 [SMILES: O=C(Cn1cc(-c2cccnc2)cn1)Nc1ccc(-c2cnccn2)cn1] | N-(5-pyrazin-2-yl-2-pyridyl)-2-[4-(3-pyridyl)pyrazol-1-yl]acetamide | 2.04 (Method 1) | 358.1 |
| 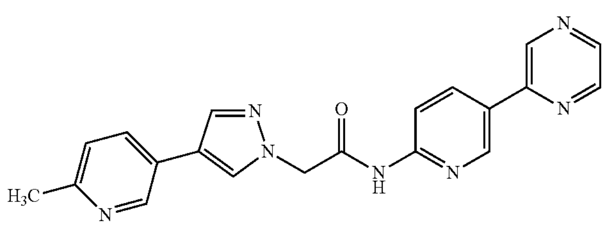 [SMILES: Cc1ccc(-c2cnn(CC(=O)Nc3ccc(-c4cnccn4)cn3)c2)cn1] | 2-[4-(6-methyl-3-pyridyl)pyrazol-1-yl]-N-(5-pyrazin-2-yl-2-pyridyl)acetamide | 2.07 (Method 1) | 372.1 |
| 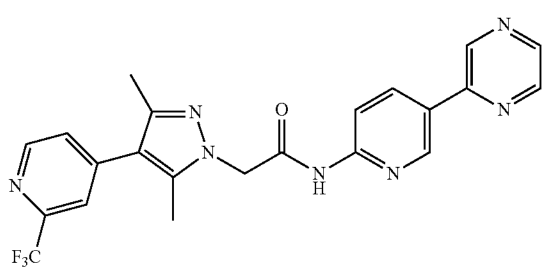 | 2-[3,5-dimethyl-4-[2-(trifluoromethyl)-4-pyridyl]pyrazol-1-yl]-N-(5-pyrazin-2-yl-2-pyridyl)acetamide | 3.49 (Method 1) | 454.1 |

-continued

| Structure | STRUCTURE NAME | LCMS RT (min) | m/z MIM |
|---|---|---|---|
| 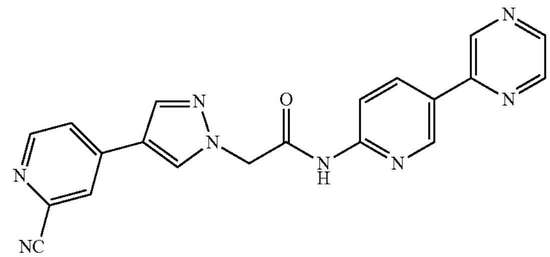 [SMILES: N#Cc1cc(-c2cnn(CC(=O)Nc3ccc(-c4cnccn4)cn3)c2)ccn1] | 2-[4-(2-cyano-4-pyridyl)pyrazol-1-yl]-N-(5-pyrazin-2-yl-2-pyridyl)acetamide | 2.87 (Method 1) | 383.1 |
| 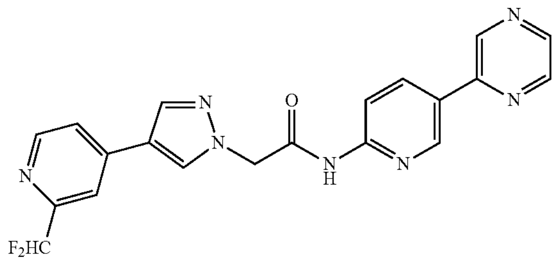 [SMILES: O=C(Cn1cc(-c2ccnc(C(F)F)c2)cn1)Nc1ccc(-c2cnccn2)cn1] | 2-[4-[2-(difluoromethyl)-4-pyridyl]pyrazol-1-yl]-N-(5-pyrazin-2-yl-2-pyridyl)acetamide | 2.95 (Method 1) | 408.1 |
| 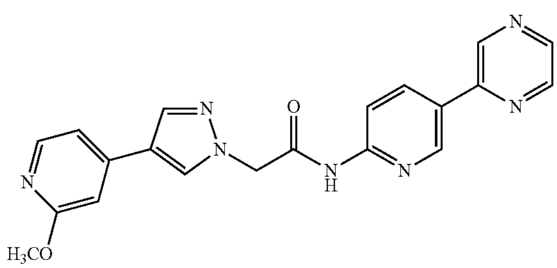 [SMILES: COc1cc(-c2cnn(CC(=O)Nc3ccc(-c4cnccn4)cn3)c2)ccn1] | 2-[4-(2-methoxy-4-pyridyl)pyrazol-1-yl]-N-(5-pyrazin-2-yl-2-pyridyl)acetamide | 2.68 (Method 1) | 388.1 |
| 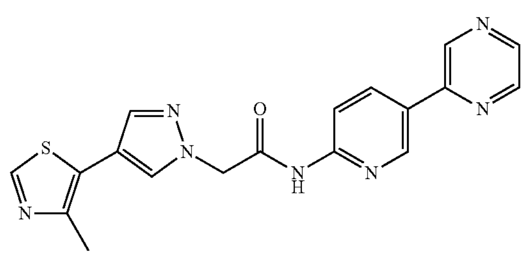 [SMILES: Cc1ncsc1-c1cnn(CC(=O)Nc2ccc(-c3cnccn3)cn2)c1] | 2-[4-(4-methylthiazol-5-yl)pyrazol-1-yl]-N-(5-pyrazin-2-yl-2-pyridyl)acetamide | 2.72 (Method 1) | 378.0 |
| 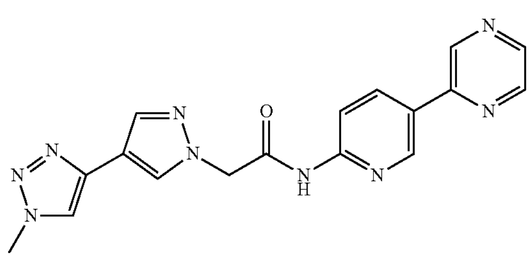 [SMILES: Cn1cc(-c2cnn(CC(=O)Nc3ccc(-c4cnccn4)cn3)c2)nn1] | 2-[4-(1-methyltriazol-4-yl)pyrazol-1-yl]-N-(5-pyrazin-2-yl-2-pyridyl)acetamide | 2.35 (Method 1) | 362.1 |
| 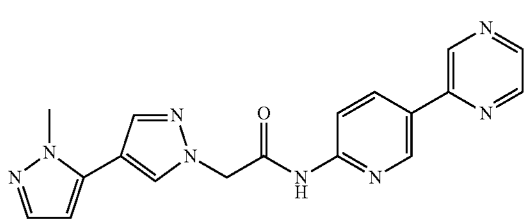 [SMILES: Cn1nccc1-c1cnn(CC(=O)Nc2ccc(-c3cnccn3)cn2)c1] | 2-[4-(2-methylpyrazol-3-yl)pyrazol-1-yl]-N-(5-pyrazin-2-yl-2-pyridyl)acetamide | 2.60 (Method 1) | 361.1 |

-continued

| Structure | STRUCTURE NAME | LCMS RT (min) | m/z MIM |
|---|---|---|---|
| 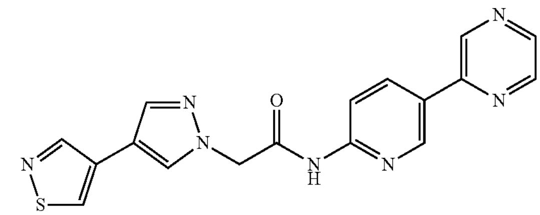 [SMILES: O=C(Cn1cc(-c2cnsc2)cn1)Nc1ccc(-c2cnccn2)cn1] | 2-(4-isothiazol-4-ylpyrazol-1-yl)-N-(5-pyrazin-2-yl-2-pyridyl)acetamide | 2.79 (Method 1) | 364.0 |
| 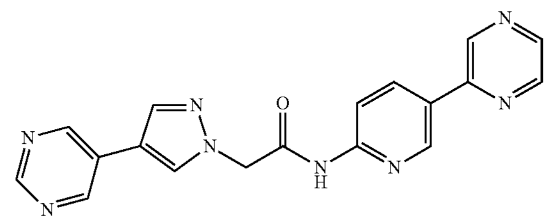 [SMILES: O=C(Cn1cc(-c2cncnc2)cn1)Nc1ccc(-c2cnccn2)cn1] | N-(5-pyrazin-2-yl-2-pyridyl)-2-(4-pyrimidin-5-ylpyrazol-1-yl)acetamide | 1.09 (Method 2) | 359.1 |
| 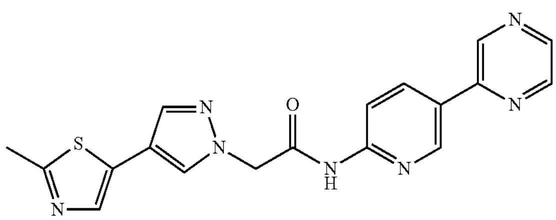 [SMILES: Cc1ncc(-c2cnn(CC(=O)Nc3ccc(-c4cnccn4)cn3)c2)s1] | 2-[4-(2-methylthiazol-5-yl)pyrazol-1-yl]-N-(5-pyrazin-2-yl-2-pyridyl)acetamide | 2.78 (Method 1) | 378.1 |
| 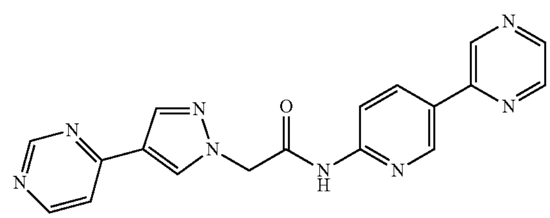 [SMILES: O=C(Cn1cc(-c2ccncn2)cn1)Nc1ccc(-c2cnccn2)cn1] | N-(5-pyrazin-2-yl-2-pyridyl)-2-(4-pyrimidin-4-ylpyrazol-1-yl)acetamide | 2.41 (Method 1) | 359.0 |
| 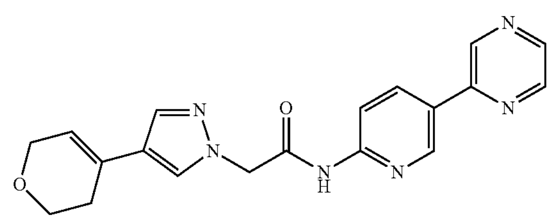 [SMILES: O=C(Cn1cc(C2=CCOCC2)cn1)Nc1ccc(-c2cnccn2)cn1] | 2-[4-(3,6-dihydro-2H-pyran-4-yl)pyrazol-1-yl]-N-(5-pyrazin-2-yl-2-pyridyl)acetamide | 2.79 (Method 1) | 363.1 |
| 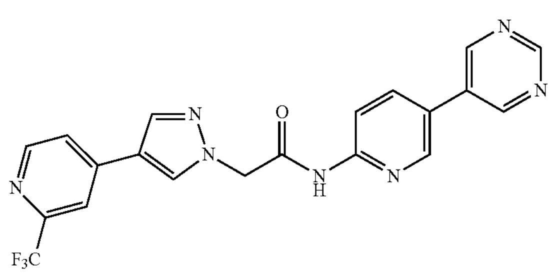 [SMILES: O=C(Cn1cc(-c2ccnc(C(F)(F)F)c2)cn1)Nc1ccc(-c2cncnc2)cn1] | N-(5-pyrimidin-5-yl-2-pyridyl)-2-[4-[2-(trifluoromethyl)-4-pyridyl]pyrazol-1-yl]acetamide | 3.10 (Method 1) | 426.1 |

| Structure | STRUCTURE NAME | LCMS RT (min) | m/z MIM |
|---|---|---|---|
| 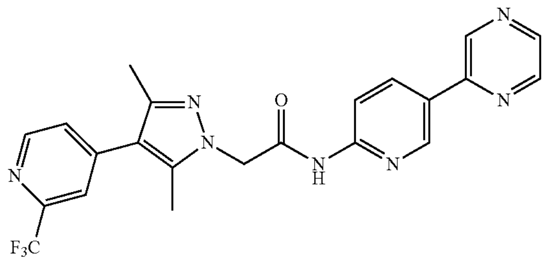 | 2-[3,5-dimethyl-4-[2-(trifluoromethyl)-4-pyridyl]pyrazol-1-yl]-N-(5-pyrimidin-5-yl-2-pyridyl)acetamide | 3.32 | 454.2 |
| 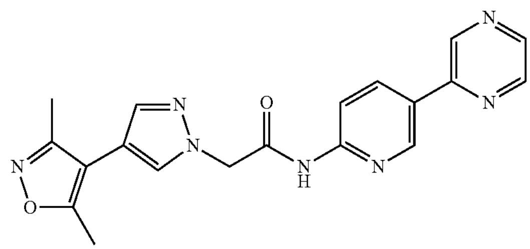 [SMILES: Cc1noc(C)c1-c1cnn(CC(=O)Nc2ccc(-c3cnccn3)cn2)c1] | 2-[4-(3,5-dimethylisoxazol-4-yl)pyrazol-1-yl]-N-(5-pyrazin-2-yl-2-pyridyl)acetamide | 2.91 | 376.1 |
| 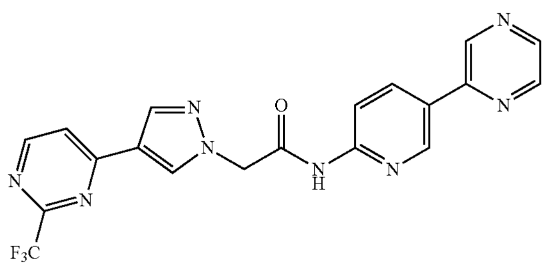 | N-(5-pyrazin-2-yl-2-pyridyl)-2-[4-[2-(trifluoromethyl)pyrimidin-4-yl]pyrazol-1-yl]acetamide | 3.31 | 427.2 |
| 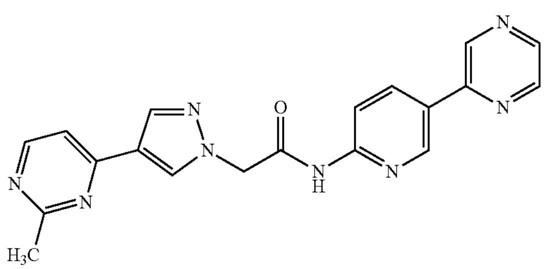 [SMILES: Cc1nccc(-c2cnn(CC(=O)Nc3ccc(-c4cnccn4)cn3)c2)n1] | 2-[4-(2-methylpyrimidin-4-yl)pyrazol-1-yl]-N-(5-pyrazin-2-yl-2-pyridyl)acetamide | 2.38 | 373.1 |
| 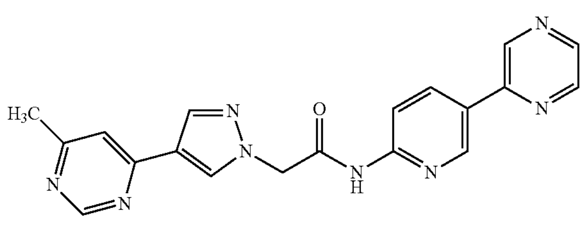 [SMILES: Cc1cc(-c2cnn(CC(=O)Nc3ccc(-c4cnccn4)cn3)c2)ncn1] | 2-[4-(6-methylpyrimidin-4-yl)pyrazol-1-yl]-N-(5-pyrazin-2-yl-2-pyridyl)acetamide | 2.47 | 373.0 |
| 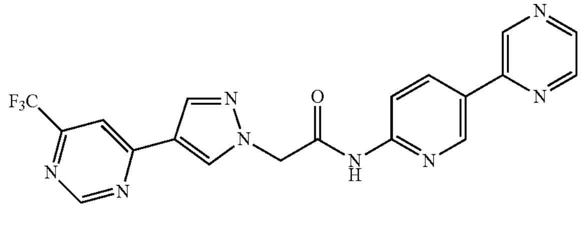 [SMILES: O=C(Cn1cc(-c2cc(C(F)(F)F)ncn2)cn1)Nc1ccc(-c2cnccn2)cn1] | N-(5-pyrazin-2-yl-2-pyridyl)-2-[4-[6-(trifluoromethyl)pyrimidin-4-yl]pyrazol-1-yl]acetamide | 3.25 | 427.0 |

-continued

| Structure | STRUCTURE NAME | LCMS RT (min) | m/z MIM |
|---|---|---|---|
| 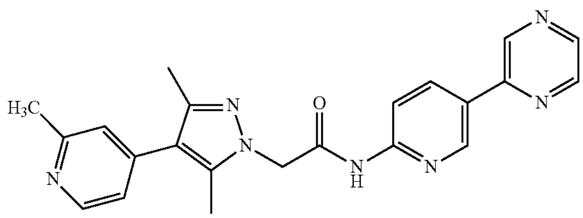 [SMILES: Cc1cc(-c2c(C)nn(CC(=O)Nc3ccc(-c4cnccn4)cn3)c2C)ccn1] | 2-[3,5-dimethyl-4-(2-methyl-4-pyridyl)pyrazol-1-yl]-N-(5-pyrazin-2-yl-2-pyridyl)acetamide | 2.19 | 400.3 |
| 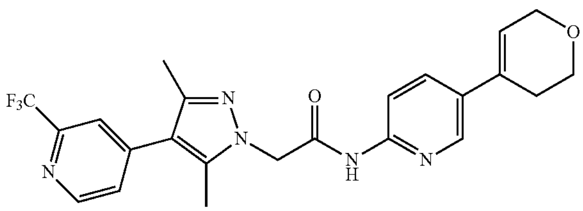 [SMILES: Cc1nn(CC(=O)Nc2ccc(C3=CCOCC3)cn2)c(C)c1-c1ccnc(C(F)(F)F)c1] | N-[5-(3,6-dihydro-2H-pyran-4-yl)-2-pyridyl]-2-[3,5-dimethyl-4-[2-(trifluoromethyl)-4-pyridyl]pyrazol-1-yl]acetamide | 3.66 | 458.1 |
| 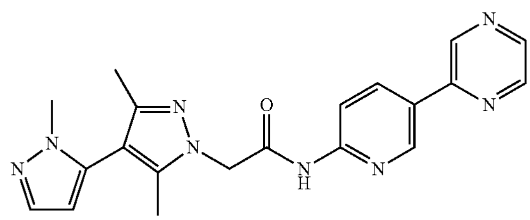 [SMILES: Cc1nn(CC(=O)Nc2ccc(-c3cnccn3)cn2)c(C)c1-c1ccnn1C] | 2-[3,5-dimethyl-4-(2-methylpyrazol-3-yl)pyrazol-1-yl]-N-(5-pyrazin-2-yl-2-pyridyl)acetamide | 2.79 | 389.1 |
| 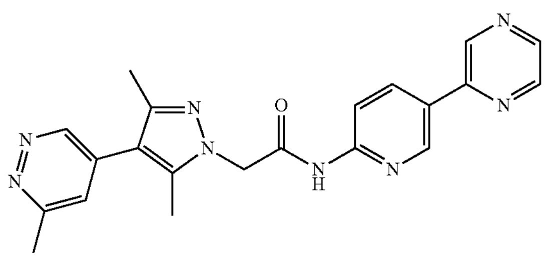 [SMILES: Cc1cc(-c2c(C)nn(CC(=O)Nc3ccc(-c4cnccn4)cn3)c2C)cnn1] | 2-[3,5-dimethyl-4-(6-methylpyridazin-4-yl)pyrazol-1-yl]-N-(5-pyrazin-2-yl-2-pyridyl)acetamide | 2.37 | 401.1 |
| 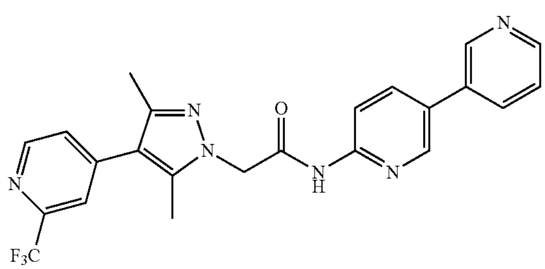 [SMILES: Cc1nn(CC(=O)Nc2ccc(-c3cccnc3)cn2)c(C)c1-c1ccnc(C(F)(F)F)c1] | 2-[3,5-dimethyl-4-[2-(trifluoromethyl)-4-pyridyl]pyrazol-1-yl]-N-[5-(3-pyridyl)-2-pyridyl]acetamide | 3.04 | 453.2 |
| 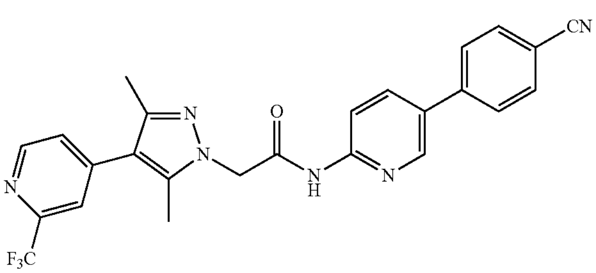 [SMILES: Cc1nn(CC(=O)Nc2ccc(-c3ccc(C#N)cc3)cn2)c(C)c1-c1ccnc(C(F)(F)F)c1] | N-[5-(4-cyanophenyl)-2-pyridyl]-2-[3,5-dimethyl-4-[2-(trifluoromethyl)-4-pyridyl]pyrazol-1-yl]acetamide | 4.04 | 477.2 |

| Structure | STRUCTURE NAME | LCMS RT (min) | m/z MIM |
|---|---|---|---|
| 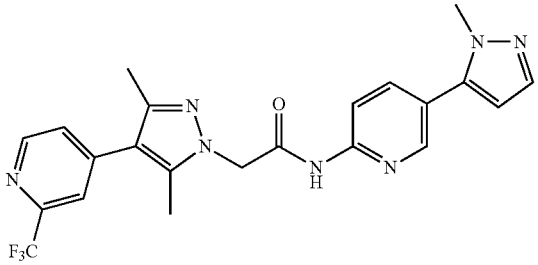 [SMILES: Cc1nn(CC(=O)Nc2ccc(-c3ccnn3C)cn2)c(C)c1-c1ccnc(C(F)(F)F)c1] | 2-[3,5-dimethyl-4-[2-(trifluoromethyl)-4-pyridyl]pyrazol-1-yl]-N-[5-(2-methylpyrazol-3-yl)-2-pyridyl]acetamide | 3.54 | 456.2 |
| 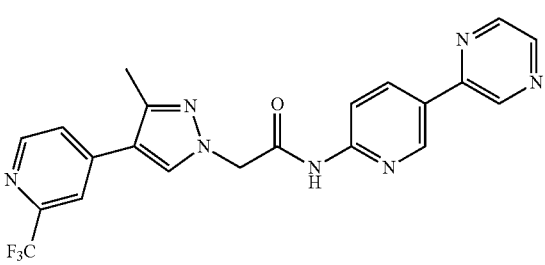 [SMILES: Cc1nn(CC(=O)Nc2ccc(-c3cnccn3)cn2)cc1-c1ccnc(C(F)(F)F)c1] | 2-[3-methyl-4-[2-(trifluoromethyl)-4-pyridyl]pyrazol-1-yl]-N-(5-pyrazin-2-yl-2-pyridyl)acetamide | 3.39 | 440.0 |
| 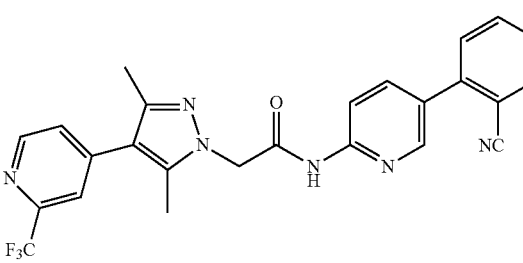 | N-[5-(2-cyanophenyl)-2-pyridyl]-2-[3,5-dimethyl-4-[2-(trifluoromethyl)-4-pyridyl]pyrazol-1-yl]acetamide | 4.02 | 477.2 |
| 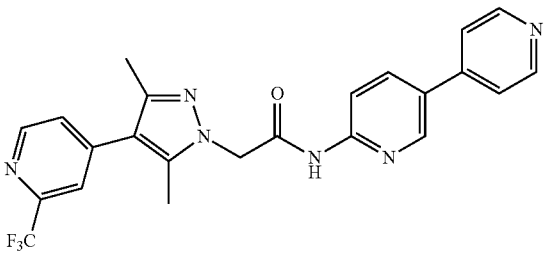 [SMILES: Cc1nn(CC(=O)Nc2ccc(-c3ccncc3)cn2)c(C)c1-c1ccnc(C(F)(F)F)c1] | 2-[3,5-dimethyl-4-[2-(trifluoromethyl)-4-pyridyl]pyrazol-1-yl]-N-[5-(4-pyridyl)-2-pyridyl]acetamide | 2.87 | 453.2 |
| 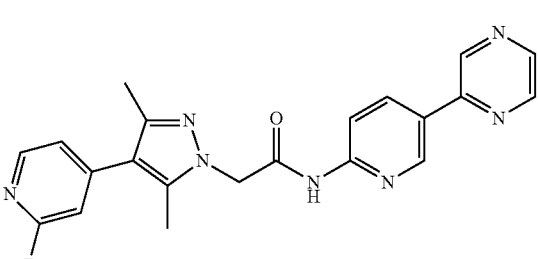 | 2-[4-(2-fluoro-4-pyridyl)-3,5-dimethyl-pyrazol-1-yl]-N-(5-pyrazin-2-yl-2-pyridyl)acetamide | 3.11 | 404.1 |

| Structure | STRUCTURE NAME | LCMS RT (min) | m/z MIM |
|---|---|---|---|
| 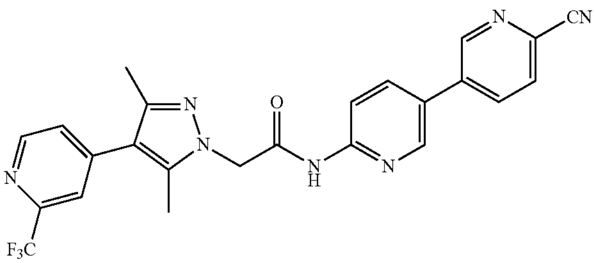 [SMILES: Cc1nn(CC(=O)Nc2ccc(-c3ccc(C#N)nc3)cn2)c(C)c1-c1ccnc(C(F)(F)F)c1] | N-[5-(6-cyano-3-pyridyl)-2-pyridyl]-2-[3,5-dimethyl-4-[2-(trifluoromethyl)-4-pyridyl]pyrazol-1-yl]acetamide | 3.76 | 478.2 |
| 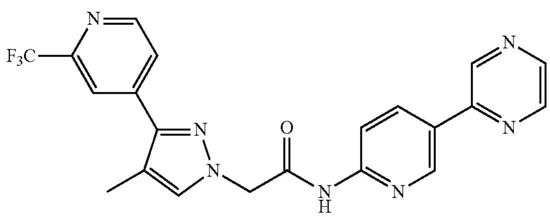 [SMILES: Cc1cn(CC(=O)Nc2ccc(-c3cnccn3)cn2)nc1-c1ccnc(C(F)(F)F)c1] | 2-[4-methyl-3-[2-(trifluoromethyl)-4-pyridyl]pyrazol-1-yl]-N-(5-pyrazin-2-yl-2-pyridyl)acetamide | 3.61 | 440.0 |
| 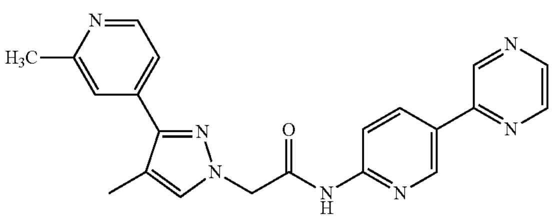 [SMILES: Cc1cc(-c2nn(CC(=O)Nc3ccc(-c4cnccn4)cn3)cc2C)ccn1] | 2-[4-methyl-3-(2-methyl-4-pyridyl)pyrazol-1-yl]-N-(5-pyrazin-2-yl-2-pyridyl)acetamide | 2.29 | 386.1 |
| 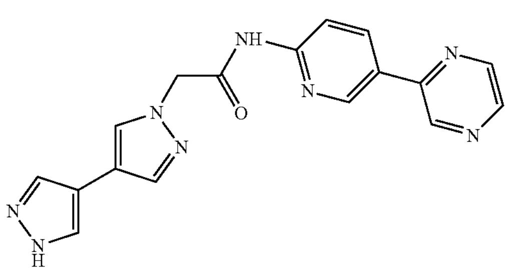 [SMILES: O=C(Cn1cc(-c2cn[nH]c2)cn1)Nc1ccc(-c2cnccn2)cn1] | N-(5-pyrazin-2-yl-2-pyridyl)-2-[4-(1H-pyrazol-4-yl)pyrazol-1-yl]acetamide | 2.34 | 347.0 |
| 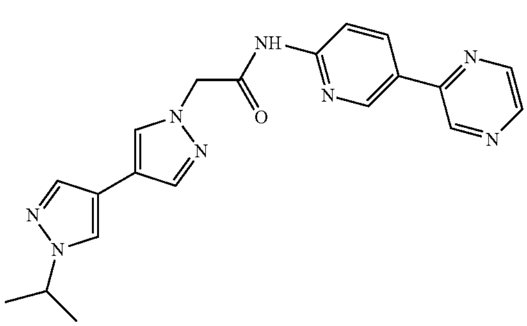 [SMILES: CC(C)n1cc(-c2cnn(CC(=O)Nc3ccc(-c4cnccn4)cn3)c2)cn1] | 2-[4-(2-isopropylpyrazol-3-yl)pyrazol-1-yl]-N-(5-pyrazin-2-yl-2-pyridyl)acetamide | 3.01 | 389.2 |

| Structure | STRUCTURE NAME | LCMS RT (min) | m/z MIM |
|---|---|---|---|
| 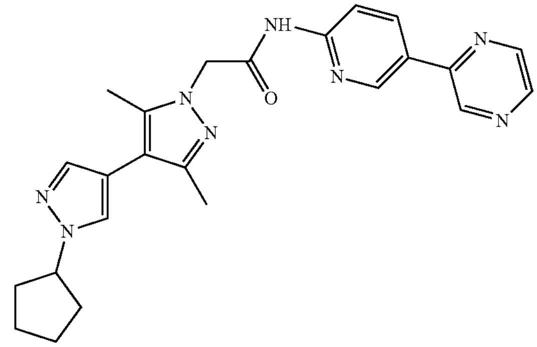 [SMILES: Cc1nn(CC(=O)Nc2ccc(-c3cnccn3)cn2)c(C)c1-c1cnn(C2CCCC2)c1] | 2-[4-(2-cyclopentylpyrazol-3-yl)pyrazol-1-yl]-N-(5-pyrazin-2-yl-2-pyridyl)acetamide | 3.36 | 415.3 |
| 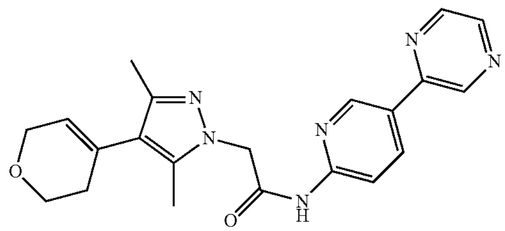 [SMILES: Cc1nn(CC(=O)Nc2ccc(-c3cnccn3)cn2)c(C)c1C1=CCOCC1] | N-[5-(3,6-dihydro-2H-pyran-4-yl)-2-pyridyl]-2-[3,5-dimethyl-4-[2-(trifluoromethyl)-4-pyridyl]pyrazol-1-yl]acetamide | 3.67 | 458.1 |

Monoaryl Alpha-Chloroacetamide: Synthesis A—Step 1

Intermediate 10 tert-butyl 4-(6-nitro-3-pyridyl)piperazine-1-carboxylate

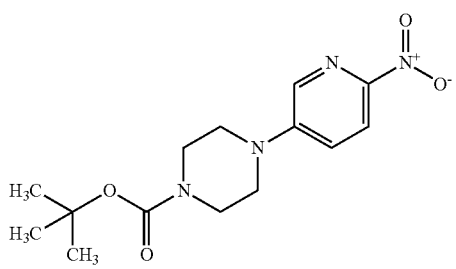 [SMILES: CC(C)(C)OC(=O)N1CCN(c2ccc([N+](=O)[O-])nc2)CC1]

A microwave vial was charged with 5-chloro-2-nitropyridine (1 g, 6.31 mmol), 1-boc-piperazine (1.29 g, 6.94 mmol) and potassium carbonate (3.3 mL, 18.92 mmol), which was suspended in DMSO (15 mL). The resulting mixture was irradiated for 1 hour at 100° C. After this time, the mixture had solidified. LC-MS showed the reaction had not gone to completion. The solid mixture was then transferred to a flask along with DMSO (5 mL) and heated to 110° C., at which point the solid mixture had melted. This was left heating overnight, after which LC-MS showed product formation and no starting material. Reaction was allowed to cool. The reaction mixture was then added to water and extracted with EtOAc (×3). The organics were then combined, washed with brine, dried over sodium sulfate, filtered and concentrated to dryness, affording an orange solid. Purification by flash column chromatography was then performed, (40 g SiO$_2$, eluting with 0-50% EtOAc in heptane). The fractions containing product were combined and concentrated to dryness, affording tert-butyl 4-(6-nitro-3-pyridyl)piperazine-1-carboxylate (1.24 g, 4.02 mmol, 63.81% yield) as a bright orange/yellow solid.

MS Method 2: RT: 1.61 min, ES$^+$ m/z 309.1 [M+H]$^+$ $^1$H NMR (400 MHz, CDCl$_3$) δ/ppm: 8.10-8.13 (d, J=9.1 Hz, 1H), 8.06-8.07 (d, J=3.0 Hz, 1H), 7.12-7.16 (dd, J=9.2, 3.0 Hz, 1H), 3.55-3.59 (m, 4H), 3.36-3.41 (m, 4H), 1.42 (s, 9H).

Monoaryl Alpha-Chloroacetamide: Synthesis A—Step 2

Intermediate 11 tert-butyl 4-(6-aminopyridin-3-yl)piperazine-1-carboxylate

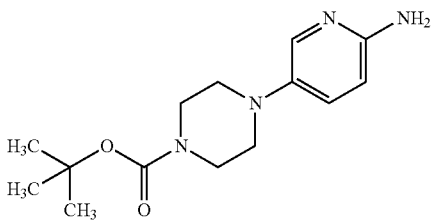 [SMILES: CC(C)(C)OC(=O)N1CCN(c2ccc(N)nc2)CC1]

A flask was charged with tert-butyl 4-(6-nitropyridin-3-yl)piperazine-1-carboxylate (1 g, 4 mmol) which was dissolved in methanol (100 mL). The resulting solution was then degassed by evacuation and the vessel back-filled with nitrogen (repeated twice). Palladium, 10 wt. % on carbon powder, dry (42 mg, 0.40 mmol) was then added in one portion and the system closed and evacuated again, backfilling with hydrogen (repeated twice). This was left to stir at room temp. After 4 hours, LC-MS showed the reaction was mostly complete, so the system was evacuated and back-filled with nitrogen (repeated twice), the solution filtered through celite and the filtrate concentrated to dryness, affording a brown oily solid tert-butyl 4-(6-aminopyridin-3-yl)piperazine-1-carboxylate (800 mg, 3.63 mmol, 90.88% yield).

MS Method 2: RT: 1.22 min, ES$^+$ m/z 279.2 [M+H]$^+$ $^1$H NMR (400 MHz, CDCl$_3$) δ/ppm: 7.70-7.71 (d, J=3.1 Hz, 1H), 7.08-7.11 (d, J=8.0 Hz, 1H), 6.40-6.43 (dd, J=8.0, 3.1 Hz, 1H), 4.11-4.15 (bs, 2H), 3.50-3.54 (m, 4H), 2.86-2.89 (m, 4H), 1.42 (s, 9H).

Monoaryl Alpha-Chloroacetamid: Synthesis A—Step 3

Intermediate 12 tert-butyl 4-[6-[(2-chloroacetyl)amino]-3-pyridyl]piperazine-1-carboxylate

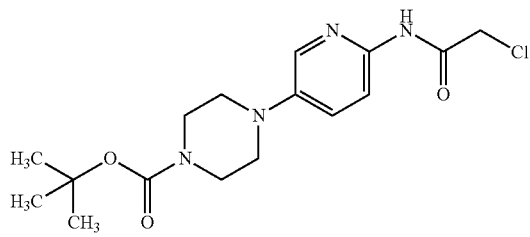 [SMILES: CC(C)(C)OC(=O)N1CCN(c2ccc(NC(=O)CCl)nc2)CC1]

A flask was charged with tert-butyl 4-(6-amino-3-pyridyl)piperazine-1-carboxylate (360 mg, 1.29 mmol) and potassium carbonate (357.5 mg, 2.59 mmol) which was suspended in 1,4-Dioxane (5 mL). Once the organic components had dissolved, the vessel was put under a nitrogen atmosphere and chloroacetyl chloride (0.15 mL, 1.94 mmol) was added to the stirring solution at room temp. This was left to stir overnight. LC-MS after this time showed conversion to the desired product and a peak that corresponded to starting material, but appeared at a slightly lower retention time. Another equivalent of acid chloride was added and the reaction left to stir at room temp for another hour. Methanol was added to the reaction mixture to quench any excess acid chloride and the resulting mixture was concentrated to dryness. The residue was then partitioned between water and EtOAc. The layers were then separated and the organics were washed with water, then with brine, dried over sodium sulfate, filtered and concentrated to dryness, affording a dark purple solid. Further purification by flash column chromatography was performed (25 g SiO$_2$, eluting with 50-60% EtOAc in heptane). Fractions collected were combined and concentrated to dryness, affording tert-butyl 4-[6-[(2-chloroacetyl)amino]-3-pyridyl]piperazine-1-carboxylate (265 mg, 0.75 mmol, 57.74% yield) as a pink/purple solid.

MS Method 2: RT: 1.57 min, ES$^+$ m/z 355.9 [M+H]$^+$ $^1$H NMR (400 MHz, CDCl$_3$) δ/ppm: 8.61 (s, 1H) 7.97-8.02 (d, J=9.0 Hz, 1H), 7.90-7.92 (d, J=2.6 Hz, 1H), 7.20-7.25 (dd, J=9.0, 2.5 Hz, 1H), 4.15 (s, 2H), 3.51-3.55 (m, 4H), 3.04-3.07 (m, 4H), 1.42 (s, 9H).

Example 7 tert-butyl 4-[6-[[2-[4-[2-(trifluoromethyl)-4-pyridyl]imidazol-1-yl]acetyl]amino]-3-pyridyl]piperazine-1-carboxylate

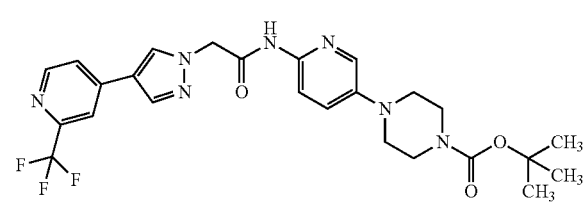 [SMILES: CC(C)(C)OC(=O)N1CCN(c2ccc(NC(=O)Cn3cc(-c4ccnc(C(F)(F)F)c4)cn3)nc2)CC1]

A vial was charged with tert-butyl 4-[6-[(2-chloroacetyl)amino]-3-pyridyl]piperazine-1-carboxylate (40 mg, 0.11 mmol) and potassium carbonate (31.16 mg, 0.23 mmol) which was taken up in DMF (1 mL). The solution was set stirring and 4-(1H-imidazol-4-yl)-2-(trifluoromethyl)pyridine (36.04 mg, 0.17 mmol) was then added. The vial was then sealed, flushed with nitrogen, and left to stir at room temp over the weekend. LC-MS after this time showed conversion to the desired product and some starting material remaining (the excess), so reaction was worked up.

The reaction mixture was diluted with water and extracted with EtOAc (×2). The organics were then combined, washed with brine, dried over sodium sulfate, filtered and concentrated to dryness, affording a lightly purple residue. This was dryloaded on to silica gel and purified by flash column chromatography, (12 g SiO$_2$, eluting with 50-100% EtOAc in heptane. The fractions were combined and concentrated to dryness, affording a white solid. Further purification via prep-LCMS yielded tert-butyl 4-[6-[[2-[4-[2-(trifluoromethyl)-4-pyridyl]imidazol-1-yl]acetyl]amino]-3-pyridyl]piperazine-1-carboxylate (18 mg, 0.034 mmol, 29.74% yield) as a white solid.

MS Method 1: RT: 3.73 min, ES$^+$ m/z 532.2 [M+H]$^+$ $^1$H NMR (400 MHz, CDCl$_3$) δ/ppm: 8.68-8.71 (d, J=5.1 Hz 1H) 8.01-8.09 (m, 2H), 7.81-7.95 (m, 2H), 7.69 (s, 1H), 7.58 (s, 1H), 7.27-7.29 (m, 1H), 4.85 (s, 2H), 3.53-3.64 (m, 4H), 3.08-3.14 (m, 4H), 1.47 (s, 9H).

Example 8

The following compounds were prepared using monoaryl alpha-chloroacetamide synthesis A in an analogous manner, varying the non-aromatic group, or the aryl substituted pyrazole or imidazole (from General Scheme 1 or 2) accordingly:

| Structure | STRUCTURE NAME | LCMS RT (min) | m/z MIM |
|---|---|---|---|
| 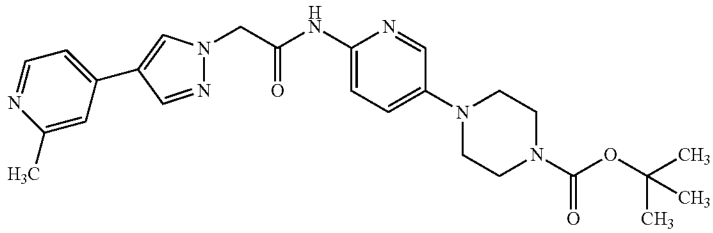 [SMILES: Cc1cc(-c2cnn(CC(=O)Nc3ccc(N4CCN(C(=O)OC(C)(C)C)CC4)cn3)c2)ccn1] | tert-butyl 4-[6-[[2-[4-(2-methyl-4-pyridyl)pyrazol-1-yl]acetyl]amino]-3-pyridyl]piperazine-1-carboxylate | 2.81 (Method 1) | 478.3 |
| 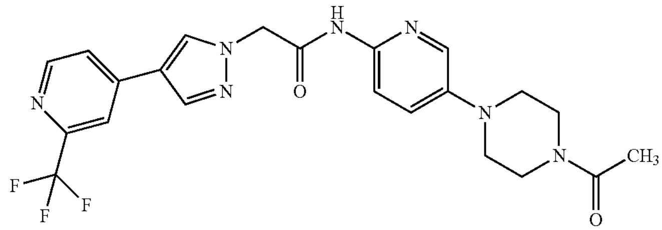 [SMILES: CC(=O)N1CCN(c2ccc(NC(=O)Cn3cc(-c4ccnc(C(F)(F)F)c4)cn3)nc2)CC1] | N-[5-(4-acetylpiperazin-1-yl)-2-pyridyl]-2-[4-[2-(trifluoromethyl)-4-pyridyl]pyrazol-1-yl]acetamide | 3.00 (Method 1) | 473.2 |
| 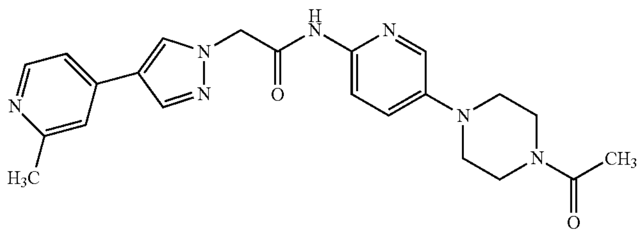 [SMILES: CC(=O)N1CCN(c2ccc(NC(=O)Cn3cc(-c4ccnc(C)c4)cn3)nc2)CC1] | N-[5-(4-acetylpiperazin-1-yl)-2-pyridyl]-2-[4-(2-methyl-4-pyridyl)pyrazol-1-yl]acetamide | 1.94 (Method 1) | 420.2 |
| 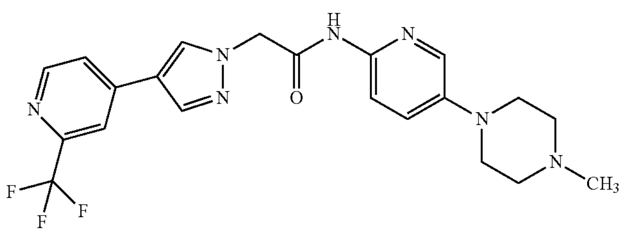 [SMILES: CN1CCN(c2ccc(NC(=O)Cn3cc(-c4ccnc(C(F)(F)F)c4)cn3)nc2)CC1] | N-[5-(4-methylpiperazin-1-yl)-2-pyridyl]-2-[4-[2-(trifluoromethyl)-4-pyridyl]pyrazol-1-yl]acetamide | 2.51 (Method 1) | 446.2 |
| 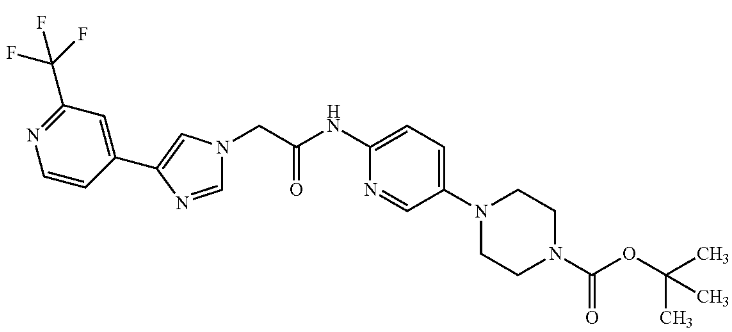 [SMILES: CC(C)(C)OC(=O)N1CCN(c2ccc(NC(=O)Cn3cnc(-c4ccnc(C(F)(F)F)c4)c3)nc2)CC1] | tert-butyl 4-[6-[[2-[4-[2-(trifluoromethyl)-4-pyridyl]imidazol-1-yl]acetyl]amino]-3-pyridyl]piperazine-1-carboxylate | 3.73 (Method 1) | 532.2 |
| 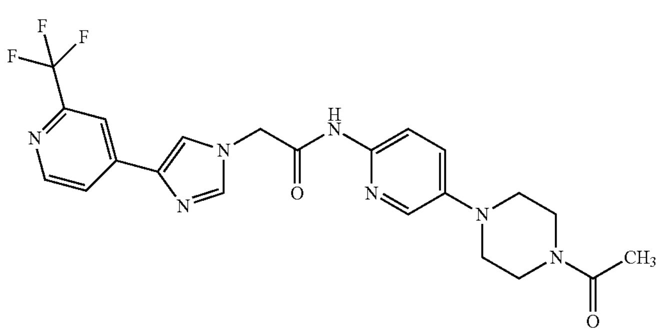 [SMILES: CC(=O)N1CCN(c2ccc(NC(=O)Cn3cnc(-c4ccnc(C(F)(F)F)c4)c3)nc2)CC1] | N-[5-(4-acetylpiperazin-1-yl)-2-pyridyl]-2-[4-[2-(trifluoromethyl)-4-pyridyl]imidazol-1-yl]acetamide | 2.77 (Method 1) | 474.2 |

| Structure | STRUCTURE NAME | LCMS RT (min) | m/z MIM |
|---|---|---|---|
| 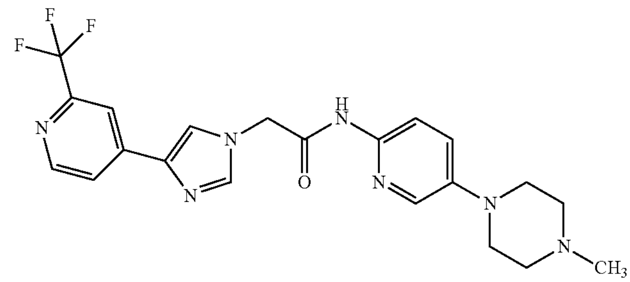 [SMILES: CN1CCN(c2ccc(NC(=O)Cn3cnc(-c4ccnc(C(F)(F)F)c4)c3)nc2)CC1] | N-[5-(4-methylpiperazin-1-yl)-2-pyridyl]-2-[4-[2-(trifluoromethyl)-4-pyridyl]imidazol-1-yl]acetamide | 2.27 (Method 1) | 446.2 |

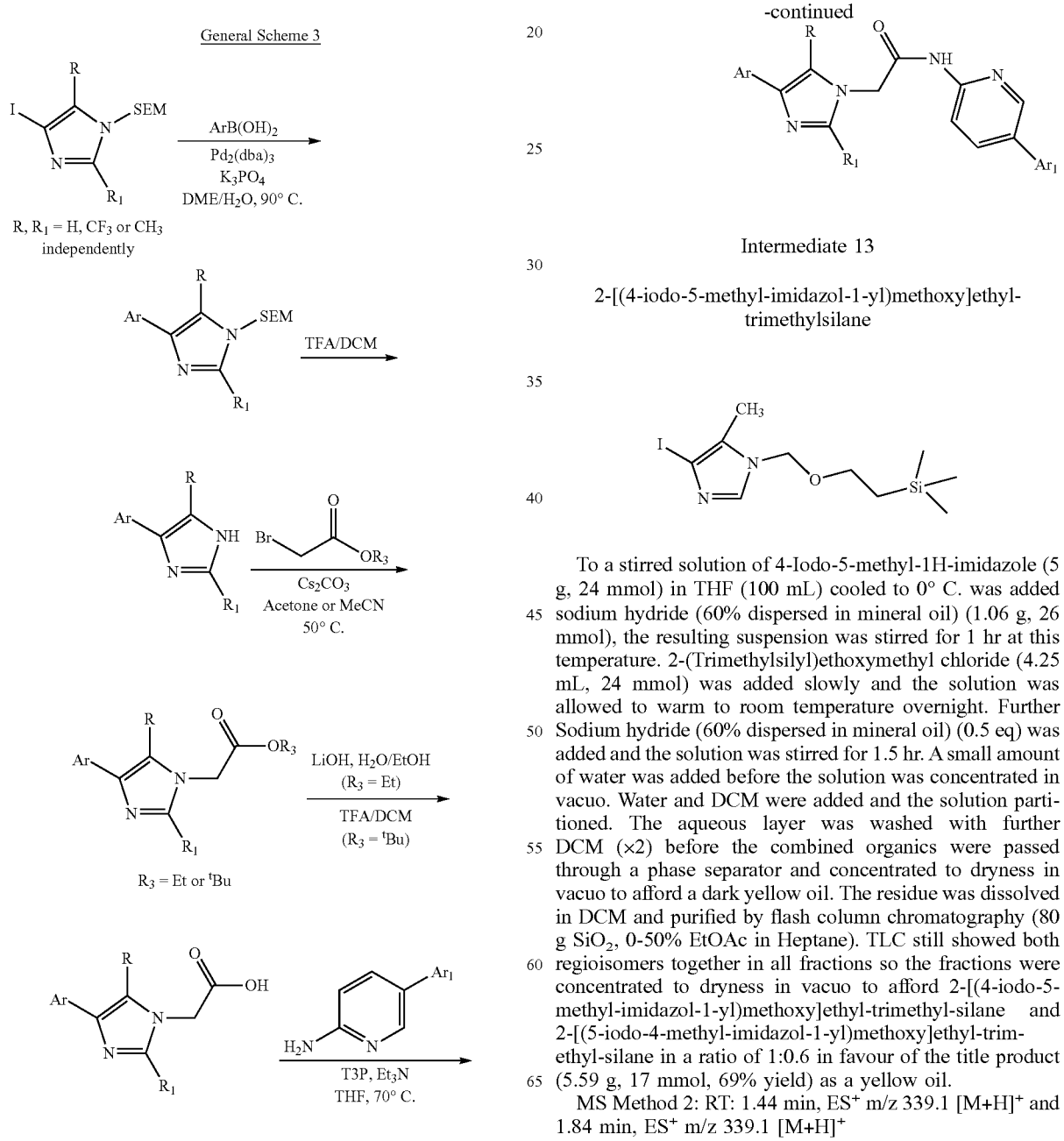

Intermediate 13

2-[(4-iodo-5-methyl-imidazol-1-yl)methoxy]ethyl-trimethylsilane

To a stirred solution of 4-Iodo-5-methyl-1H-imidazole (5 g, 24 mmol) in THF (100 mL) cooled to 0° C. was added sodium hydride (60% dispersed in mineral oil) (1.06 g, 26 mmol), the resulting suspension was stirred for 1 hr at this temperature. 2-(Trimethylsilyl)ethoxymethyl chloride (4.25 mL, 24 mmol) was added slowly and the solution was allowed to warm to room temperature overnight. Further Sodium hydride (60% dispersed in mineral oil) (0.5 eq) was added and the solution was stirred for 1.5 hr. A small amount of water was added before the solution was concentrated in vacuo. Water and DCM were added and the solution partitioned. The aqueous layer was washed with further DCM (×2) before the combined organics were passed through a phase separator and concentrated to dryness in vacuo to afford a dark yellow oil. The residue was dissolved in DCM and purified by flash column chromatography (80 g $SiO_2$, 0-50% EtOAc in Heptane). TLC still showed both regioisomers together in all fractions so the fractions were concentrated to dryness in vacuo to afford 2-[(4-iodo-5-methyl-imidazol-1-yl)methoxy]ethyl-trimethyl-silane and 2-[(5-iodo-4-methyl-imidazol-1-yl)methoxy]ethyl-trimethyl-silane in a ratio of 1:0.6 in favour of the title product (5.59 g, 17 mmol, 69% yield) as a yellow oil.

MS Method 2: RT: 1.44 min, $ES^+$ m/z 339.1 $[M+H]^+$ and 1.84 min, $ES^+$ m/z 339.1 $[M+H]^+$ ¹H NMR (400 MHz, CDCl₃) δ/ppm: 7.73 (s, 1H, minor), 7.49 (s, 1H, major), 5.22 (s, 2H, both regioisomers), 3.40-3.50 (m, 2H, both regioisomers), 2.27 (s, 3H, major), 2.26 (s, 3H, minor), 0.85-0.93 (m, 2H, both regioisomers), 0.03 (s, 9H, both regioisomers).

Intermediate 14 trimethyl-[2-[[5-methyl-4-[2-(trifluoromethyl)-4-pyridyl]imidazol-1-yl]methoxy]ethyl]silane

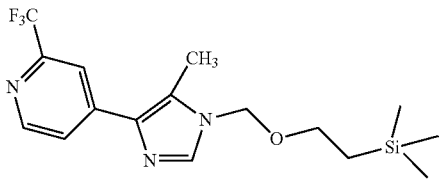 [SMILES: Cc1c(-c2ccnc(C(F)(F)F)c2)ncn1COCC[Si](C)(C)C]

A stirred solution of 2-[(5-iodo-4-methyl-imidazol-1-yl)methoxy]ethyltrimethyl-silane (1 g, 2.96 mmol) and [2-(trifluoromethyl)-4-pyridyl]boronic acid (847 mg, 4.43 mmol) in monoglyme (18 mL) was degassed and back filled with N₂ (×3). To this was added potassium phosphate (tribasic) (1.88 g, 8.87 mmol) in Water (9 mL) followed by Tricyclohexylphosphine (166 mg, 0.59 mmol) and tris (dibenzylideneacetone)dipalladium (0) (271 mg, 0.30 mmol) before the resulting solution was degassed and back filled with N₂ (×3) then heated to 90° C. and stirred at this temperature overnight. The solution was allowed to cool to room temperature. The mixture was filtered though a pad of celite before being concentrated to dryness in vacuo to afford the crude as a thick brown oil. The residue was dissolved in the minimum amount of DCM and purified by flash column chromatography (80 g SiO₂, 0-100% EtOAc in heptane). Like fractions were identified, combined and concentrated to dryness in vacuo to afford trimethyl-[2-[[5-methyl-4-[2-(trifluoromethyl)-4-pyridyl]imidazol-1-yl]methoxy]ethyl]silane (478 mg, 1.34 mmol, 45% yield) as a single regioisomer and yellow oil which solidified on standing.

MS Method 2: RT: 1.90 min, ES⁺ m/z 358.2 [M+H]⁺

¹H NMR (400 MHz, CDCl₃) δ/ppm: 8.70-8.72 (d, J=5.1 Hz, 1H) 8.05 (s, 1H), 7.76, 7.80 (dd, J=5.1, 2.6 Hz 1H), 7.61 (s, 1H), 5.29 (s, 2H), 3.50-3.57 (m, 2H), 2.27 (s, 3H, major), 2.55 (s, 3H), 0.90-0.96 (m, 2H), 0.00 (s, 9H).

Intermediate 15

4-(5-methyl-1H-imidazol-4-yl)-2-(trifluoromethyl)pyridine

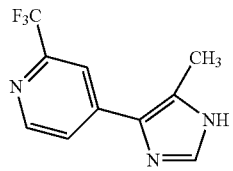 [SMILES: Cc1[nH]cnc1-c1ccnc(C(F)(F)F)c1]

To a stirred solution of trimethyl-[2-[[5-methyl-4-[2-(trifluoromethyl)-4-pyridyl]imidazol-1-yl]methoxy]ethyl]silane (1.57 g, 4.4 mmol) in DCM (25 mL) was added trifluoroacetic acid (16 .mL, 209 mmol) and the resulting solution stirred at RT overnight. The solution was concentrated to dryness in vacuo before being dissolved in MeOH and loaded onto a MeOH primed 10 g SCX cartridge, washing with MeOH and eluting with 1M NH₃ solution. The ammonia MeOH solution was concentrated to dryness in vacuo to afford 4-(5-methyl-1H-imidazol-4-yl)-2-(trifluoromethyl)pyridine (950 mg, 4.18 mmol, 94% yield) as a pale yellow powder.

MS Method 2: RT: 1.07 min, ES⁺ m/z 228.1 [M+H]⁺

¹H NMR (400 MHz, MeOD) δ/ppm: 8.67-8.68 (d, J=5.2 Hz, 1H), 8.10 (s, 1H), 7.88 (s, 1H), 7.74 (s, 1H), 2.57 (s, 3H).

Intermediate 16

2-fluoro-4-(5-methyl-1H-imidazol-4-yl)pyridine

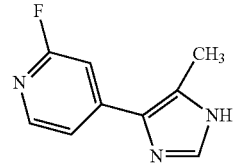

2-Fluoro-4-(5-methyl-1H-imidazol-4-yl)pyridine was prepared in an analogous manner.

MS Method 2: RT: 0.72 min, ES⁺ m/z 178.0 [M+H]⁺

¹H NMR (400 MHz, MeOD) δ/ppm: 8.18-8.20 (d, J=5.2 Hz, 1H), 7.73 (s, 1H), 7.56-7.60 (dt, J=1.7, 5.6 Hz, 1H), 7.29 (s, 1H), 2.54 (s, 3H).

Intermediate 17

2-[5-methyl-4-[2-(trifluoromethyl)-4-pyridyl]imidazol-1-yl]acetate

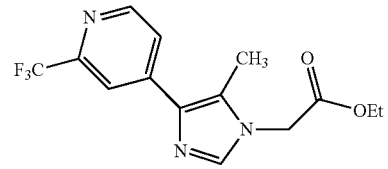 [SMILES: CCOC(=O)Cn1cnc(-c2ccnc(C(F)(F)F)c2)c1C]

Under N₂ to a stirred solution of 4-(5-methyl-1H-imidazol-4-yl)-2-(trifluoromethyl)pyridine (950 mg, 4.18 mmol) in MeCN (30 mL) was added potassium carbonate (1.73 g, 12.6 mmol) and ethyl bromoacetate (0.56 mL, 5.02 mmol) before the resulting solution was heated to 80° C. and stirred at this temperature for 1 hr. The solution was allowed to cool to room temperature and stirred overnight. The solution was filtered with the solid being washed with MeCN before the filtrate was concentrated to dryness in vacuo to afford the crude as a dark yellow crystalline solid. The residue was dissolved in DCM and purified by flash column chromatography (40 g SiO₂, 40-100% EtOAc in heptane). Appropriate fractions were identified, combined and concentrated to dryness in vacuo to afford ethyl 2-[5-methyl-4-[2-(trifluoromethyl)-4-pyridyl]imidazol-1-yl]acetate (1.12 g, 3.57 mmol, 85% yield) as a pale yellow crystalline solid.

MS Method 2: RT: 1.50 min, ES⁺ m/z 314.1 [M+H]⁺

¹H NMR (400 MHz, CDCl₃) δ/ppm: 8.72-8.34 (d, J=4.8 Hz, 1H), 8.06 (s, 1H), 7.79-7.80 (d, J=4.8 Hz, 1H), 7.58 (s, 1H), 4.71 (s, 2H), 4.29-4.34 (q, J=7.1 Hz, 2H), 2.36 (s, 3H) 1.32-1.36 (t, J=7.1 Hz, 3H).

Intermediate 18 tert-butyl 2-[4-(2-fluoro-4-pyridyl)-1-methyl-imidazol-1-yl]acetate

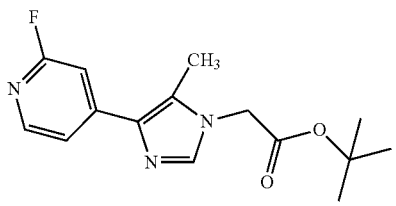 [SMILES: Cc1c(-c2ccnc(F)c2)ncn1CC(=O)OC(C)(C)C]

A flask was charged with 2-fluoro-4-(5-methyl-1H-imidazol-4-yl)pyridine (100 mg, 0.56 mmol) and cesium carbonate (276 mg, 0.85 mmol) which were suspended in acetone (2.5 mL). tert-Butyl 2-bromoacetate (0.09 mL, 0.62 mmol) was then added and the reaction heated to 50° C. for 1 hour, then cooled to room temp. The reaction mixture was then diluted with more acetone and passed through a phase separator. The filter cake was washed with acetone and the resulting filtrate then concentrated to dryness, giving tert-butyl 2-[4-(2-fluoro-4-pyridyl)-5-methyl-imidazol-1-yl]acetate (160 mg, 0.55 mmol, 97% yield) as a yellow solid.

MS Method 2: RT: 1.41 min, ES⁺ m/z 292.1 [M+H]⁺

Intermediate 19

2-[5-methyl-4-[2-(trifluoromethyl)-4-pyridyl]imidazol-1-yl]acetic acid

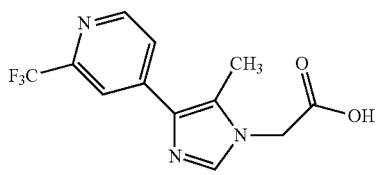

To a stirred solution of ethyl 2-[5-methyl-4-[2-(trifluoromethyl)-4-pyridyl]imidazol-1-yl]acetate (1.12 g, 3.57 mmol) in ethanol (27 mL) was added lithium hydroxide (231 mg, 9.64 mmol) in water (2.7 mL) before the resulting solution was stirred at room temperature overnight.

LCMS indicated complete conversion to product. The solution was concentrated to dryness in vacuo to afford lithium 2-[5-methyl-4-[2-(trifluoromethyl)-4-pyridyl]imidazol-1-yl]acetate (1.04 g, 3.57 mmol, 99.% yield) as an off white powder. The material was used as is in the next step.

MS Method 2: RT: 1.09 min, ES⁺ m/z 286.1 [M+H]⁺

¹H NMR (400 MHz, DMSO) δ/ppm: 8.65-8.67 (d, J=5.2 Hz, 1H), 8.05 (s, 1H), 7.86-7.89 (d, J=5.2 Hz, 1H), 7.60 (s, 1H), 4.19 (s, 2H), 2.36 (s, 3H).

Intermediate 20

2-[4-(2-fluoro-4-pyridyl)-6-methyl-imidazol-1-yl] acetic acid

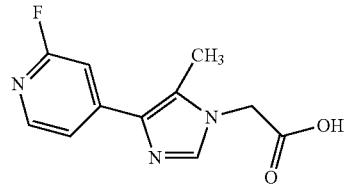 [SMILES: Cc1c(-c2ccnc(F)c2)ncn1CC(=O)O]

A flask was charged with tert-butyl 2-[4-(2-fluoro-4-pyridyl)-5-methyl-imidazol-1-yl]acetate (160 mg, 0.55 mmol) which was taken up in Hydrogen Chloride (4M in dioxane) (3 mL, 12 mmol). The reaction mixture was then left to stir overnight at room temp. A precipitate had formed after this time. The reaction was concentrated to dryness, giving 2-[4-(2-fluoro-4-pyridyl)-5-methyl-imidazol-1-yl] acetic acid (150 mg, 0.6377 mmol, 116.12% yield) as a yellow solid which turned darker after standing in air.

MS Method 2: RT: 0.67 min, ES⁺ m/z 236.0 [M+H]⁺

¹H NMR (400 MHz, MeOD) δ/ppm: 9.17 (s, 1H), 8.42-8.44 (d, J=5.2 Hz, 1H), 7.56-7.58 (dt, J=1.7, 5.2 Hz, 1H), 7.36 (s, 1H), 5.24 (s, 2H), 2.52 (s, 3H).

Intermediate 21

5-pyrazin-2-ylpyridin-2-amine

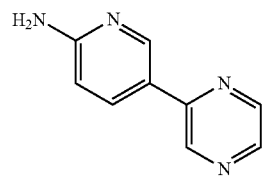 [SMILES: Nc1ccc(-c2cnccn2)cn1]

5-pyrazin-2-ylpyridin-2-amine was prepared in an analogous manner to that described for intermediate 4 in Biaryl alpha-chloroacetamide: Synthesis A—Step 1.

MS Method 2: RT: 0.42 min, ES⁺ m/z 173.1 [M+H]⁺

¹H NMR (400 MHz, DMSO) δ/ppm: 9.11-9.22 (d, J=1.6 Hz, 1H), 8.72-8.73 (dd, J=0.4, 1.6 Hz, 1H), 8.59-8.60 (dd, J=1.6, 2.4 Hz, 1H), 8.45-8.61 (d, J=2.4 Hz, 1H), 8.10-8.13 (dd, J=2.4, 8.4 Hz, 1H), 6.55-6.57 (dd, J=0.8, 8.8 Hz, 1H), 6.41-6.44 (bs, 2H).

Example 9

2-[5-methyl-4-[2-(trifluoromethyl)-4-pyridyl]imidazol-1-yl]-N-(5-pyrazin-2-yl-2-pyridyl)acetamide

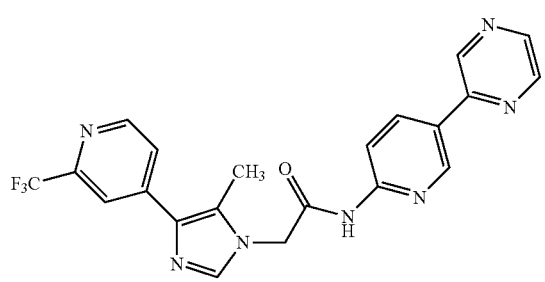 [SMILES: Cc1c(-c2ccnc(C(F)(F)F)c2)ncn1CC(=O)Nc1ccc(-c2cnccn2)cn1]

To a stirred solution of lithium 2-[5-methyl-4-[2-(trifluoromethyl)-4-pyridyl]imidazol-1-yl]acetate (1.04 g, 3.57 mmol) and 5-pyrazin-2-ylpyridin-2-amine (738 mg, 4.29 mmol) in THF (35 mL) was added N,N-diisopropylethylamine (1.58 mL, 8.93 mmol) and propylphosphonic anhydride (6.38 mL, 10.7 mmol) and the resulting solution heated to 70° C. Reaction was monitored by LCMS and after 2 hrs further propylphosphonic anhydride (2.13 mL, 3.57 mmol) and N,N-diisopropylethylamine (0.6 mL) were added the solution was allowed to cool to room temperature and stirred over the weekend. The solution was diluted with water and EtOAc and partitioned. The aqueous was washed with EtOAc (×2) before the combined organics were washed with brine. Product precipitated and was isolated by filtration and loaded onto a MeOH primed 10 g SCX cartridge, washing with MeOH and eluting with 1M $NH_3$ MeOH solution. The ammonia methanol solution was concentrated to dryness in vacuo to afford an off white solid which was then dried in a vacuum oven for 2 hrs. The organics were separated from the filtrate, dried (sodium sulphate), filtered and concentrated to dryness in vacuo to afford a light brown foam containing product of ~95% purity. This was dissolved in DCM and purified by flash column chromatography (25 g $SiO_2$, 70-100% EtOAc in heptane, then 0-5% MeOH/EtOAc). Appropriate fractions were combined and concentrated to dryness in vacuo to afford an off white solid. The solids were combined to give 2-[5-methyl-4-[2-(trifluoromethyl)-4-pyridyl]imidazol-1-yl]-N-(5-pyrazin-2-yl-2-pyridyl)acetamide (1.22 g, 2.77 mmol, 78% yield) as an off white solid.

MS Method 2: RT: 1.45 min, $ES^+$ m/z 440.1 $[M+H]^+$ $^1$H NMR (400 MHz, DMSO) δ/ppm: 11.27 (bs, 1H), 9.32-9.33 (d, J=1.6 Hz, 1H), 8.70-8.75 (m, 2H), 8.64-8.65 (d, J=2.4 Hz, 1H), 8.54-8.58 (dd, J=2.4, 8.8 Hz, 1H), 8.17-8.19 (d, J=9.2 Hz, 1H), 8.09 (s, 1H), 7.92-7.94 (d, J=4.4 Hz, 1H), 7.85 (s, 1H), 5.12 (s, 2H), 2.45 (s, 3H).

The compound of Example 9 could also be made by the procedure outlined in General Scheme 1.

Example 10

2-[4-(2-fluoro-4-pyridyl)-5-methyl-imidazol-1-yl]-N-(5-pyrazin-2-yl-2-pyridyl)acetamide

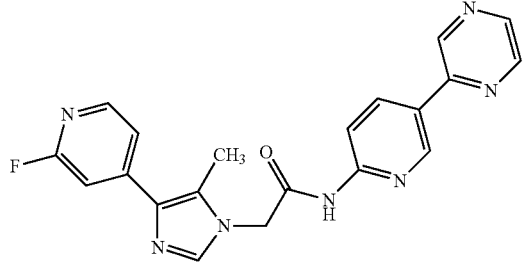 [SMILES: Cc1c(-c2ccnc(F)c2)ncn1CC(=O)Nc1ccc(-c2cnccn2)cn1]

A flask was charged with 2-[4-(2-fluoro-4-pyridyl)-5-methyl-imidazol-1-yl]acetic acid (125 mg, 0.53 mmol) and 5-pyrazin-2-ylpyridin-2-amine (110 mg, 0.64 mmol) which were taken up in dry THF (2.5 mL). N,N-diisopropylethylamine (0.46 mL, 2.66 mmol) was then added, followed by propylphosphonic anhydride (0.63 mL, 1.06 mmol). The resulting mixture was then heated to reflux for 2 hours then allowed to cool to room temp. The reaction mixture was concentrated to dryness, giving a brown oil. This was then dry-loaded on to silica gel and purified by flash chromatography, (12 g SiO2, eluting with 0-10% MeOH in EtOAc. Fractions containing desired compound were combined and concentrated to dryness, giving an off-white solid. This was then dry-loaded on to celite and further purified by reverse-phase chromatography, (12 g C-18 column, eluting with 5-40% MeCN in water+0.1% formic acid additive). Fractions containing desired compound were combined and concentrated to dryness, giving 2-[4-(2-fluoro-4-pyridyl)-5-methyl-imidazol-1-yl]-N-(5-pyrazin-2-yl-2-pyridyl)acetamide (86 mg, 0.22 mmol, 41% yield) as a white solid.

MS Method 2: RT: 1.20 min, $ES^+$ m/z 390.1 $[M+H]^+$ $^1$H NMR (400 MHz, DMSO) δ/ppm: 11.26 (bs, 1H), 9.32-9.33 (d, J=1.4 Hz, 1H), 9.14-9.15 (d, J=1.8 Hz 1H) 8.72-8.74 (m, 1H), 8.64-8.65 (d, J=2.5 Hz, 1H), 8.54-8.57 (dd, J=2.4, 8.8 Hz), 8.17-8.21 (m, 2H), 7.81 (s, 1H), 7.61-7.63 (m, 1H), 7.32 (m, 1H), 5.09 (s, 2H), 2.42 (s, 3H).

Example 11

The following compounds were prepared by analogy with examples 9 and 10 following general route 3, varying the substitution on the iodo imidazole and the aryl boronate ester. The method of biaryl alpha-chloroacetamide synthesis A was used to prepare the coupling partner for the final step, varying the arylhalide and/or arylboronate used.

| Structure | STRUCTURE NAME | LCMS RT (min) | m/z MIM |
|---|---|---|---|
| 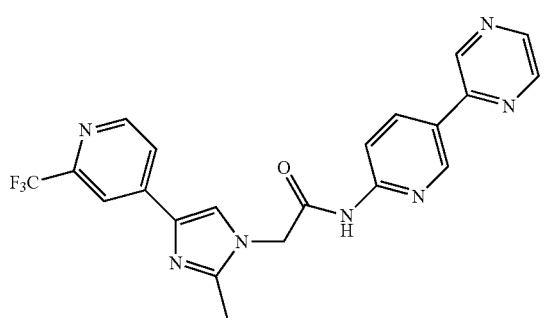 [SMILES: Cc1nc(-c2ccnc(C(F)(F)F)c2)cn1CC(=O)Nc1ccc(-c2cnccn2)cn1] | 2-[2-methyl-4-[2-(trifluoromethyl)-4-pyridyl]imidazol-1-yl]-N-(5-pyrazin-2-yl-2-pyridyl)acetamide | 2.77 (Method 1) | 440.1 |

-continued

| Structure | STRUCTURE NAME | LCMS RT (min) | m/z MIM |
|---|---|---|---|
| 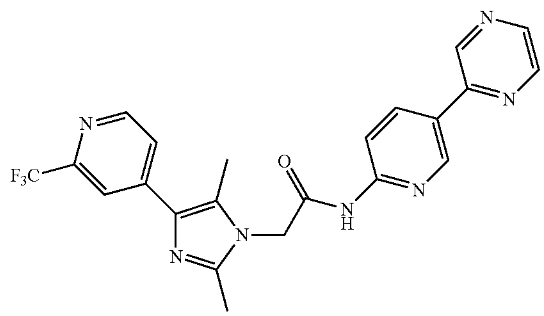 [SMILES: Cc1nc(-c2ccnc(C(F)(F)F)c2)c(C)n1CC(=O)Nc1ccc(-c2cnccn2)cn1] | 2-[2,5-dimethyl-4-[2-(trifluoromethyl)-4-pyridyl]imidazol-1-yl]-N-(5-pyrazin-2-yl-2-pyridyl)acetamide | 2.71 (Method 1) | 454.2 |
| 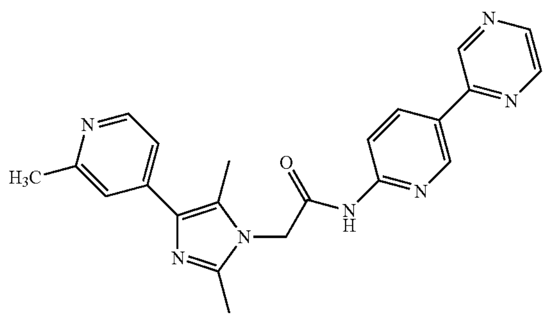 [SMILES: Cc1cc(-c2nc(C)n(CC(=O)Nc3ccc(-c4cnccn4)cn3)c2C)ccn1] | 2-[2,5-dimethyl-4-(2-methyl-4-pyridyl)imidazol-1-yl]-N-(5-pyrazin-2-yl-2-pyridyl)acetamide | 2.07 (Method 1) | 400.2 |
| 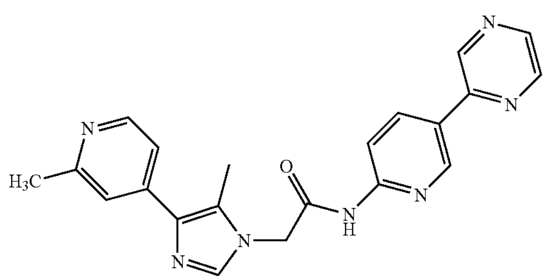 [SMILES: Cc1cc(-c2ncn(CC(=O)Nc3ccc(-c4cnccn4)cn3)c2C)ccn1] | 2-[5-methyl-4-(2-methyl-4-pyridyl)imidazol-1-yl]-N-(5-pyrazin-2-yl-2-pyridyl)acetamide | 2.10 (Method 1) | 386.2 |
| 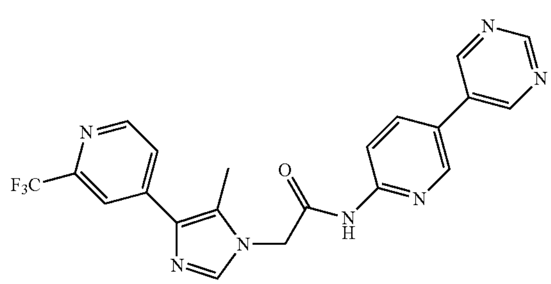 [SMILES: Cc1c(-c2ccnc(C(F)(F)F)c2)ncn1CC(=O)Nc1ccc(-c2cncnc2)cn1] | 2-[5-methyl-4-[2-(trifluoromethyl)-4-pyridyl]imidazol-1-yl]-N-(5-pyrimidin-5-yl-2-pyridyl)acetamide | 2.76 (Method 1) | 440.1 |
| 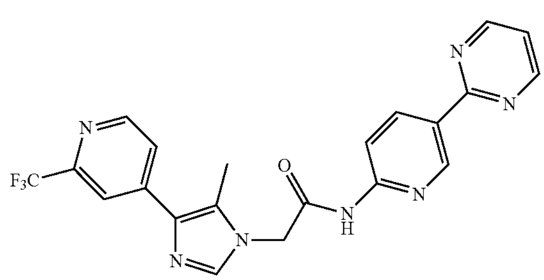 [SMILES: Cc1c(-c2ccnc(C(F)(F)F)c2)ncn1CC(=O)Nc1ccc(-c2ncccn2)cn1] | 2-[5-methyl-4-[2-(trifluoromethyl)-4-pyridyl]imidazol-1-yl]-N-(5-pyrimidin-2-yl-2-pyridyl)acetamide | 3.05 (Method 1) | 440.1 |

-continued

| Structure | STRUCTURE NAME | LCMS RT (min) | m/z MIM |
|---|---|---|---|
| 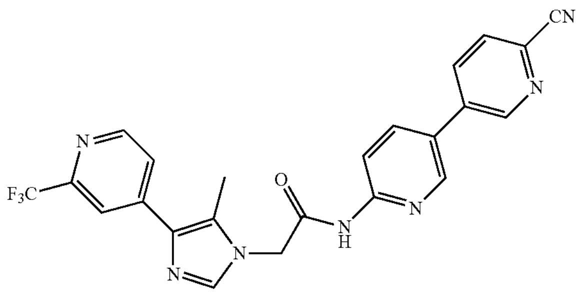 [SMILES: Cc1c(-c2ccnc(C(F)(F)F)c2)ncn1CC(=O)Nc1ccc(-c2ccc(C#N)nc2)cn1] | N-[5-(6-cyano-3-pyridyl)-2-pyridyl]-2-[5-methyl-4-[2-(trifluoromethyl)-4-pyridyl]imidazol-1-yl]acetamide | 3.24 (Method 1) | 464.1 |
| 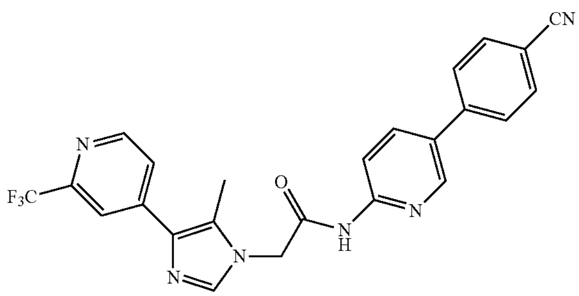 [SMILES: Cc1c(-c2ccnc(C(F)(F)F)c2)ncn1CC(=O)Nc1ccc(-c2ccc(C#N)cc2)cn1] | N-[5-(4-cyanophenyl)-2-pyridyl]-2-[5-methyl-4-[2-(trifluoromethyl)-4-pyridyl]imidazol-1-yl]acetamide | 3.57 (Method 1) | 463.2 |
| 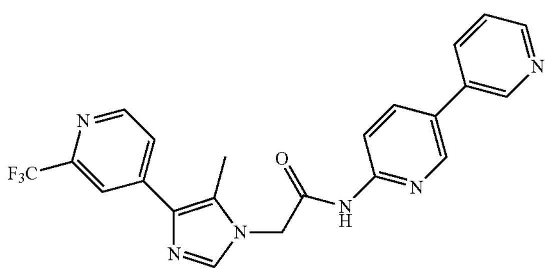 [SMILES: Cc1c(-c2ccnc(C(F)(F)F)c2)ncn1CC(=O)Nc1ccc(-c2cccnc2)cn1] | 2-[5-methyl-4-[2-(trifluoromethyl)-4-pyridyl]imidazol-1-yl]-N-[5-(3-pyridyl)-2-pyridyl]acetamide | 2.58 (Method 1) | 439.1 |
| 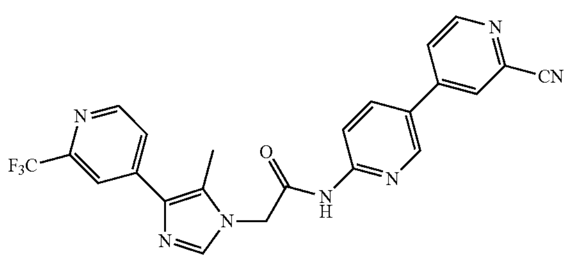 [SMILES: Cc1c(-c2ccnc(C(F)(F)F)c2)ncn1CC(=O)Nc1ccc(-c2ccnc(C#N)c2)cn1] | N-[5-(2-cyano-4-pyridyl)-2-pyridyl]-2-[5-methyl-4-[2-(trifluoromethyl)-4-pyridyl]imidazol-1-yl]acetamide | 3.29 (Method 1) | 464.2 |
| 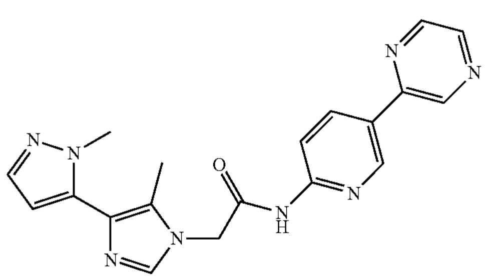 [SMILES: Cc1c(-c2ccnn2C)ncn1CC(=O)Nc1ccc(-c2cnccn2)cn1] | 2-[5-methyl-4-(2-methylpyrazol-3-yl)imidazol-1-yl]-N-(5-pyrazin-2-yl-2-pyridyl)acetamide | 2.37 (Method 1) | 375.2 |

General Scheme 4

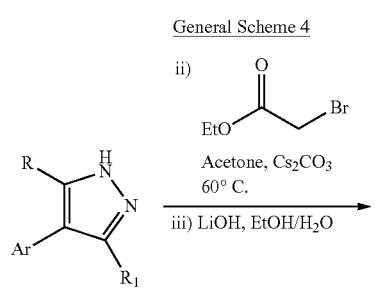

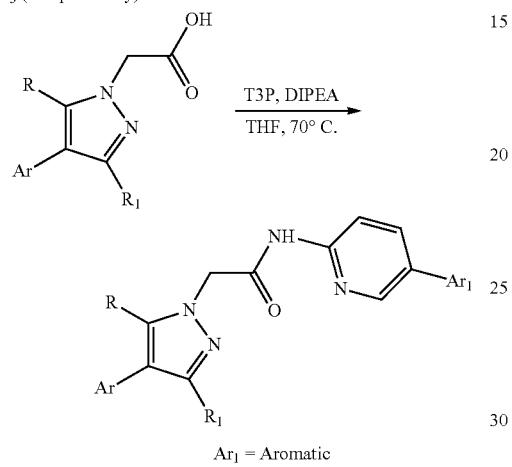

Ar = Aromatic
R, R₁ = H, CH₃ (independently)

Ar₁ = Aromatic

Aryl Pyrazoles starting materials were prepared according to the method described previously as illustrated in general scheme 2, varying the substitution on the pyrazole boronate ester and the aryl halide. The method of biaryl alpha-chloroacetamide synthesis A was used to prepare the coupling partner for the final step, varying the arylhalide and/or arylboronate used.

Intermediate 22

2-[4-(2-cyclopentylpyrazol-3-yl)-3,5-dimethyl-pyrazol-1-yl]acetate

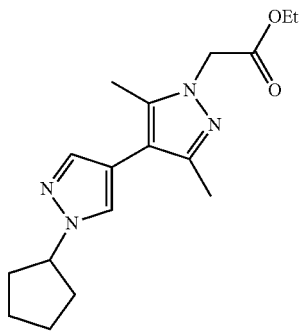 [SMILES: CCOC(=O)Cn1nc(C)c(-c2cnn(C3CCCC3)c2)c1C]

Ethyl bromoacetate (0.02 mL, 0.17 mmol), 4-(2-cyclopentylpyrazol-3-yl)-3,5-dimethyl-1H-pyrazole (35.7 mg, 0.16 mmol) and caesium carbonate (95.3 mg, 0.47 mmol) were added to Acetone (4 mL) forming a suspension. The flask was then heated to reflux and left to stir overnight.

The precipitate was filtered off, the filtrate was evaporated to dryness. The residue was dissolved in EtOAc and dried over sodium sulphate. The solvent was evaporated, affording ethyl 2-[4-(2-cyclopentylpyrazol-3-yl)-3,5-dimethyl-pyrazol-1-yl]acetate (51.2 mg, 0.16 mmol, 100% yield) as a yellow oil. The product was used without any further purification.

MS Method 2: RT: 1.71 min, ES⁺ m/z 317.0 [M+H]⁺
¹H NMR (400 MHz, CDCl3) δ/ppm: 7.43 (s, 1H), 7.73 (s, 1H), 6.25 (s, 1H), 4.81 (s, 2H), 4.65-4.67 (m, 1H), 4.21-4.25 (q, J=6.9 Hz, 2H), 2.39 (s, 3H), 2.36 (s, 3H), 2.04-2.18 (m, 4H), 1.85-1.91 (m, 2H), 1.66-1.71 (m, 2H), 1.21-1.24 (t, J=6.9 Hz, 3H).

Intermediate 23

2-[4-(2-cyclopentylpyrazol-3-yl)-3,5-dimethyl-pyrazol-1-yl]acetic

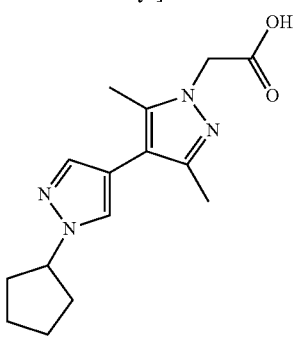

Ethyl 2-[4-(2-cyclopentylpyrazol-3-yl)-3,5-dimethyl-pyrazol-1-yl]acetate (51.2 mg, 0.16 mmol) was dissolved in ethanol (3 mL), lithium hydroxide (10.46 mg, 0.44 mmol) in water (0.30 mL) was added and the reaction was stirred at RT for 1 h. The mixture was acidified by using a 1M HCl solution. The solvent was evaporated. The residue was taken up into EtOAc and washed with brine. The organic phase was separated and dired over Na₂SO₄. Evaporation of the solvent afforded 2-[4-(2-cyclopentylpyrazol-3-yl)-3,5-dimethyl-pyrazol-1-yl]acetic acid (40.4 mg, 0.14 mmol, 87% yield) as a yellow oil which crystallized on standing.

MS Method 2: RT: 1.66 min, ES⁺ m/z 308.1 [M+H]⁺
¹H NMR (400 MHz, CDCl3) δ/ppm: 7.46 (s, 1H), 6.24 (s, 1H), 4.81 (s, 2H), 4.66-4.69 (m, 1H), 3.50-4.20 (bs, 1H), 2.39 (s, 3H), 2.37 (s, 3H), 2.13-2.21 (m, 2H), 2.00-2.10 (m, 2H), 1.89-1.99 (m, 2H), 1.66-1.71 (m, 2H).

Example 12

2-[4-(2-cyclopentylpyrazol-3-yl)-3,5-dimethyl-pyrazol-1-yl]-N-(5-pyrazin-2-yl-2-pyridyl)acetamide

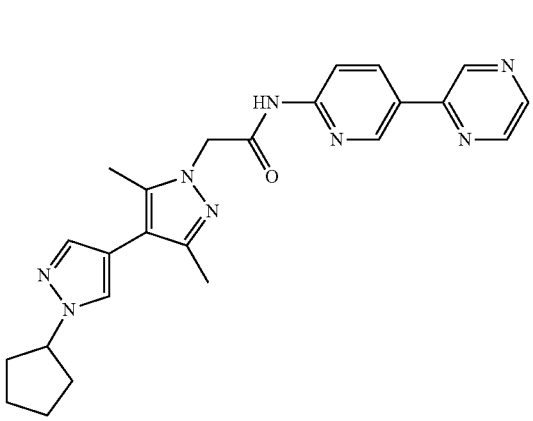 [SMILES: Cc1nn(CC(=O)Nc2ccc(-c3cnccn3)cn2)c(C)c1-c1cnn(C2CCCC2)c1]

A stirred solution of 2-[4-(2-cyclopentylpyrazol-3-yl)-3,5-dimethyl-pyrazol-1-yl]acetic acid (40.4 mg, 0.14 mmol), 5-pyrazin-2-ylpyridin-2-amine (24.13 mg, 0.1400 mmol), propylphosphonic anhydride (0.13 mL, 0.2100 mmol) and N,N-Diisopropylethylamine (0.06 mL, 0.35 mmol) in THF (5 mL) was heated to reflux overnight. LCMS indicated complete conversion to product. The THF was removed in vacuo then EtOAc and water were added to the mixture and the layers separated. The organic layer was washed with water then brine, dried, then concentrated in vacuo to afford a yellow gum, that was purified by LC (50-100% EtOAc in Heptane) to afford 2-[4-(2-cyclopentylpyrazol-3-yl)-3,5-dimethyl-pyrazol-1-yl]-N-(5-pyrazin-2-yl-2-pyridyl)acetamide (5.9 mg, 0.01 mmol, 10% yield).

MS Method 2: RT: 1.62 min, ES+ m/z 433.3 [M+H]+

$^1$H NMR (400 MHz, DMSO) δ/ppm: 11.03 (s, 1H), 9.31-9.33 (d, J=1.4 Hz, 1H), 9.13-9.14 (d, J=1.8 Hz, 1H), 8.71-8.75 (m, 1H), 8.62-8.43 (d, J=1 Hz, 1H), 8.53-8.57 (dd, J=2.4, 8.7 Hz, 1H), 8.17-8.20 (d, J=8.7 Hz, 1H), 7.75-7.78 (d, J=2.24 Hz, 1H), 6.28-6.29 (d, J=2.4 Hz, 1H), 5.06 (s, 2H), 4.66-4.75 (q, J=6.7 Hz, 1H), 2.38 (s, 3H), 2.24 (s, 3H), 1.91-2.13 (m, 4H), 1.77-1.83 (m, 2H), 1.62-1.69 (m, 2H).

Example 13

Further examples were prepared following general scheme 4 varying the substitution on the pyrazole boronate ester and the aryl halide. The method of biaryl alpha-chloroacetamide synthesis A was used to prepare the coupling partner for the final step, varying the arylhalide and/or arylboronate used.

| Structure | Structure Name | LCMS (min) | m/z MIM |
|---|---|---|---|
| 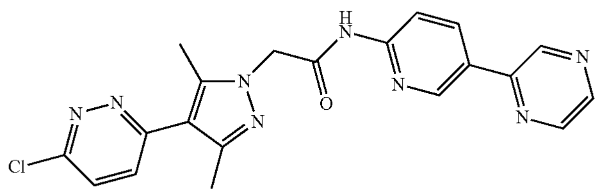 [SMILES: Cc1nn(CC(=O)Nc2ccc(-c3cnccn3)cn2)c(C)c1-c1ccc(Cl)nn1] | 2-[4-(6-chloropyridazin-3-yl)-3,5-dimethyl-pyrazol-1-yl]-N-(5-pyrazin-2-yl-2-pyridyl)acetamide | 2.96 (Method 1) | 421.1/ 423.2 |
| 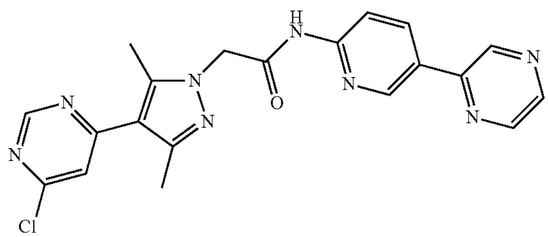 [SMILES: Cc1nn(CC(=O)Nc2ccc(-c3cnccn3)cn2)c(C)c1-c1cc(Cl)ncn1] | 2-[4-(6-chloropyrimidin-4-yl)-3,5-dimethyl-pyrazol-1-yl]-N-(5-pyrazin-2-yl-2-pyridyl)acetamide | 3.19 (Method 1) | 421.0/ 422.9 |
| 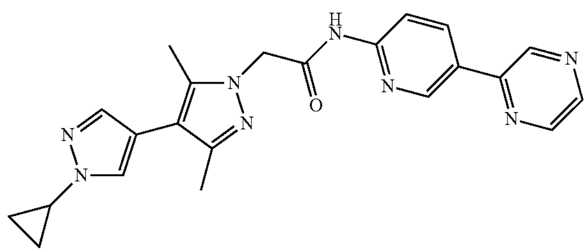 [SMILES: Cc1nn(CC(=O)Nc2ccc(-c3cnccn3)cn2)c(C)c1-c1cnn(C2CC2)c1] | 2-[4-(1-cyclopropylpyrazol-4-yl)-3,5-dimethyl-pyrazol-1-yl]-N-(5-pyrazin-2-yl-2-pyridyl)acetamide | 2.98 (Method 1) | 415.3 |
| 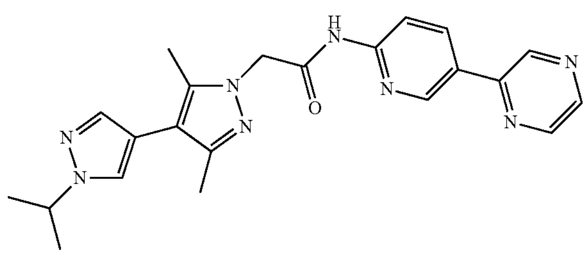 [SMILES: Cc1nn(CC(=O)Nc2ccc(-c3cnccn3)cn2)c(C)c1-c1cnn(C(C)C)c1] | 2-[4-(1-isopropylpyrazol-4-yl)-3,5-dimethyl-pyrazol-1-yl]-N-(5-pyrazin-2-yl-2-pyridyl)acetamide | 3.09 (Method 1) | 417.2 |
| 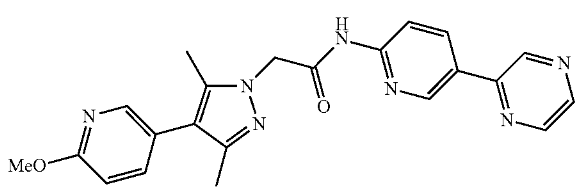 [SMILES: COc1ccc(-c2c(C)nn(CC(=O)Nc3ccc(-c4cnccn4)cn3)c2C)cn1] | 2-[4-(6-methoxy-3-pyridyl)-3,5-dimethyl-pyrazol-1-yl]-N-(5-pyrazin-2-yl-2-pyridyl)acetamide | 3.23 (Method 1) | 416.3 |

-continued

| Structure | Structure Name | LCMS (min) | m/z MIM |
|---|---|---|---|
| 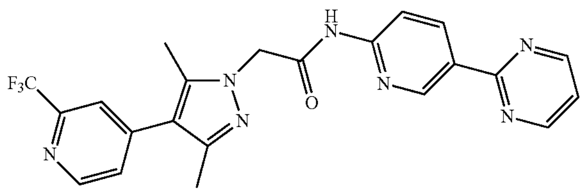 [SMILES: Cc1nn(CC(=O)Nc2ccc(-c3ncccn3)cn2)c(C)c1-c1ccnc(C(F)(F)F)c1] | 2-[3,5-dimethyl-4-[2-(trifluoromethyl)-4-pyridyl]pyrazol-1-yl]-N-(5-pyrimidin-2-yl-2-pyridyl)acetamide | 3.60 (Method 1) | 454.2 |
| 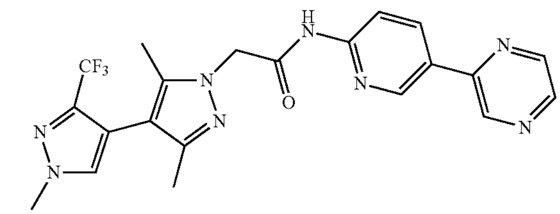 [SMILES: Cc1nn(CC(=O)Nc2ccc(-c3cnccn3)cn2)c(C)c1-c1cn(C)nc1C(F)(F)F] | 2-[3,5-dimethyl-4-[1-methyl-3-(trifluoromethyl)pyrazol-4-yl]pyrazol-1-yl]-N-(5-pyrazin-2-yl-2-pyridyl)acetamide | 3.31 (Method 1) | 457.1 |
| 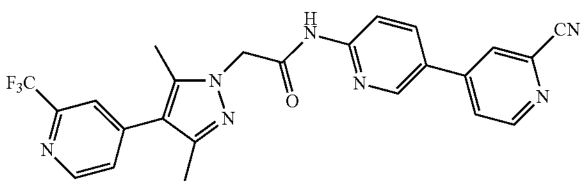 [SMILES: Cc1nn(CC(=O)Nc2ccc(-c3ccnc(C#N)c3)cn2)c(C)c1-c1ccnc(C(F)(F)F)c1] | N-[5-(2-cyano-4-pyridyl)-2-pyridyl]-2-[3,5-dimethyl-4-[2-(trifluoromethyl)-4-pyridyl]pyrazol-1-yl]acetamide | 3.75 (Method 1) | 478.2 |
| 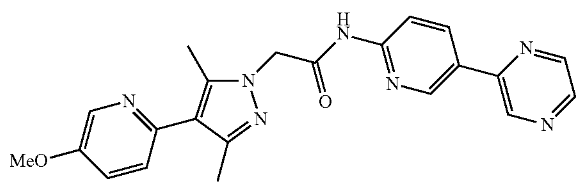 [SMILES: COc1ccc(-c2c(C)nn(CC(=O)Nc3ccc(-c4cnccn4)cn3)c2C)nc1] | 2-[4-(5-methoxy-2-pyridyl)-3,5-dimethyl-pyrazol-1-yl]-N-(5-pyrazin-2-yl-2-pyridyl)acetamide | 2.54 (Method 1) | 416.2 |
| 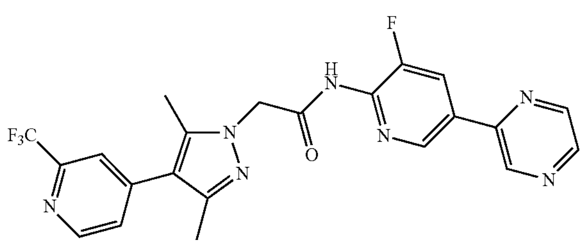 [SMILES: Cc1nn(CC(=O)Nc2ncc(-c3cnccn3)cc2F)c(C)c1-c1ccnc(C(F)(F)F)c1] | 2-[3,5-dimethyl-4-[2-(trifluoromethyl)-4-pyridyl]pyrazol-1-yl]-N-(3-fluoro-5-pyrazin-2-yl-2-pyridyl)acetamide | 3.37 (Method 1) | 472.0 |
| 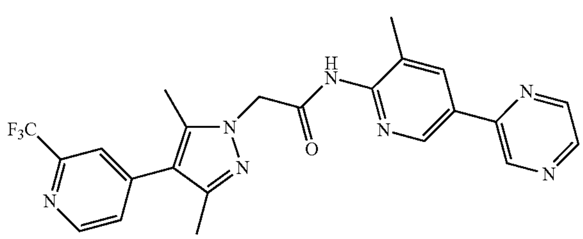 [SMILES: Cc1cc(-c2cnccn2)cnc1NC(=O)Cn1nc(C)c(-c2ccnc(C(F)(F)F)c2)c1C] | 2-[3,5-dimethyl-4-[2-(trifluoromethyl)-4-pyridyl]pyrazol-1-yl]-N-(3-methyl-5-pyrazin-2-yl-2-pyridyl)acetamide | 3.31 (Method 1) | 468.2 |
| 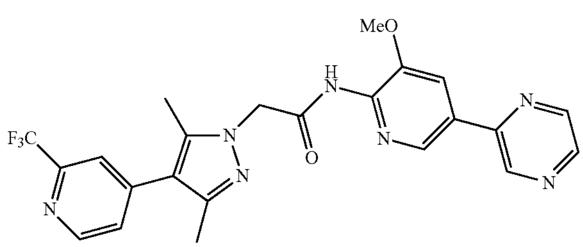 [SMILES: COc1cc(-c2cnccn2)cnc1NC(=O)Cn1nc(C)c(-c2ccnc(C(F)(F)F)c2)c1C] | 2-[3,5-dimethyl-4-[2-(trifluoromethyl)-4-pyridyl]pyrazol-1-yl]-N-(3-methoxy-5-pyrazin-2-yl-2-pyridyl)acetamide | 3.33 (Method 1) | 484.2 |

-continued

| Structure | Structure Name | LCMS (min) | m/z MIM |
|---|---|---|---|
| 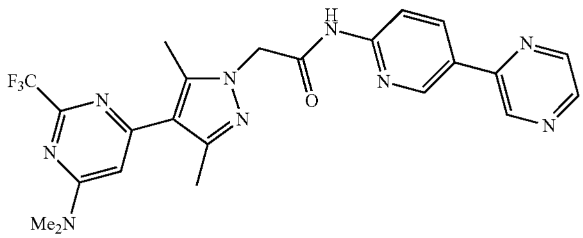 [SMILES: Cc1nn(CC(=O)Nc2ccc(-c3cnccn3)cn2)c(C)c1-c1cc(N(C)C)nc(C(F)(F)F)n1] | 2-[4-[6-(dimethylamino)-2-(trifluoromethyl)pyrimidin-4-yl]-3,5-dimethyl-pyrazol-1-yl]-N-(5-pyrazin-2-yl-2-pyridyl)acetamide | 3.97 (Method 1) | 498.3 |
| 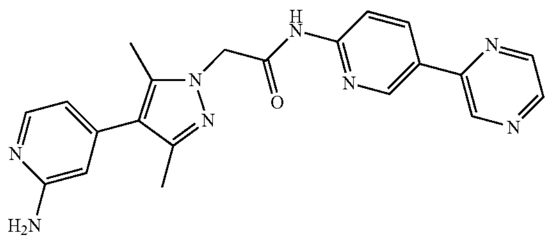 [SMILES: Cc1nn(CC(=O)Nc2ccc(-c3cnccn3)cn2)c(C)c1-c1ccnc(N)c1] | 2-[4-(2-amino-4-pyridyl)-3,5-dimethyl-pyrazol-1-yl]-N-(5-pyrazin-2-yl-2-pyridyl)acetamide | 2.19 (Method 1) | 401.1 |
| 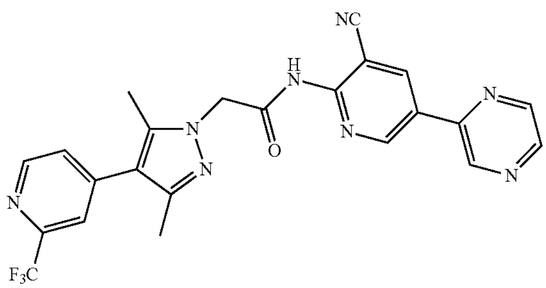 [SMILES: Cc1nn(CC(=O)Nc2ncc(-c3cnccn3)cc2C#N)c(C)c1-c1ccnc(C(F)(F)F)c1] | N-(3-cyano-5-pyrazin-2-yl-2-pyridyl)-2-[3,5-dimethyl-4-[2-(trifluoromethyl)-4-pyridyl]pyrazol-1-yl] acetamide | 3.41 (Method 1) | 479.1 |
| 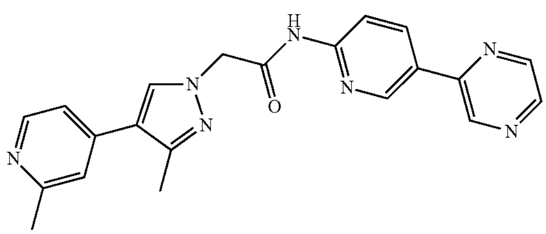 [SMILES: Cc1cc(-c2cn(CC(=O)Nc3ccc(-c4cnccn4)cn3)nc2C)ccn1] | 2-[3-methyl-4-(2-methyl-4-pyridyl)pyrazol-1-yl]-N-(5-pyrazin-2-yl-2-pyridyl)acetamide | 2.20 (Method 1) | 386.2 |
| 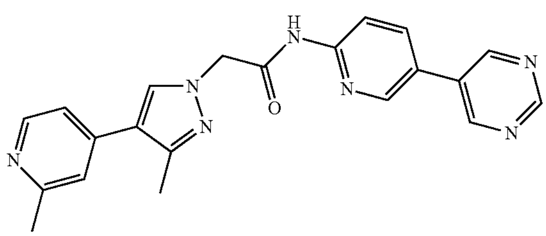 [SMILES: Cc1cc(-c2cn(CC(=O)Nc3ccc(-c4cncnc4)cn3)nc2C)ccn1] | 2-[3-methyl-4-(2-methyl-4-pyridyl)pyrazol-1-yl]-N-(5-pyrimidin-5-yl-2-pyridyl)acetamide | 2.07 (Method 1) | 386.2 |
| 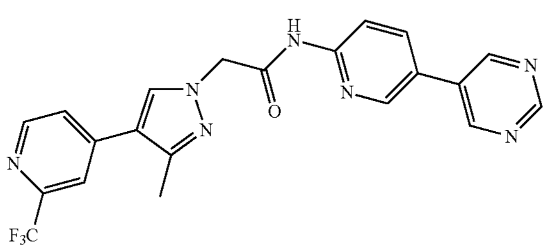 [SMILES: Cc1nn(CC(=O)Nc2ccc(-c3cncnc3)cn2)cc1-c1ccnc(C(F)(F)F)c1] | 2-[3-methyl-4-[2-(trifluoromethyl)-4-pyridyl]pyrazol-1-yl]-N-(5-pyrimidin-5-yl-2-pyridyl)acetamide | 3.22 (Method 1) | 440.2 |

-continued

| Structure | Structure Name | LCMS (min) | m/z MIM |
|---|---|---|---|
| | N-[5-[2-(dimethylamino)-4-pyridyl]-2-pyridyl]-2-[3-methyl-4-[2-(trifluoromethyl)-4-pyridyl]pyrazol-1-yl]acetamide | 2.93 (Method 1) | 482.3 |
| 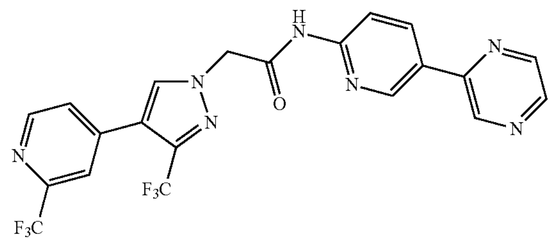 [SMILES: O=C(Cn1cc(-c2ccnc(C(F)(F)F)c2)c(C(F)(F)F)n1)Nc1ccc(-c2cnccn2)cn1] | N-(5-pyrazin-2-yl-2-pyridyl)-2-[3-(trifluoromethyl)-4-[2-(trifluoromethyl)-4-pyridyl]pyrazol-1-yl]acetamide | 3.97 (Method 1) | 494.2 |
| 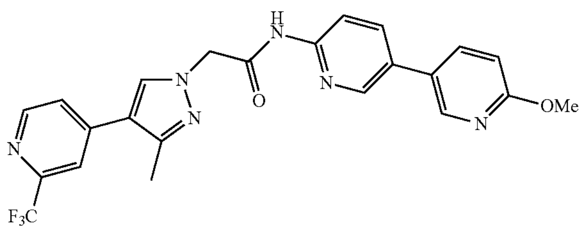 [SMILES: COc1ccc(-c2ccc(NC(=O)Cn3cc(-c4ccnc(C(F)(F)F)c4)c(C)n3)nc2)cn1] | N-[5-(6-methoxy-3-pyridyl)-2-pyridyl]-2-[3-methyl-4-[2-(trifluoromethyl)-4-pyridyl]pyrazol-1-yl]acetamide | 1.28 (Method 2) | 482.3 |
| | N-[5-[6-(dimethylamino)-3-pyridyl]-2-pyridyl]-2-[3-methyl-4-[2-(trifluoromethyl)-4-pyridyl]pyrazol-1-yl]acetamide | 2.90 (Method 1) | 482.2 |
| 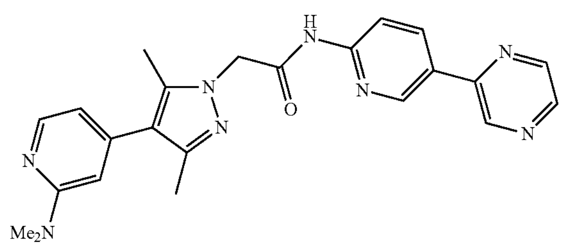 [SMILES: Cc1nn(CC(=O)Nc2ccc(-c3cnccn3)cn2)c(C)c1-c1ccnc(N(C)C)c1] | 2-[4-[2-(dimethylamino)-4-pyridyl]-3,5-dimethyl-pyrazol-1-yl]-N-(5-pyrazin-2-yl-2-pyridyl)acetamide | 2.37 (Method 1) | 429.2 |
| 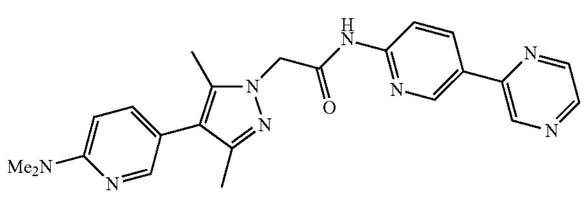 [SMILES: Cc1nn(CC(=O)Nc2ccc(-c3cnccn3)cn2)c(C)c1-c1ccc(N(C)C)nc1] | 2-[4-[6-(dimethylamino)-3-pyridyl]-3,5-dimethyl-pyrazol-1-yl]-N-(5-pyrazin-2-yl-2-pyridyl)acetamide | 2.34 (Method 1) | 429.2 |
| 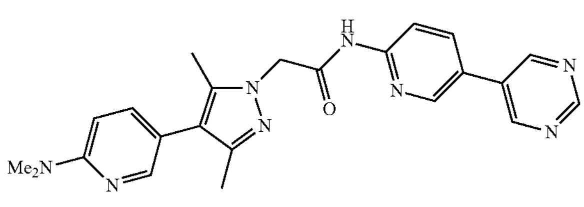 [SMILES: Cc1nn(CC(=O)Nc2ccc(-c3cncnc3)cn2)c(C)c1-c1ccc(N(C)C)nc1] | 2-[4-[6-(dimethylamino)-3-pyridyl]-3,5-dimethyl-pyrazol-1-yl]-N-(5-pyrimidin-5-yl-2-pyridyl)acetamide | 2.27 (Method 2) | 429.3 |

| Structure | Structure Name | LCMS (min) | m/z MIM |
|---|---|---|---|
| 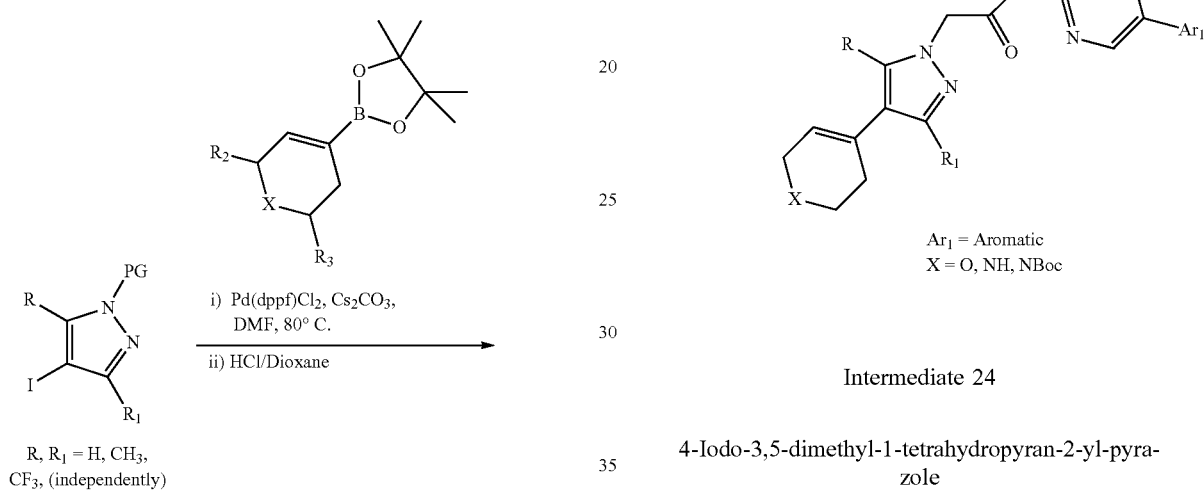 | N-[5-(6-acetamido-3-pyridyl)-2-pyridyl]-2-[3-methyl-4-[2-(trifluoromethyl)-4-pyridyl]pyrazol-1-yl]acetamide | 3.31 (Method 2) | 496.2 |

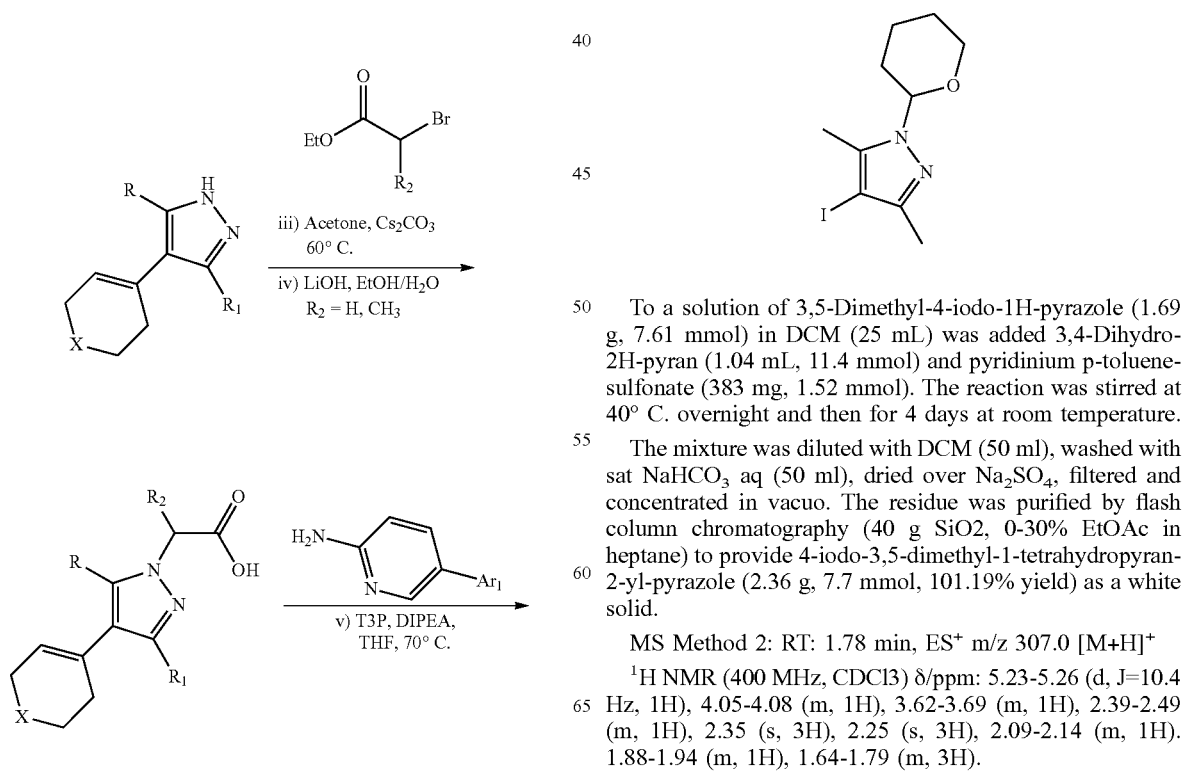

Ar₁ = Aromatic
X = O, NH, NBoc

Intermediate 24

4-Iodo-3,5-dimethyl-1-tetrahydropyran-2-yl-pyrazole

To a solution of 3,5-Dimethyl-4-iodo-1H-pyrazole (1.69 g, 7.61 mmol) in DCM (25 mL) was added 3,4-Dihydro-2H-pyran (1.04 mL, 11.4 mmol) and pyridinium p-toluenesulfonate (383 mg, 1.52 mmol). The reaction was stirred at 40° C. overnight and then for 4 days at room temperature.

The mixture was diluted with DCM (50 ml), washed with sat NaHCO₃ aq (50 ml), dried over Na₂SO₄, filtered and concentrated in vacuo. The residue was purified by flash column chromatography (40 g SiO2, 0-30% EtOAc in heptane) to provide 4-iodo-3,5-dimethyl-1-tetrahydropyran-2-yl-pyrazole (2.36 g, 7.7 mmol, 101.19% yield) as a white solid.

MS Method 2: RT: 1.78 min, ES⁺ m/z 307.0 [M+H]⁺

¹H NMR (400 MHz, CDCl3) δ/ppm: 5.23-5.26 (d, J=10.4 Hz, 1H), 4.05-4.08 (m, 1H), 3.62-3.69 (m, 1H), 2.39-2.49 (m, 1H), 2.35 (s, 3H), 2.25 (s, 3H), 2.09-2.14 (m, 1H). 1.88-1.94 (m, 1H), 1.64-1.79 (m, 3H).

Intermediate 25

4-(3,6-dihydro-2H-pyran-4-yl)-3,5-dimethyl-1-tetrahydropyran-2-yl-pyrazole

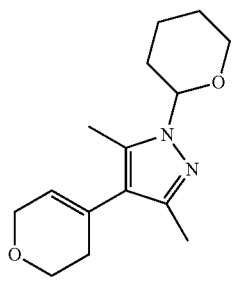 [SMILES: Cc1nn(C2CCCCO2)c(C)c1C1=CCOCC1]

A flask was charged with 4-iodo-3,5-dimethyl-1-tetrahydropyran-2-yl-pyrazole (1.3 g, 4.25 mmol), cesium carbonate (4.15 g, 12.7 mmol) and 3,6-dihydro-2H-pyran-4-boronic acid pinacol ester (1.78 g, 8.49 mmol) which was taken up in DMF (18.7 mL). The resulting solution was then degassed by evacuation and back-filled with nitrogen (repeated twice).

[1,1'-bis(diphenylphosphino)ferrocene]Palladium(II) chloride dichloromethane complex (347 mg, 0.42 mmol) was then added, the system evacuated and back-filled with nitrogen once more, then the reaction mixture heated up to 80° C. for 4 hours. The reaction mixture was partitioned between EtOAc and water. The organic layer washed with saturated aqueous NaHCO$_3$, then with brine, dried over sodium sulfate, filtered and concentrated to dryness, affording a thick brown oil. This was purified by column chromatography, (80 g SiO$_2$, eluting with 20-60% EtOAc in heptane). The fractions containing product were combined and concentrated to dryness, affording 4-(3,6-dihydro-2H-pyran-4-yl)-3,5-dimethyl-1-tetrahydropyran-2-yl-pyrazole (200 mg, 0.76 mmol, 18% yield) as a yellow oil.

MS Method 2: RT: 1.46 min, ES$^+$ m/z 263.5 [M+H]$^+$ $^1$H NMR (400 MHz, CDCl3) δ/ppm: 5.51-5.58 (m, 1H), 5.15-5.19 (dd, J=2.4, 10.4 Hz, 1H), 4.26-4.30 (q, J=2.7 Hz, 2H), 4.04-4.10 (m, 1H), 3.85-3.90 (t, J=5.4 Hz, 2H), 3.60-3.68 (dt, J=2.4, 11.6 Hz, 1H), 2.42-2.54 (m, 1H), 2.26-2.31 (m, 2H), 2.24 (s, 3H), 2.20 (s, 3H), 2.05-2.12 (m, 1H), 1.89-1.94 (m, 1H), 1.62-1.76 (m, 2H), 1.25-1.29 (m, 1H).

Intermediate 26

3,5-dimethyl-1-tetrahydropyran-2-yl-4-tetrahydropyran-4-yl-pyrazole

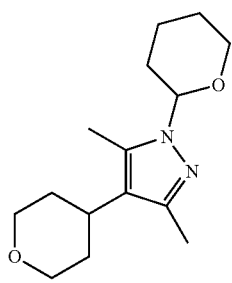 [SMILES: Cc1nn(C2CCCCO2)c(C)c1C1CCOCC1]

To a round bottomed flask was added 4-(3,6-dihydro-2H-pyran-4-yl)-3,5-dimethyl-1-tetrahydropyran-2-yl-pyrazole (100 mg, 0.38 mmol) and methanol (5 mL). The solution was purged and evacuated with nitrogen several times before the addition of palladium, 10 wt. % on carbon powder, wet (81 mg, 0.08 mmol) after which the system was again purged and evacuated several times. The reaction vessel was then filled with hydrogen and stirred vigorously overnight.

The mixture was filtered over a celite pad, washed with MeOH and dried, affording 3,5-dimethyl-1-tetrahydropyran-2-yl-4-tetrahydropyran-4-yl-pyrazole (90 mg, 0.34 mmol, 90% yield) as a colourless oil.

MS Method 2: RT: 1.41 min, ES$^+$ m/z 265.0 [M+H]$^+$ $^1$H NMR (400 MHz, CDCl3) δ/ppm: 5.15-5.19 (dd, J=2.4, 10.4 Hz, 1H), 4.03-4.11 (m, 3H), 3.60-3.68 (dt, J=2.4, 12.5 Hz, 1H), 3.44-3.52 (dt, J=2.0, 12.5 Hz, 2H), 2.61-2.68 (tt, J=4.0, 12.5 Hz, 1H), 2.44-2.55 (m, 1H), 2.29 (s, 3H), 2.28 (s, 3H), 2.05-2.12 (m, 1H), 1.89-2.03 (m, 3H), 1.52-1.79 (m, 5H).

Intermediate 27

4-(3,6-dihydro-2H-pyran-4-yl)-3,5-dimethyl-1H-pyrazole

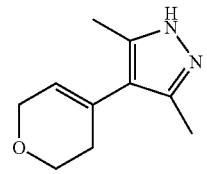

To a round bottomed flask was added 4-(3,6-dihydro-2H-pyran-4-yl)-3,5-dimethyl-1-tetrahydropyran-2-yl-pyrazole (505 mg, 1.92 mmol) and 4M hydrogen chloride in dioxane (4.81 mL, 19.3 mmol) was added dropwise. The reaction was stirred at room temperature over the weekend. The pH was adjusted to basic by addition of saturated NaHCO3. The organic layer was separated, washed with brine, dried over sodium sulphate and evaporated, affording a yellow oil. The resulting residue was loaded onto a methanol primed SCX cartridge and eluted with methanol (3CV) and 1M ammonia in methanol (3CV). The ammonia flush was then concentrated affording 4-(3,6-dihydro-2H-pyran-4-yl)-3,5-dimethyl-1H-pyrazole (280 mg, 1.57 mmol, 82% yield) as a colourless oil.

MS Method 2: RT: 0.96 min, ES+ m/z 179.0 [M+H]+

1H NMR (400 MHz, CDCl3) δ/ppm: 5.55-5.62 (m, 1H), 4.27-4.31 (q, J=2.7 Hz, 2H), 3.87-3.92 (t, J=5.4 Hz, 2H), 2.30-2.36 (m, 2H), 2.52 (s, 6H).

Intermediate 28

4-tetrahydropyran-4-yl-1H-pyrazole

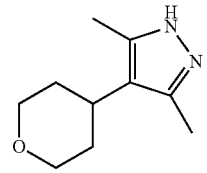

1-Tetrahydropyran-2-yl-4-tetrahydropyran-4-yl-pyrazole (120 mg, 0.51 mmol) was dissolved in 1,4-dioxane (2 mL) and 4M HCl in dioxane (1.27 mL, 5.09 mmol) was added dropwise. The reaction was stirred at room temperature overnight. The pH was adjusted to basic by addition of saturated NaHCO₃. The organic layer was extracted with EtOAc, separated, washed with brine, dried over sodium sulphate and evaporated, affording 4-tetrahydropyran-4-yl-1H-pyrazole (72.8 mg, 0.47 mmol, 94% yield) as a white solid that was used without any further purification.

MS Method 2: RT: 0.88 min, ES⁺ m/z 181.0 [M+H]⁺

¹H NMR (400 MHz, CDCl3) δ/ppm: 4.04-4.12 (m, 2H), 3.46-3.56 (m, 2H), 2.63-2.72 (tt, J=3.8, 12.5 Hz, 1H), 2.29 (s, 6H), 1.90-2.01 (m, 2H), 1.51-1.63 (m, 3H).

Intermediate 29

2-[4-(3,6-dihydro-2H-pyran-4-yl)-3,5-dimethyl-pyrazol-1-yl]acetic acid

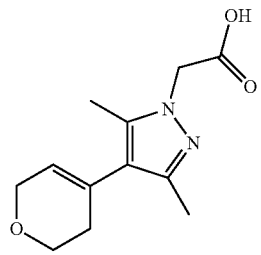 [SMILES: Cc1nn(CC(=O)O)c(C)c1C1=CCOCC1]

Following the two step procedure described for alkylation and hydrolysis of intermediate 23 in general scheme 4 2-[4-(3,6-dihydro-2H-pyran-4-yl)-3,5-dimethyl-pyrazol-1-yl]acetic acid was prepared.

MS Method 2: RT: 1.06 min, ES⁺ m/z 237.0 [M+H]⁺

¹H NMR (400 MHz, CDCl₃) δ/ppm: 5.57-5.63 (m, 1H), 4.77 (s, 2H), 4.27-4.30 (m, 2H), 3.86-3.92 (m, 2H), 2.90-3.50 (bs, 1H), 2.26-2.33 (m, 2H), 2.22 (s, 3H), 2.20 (s, 3H).

Intermediate 30 ethyl 2-[4-(3,6-dihydro-2H-pyran-4-yl)-3,5-dimethyl-pyrazol-1-yl]propanoate

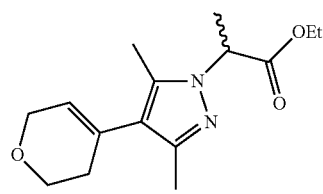 [SMILES: CCOC(=O)C(C)n1nc(C)c(C2=CCOCC2)c1C]

A flask was charged with 4-(3,6-dihydro-2H-pyran-4-yl)-3,5-dimethyl-1H-pyrazole (150 mg, 0.84 mmol), ethyl 2-bromopropionate (0.16 mL, 1.26 mmol) and potassium carbonate (345 mg, 2.52 mmol) which was suspended in MeCN (5 mL). The flask was then heated to reflux and left to stir overnight. After this time, a TLC analysis show SM left, so ethyl 2-bromopropionate (0.16 mL, 1.26 mmol) was added again and the reaction was stirred for further 24 hours. The precipitated solid was filtered off and washed with EtOAc. The filtrate was evaporated to dryness, affording a yellow oil which was purified by flash column chromatography (12 g, SiO₂, 20-100% EtOAc in heptane). Ethyl 2-[4-(3,6-dihydro-2H-pyran-4-yl)-3,5-dimethyl-pyrazol-1-yl]propanoate was isolated as a colourless oil (31 mg, 0.11 mmol, 13% yield).

¹H NMR (400 MHz, CDCl₃) δ/ppm: 5.50-5.58 (m, 1H), 4.84-4.88 (q, J=7.1 Hz, 1H), 4.15-4.30 (m, 4H), 3.86-3.92 (m, 2H), 2.29-2.34 (m, 2H), 2.20 (s, 3H), 2.27 (s, 3H), 1.81-1.82 (d, J=7.1 Hz, 3H), 1.19-1.25 (q, J=6.2 Hz, 3H).

Intermediate 31

2-[4-(3,6-dihydro-2H-pyran-4-yl)-3,5-dimethyl-pyrazol-1-yl]propanoic acid

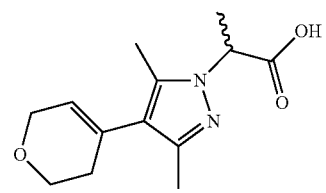 [SMILES: Cc1nn(C(C)C(=O)O)c(C)c1C1=CCOCC1]

Ethyl 2-[4-(3,6-dihydro-2H-pyran-4-yl)-3,5-dimethyl-pyrazol-1-yl]propanoate (31.2 mg, 0.11 mmol) was dissolved in ethanol (5 mL), lithium hydroxyde (6.71 mg, 0.28 mmol) in water (0.20 mL) was added and the reaction was stirred at RT for 16 h. Evaporation of the solvent afforded 2-[4-(3,6-dihydro-2H-pyran-4-yl)-3,5-dimethyl-pyrazol-1-yl]propanoic acid.

MS Method 2: RT: 1.51 min, ES⁺ m/z 251.1 [M+H]⁺

Intermediate 32

2-[4-(1-tert-butoxycarbonyl-3,6-dihydro-2H-pyridin-4-yl)pyrazol-1-yl]acetic acid

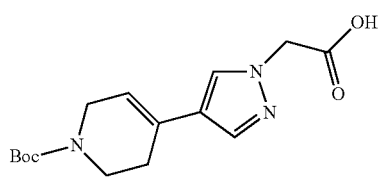 [SMILES: CC(C)(C)OC(=O)N1CC=C(c2cnn(CC(=O)O)c2)CC1]

Following steps i-iv) in general scheme 5 2-[4-(1-tert-butoxycarbonyl-3,6-dihydro-2H-pyridin-4-yl)pyrazol-1-yl] acetic acid was prepared starting from 4-iodo-1H-pyrazole and N-Boc-1,2,3,6-tetrahydropyridine-4-boronic acid pinacol ester.

MS Method 2: RT: 1.66 min, ES⁺ m/z 308.1 [M+H]⁺

¹H NMR (400 MHz, CDCl₃) δ/ppm: 7.63 (s, 1H), 7.43 (s, 1H), 5.84-5.95 (bs, 1H), 5.04 (s, 2H), 3.98-4.04 (m, 2H), 3.55-3.63 (t, J=6.0 Hz, 2H), 2.34-2.40 (m, 2H), 1.43-1.54 (m, 9H)

Example 14

2-[4-(3,6-dihydro-2H-pyran-4-yl)-3,5-dimethyl-pyrazol-1-yl]-N-(5-pyrazin-2-yl-2-pyridyl)acetamide

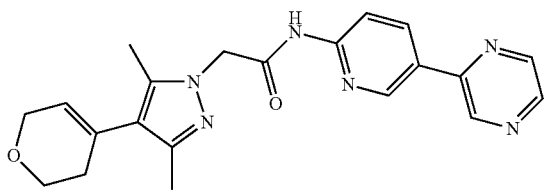 [SMILES: Cc1nn(CC(=O)Nc2ccc(-c3cnccn3)cn2)c(C)c1C1=CCOCC1]

A stirred solution of 2-[4-(3,6-dihydro-2H-pyran-4-yl)-3,5-dimethyl-pyrazol-1-yl]acetic acid (108 mg, 0.46 mmol), 5-pyrazin-2-ylpyridin-2-amine (103 mg, 0.60 mmol), propylphosphonic anhydride (0.55 mL, 0.92 mmol) and N,N-diisopropylethylamine (0.2 mL, 1.15 mmol) in THF (5 mL) was heated to reflux and stirred for 2 h. The THF was removed in vacuo to afford a yellow gum, that was purified by flash column chromatography (12 g SiO$_2$, 50-100% EtOAc in heptane) to afford 2-[4-(3,6-dihydro-2H-pyran-4-yl)-3,5-dimethyl-pyrazol-1-yl]-N-(5-pyrazin-2-yl-2-pyridyl)acetamide ((45 mg, 0.12 mmol, 25% yield) as a colourless solid.

MS Method 2: RT: 1.34 min, ES$^+$ m/z 391.2 [M+H]$^+$ $^1$H NMR (400 MHz, DMSO) δ/ppm: 11.05 (s, 1H), 9.30-9.34 (d, J=1.4 Hz, 1H), 9.12-9.14 (d, J=1.9 Hz, 1H), 8.72-8.74 (m, 1H), 8.63-8.65 (d, J=2.4 Hz, 1H), 8.53-8.57 (dd, J=2.4, 8.7 Hz, 1H), 8.16-8.20 (d, J=8.8 Hz, 1H), 5.57 (s, 1H), 5.00 (s, 2H), 4.17-4.21 (m, 2H), 3.77-3.82 (t, J=5.6 Hz, 2H), 2.24-2.39 (m, 2H), 2.18 (s, 3H), 2.09 (s, 3H).

Example 15

2-[4-(3,6-dihydro-2H-pyran-4-yl)-3,5-dimethyl-pyrazol-1-yl]-N-(5-pyrazin-2-yl-2-pyridyl)propanamide

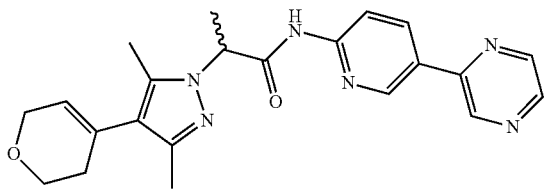 [SMILES: Cc1nn(C(C)C(=O)Nc2ccc(-c3cnccn3)cn2)c(C)c1C1=CCOCC1]

A stirred solution of lithium 2-[4-(3,6-dihydro-2H-pyran-4-yl)-3,5-dimethyl-pyrazol-1-yl]propanoate (29 mg, 0.11 mmol), 5-pyrazin-2-ylpyridin-2-amine (19 mg, 0.11 mmol), propylphosphonic anhydride (0.13 mL, 0.22 mmol) and N,N-diisopropylethylamine (0.05 mL, 0.28 mmol) in THF (5 mL) was heated to reflux and stirred for 24 h. After this time, LC-MS showed no conversion to the desired product so propylphosphonic anhydride (0.26 mL, 0.44 mmol), N,N-diisopropylethylamine (0.1 mL, 0.56 mmol) and 5-pyrazin-2-ylpyridin-2-amine (19 mg, 0.1100 mmol) were added. The reaction was stirred for further 24 h. The THF was removed in vacuo to afford a yellow gum, that was purified by flash column chromatography (4 g SiO$_2$, 50-100% EtOAc in Heptane), followed by reverse phase preparative HPLC affording 2-[4-(3,6-dihydro-2H-pyran-4-yl)-3,5-dimethyl-pyrazol-1-yl]-N-(5-pyrazin-2-yl-2-pyridyl)propanamide as a white solid (10.3 mg, 0.03 mmol, 22% yield).

MS Method 1: RT: 3.28 min, ES$^+$ m/z 405.3 [M+H]$^+$ $^1$H NMR (400 MHz, DMSO) δ/ppm: 10.77 (s, 1H), 9.29-9.32 (d, J=1.4 Hz, 1H), 9.09-9.11 (d, J=1.9 Hz, 1H), 8.71-8.75 (m, 1H), 8.62-8.65 (d, J=2.4 Hz, 1H), 8.53-8.57 (dd, J=2.4, 8.7 Hz, 1H), 8.19-8.24 (d, J=8.8 Hz, 1H), 5.57 (s, 1H), 5.16-5.23 (q, J=7 Hz 1H), 4.17-4.21 (m, 2H), 3.76-3.8 (t, J=5.9 Hz, 2H), 2.22-2.37 (m, 2H), 2.21 (s, 3H), 2.12 (s, 3H), 1.63-1.67 (d, J=7 Hz, 3H).

Example 16 tert-butyl 4-[1-[2-oxo-2-[(5-pyrazin-2-yl-2-pyridyl)amino]ethyl]pyrazol-4-yl]-3,6-dihydro-2H-pyridine-1-carboxylate

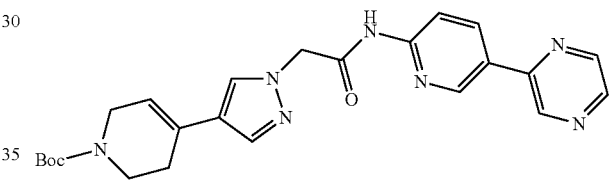

Intermediate 32 was subject to coupling according to step v) of general scheme 5 to form tert-butyl 4-[1-[2-oxo-2-[(5-pyrazin-2-yl-2-pyridyl)amino]ethyl]pyrazol-4-yl]-3,6-dihydro-2H-pyridine-1-carboxylate.

MS Method 1: RT: 3.68 min, ES$^+$ m/z 462.3 [M+H]$^+$ $^1$H NMR (400 MHz, DMSO) δ/ppm: 11.06 (s, 1H), 9.31-9.32 (d, J=1.3 Hz, 1H), 9.11-9.14 (d, J=2.2 Hz, 1H), 8.71-8.74 (m, 1H), 8.63-8.65 (d, J=2.5 Hz, 1H), 8.52-8.57 (1H, dd, J=2.4, 8.8 Hz, 1H), 8.15-8.21 (d, J=8.8 Hz, 1H), 7.84 (s, 1H), 7.66 (s, 1H), 5.94-5.99 (bs, 1H), 5.11 (s, 2H), 3.92-3.98 (bs, 2H), 3.49-3.54 (t, J=5.6 Hz, 2H), 2.30-2.37 (m, 2H), 1.42 (s, 9H).

Example 17

In an analogous fashion the following examples were also prepared.

| Structure | STRUCTURE NAME | LCMS RT (min) | m/z MIM |
|---|---|---|---|
| 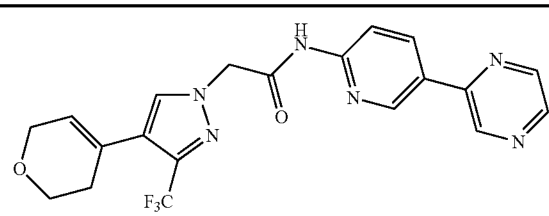 | 2-[4-(3,6-dihydro-2H-pyran-4-yl)-3-(trifluoromethyl)pyrazol-1-yl]-N-(5-pyrazin-2-yl-2-pyridyl)acetamide | 1.59 (Method 2) | 431.2 |

| Structure | STRUCTURE NAME | LCMS RT (min) | m/z MIM |
|---|---|---|---|
| 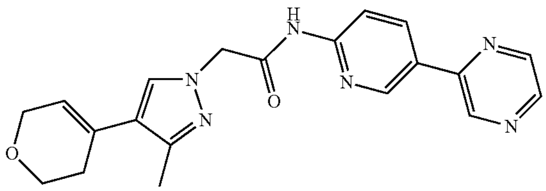 [SMILES: Cc1nn(CC(=O)Nc2ccc(-c3cnccn3)cn2)cc1C1=CCOCC1] | 2-[4-(3,6-dihydro-2H-pyran-4-yl)-3-methyl-pyrazol-1-yl]-N-(5-pyrazin-2-yl-2-pyridyl)acetamide | 1.36 (Method 2) | 377.2 |
| 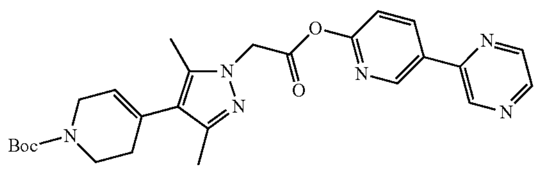 [SMILES: Cc1nn(CC(=O)Oc2ccc(-c3cnccn3)cn2)c(C)c1C1=CCN(C(=O)OC(C)(C)C)CC1] | tert-butyl 4-[3,5-dimethyl-1-[2-oxo-2-[(5-pyrazin-2-yl-2-pyridyl)amino]ethyl]pyrazol-4-yl]-3,6-dihydro-2H-pyridine-1-carboxylate | 3.87 (Method 1) | 490.3 |

Example 18

2-[3,5-dimethyl-4-(1,2,3,6-tetrahydropyridin-4-yl)pyrazol-1-yl]-N-(5-pyrazin-2-yl-2-pyridyl)acetamide

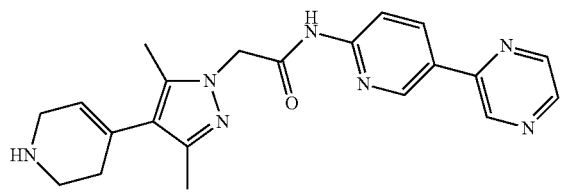 [SMILES: Cc1nn(CC(=O)Nc2ccc(-c3cnccn3)cn2)c(C)c1C1=CCNCC1]

tert-butyl 4-[3,5-dimethyl-1-[2-oxo-2-[(5-pyrazin-2-yl-2-pyridyl)amino]ethyl]pyrazol-4-yl]-3,6-dihydro-2H-pyridine-1-carboxylate (37.2 mg, 0.08 mmol) was dissolved in DCM (5 mL) and trifluoroacetic acid (0.58 mL, 7.6 mmol) was added dropwise. The reaction was stirred at RT for 1 hour. The mixture was washed with saturated NaHCO₃ and brine.

The organic layer was dried over sodium sulphate and evaporated in vacuo, affording a pale yellow solid analysed as 2-[3,5-dimethyl-4-(1,2,3,6-tetrahydropyridin-4-yl)pyrazol-1-yl]-N-(5-pyrazin-2-yl-2-pyridyl)acetamide (6 mg, 0.01 mmol, 20% yield).

MS Method 1: RT: 2.07 min, ES⁺ m/z 390.1 [M+H]⁺

¹H NMR (400 MHz, DMSO) δ/ppm: 11.05 (s, 1H), 9.31-9.34 (d, J=1.4 Hz, 1H), 9.10-9.14 (d, J=1.9 Hz, 1H), 8.72-8.75 (m, 1H), 8.63-8.65 (d, J=2.5 Hz, 1H), 8.52-8.56 (m, 1H), 8.15-8.21 (m, 1H), 5.52 (bs, 1H), 4.99 (s, 2H), 3.37-3.40 (m, 2H), 2.91-2.97 (m, 2H), 2.15-2.22 (m, 5H), 2.08 (s, 3H).

Intermediate 33

(2,6-dimethyl-3,6-dihydro-2H-pyran-4-yl)trifluoromethanesulfonate

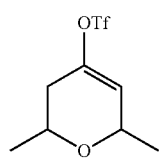

To a round bottomed flask which has been dried in the vacuum oven overnight was added 2,6-dimethyltetrahydropyran-4-one (830 mg, 6.48 mmol) in THF (20 ml). The solution was cooled to −78° C. and lithium bis(trimethylsilyl)amide 1.0 M solution in THF (9.07 mL, 9.07 mmol) was added dropwise. The solution was allowed to stir for 1 hour at −78° C. before the addition of N-phenyl bis-trifluoromethane sulfonimide (2776 mg, 7.77 mmol) in THF (5 ml). The reaction formed a cream suspension and was then allowed to rise to room temperature over 4 hours after which an orange solution had formed. Analysis by TLC (5% EtOAc in heptane) showed no remaining 2,6 dimethyltetrahydropyranone and a new spot. The reaction diluted with EtOAc and was quenched with 1M HCl. The phases were separated and the organic layer was then washed with 1M NaOH. The organic layer was dried over sodium sulphate, filtered and concentrated and columned on silica gel (0-15% EtOAc in heptane) to give (2,6-dimethyl-3,6-dihydro-2H-pyran-4-yl) trifluoromethanesulfonate (1.1 g, 4.13 mmol, 64% yield) as a clear liquid and a mixture of stereoisomers.

¹H NMR (400 MHz, CDCl₃) δ/ppm: 5.69-5.71 (m, 1H), 4.31-4.39 (m, 1H), 3.73-3.82 (m, 1H), 2.19-2.38 (m, 2H), 1.31-1.33 (d, J=3.6 Hz, 3H), 1.29-1.31 (d, J=4.1 Hz, 3H)

Intermediate 34

4-(2,6-dimethyl-3,6-dihydro-2H-pyran-4-yl)-3,5-dimethyl-1H-pyrazole

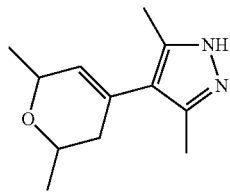

2,6-dimethyl-3,6-dihydro-2H-pyran-4-yl) trifluoromethanesulfonate (1075 mg, 4.13 mmol) and tert-butyl 3,5-dimethyl-4-(4,4,5,5-tetramethyl-1,3,2-dioxaborolan-2-yl) pyrazole-1-carboxylate (1464.15 mg, 4.54 mmol) were dissolved in 1,4-dioxane (9 mL) before adding potassium phosphate tribasic (1315 mg, 6.2 mmol) in Water (2 mL) and degassing by bubbling N₂ through the mixture for 10 mins. Tricyclohexylphosphine (58 mg, 0.21 mmol) and tris(dibenzylideneacetone)dipalladium (0) (95 mg, 0.10 mmol) were added, degassing continued for a further 2 mins prior to heating thermally 100° C. (external probe) for 18 hrs. The reaction was cooled and then the dioxane was removed in vacuo. The mixture was then partitioned between water and EtOAc. The organic layer was washed with water several times, then dried over sodium sulphate filtered and concentrated. The resulting residue was then loaded onto a methanol primed SCX cartridge. The column was eluted with methanol (3CV) and 1M ammonia in methanol (3CV). The ammonia flush was concentrated to give 4-(2,6-dimethyl-3,6-dihydro-2H-pyran-4-yl)-3,5-dimethyl-1H-pyrazole (854 mg, 4.14 mmol, 100.% yield) as a mixture of stereoisomers.

MS Method 2: RT: 1.66 min, ES⁺ m/z 391.3 [M+H]⁺

¹H NMR (400 MHz, CDCl₃) δ/ppm: 5.46-5.48 (m, 1H), 4.35-4.43 (m, 1H), 3.76-3.85 (m, 1H), 2.25 (s, 6H), 2.05-2.22 (m, 2H), 1.28-1.32 (m, 6H).

Example 19

2-[4-(2,6-dimethyltetrahydropyran-4-yl)-3,5-dimethyl-pyrazol-1-yl]-N-(5-pyrazin-2-yl-2-pyridyl)acetamide

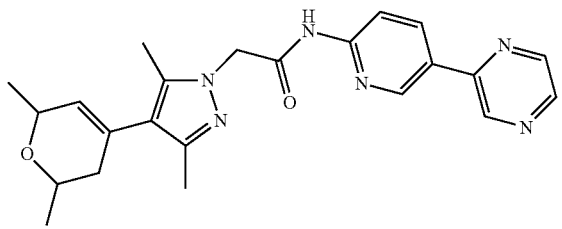 [SMILES: Cc1nn(CC(=O)Nc2ccc(-c3cnccn3)cn2)c(C)c1C1=CC(C)OC(C)C1]

Using steps 3-5 of general scheme 5 2-[4-(2,6-dimethyltetrahydropyran-4-yl)-3,5-dimethyl-pyrazol-1-yl]-N-(5-pyrazin-2-yl-2-pyridyl)acetamide was prepared.

MS Method 1: RT: 3.41 min, ES⁺ m/z 419.3 [M+H]⁺

¹H NMR (400 MHz, CDCl₃) δ/ppm: 9.00-9.02 (d, J=1.5 Hz, 1H), 8.91-8.93 (m, 1H), 8.79-8.82 (bs, 1H), 8.63-8.65 (m, 1H), 8.53-8.56 (d, J=2.5 Hz, 1H), 8.34-8.37 (m, 2H), 5.48-5.51 (m, 1H), 4.84 (s, 2H), 4.35-4.43 (m, 1H), 3.77-3.85 (m, 1H), 2.29 (s, 3H), 2.24 (s, 3H), 2.16-2.23 (m, 1H), 2.04-2.11 (m, 1H), 1.31-1.34 (d, J=2.8 Hz, 3H), 1.28-1.31 (d, J=2.3 Hz, 3H).

Intermediate 35

2-[4-(2,6-dimethyltetrahydropyran-4-yl)-3,5-dimethyl-pyrazol-1-yl]acetic acid

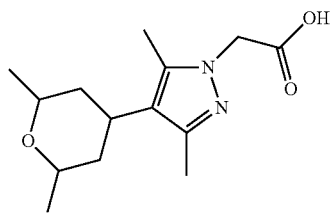 [SMILES: Cc1nn(CC(=O)O)c(C)c1C1CC(C)OC(C)C1]

To a round bottomed flask was added ethyl 2-[4-(2,6-dimethyl-3,6-dihydro-2H-pyran-4-yl)-3,5-dimethyl-pyrazol-1-yl]acetate (340 mg, 1.16 mmol) and methanol (2 mL). The solution was purged and evacuated with nitrogen several times before the addition of palladium, 10 wt. % on carbon, wet (618 mg, 0.58 mmol), after which the system was again purged and evacuated several times. The reaction vessel was then filled with hydrogen and stirred vigorously overnight.

The reaction was flushed with nitrogen and filtered through a pad of celite and washed with methanol. The methanol was concentrated to give the reduced product to which was added water (0.58 mL), ethanol (3 mL) and lithium hydroxide monohydrate (44 mg, 1.05 mmol). The reaction was stirred for 30 mins at room temperature. The ethanol was removed by vacuum concentration, the aqueous layer was then acidified to pH3 with 1M HCl. The aqueous layer was then extracted 3 times with EtOAc. The organic layers were combined, dried over sodium sulphate, filtered and then concentrated to afford 2-[4-(2,6-dimethyltetrahydropyran-4-yl)-3,5-dimethyl-pyrazol-1-yl]acetic acid (168 mg, 0.63 mmol, 60% yield) as a white solid.

MS Method 2: RT: 1.26 min, ES⁺ m/z 267.2 [M+H]⁺

¹H NMR (400 MHz, CDCl₃) δ/ppm: 4.80 (s, 2H), 4.00-4.60 (bs, 1H), 3.50-3.53 (m, 2H), 2.59-2.62 (m, 1H), 2.20 (s, 3H), 2.05 (s, 3H), 1.39-1.60 (m, 4H), 1.23-1.26 (m, 6H).

Example 20

2-[4-(2,6-dimethyltetrahydropyran-4-yl)-3,5-dimethyl-pyrazol-1-yl]-N-(5-pyrazin-2-yl-2-pyridyl)acetamide

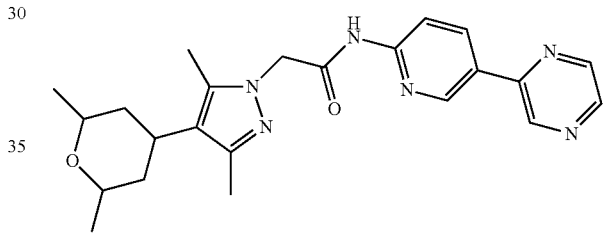

A stirred solution of 2-[4-(2,6-dimethyltetrahydropyran-4-yl)-3,5-dimethyl-pyrazol-1-yl]acetic acid (50 mg, 0.19 mmol), 5-pyrazin-2-ylpyridin-2-amine (39 mg, 0.23 mmol), propylphosphonic anhydride (0.22 mL, 0.38 mmol) and N,N-Diisopropylethylamine (0.08 mL, 0.47 mmol) in THF (2 mL) was heated to reflux and stirred overnight at 80° C. The THF was removed in vacuo to afford a yellow gum that was purified by silica gel column chromatography using 0-100% EtOAc in heptane then 0-10% MeOH in EtOAc. Fractions containing the product were combined and concentrated. The residue was columned again (0-3% MeOH in EtOAc) and further purified by preparative LCMS. The clean fractions were concentrated to give 2-[4-(2,6-dimethyltetrahydropyran-4-yl)-3,5-dimethyl-pyrazol-1-yl]-N-(5-pyrazin-2-yl-2-pyridyl)acetamide (16 mg, 0.04 mmol, 20% yield) as a white solid.

MS Method 1: RT: 3.35 min, ES⁺ m/z 421.3 [M+H]⁺

¹H NMR (400 MHz, CDCl₃) δ/ppm: 9.01-9.03 (d, J=1.6 Hz, 1H), 8.93-8.95 (m, 1H), 8.74-8.78 (bs, 1H), 8.65-8.72 (m, 1H), 8.55-8.57 (d, J=2.5 Hz, 1H), 8.36-8.39 (m, 2H), 4.84 (s, 2H), 3.54-3.64 (m, 2H), 2.71-2.80 (dt, J=2.1, 6.0 Hz, 1H), 2.35 (s, 3H), 2.28 (s, 3H), 1.48-1.68 (m, 4H), 1.25-1.29 (d, J=6.2 Hz, 6H).

Example 21

The following dihydropyrans were prepared in an analogous manner to example 19, the tetraydropyrans were prepared in an analogous manner to example 20.

| Structure | STRUCTURE NAME | LCMS RT (min) | m/z MIM |
|---|---|---|---|
| 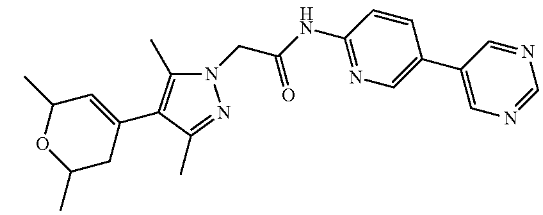 [SMILES: Cc1nn(CC(=O)Nc2ccc(-c3cncnc3)cn2)c(C)c1C1=CC(C)OC(C)C1] | 2-[4-(2,6-dimethyl-3,6-dihydro-2H-pyran-4-yl)-3,5-dimethyl-pyrazol-1-yl]-N-(5-pyrimidin-5-yl-2-pyridyl)acetamide | 3.22 (Method 1) | 419.4 |
| 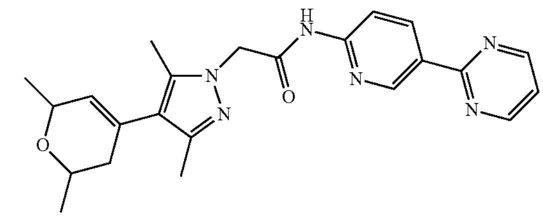 [SMILES: Cc1nn(CC(=O)Nc2ccc(-c3ncccn3)cn2)c(C)c1C1=CC(C)OC(C)C1] | 2-[4-(2,6-dimethyl-3,6-dihydro-2H-pyran-4-yl)-3,5-dimethyl-pyrazol-1-yl]-N-(5-pyrimidin-2-yl-2-pyridyl)acetamide | 3.53 (Method 1) | 419.3 |
| 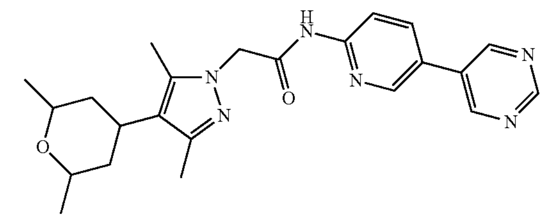 [SMILES: Cc1nn(CC(=O)Nc2ccc(-c3cncnc3)cn2)c(C)c1C1CC(C)OC(C)C1] | 2-[4-(2,6-dimethyltetrahydropyran-4-yl)-3,5-dimethyl-pyrazol-1-yl]-N-(5-pyrimidin-5-yl-2-pyridyl)acetamide | 3.15 (Method 1) | 421.5 |
| 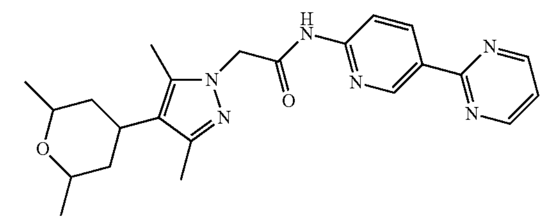 | 2-[4-(2,6-dimethyltetrahydropyran-4-yl)-3,5-dimethyl-pyrazol-1-yl]-N-(5-pyrimidin-2-yl-2-pyridyl)acetamide | 3.46 (Method 1) | 421.3 |

Further compounds of the invention could be prepared by analogy with the following route:

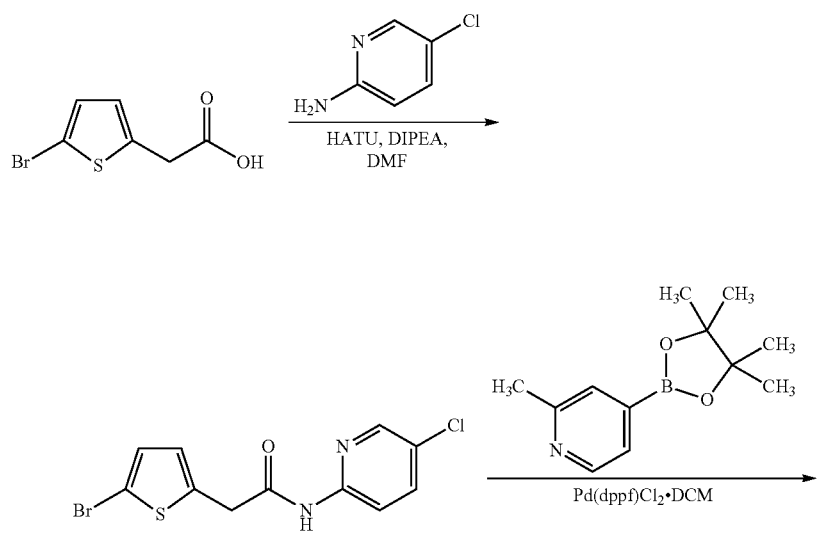

General Scheme 6

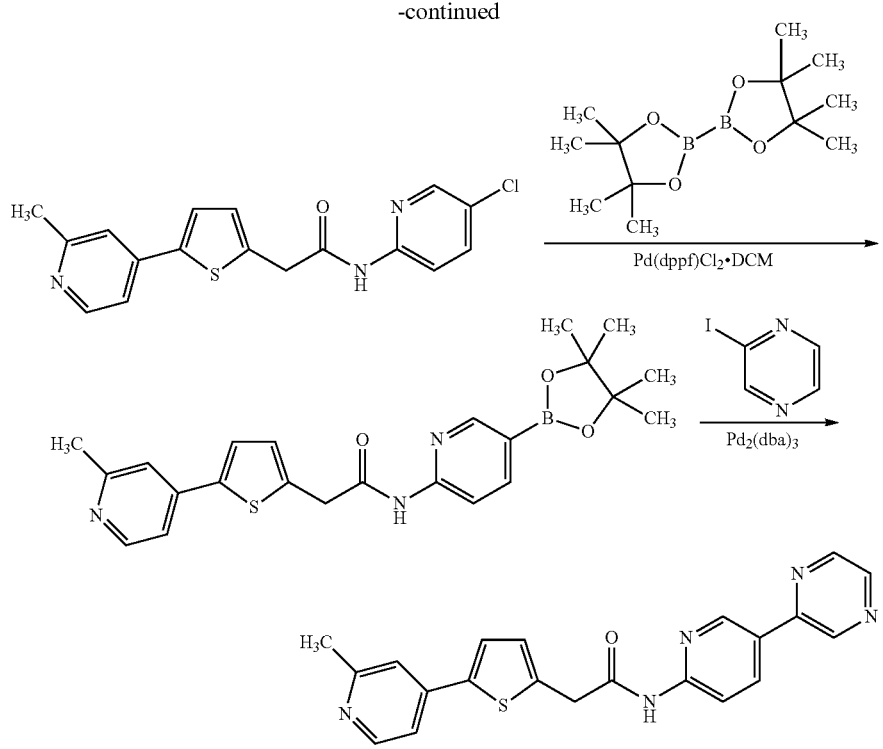

Intermediate 36

2-(5-bromo-2-thienyl)-N-(5-chloro-2-pyridyl)acetamide

A flask was charged with 2-(5-bromo-2-thienyl)acetic acid (300 mg, 1.36 mmol) and 5-chlor-2-pyridinamine (174 mg, 1.36 mmol), which was taken up in DMF (5 mL) and N,N-diisopropylethylamine (0.47 mL, 2.71 mmol) was added. The solution was set stirring and HATU (567 mg, 1.49 mmol) was added. The resulting solution was left to stir overnight. The reaction mixture was diluted with water and partitioned with EtOAc. Separation was difficult, so some brine was added in aid. The phases were then separated and the organic layer was washed with 1:1 brine and water mixture (×2). The aqueous washes were then combined and extracted once with EtOAc. The organics were then combined, washed with brine, dried over sodium sulfate, filtered and concentrated to dryness, affording a brown oil. Purification by flash column chromatography was performed, (25 g $SiO_2$, eluting with 0-50% EtOAc in heptane). Fractions containing the product were combined and concentrated to dryness, affording 2-(5-bromo-2-thienyl)-N-(5-chloro-2-pyridyl)acetamide (104 mg, 0.31 mmol, 23.11% yield) as a brown crystalline solid.

MS Method 2: RT: 1.83 min, $ES^+$ m/z 332.8 $[M+H]^+$ $^1H$ NMR (400 MHz, $CDCl_3$) δ/ppm: 8.10-8.15 (m, 2H), 7.82-7.91 (bs, 1H), 7.58-7.63 (dd, J=9.0, 2.9 Hz, 1H), 6.90-6.92 (d, J=3.8 Hz, 1H), 6.71-6.73, (dt, J=3.8, 0.9 Hz, 1H), 3.81 (s, 2H).

Intermediate 37

N-(5-chloro-2-pyridyl)-2-[5-(2-methyl-4-pyridyl)-2-thienyl]acetamide

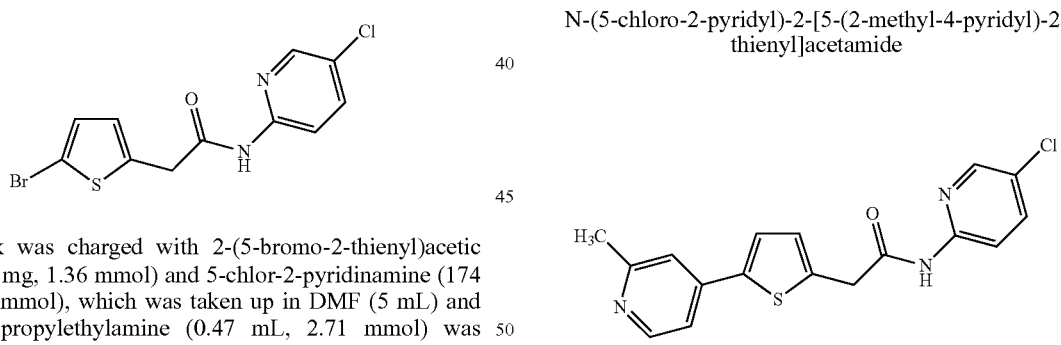

A flask was charged with 2-(5-bromo-2-thienyl)-N-(5-chloro-2-pyridyl)acetamide (100 mg, 0.30 mmol), 1,4-dioxane (2 mL) and water (1 mL). The resulting solution was then degassed under vacuum and the system back-filled with nitrogen. This was repeated twice before adding [1,1_apos_-bis(diphenylphosphino)ferrocene]palladium (II) chloride dichloromethane complex (24 mg, 0.03 mmol). Then the system was purged with nitrogen again and the reaction mixture heated to 85° C. for 1 hour thermally. The reaction mixture was concentrated to dryness and the solid purified by flash column chromatography, (12 g $SiO_2$, eluting with 20-100% EtOAc in heptane). Fractions containing the product were combined and concentrated to dryness, affording N-(5-chloro-2-pyridyl)-2-[5-(2-methyl-4-pyridyl)-2-thienyl]acetamide (75 mg, 0.22 mmol, 72.33% yield) as a yellow solid.

MS Method 2: RT: 1.27 min, ES+ m/z 344.0 [M+H]+

$^1$H NMR (400 MHz, CDCl$_3$) δ/ppm: 8.39-8.43 (d, J=5.6 Hz, 1H), 8.12-8.16 (d, J=9.0 Hz, 1H), 8.11-8.13 (d, J=2.6 Hz, 1H), 7.91-7.95 (bs, 1H), 7.59-7.62 (dd, J=9.0, 2.6 Hz, 1H), 7.32-7.34 (d, J=3.7 Hz, 1H), 7.23-7.25 (m, 1H), 7.17-7.21 (m, 1H), 6.96-6.98 (1H, d, J=3.7 Hz, 1H), 3.91 (s, 2H), 2.53 (s, 3H).

Example 22

2-[5-(2-methyl-4-pyridyl)-2-thienyl]-N-(5-pyrazin-2-yl-2-pyridyl)acetamide

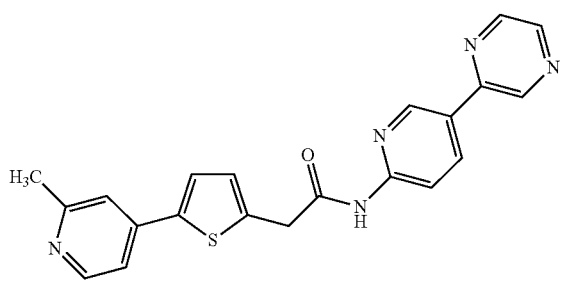 [SMILES: Cc1cc(-c2ccc(CC(=O)Nc3ccc(-c4cnccn4)cn3)s2)ccn1]

A flask was charged with N-(5-chloro-2-pyridyl)-2-[5-(2-methyl-4-pyridyl)-2-thienyl]acetamide (70 mg, 0.20 mmol), bis(pinacolato)diboron (56 mg, 0.22 mmol), tris(dibenzylideneacetone)dipalladium (0) (9 mg, 0.01 mmol) was then added to the solution, the system flushed with nitrogen again and the reaction heated to 110° C. for 2 hours. The reaction mixture was diluted with EtOAc and filtered through a thin pad of celite, eluting with EtOAc. The filtrate was then concentrated to dryness, affording crude 2-[5-(2-methyl-4-pyridyl)-2-thienyl]-N-[5-(4,4,5,5-tetramethyl-1,3,2-dioxaborolan-2-yl)-2-pyridyl]acetamide (130 mg, 0.2986 mmol, 146.% yield) as an red/orange oil which was immediately take on into the final Suzuki reaction without purification.

Iodopyrazine (85 mg, 0.41 mmol), and sodium carbonate (87 mg, 0.83 mmol). This was taken up in toluene (1.6 mL), Ethanol (0.40 mL) and Water (0.40 mL). The resulting solution was then degassed through evacuation and the system back-filled with nitrogen (×3).

Tetrakis(triphenylphosphine)palladium(0) (31.85 mg, 0.03 mmol) was then added to the solution, the system evacuated and filled with nitrogen again, and the solution heated to 85° C. for 2 hrs.

The reaction was concentrated to dryness and purified by flash column chromatography (12 g SiO$_2$ eluting with 50-100% EtOAc with 2% triethylamine in heptane). The fractions containing product were combined and concentrated to dryness, affording a light orange solid. The compound was purified further by prep-LCMS, which afforded 2-[5-(2-methyl-4-pyridyl)-2-thienyl]-N-(5-pyrazin-2-yl-2-pyridyl)acetamide (7 mg, 0.018 mmol, 6.5% yield) as an off white solid.

MS Method 2: RT: 1.13 min, ES+ m/z 388.1 [M+H]+

$^1$H NMR (400 MHz, DMSO) δ/ppm: 11.09 (s, 1H), 9.31.9.33 (d, J=1.3 Hz, 1H), 9.11-9.13 (d, J=2.1 Hz, 1H), 8.72-8.74 (m, 1H), 8.63-8.65 (d, J=2.6 Hz, 1H), 8.52-8.56 (dd, J=8.7, 2.4 Hz, 1H), 8.40-8.43 (d, J=5.5 Hz, 1H), 8.22-8.26 (d, J=9.2 Hz, 1H), 7.63-7.65 (d, J=3.7 Hz, 1H), 7.48 (s, 1H), 7.39-7.42, (m, 1H), 7.08-7.10 (d, J=3.5 Hz, 1H), 4.10 (s, 2H), 2.51 (s, 3H).

Example 23

The following compounds were prepared in an analogous manner using the appropriately substituted thiophenes, aryl/vinyl boronates and aryl halides.

| Structure | STRUCTURE NAME | LCMS RT (min) | m/z MIM |
|---|---|---|---|
| 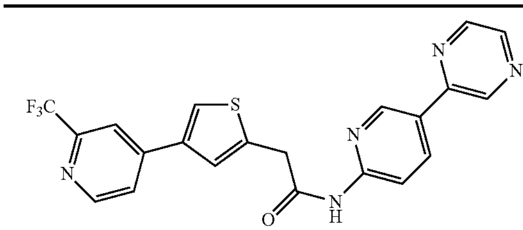 | N-(5-pyrazin-2-yl-2-pyridyl)-2-[4-[2-(trifluoromethyl)-4-pyridyl]-2-thienyl]acetamide | 3.78 (Method 1) | 442.0 |
| 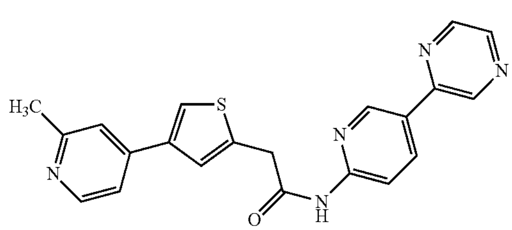 [SMILES: Cc1cc(-c2csc(CC(=O)Nc3ccc(-c4cnccn4)cn3)c2)ccn1] | 2-[4-(2-methyl-4-pyridyl)-2-thienyl]-N-(5-pyrazin-2-yl-2-pyridyl)acetamide | 2.39 (Method 1) | 388.1 |
| 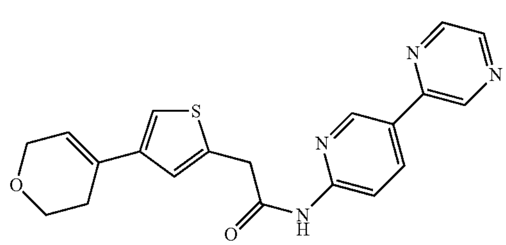 [SMILES: O=C(Cc1cc(C2=CCOCC2)cs1)Nc1ccc(-c2cnccn2)cn1] | 2-[4-(3,6-dihydro-2H-pyran-4-yl)-2-thienyl]-N-(5-pyrazin-2-yl-2-pyridyl)acetamide | 3.35 (Method 1) | 379.1 |

| Structure | STRUCTURE NAME | LCMS RT (min) | m/z MIM |
|---|---|---|---|
| 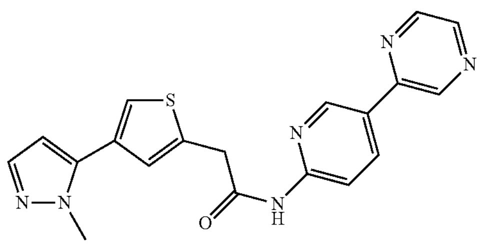 [SMILES: Cn1nccc1-c1csc(CC(=O)Nc2ccc(-c3cnccn3)cn2)c1] | 2-[4-(2-methylpyrazol-3-yl)-2-thienyl]-N-(5-pyrazin-2-yl-2-pyridyl)acetamide | 3.10 (Method 1) | 377.1 |

Dual-Cell β-Catenin Reporter Assay

Mouse L cells transfected to constitutively produce biologically active murine Wnt-3a, referred to as L-Wnt cells, were purchased from the American Type Culture Collection, ATCC, Manassas, Va. (ATCC). These cells were cultured in DMEM supplemented with 10% FCS (Gibco/Invitrogen, Carlsbad, Calif.), 1% geneticin and 1% sodium pyruvate (Sigma) at 37° C. with 5% $CO_2$. The cells were seeded into 96 well plates and treated with serial dilutions of compound diluted to 0.1% DMSO concentration. After 24 hours, cell supernatants were transferred to a 96 well plate previously seeded with Leading Light® Wnt Reporter Cells, stably transfected with a luciferase gene under control of Wnt pathway response elements. After a further 24 hours, cells are treated with One-glo luciferase assay system (Promega, Madison, Wis.) and the luminescent signal read by envision. The $IC_{50}$ of the compound is determined as the concentration that reduces the induced luciferase signal to 50% of the DMSO control.

The results of the assay for certain compounds of the invention are given below. The table shows the $IC_{50}$ value of the compound categorised as "+", " ", "++" and "+++". The category "+" refers to compounds with an $IC_{50}$ of >100 μM. The category "++" refers to compounds with an $IC_{50}$ of 5 to 100 μM. The category "+++" refers to compounds with an $IC_{50}$<5 μM.

| ID No. | Compound | IC50 (nM) |
|---|---|---|
| 1 | 2-[4-(2-methyl-4-pyridyl)imidazol-1-yl]-N-(5-pyrazin-2-yl-2-pyridyl)acetamide | ++ |
| 2 | 2-[5-(2-methyl-4-pyridyl)-2-thienyl]-N-(5-pyrazin-2-yl-2-pyridyl)acetamide | +++ |
| 3 | 2-[4-(2-methyl-4-pyridyl)pyrazol-1-yl]-N-(5-pyrazin-2-yl-2-pyridyl)acetamide | ++ |
| 4 | N-(5-pyrazin-2-yl-2-pyridyl)-2-[4-[2-(trifluoromethyl)-4-pyridyl]imidazol-1-yl]acetamide | +++ |
| 5 | N-(5-pyrazin-2-yl-2-pyridyl)-2-[4-(4-pyridyl)imidazol-1-yl]acetamide | ++ |
| 6 | tert-butyl 4-[6-[[2-[4-[2-(trifluoromethyl)-4-pyridyl]imidazol-1-yl]acetyl]amino]-3-pyridyl]piperazine-1-carboxylate | +++ |
| 7 | N-(5-pyrimidin-5-yl-2-pyridyl)-2-[4-[2-(trifluoromethyl)-4-pyridyl]imidazol-1-yl]acetamide | +++ |
| 8 | tert-butyl 4-[6-[[2-[4-(2-methyl-4-pyridyl)pyrazol-1-yl]acetyl]amino]-3-pyridyl]piperazine-1-carboxylate | ++ |
| 9 | tert-butyl 4-[6-[[2-[4-[2-(trifluoromethyl)-4-pyridyl]pyrazol-1-yl]acetyl]amino]-3-pyridyl]piperazine-1-carboxylate | ++ |
| 10 | N-[5-(4-acetylpiperazin-1-yl)-2-pyridyl]-2-[4-[2-(trifluoromethyl)-4-pyridyl]pyrazol-1-yl]acetamide | ++ |
| 11 | N-(6-pyrimidin-5-yl-3-pyridyl)-2-[4-[2-(trifluoromethyl)-4-pyridyl]imidazol-1-yl]acetamide | + |
| 12 | N-[5-(4-acetylpiperazin-1-yl)-2-pyridyl]-2-[4-[2-(trifluoromethyl)-4-pyridyl]imidazol-1-yl]acetamide | ++ |
| 13 | N-(6-pyrazin-2-yl-3-pyridyl)-2-[4-[2-(trifluoromethyl)-4-pyridyl]imidazol-1-yl]acetamide | ++ |
| 14 | N-(5-pyrimidin-2-yl-2-pyridyl)-2-[4-[2-(trifluoromethyl)-4-pyridyl]imidazol-1-yl]acetamide | +++ |
| 15 | N-[5-(4-methylpiperazin-1-yl)-2-pyridyl]-2-[4-[2-(trifluoromethyl)-4-pyridyl]imidazol-1-yl]acetamide | + |
| 16 | N-(5-pyrimidin-4-yl-2-pyridyl)-2-[4-[2-(trifluoromethyl)-4-pyridyl]imidazol-1-yl]acetamide | ++ |
| 17 | N-(5-pyrazin-2-yl-2-pyridyl)-2-[4-[2-(trifluoromethyl)-4-pyridyl]pyrazol-1-yl]acetamide | +++ |
| 18 | N-(5-pyrazin-2-yl-2-pyridyl)-2-[4-[6-(trifluoromethyl)-3-pyridyl]pyrazol-1-yl]acetamide | + |
| 19 | 2-[3,5-dimethyl-4-[2-(trifluoromethyl)-4-pyridyl]pyrazol-1-yl]-N-(5-pyrazin-2-yl-2-pyridyl)acetamide | +++ |
| 20 | 2-[4-(2-cyano-4-pyridyl)pyrazol-1-yl]-N-(5-pyrazin-2-yl-2-pyridyl)acetamide | + |

| ID No. | Compound | IC50 (nM) |
|---|---|---|
| 21 | 2-[4-[2-(difluoromethyl)-4-pyridyl]pyrazol-1-yl]-N-(5-pyrazin-2-yl-2-pyridyl)acetamide | +++ |
| 22 | 2-[4-(2-methoxy-4-pyridyl)pyrazol-1-yl]-N-(5-pyrazin-2-yl-2-pyridyl)acetamide | ++ |
| 23 | N-(5-pyrazin-2-yl-2-pyridyl)-2-[4-[2-(trifluoromethyl)-4-pyridyl]-2-thienyl]acetamide | +++ |
| 24 | 2-[4-(2-methyl-4-pyridyl)-2-thienyl]-N-(5-pyrazin-2-yl-2-pyridyl)acetamide | +++ |
| 25 | 2-[4-(4-methylthiazol-5-yl)pyrazol-1-yl]-N-(5-pyrazin-2-yl-2-pyridyl)acetamide | ++ |
| 26 | 2-[4-(2-methylpyrazol-3-yl)pyrazol-1-yl]-N-(5-pyrazin-2-yl-2-pyridyl)acetamide | ++ |
| 27 | 2-(4-isothiazol-4-ylpyrazol-1-yl)-N-(5-pyrazin-2-yl-2-pyridyl)acetamide | ++ |
| 28 | 2-[4-(3,6-dihydro-2H-pyran-4-yl)-2-thienyl]-N-(5-pyrazin-2-yl-2-pyridyl)acetamide | ++ |
| 29 | 2-[4-(2-methylthiazol-5-yl)pyrazol-1-yl]-N-(5-pyrazin-2-yl-2-pyridyl)acetamide | + |
| 30 | N-(5-pyrazin-2-yl-2-pyridyl)-2-(4-pyrimidin-4-ylpyrazol-1-yl)acetamide | + |
| 31 | 2-[4-(2-methylpyrazol-3-yl)-2-thienyl]-N-(5-pyrazin-2-yl-2-pyridyl)acetamide | ++ |
| 32 | 2-[4-(2-methylpyrazol-3-yl)imidazol-1-yl]-N-(5-pyrazin-2-yl-2-pyridyl)acetamide | + |
| 33 | N-(5-pyrazin-2-yl-2-pyridyl)-2-[4-(1H-pyrazol-4-yl)pyrazol-1-yl]acetamide | + |
| 34 | N-(5-pyrimidin-5-yl-2-pyridyl)-2-[4-[2-(trifluoromethyl)-4-pyridyl]pyrazol-1-yl]acetamide | +++ |
| 35 | 2-[3,5-dimethyl-4-[2-(trifluoromethyl)-4-pyridyl]pyrazol-1-yl]-N-(5-pyrimidin-5-yl-2-pyridyl)acetamide | +++ |
| 36 | 2-[4-(3,5-dimethylisoxazol-4-yl)pyrazol-1-yl]-N-(5-pyrazin-2-yl-2-pyridyl)acetamide | ++ |
| 37 | N-(5-pyrazin-2-yl-2-pyridyl)-2-[4-[2-(trifluoromethyl)pyrimidin-4-yl]pyrazol-1-yl]acetamide | +++ |
| 38 | 2-[4-(2-methylpyrimidin-4-yl)pyrazol-1-yl]-N-(5-pyrazin-2-yl-2-pyridyl)acetamide | ++ |
| 39 | 2-[4-(6-methylpyrimidin-4-yl)pyrazol-1-yl]-N-(5-pyrazin-2-yl-2-pyridyl)acetamide | + |
| 40 | 2-(3,5-dimethyl-4-tetrahydropyran-4-yl-pyrazol-1-yl)-N-(5-pyrazin-2-yl-2-pyridyl)acetamide | +++ |
| 41 | N-(5-pyrazin-2-yl-2-pyridyl)-2-[4-[6-(trifluoromethyl)pyrimidin-4-yl]pyrazol-1-yl]acetamide | ++ |
| 42 | N-(5-pyrazin-2-yl-2-pyridyl)-2-[4-(1,2,3,6-tetrahydropyridin-4-yl)imidazol-1-yl]acetamide | + |
| 43 | 2-[4-(2-isopropylpyrazol-3-yl)pyrazol-1-yl]-N-(5-pyrazin-2-yl-2-pyridyl)acetamide | + |
| 44 | 2-[3,5-dimethyl-4-(2-methyl-4-pyridyl)pyrazol-1-yl]-N-(5-pyrazin-2-yl-2-pyridyl)acetamide | +++ |
| 45 | 2-[4-(2-cyclopentylpyrazol-3-yl)pyrazol-1-yl]-N-(5-pyrazin-2-yl-2-pyridyl)acetamide | + |
| 46 | tert-butyl 4-[3,5-dimethyl-1-[2-oxo-2-[(5-pyrazin-2-yl-2-pyridyl)amino]ethyl]pyrazol-4-yl]-3,6-dihydro-2H-pyridine-1-carboxylate | ++ |
| 47 | 2-[4-(2-cyclopentylpyrazol-3-yl)-3,5-dimethyl-pyrazol-1-yl]-N-(5-pyrazin-2-yl-2-pyridyl)acetamide | + |
| 48 | 2-[4-(3,6-dihydro-2H-pyran-4-yl)-3,5-dimethyl-pyrazol-1-yl]-N-(5-pyrazin-2-yl-2-pyridyl)acetamide | +++ |
| 49 | N-[5-(3,6-dihydro-2H-pyran-4-yl)-2-pyridyl]-2-[3,5-dimethyl-4-[2-(trifluoromethyl)-4-pyridyl]pyrazol-1-yl]acetamide | ++ |
| 50 | 2-[3,5-dimethyl-4-(2-methylpyrazol-3-yl)pyrazol-1-yl]-N-(5-pyrazin-2-yl-2-pyridyl)acetamide | ++ |
| 51 | 2-[3,5-dimethyl-4-(6-methylpyridazin-4-yl)pyrazol-1-yl]-N-(5-pyrazin-2-yl-2-pyridyl)acetamide | ++ |
| 52 | 2-[3,5-dimethyl-4-[2-(trifluoromethyl)-4-pyridyl]pyrazol-1-yl]-N-[5-(3-pyridyl)-2-pyridyl]acetamide | +++ |
| 53 | 2-[3,5-dimethyl-4-(1,2,3,6-tetrahydropyridin-4-yl)pyrazol-1-yl]-N-(5-pyrazin-2-yl-2-pyridyl)acetamide | + |
| 54 | N-[5-(4-cyanophenyl)-2-pyridyl]-2-[3,5-dimethyl-4-[2-(trifluoromethyl)-4-pyridyl]pyrazol-1-yl]acetamide | +++ |
| 55 | 2-[3,5-dimethyl-4-[2-(trifluoromethyl)-4-pyridyl]pyrazol-1-yl]-N-[5-(2-methylpyrazol-3-yl)-2-pyridyl]acetamide | +++ |
| 56 | 2-[3-methyl-4-[2-(trifluoromethyl)-4-pyridyl]pyrazol-1-yl]-N-(5-pyrazin-2-yl-2-pyridyl)acetamide | +++ |
| 57 | 2-[4-(6-chloropyrimidin-4-yl)-3,5-dimethyl-pyrazol-1-yl]-N-(5-pyrazin-2-yl-2-pyridyl)acetamide | ++ |
| 58 | 2-[4-(1-cyclopropylpyrazol-4-yl)-3,5-dimethyl-pyrazol-1-yl]-N-(5-pyrazin-2-yl-2-pyridyl)acetamide | ++ |

-continued

| ID No. | Compound | IC50 (nM) |
|---|---|---|
| 59 | N-[5-(2-cyanophenyl)-2-pyridyl]-2-[3,5-dimethyl-4-[2-(trifluoromethyl)-4-pyridyl]pyrazol-1-yl]acetamide | +++ |
| 60 | 2-[3,5-dimethyl-4-[2-(trifluoromethyl)-4-pyridyl]pyrazol-1-yl]-N-[5-(4-pyridyl)-2-pyridyl]acetamide | ++ |
| 61 | 2-[4-(2-fluoro-4-pyridyl)-3,5-dimethyl-pyrazol-1-yl]-N-(5-pyrazin-2-yl-2-pyridyl)acetamide | +++ |
| 62 | 2-[4-(1-isopropylpyrazol-4-yl)-3,5-dimethyl-pyrazol-1-yl]-N-(5-pyrazin-2-yl-2-pyridyl)acetamide | ++ |
| 63 | 2-[3,5-dimethyl-4-[2-(trifluoromethyl)-4-pyridyl]pyrazol-1-yl]-N-[5-(1,1-dioxo-3,6-dihydro-2H-thiopyran-4-yl)-2-pyridyl]acetamide | ++ |
| 64 | 2-[4-(6-methoxy-3-pyridyl)-3,5-dimethyl-pyrazol-1-yl]-N-(5-pyrazin-2-yl-2-pyridyl)acetamide | ++ |
| 65 | 2-[3,5-dimethyl-4-[2-(trifluoromethyl)-4-pyridyl]pyrazol-1-yl]-N-(5-pyrimidin-2-yl-2-pyridyl)acetamide | +++ |
| 66 | N-[5-(6-cyano-3-pyridyl)-2-pyridyl]-2-[3,5-dimethyl-4-[2-(trifluoromethyl)-4-pyridyl]pyrazol-1-yl]acetamide | +++ |
| 67 | 2-[4-methyl-3-[2-(trifluoromethyl)-4-pyridyl]pyrazol-1-yl]-N-(5-pyrazin-2-yl-2-pyridyl)acetamide | +++ |
| 68 | 2-[2-methyl-4-[2-(trifluoromethyl)-4-pyridyl]imidazol-1-yl]-N-(5-pyrazin-2-yl-2-pyridyl)acetamide | +++ |
| 69 | 2-[3,5-dimethyl-4-[2-(trifluoromethyl)-4-pyridyl]pyrazol-1-yl]-N-(5-tetrahydropyran-4-yl-2-pyridyl)acetamide | ++ |
| 70 | 2-[3,5-dimethyl-4-[1-methyl-3-(trifluoromethyl)pyrazol-4-yl]pyrazol-1-yl]-N-(5-pyrazin-2-yl-2-pyridyl)acetamide | ++ |
| 71 | N-[5-(2-cyano-4-pyridyl)-2-pyridyl]-2-[3,5-dimethyl-4-[2-(trifluoromethyl)-4-pyridyl]pyrazol-1-yl]acetamide | +++ |
| 72 | 2-[2,5-dimethyl-4-[2-(trifluoromethyl)-4-pyridyl]imidazol-1-yl]-N-(5-pyrazin-2-yl-2-pyridyl)acetamide | +++ |
| 73 | 2-[3,5-dimethyl-4-[2-(trifluoromethyl)-4-pyridyl]pyrazol-1-yl]-N-(3-fluoro-5-pyrazin-2-yl-2-pyridyl)acetamide | ++ |
| 74 | 2-[5-methyl-4-[2-(trifluoromethyl)-4-pyridyl]imidazol-1-yl]-N-(5-pyrazin-2-yl-2-pyridyl)acetamide | +++ |
| 75 | 2-[4-methyl-3-(2-methyl-4-pyridyl)pyrazol-1-yl]-N-(5-pyrazin-2-yl-2-pyridyl)acetamide | +++ |
| 76 | 2-[3,5-dimethyl-4-[2-(trifluoromethyl)-4-pyridyl]pyrazol-1-yl]-N-(3-methyl-5-pyrazin-2-yl-2-pyridyl)acetamide | + |
| 77 | 2-[3,5-dimethyl-4-[2-(trifluoromethyl)-4-pyridyl]pyrazol-1-yl]-N-(3-methoxy-5-pyrazin-2-yl-2-pyridyl)acetamide | ++ |
| 78 | 2-[4-[6-(dimethylamino)-2-(trifluoromethyl)pyrimidin-4-yl]-3,5-dimethyl-pyrazol-1-yl]-N-(5-pyrazin-2-yl-2-pyridyl)acetamide | +++ |
| 79 | 2-[4-(2-amino-4-pyridyl)-3,5-dimethyl-pyrazol-1-yl]-N-(5-pyrazin-2-yl-2-pyridyl)acetamide | ++ |
| 80 | N-(3-cyano-5-pyrazin-2-yl-2-pyridyl)-2-[3,5-dimethyl-4-[2-(trifluoromethyl)-4-pyridyl]pyrazol-1-yl]acetamide | ++ |
| 81 | 2-[4-(3,6-dihydro-2H-pyran-4-yl)-3,5-dimethyl-pyrazol-1-yl]-N-(5-pyrazin-2-yl-2-pyridyl)propanamide | +++ |
| 82 | 2-[4-(2,6-dimethyl-3,6-dihydro-2H-pyran-4-yl)-3,5-dimethyl-pyrazol-1-yl]-N-(5-pyrazin-2-yl-2-pyridyl)acetamide | +++ |
| 83 | 1-[4-(3,6-dihydro-2H-pyran-5-yl)-3,5-dimethyl-pyrazol-1-yl]-2-methyl-2-[(5-pyrazin-2-yl-2-pyridyl)amino]propan-1-one | ++ |
| 84 | 2-[4-(2,6-dimethyl-3,6-dihydro-2H-pyran-4-yl)-3,5-dimethyl-pyrazol-1-yl]-N-(5-pyrimidin-5-yl-2-pyridyl)acetamide | +++ |
| 85 | 2-[4-(2,6-dimethyl-3,6-dihydro-2H-pyran-4-yl)-3,5-dimethyl-pyrazol-1-yl]-N-(5-pyrimidin-2-yl-2-pyridyl)acetamide | ++ |
| 86 | 2-[2,5-dimethyl-4-(2-methyl-4-pyridyl)imidazol-1-yl]-N-(5-pyrazin-2-yl-2-pyridyl)acetamide | +++ |
| 87 | 2-[5-methyl-4-(2-methyl-4-pyridyl)imidazol-1-yl]-N-(5-pyrazin-2-yl-2-pyridyl)acetamide | +++ |
| 88 | 2-[4-(3,6-dihydro-2H-pyran-4-yl)-3-(trifluoromethyl)pyrazol-1-yl]-N-(5-pyrazin-2-yl-2-pyridyl)acetamide | +++ |
| 89 | 2-[4-(3,6-dihydro-2H-pyran-4-yl)-3-methyl-pyrazol-1-yl]-N-(5-pyrazin-2-yl-2-pyridyl)acetamide | ++ |
| 90 | 2-[3-methyl-4-(2-methyl-4-pyridyl)pyrazol-1-yl]-N-(5-pyrazin-2-yl-2-pyridyl)acetamide | +++ |
| 91 | 2-[3-methyl-4-(2-methyl-4-pyridyl)pyrazol-1-yl]-N-(5-pyrimidin-5-yl-2-pyridyl)acetamide | +++ |
| 92 | 2-[4-(2,6-dimethyltetrahydropyran-4-yl)-3,5-dimethyl-pyrazol-1-yl]-N-(5-pyrazin-2-yl-2-pyridyl)acetamide | ++ |
| 93 | 2-[3-methyl-4-[2-(trifluoromethyl)-4-pyridyl]pyrazol-1-yl]-N-(5-pyrimidin-5-yl-2-pyridyl)acetamide | +++ |
| 94 | N-[5-[2-(dimethylamino)-4-pyridyl]-2-pyridyl]-2-[3-methyl-4-[2-(trifluoromethyl)-4-pyridyl]pyrazol-1-yl]acetamide | ++ |
| 95 | N-(5-pyrazin-2-yl-2-pyridyl)-2-[3-(trifluoromethyl)-4-[2-(trifluoromethyl)-4-pyridyl]pyrazol-1-yl]acetamide | +++ |
| 96 | 2-[4-(2,6-dimethyltetrahydropyran-4-yl)-3,5-dimethyl-pyrazol-1-yl]-N-(5-pyrimidin-5-yl-2-pyridyl)acetamide | ++ |

| ID No. | Compound | IC50 (nM) |
|---|---|---|
| 97 | 2-[4-(2,6-dimethyltetrahydropyran-4-yl)-3,5-dimethyl-pyrazol-1-yl]-N-(5-pyrimidin-2-yl-2-pyridyl)acetamide | ++ |
| 98 | N-[5-(6-methoxy-3-pyridyl)-2-pyridyl]-2-[3-methyl-4-[2-methyl(trifluoromethyl)-4-pyridyl]pyrazol-1-yl]acetamide | ++ |
| 99 | N-[5-[6-(dimethylamino)-3-pyridyl]-2-pyridyl]-2-[3-methyl-4-[2-(trifluoromethyl)-4-pyridyl]pyrazol-1-yl]acetamide | +++ |
| 100 | 2-[4-[2-(dimethylamino)-4-pyridyl]-3,5-dimethyl-pyrazol-1-yl]-N-(5-pyrazin-2-yl-2-pyridyl)acetamide | ++ |
| 101 | 2-[4-[6-(dimethylamino)-3-pyridyl]-3,5-dimethyl-pyrazol-1-yl]-N-(5-pyrazin-2-yl-2-pyridyl)acetamide | ++ |
| 102 | 2-[4-[6-(dimethylamino)-3-pyridyl]-3,5-dimethyl-pyrazol-1-yl]-N-(5-pyrimidin-5-yl-2-pyridyl)acetamide | ++ |
| 103 | N-[5-(6-acetamido-3-pyridyl)-2-pyridyl]-2-[3-methyl-4-[2-(trifluoromethyl)-4-pyridyl]pyrazol-1-yl]acetamide | +++ |
| 104 | 2-[5-methyl-4-[2-(trifluoromethyl)-4-pyridyl]imidazol-1-yl]-N-(5-pyrimidin-5-yl-2-pyridyl)acetamide | +++ |
| 105 | 2-[5-methyl-4-[2-(trifluoromethyl)-4-pyridyl]imidazol-1-yl]-N-(5-pyrimidin-2-yl-2-pyridyl)acetamide | +++ |
| 106 | N-[5-(6-cyano-3-pyridyl)-2-pyridyl]-2-[5-methyl-4-[2-(trifluoromethyl)-4-pyridyl]imidazol-1-yl]acetamide | +++ |
| 107 | N-[5-(4-cyanophenyl)-2-pyridyl]-2-[5-methyl-4-[2-(trifluoromethyl)-4-pyridyl]imidazol-1-yl]acetamide | +++ |
| 108 | 2-[5-methyl-4-[2-(trifluoromethyl)-4-pyridyl]imidazol-1-yl]-N-[5-(3-pyridyl)-2-pyridyl]acetamide | +++ |
| 109 | N-[5-(2-cyano-4-pyridyl)-2-pyridyl]-2-[5-methyl-4-[2-(trifluoromethyl)-4-pyridyl]imidazol-1-yl]acetamide | ++ |
| 110 | 2-[4-(2-fluoro-4-pyridyl)-5-methyl-imidazol-1-yl]-N-(5-pyrazin-2-yl-2-pyridyl)acetamide | +++ |
| 111 | 2-[5-methyl-4-(2-methylpyrazol-3-yl)imidazol-1-yl]-N-(5-pyrazin-2-yl-2-pyridyl)acetamide | ++ |
| 1 | 2-[4-(2-methyl-4-pyridyl)imidazol-1-yl]-N-(5-pyrazin-2-yl-2-pyridyl)acetamide | 18.22 |
| 2 | 2-[5-(2-methyl-4-pyridyl)-2-thienyl]-N-(5-pyrazin-2-yl-2-pyridyl)acetamide | 0.14 |
| 3 | 2-[4-(2-methyl-4-pyridyl)pyrazol-1-yl]-N-(5-pyrazin-2-yl-2-pyridyl)acetamide | 12.18 |
| 4 | N-(5-pyrazin-2-yl-2-pyridyl)-2-[4-[2-(trifluoromethyl)-4-pyridyl]imidazol-1-yl]acetamide | 0.90 |
| 5 | N-(5-pyrazin-2-yl-2-pyridyl)-2-[4-(4-pyridyl)imidazol-1-yl]acetamide | 47.04 |
| 6 | tert-butyl 4-[6-[[2-[4-[2-(trifluoromethyl)-4-pyridyl]imidazol-1-yl]acetyl]amino]-3-pyridyl]piperazine-1-carboxylate | 0.91 |
| 19 | 2-[3,5-dimethyl-4-[2-(trifluoromethyl)-4-pyridyl]pyrazol-1-yl]-N-(5-pyrazin-2-yl-2-pyridyl)acetamide | 0.10 |
| 23 | N-(5-pyrazin-2-yl-2-pyridyl)-2-[4-[2-(trifluoromethyl)-4-pyridyl]-2-thienyl]acetamide | 0.34 |
| 35 | 2-[3,5-dimethyl-4-[2-(trifluoromethyl)-4-pyridyl]pyrazol-1-yl]-N-(5-pyrimidin-5-yl-2-pyridyl)acetamide | 0.34 |
| 54 | N-[5-(4-cyanophenyl)-2-pyridyl]-2-[3,5-dimethyl-4-[2-(trifluoromethyl)-4-pyridyl]pyrazol-1-yl]acetamide | 0.14 |
| 74 | 2-[5-methyl-4-[2-(trifluoromethyl)-4-pyridyl]imidazol-1-yl]-N-(5-pyrazin-2-yl-2-pyridyl)acetamide | 0.05 |
| 75 | 2-[4-methyl-3-(2-methyl-4-pyridyl)pyrazol-1-yl]-N-(5-pyrazin-2-yl-2-pyridyl)acetamide | 0.61 |
| 93 | 2-[3-methyl-4-[2-(trifluoromethyl)-4-pyridyl]pyrazol-1-yl]-N-(5-pyrimidin-5-yl-2-pyridyl)acetamide | 0.66 |
| 107 | N-[5-(4-cyanophenyl)-2-pyridyl]-2-[5-methyl-4-[2-(trifluoromethyl)-4-pyridyl]imidazol-1-yl]acetamide | 0.05 |

Specificity Immunoprecipitation

L-Wnt cells can be assessed by treatment with alkanyl-palmitate and several concentrations of compound. After 24 hours cell lysates could be washed in PBS (SOURCE) and collected in ice cold lysis buffer (LYSIS BUFFER). Dynabeads (SOURCE) can be incubated with anti-wnt-3a antibody (Abcam) for 20 minutes and incubated with lysates for an hour. Beads can be isolated by magnet and the unbound faction retained. Click chemistry can be performed on samples using Click-iT® protein buffer kit (Life technologies), following the protocol provided, to conjugate biotin to alkanyl palmitate. Elutes can be separated from the samples by magnet and the resulting samples boiled for 20 minutes to dissociate the conjugates. Beads can be removed and the elutes and unbound fraction can be run by polyacrylamide gel electrophoresis, transferred to a membrane and stained for biotin using streptavidin-horseradish peroxidase and for total Wnt by specific antibody.

Cell Death Assay

Cells in growth media (DMEM, 10% FCS) can be treated with a serial dilution of compound diluted to 0.1% DMSO for 72 hours. Viable cell number was measured by the ability to reduce resazurin to resorufin which was detected by fluorescence emission at 590 nm.

Foci Formation Assay

Capan-2 cells can be seeded onto 6 well plates in standard growth media and treated with serial dilutions of compound. Cell media was changed every four days with fresh compound added. After ten days' growth, cells can be fixed on methanol and treated with crystal violet to visualise. Area covered by cell colonies was detected by Operetta and analysed using Columbus software.

The invention claimed is:
1. A compound of formula (III):

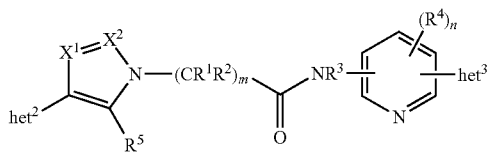

wherein
- $X^1$ and $X^2$ are selected from the group consisting of $CR^6$ and N, provided that $X^1$ and $X^2$ are not both $CR^6$;
- $het^2$ is a 5 or 6 membered heterocyclic ring which may be unsubstituted or substituted, and when substituted the ring is substituted with 1, 2 or 3 groups independently selected at each occurrence from the group consisting of halo, $C_{1-4}$ alkyl, $C_{1-4}$ haloalkyl, $-OR^{A1}$, $-NR^{A1}R^{B1}$, $-CN$, $-NO_2$, $-NR^{A1}C(O) R^{B1}$, $-C(O)NR^{A1}R^{B1}$, $NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl;
- $het^3$ is a 5 or 6 membered heterocyclic ring or a phenyl ring which may be unsubstituted or substituted, and when substituted the ring is substituted with 1, 2 or 3 groups independently selected at each occurrence from the group consisting of halo, $C_{1-4}$ alkyl, $C_{1-4}$ haloalkyl, $-OR^{A1}$, $-NR^{A1}R^{B1}$, $-CN$, $-NO_2$, $-NR^{A1}C(O)R^{B1}$, $-C(O)NR^{A1}R^{B1}$, $-NR^{A1}SO_2R^{B1}$, $-SO_2NR^{A1}R^{B1}$, $-SO2R^{A1}$, $-C(O)R^{A1}$, $-C(O)OR^{A1}$ and $C_{3-6}$ cycloalkyl;
- $R^1$ and $R^2$ are independently selected at each occurrence from the group consisting of H, halo, $C_{1-4}$ alkyl, $C_{1-4}$ haloalkyl, $-OR^{A3}$, $-NR^{A3}R^{B3}$ and $C_{3-6}$ cycloalkyl;
- $R^3$ is selected from the group consisting of H, $C_{1-4}$ alkyl, $C_{1-4}$ haloalkyl, and $C_{3-6}$ cycloalkyl;
- $R^4$ is independently selected at each occurrence from the group consisting of halo, $C_{1-4}$ alkyl, $C_{1-4}$ haloalkyl, $-CN$, $OR^{A4}$, $-NR^{A4}R^{B4}$, $-SO_2R^{A4}$, $C_{3-6}$ cycloalkyl and $C_{3-6}$ halocycloalkyl;
- $R^5$ and $R^6$ are, at each occurrence, independently selected from the group consisting of H, halo, $C_{1-4}$ alkyl, $C_{1-4}$ haloalkyl, $-OR^{A2}$, $-NR^{A2}R^{B2}$, $-CN$, $-SO_2R^{A2}$, and $C_{3-6}$ cycloalkyl;
- m is 1, 2 or 3;
- n is 0, 1 or 2; and
- $R^{A1}$, $R^{B1}$, $R^{A2}$, $R^{B2}$, $R^{A3}$, $R^{B3}$, $R^{A4}$ and $R^{B4}$ are at each occurrence independently selected from the group consisting of H, $C_{1-4}$ alkyl, and $C_{1-4}$ haloalkyl.

2. The compound of claim 1, wherein $het^2$ is a 5 or 6 membered heterocyclic ring which may be unsubstituted or substituted, and when substituted the ring is substituted with 1, 2 or 3 groups selected from the group consisting of halo, $C_{1-4}$ alkyl, $C_{1-4}$ haloalkyl, $-OR^{A1}$, $-NO_2$, $-NR^{A1}C(O) R^{B1}$, $-NR^{A1}SO_2R^{B1}$, $-SO_2NR^{A1}R^{B1}$, $-SO_2R^{A1}$, $-C(O) R^{A1}$, $-C(O)OR^{A1}$ and $C_{3-6}$ cycloalkyl;
provided that $het^2$ is not pyridyl.

3. The compound of claim 1, wherein $het^2$ represents a ring selected from the group consisting of unsubstituted or substituted: pyrazole, imidazole, pyridine, pyrazine, pyrimidine, pyridazine, pyran, tetrahydropyran, dihydropyran, piperidine, piperazine, morpholine, thiomorpholine, oxazine, dioxine, dioxane, thiazine, oxathiane and dithiane.

4. The compound of claim 1, wherein $het^3$ represents an aromatic, saturated or unsaturated 6 membered heterocyclic ring which is unsubstituted or substituted and comprises at least one nitrogen atom.

5. The compound of claim 1, wherein $het^3$ represents a ring selected from the group consisting of unsubstituted or substituted: pyrimidine, pyrazine, pyridazine, piperazine, dioxine, dioxane, morpholine and thiomorpholine.

6. The compound of claim 1, wherein $R^1$ and $R^2$ may be independently selected at each occurrence from the group consisting of H, chloro, fluoro, methyl, ethyl, trifluoromethyl, trifluoroethyl, $-OCF_3$, $-OH$, $-OMe$, $-OEt$, $-NH_2$, $-NHMe$, and $-NMe_2$.

7. The compound of claim 1, wherein $R^3$ is H or methyl.

8. The compound of claim 1, wherein $R^4$ is independently selected at each occurrence from the group consisting of H, chloro, fluoro, methyl, ethyl, trifluoromethyl, trifluoroethyl, $-OCF_3$, $-OH$, $-OMe$, $-OEt$, $-NH_2$, $-NHMe$, and $-NMe_2$.

9. The compound of claim 1, wherein m is 1.

10. The compound of claim 1, wherein n is 0.

11. The compound of claim 1, wherein the compound is selected from the group consisting of:

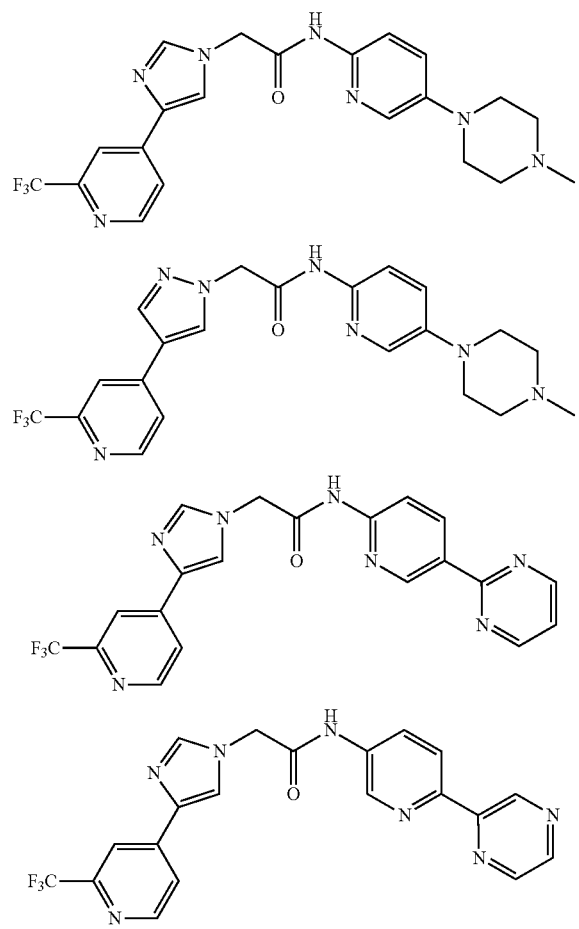

139
-continued
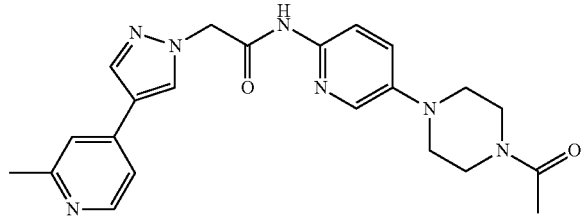
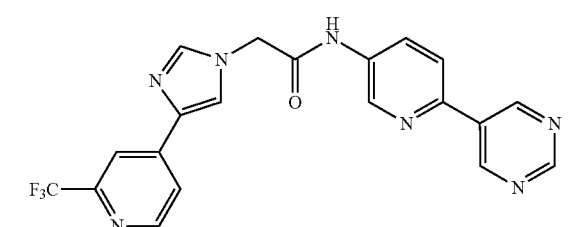
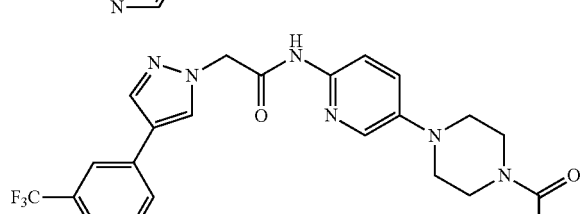
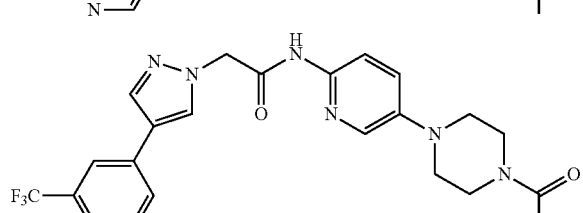
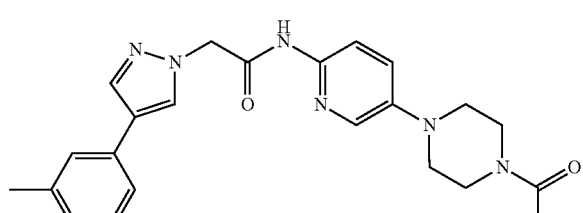
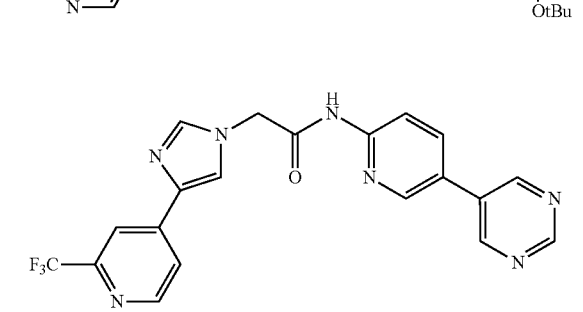
140
-continued
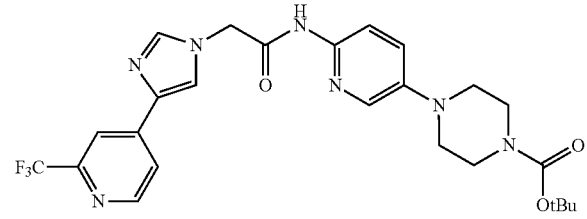
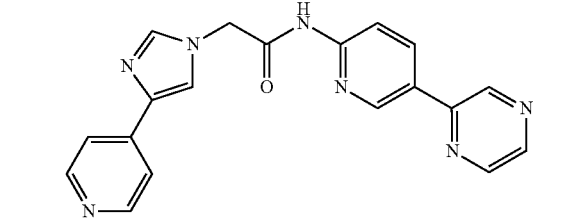
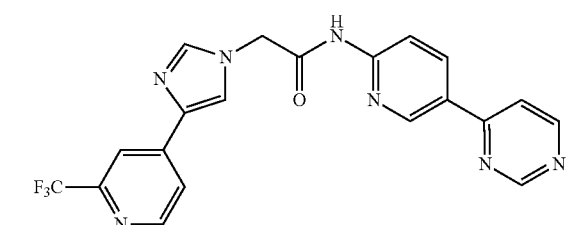
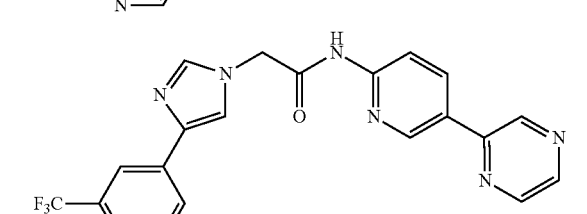
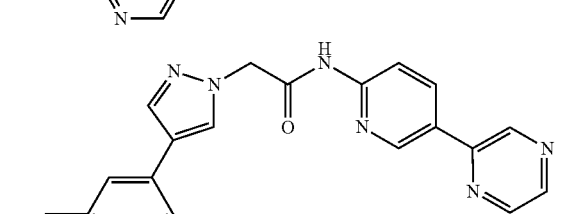
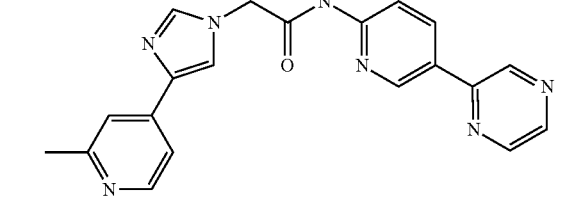
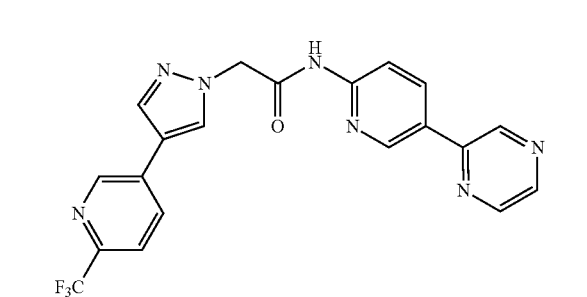

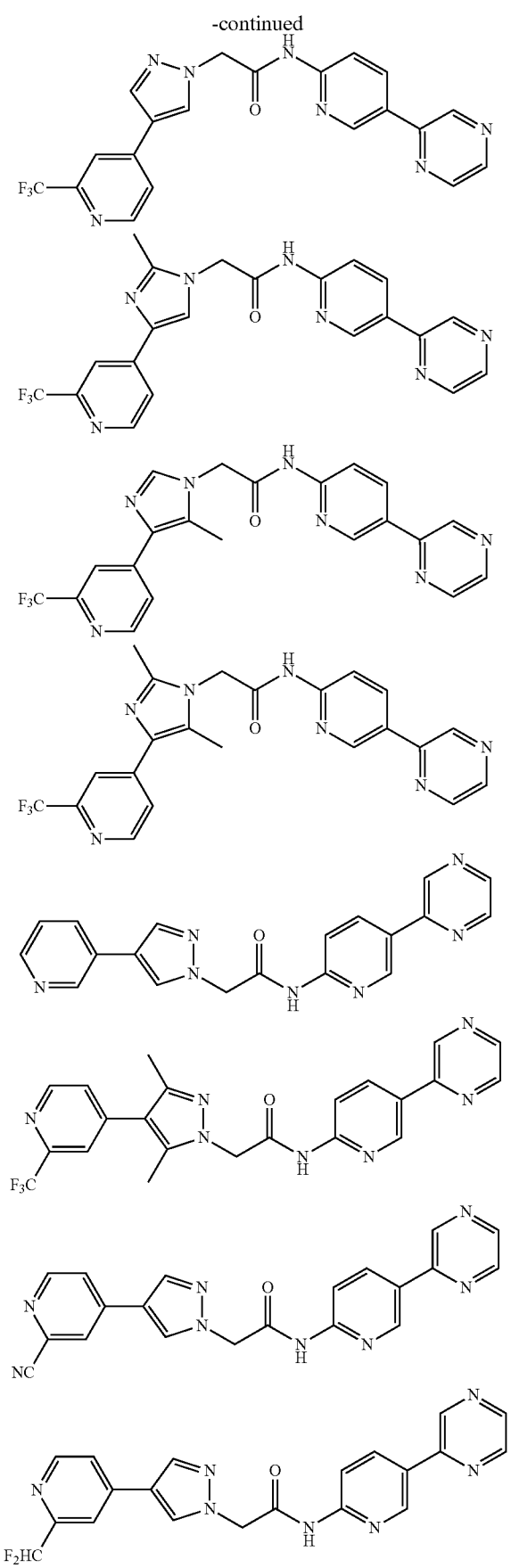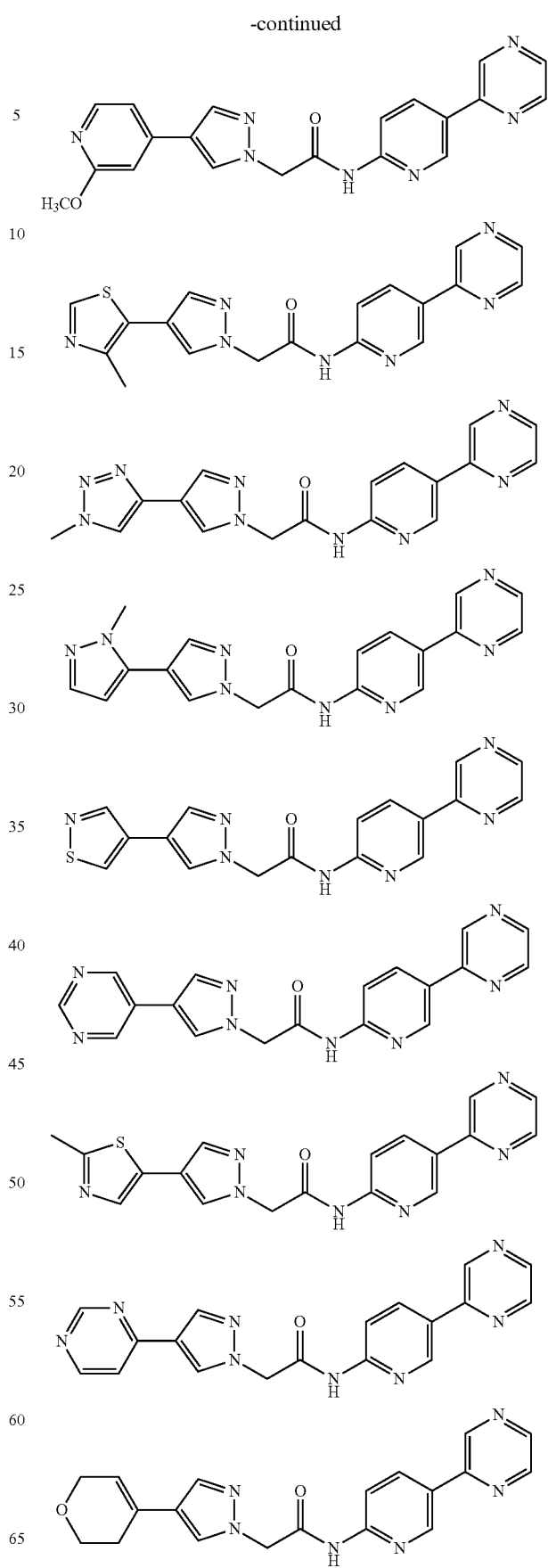

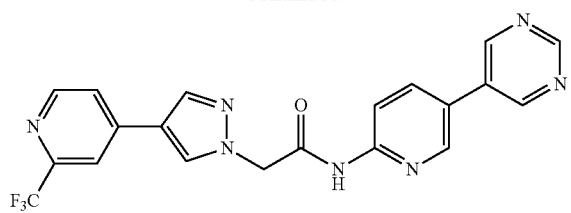
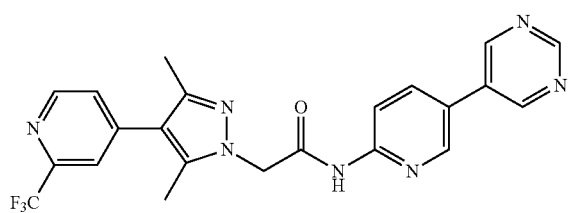
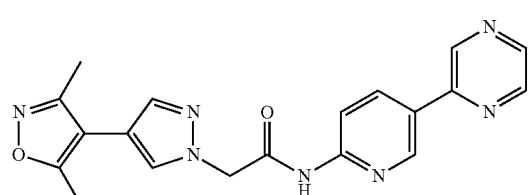
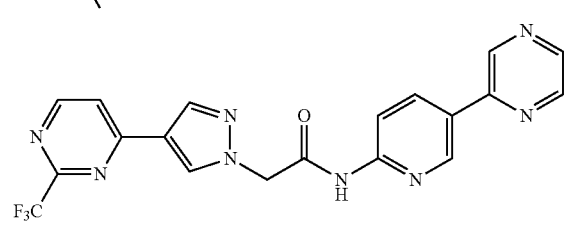
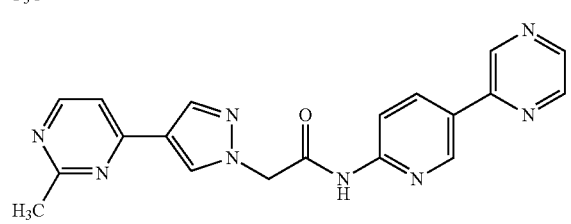
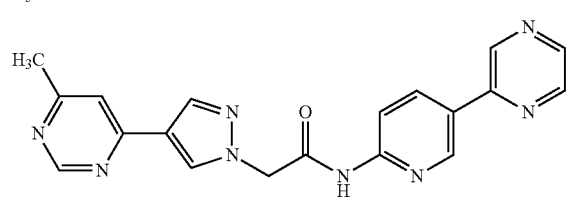
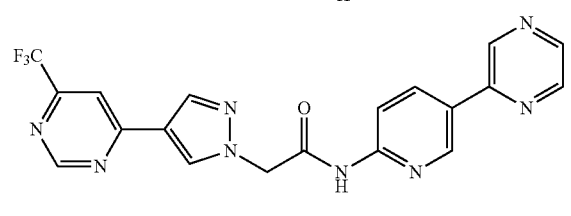
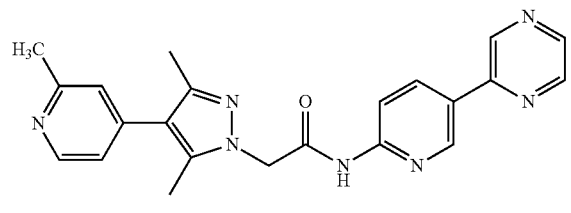
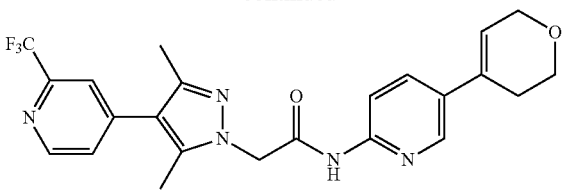
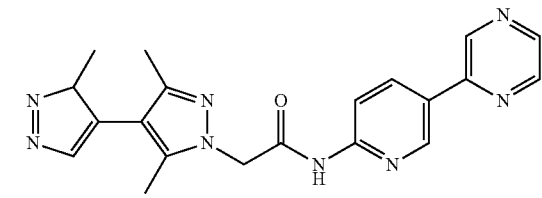
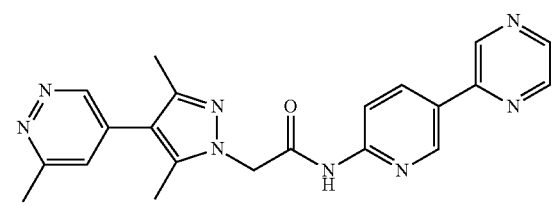
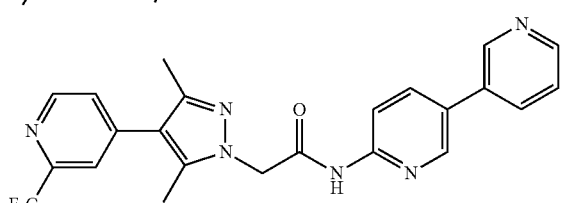
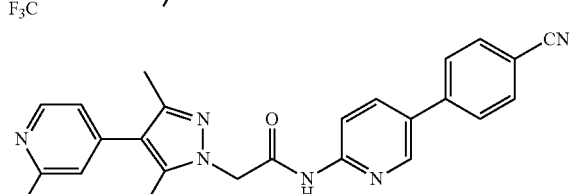
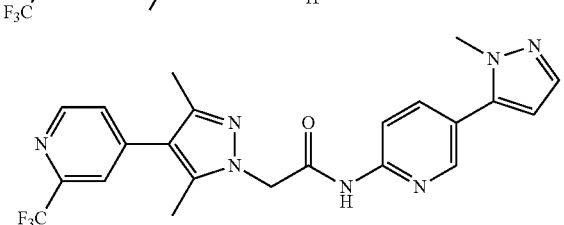
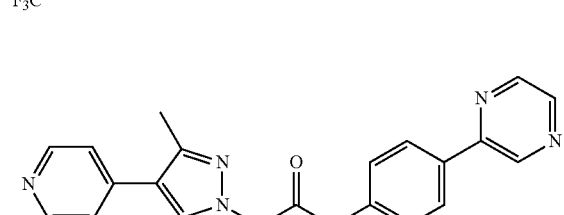
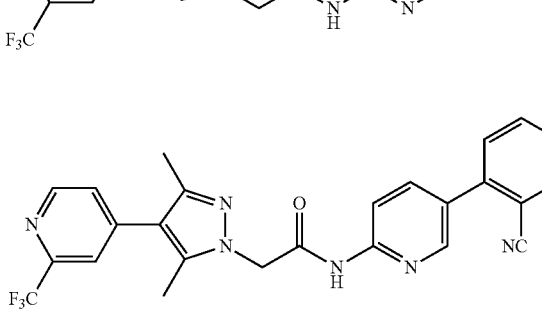

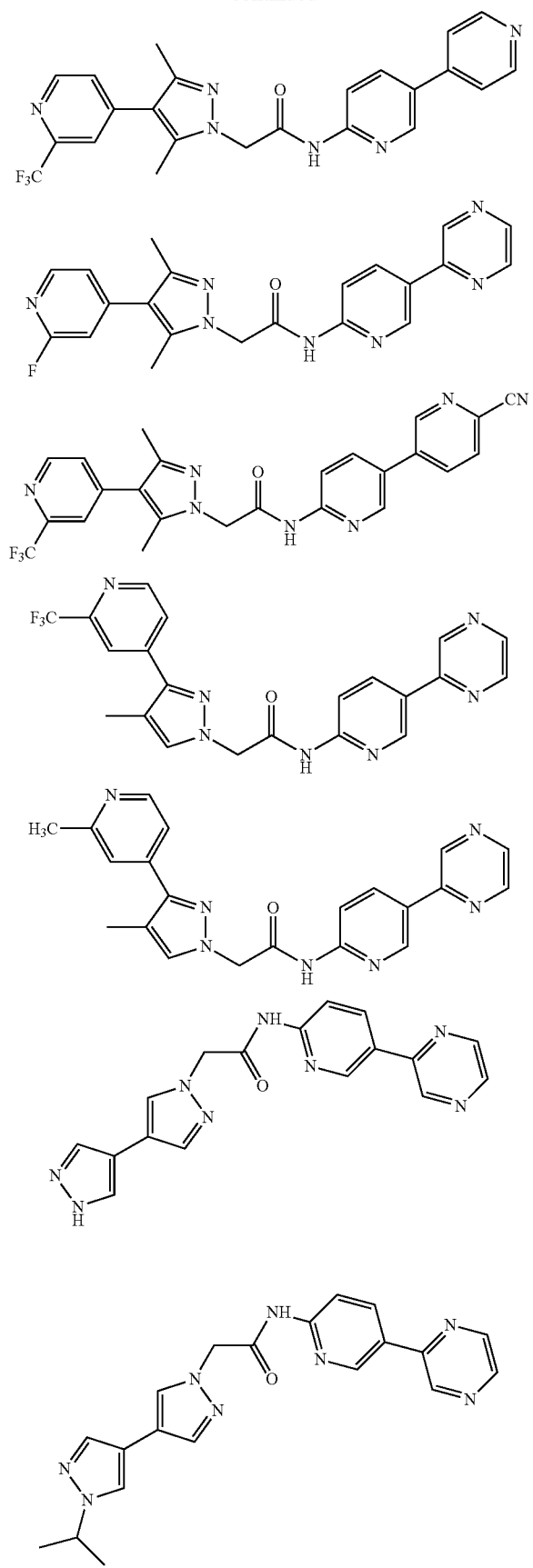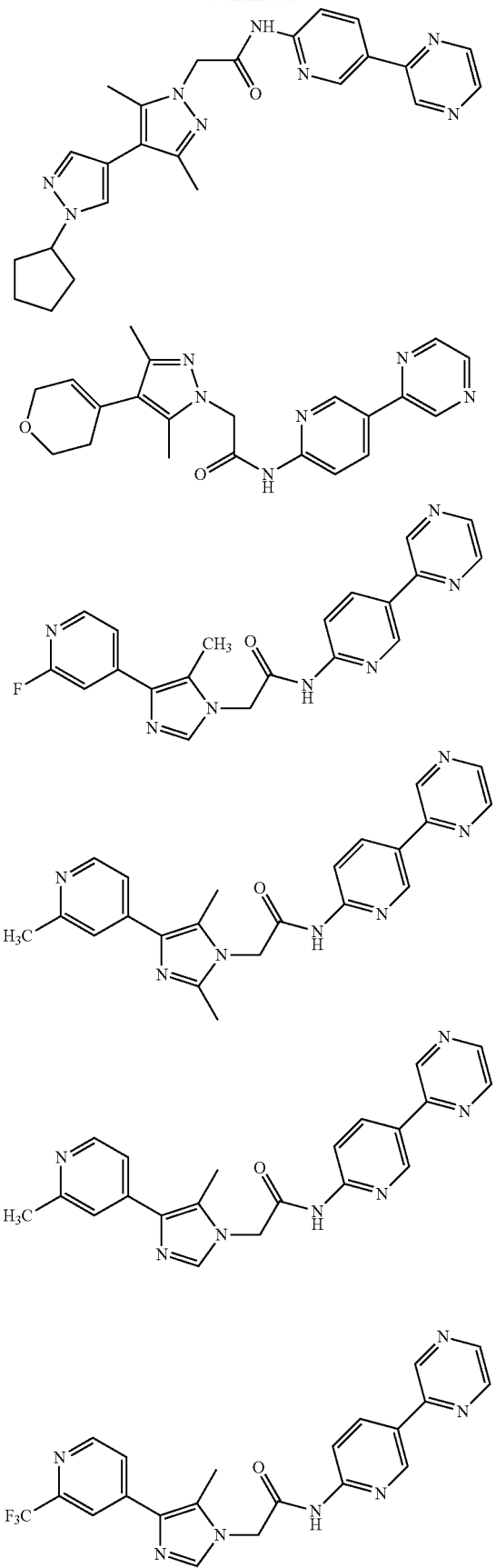

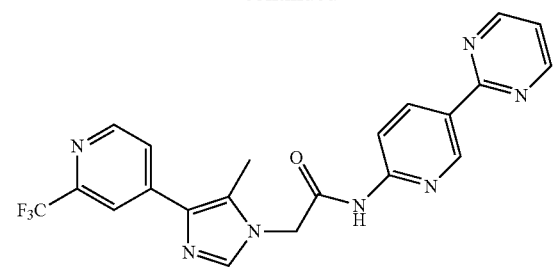
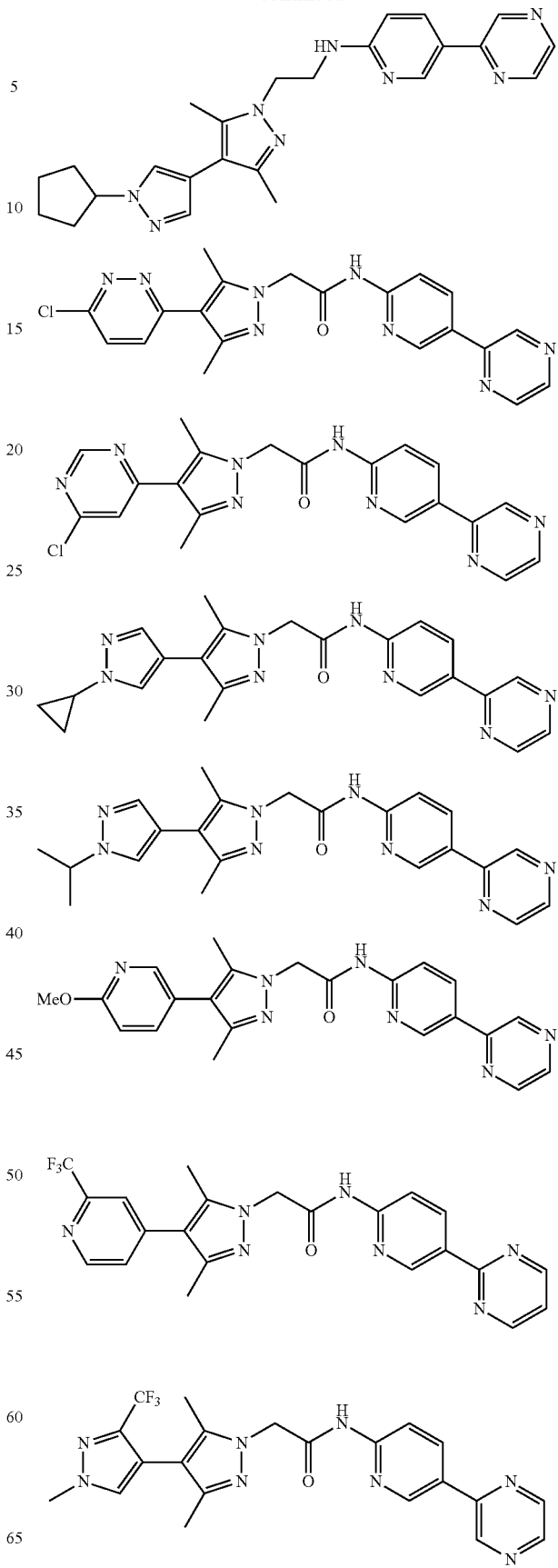

149
-continued
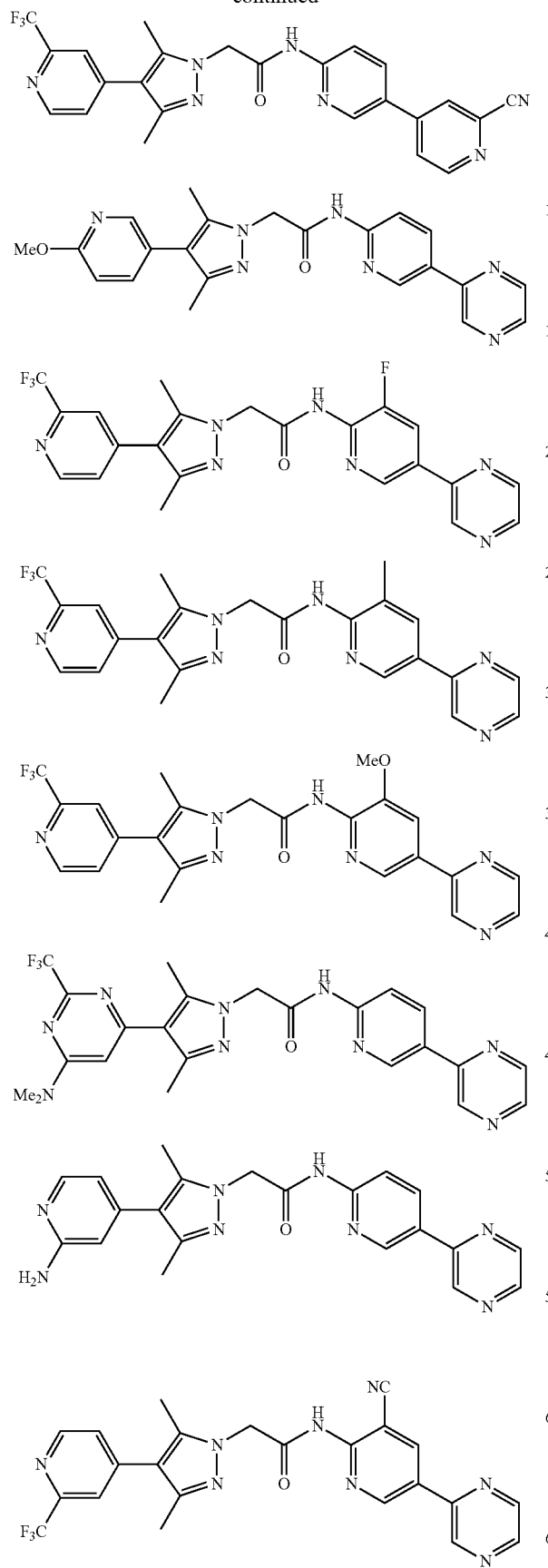
150
-continued
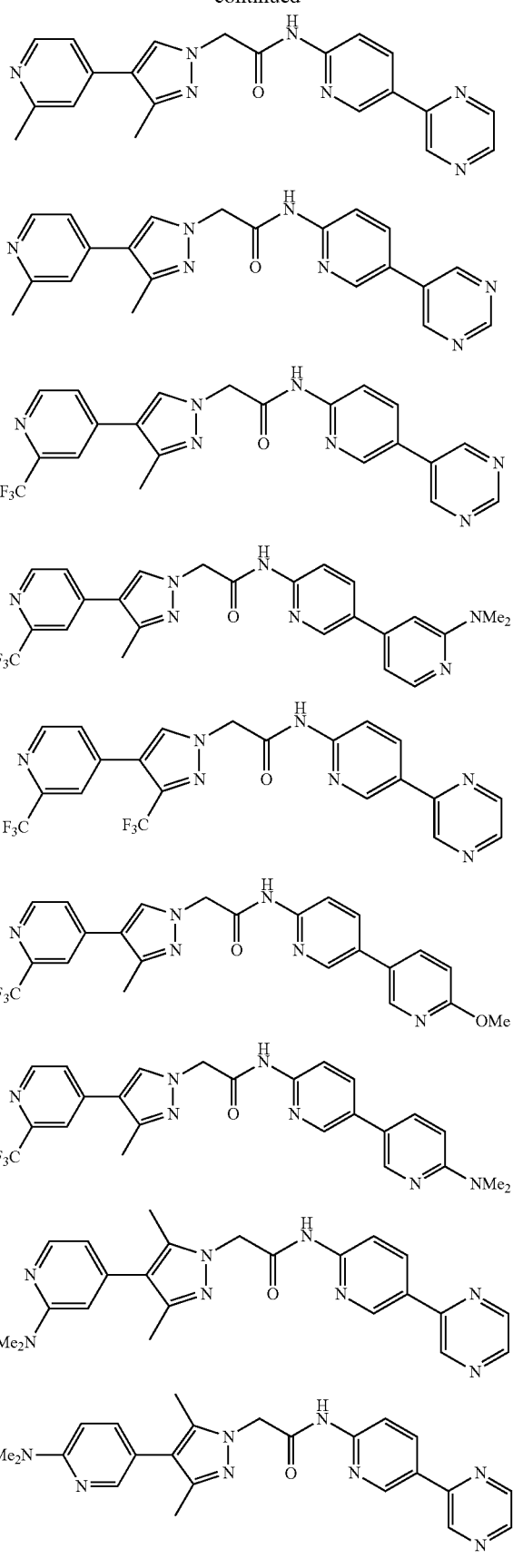

151
-continued

152
-continued

153
-continued
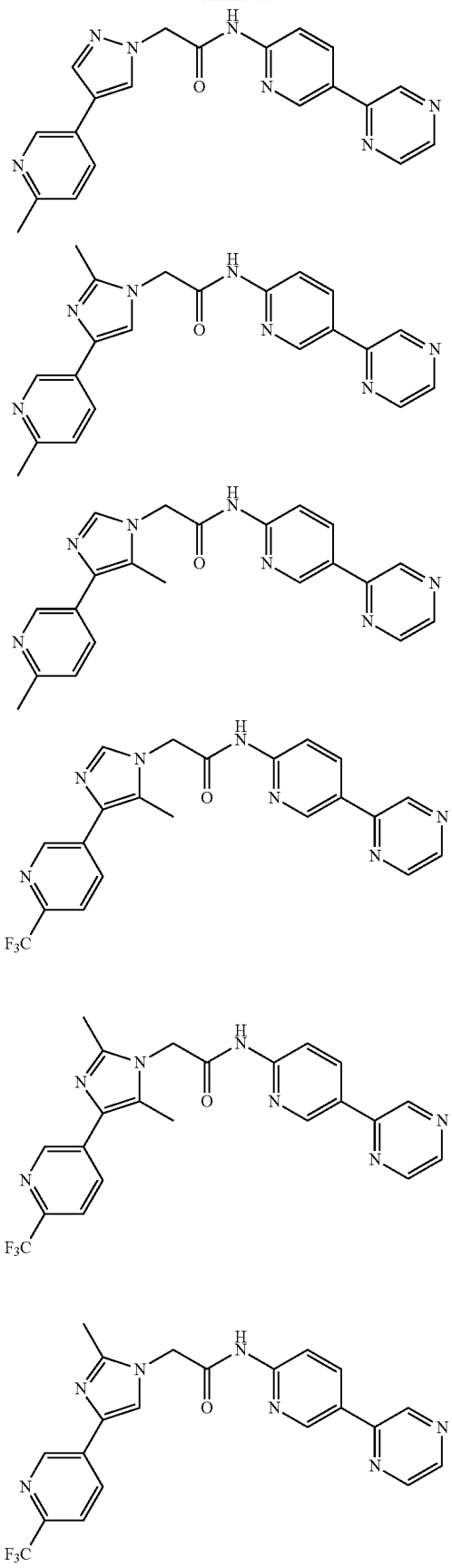
154
-continued
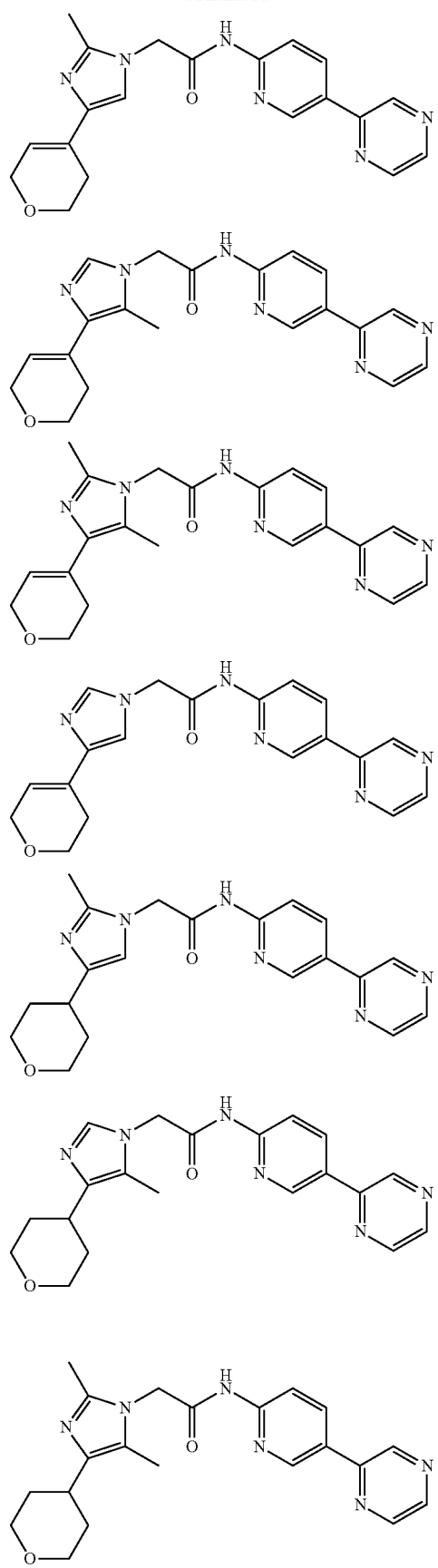

-continued

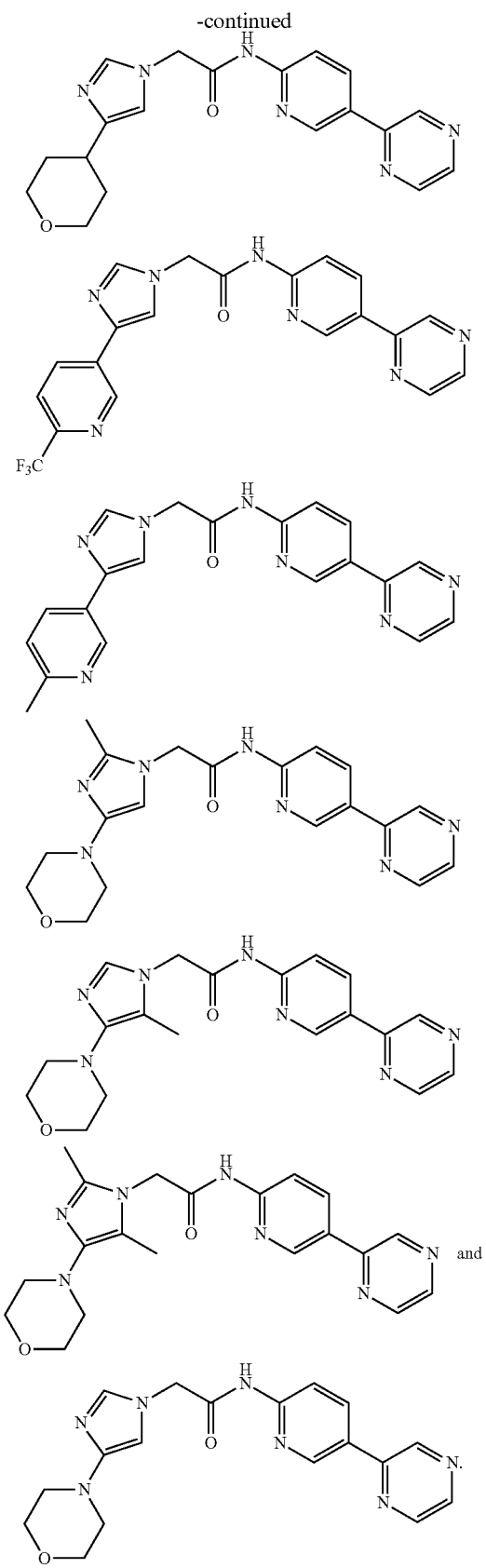

and

12. A method of treatment of a condition mediated by the Wnt signaling pathway selected from the group consisting of cancer, sarcoma, melanoma, skin cancer, haematological tumors, lymphoma, carcinoma, and leukemia, wherein the method comprises administering to a patient in need thereof a therapeutic amount of a compound of formula (III):

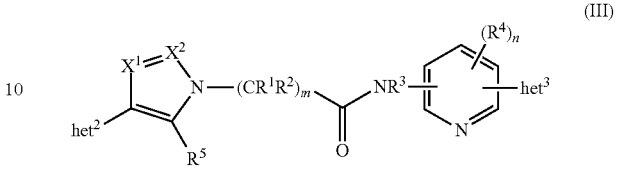

wherein
$X^1$ and $X^2$ are selected from the group consisting of $CR^6$ and N, provided that $X^1$ and $X^2$ are not both $CR^6$;
$het^2$ is a 5 or 6 membered heterocyclic ring which may be unsubstituted or substituted, and when substituted the ring is substituted with 1, 2 or 3 groups independently selected at each occurrence from the group consisting of halo, $C_{1-4}$ alkyl, $C_{1-4}$ haloalkyl, $-OR^{A1}$, $-NR^{A1}R^{B1}$, $-CN$, $-NO_2$, $-NR^{A1}C(O)R^{B1}$, $-C(O)NR^{A1}R^{B1}$, $NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl;
$het^3$ is a 5 or 6 membered heterocyclic ring or a phenyl ring which may be unsubstituted or substituted, and when substituted the ring is substituted with 1, 2 or 3 groups independently selected at each occurrence from the group consisting of halo, $C_{1-4}$ alkyl, $C_{1-4}$ haloalkyl, $-OR^{A1}$, $-NR^{A1}R^{B1}$, $-CN$, $-NO_2$, $-NR^{A1}C(O)R^{B1}$, $-C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl;
$R^1$ and $R^2$ are independently selected at each occurrence from the group consisting of H, halo, $C_{1-4}$ alkyl, $C_{1-4}$ haloalkyl, $-OR^{A3}$, $-NR^{A3}R^{B3}$ and $C_{3-6}$ cycloalkyl;
$R^3$ is selected from the group consisting of H, $C_{1-4}$ alkyl, $C_{1-4}$ haloalkyl, and $C_{3-6}$ cycloalkyl;
$R^4$ is independently selected at each occurrence from the group consisting of halo, $C_{1-4}$ alkyl, $C_{1-4}$ haloalkyl, $-CN$, $OR^{A4}$, $-NR^{A4}R^{B4}$, $-SO_2R^{A4}$, $C_{3-6}$ cycloalkyl and $C_{3-6}$ halocycloalkyl;
$R^5$ and $R^6$ are, at each occurrence, independently selected from the group consisting of H, halo, $C_{1-4}$ alkyl, $C_{1-4}$ haloalkyl, $-OR^{A2}$, $-NR^{A2}R^{B2}$, $-CN$, $-SO_2R^{A2}$, and $C_{3-6}$ cycloalkyl;
m is 1, 2 or 3;
n is 0, 1 or 2; and
$R^{A1}$, $R^{B1}$, $R^{A2}$, $R^{B2}$, $R^{A3}$, $R^{B3}$, $R^{A4}$ and $R^{B4}$ are at each occurrence independently selected from the group consisting of H, $C_{1-4}$ alkyl, and $C_{1-4}$ haloalkyl.

13. The method of claim 12, wherein the condition is selected from the group consisting of esophageal squamous cell carcinoma, gastric cancer, glioblastomas, astrocytomas, retinoblastoma, osteosarcoma, chondosarcoma, Ewing's sarcoma, rabdomysarcoma, Wilm's tumor, basal cell carcinoma, non-small cell lung cancer, brain tumour, hormone refractory prostate cancer, prostate cancer, metastatic breast cancer, breast cancer, metastatic pancreatic cancer, pancreatic cancer, colorectal cancer, cervical cancer, head and neck squamous cell carcinoma, and cancer of the head and neck.

14. The method of claim 12, wherein the condition is selected from the group consisting of skin fibrosis, idiopathic pulmonary fibrosis, renal interstitial fibrosis, liver fibrosis, proteinuria, kidney graft rejection, osteoarthritis, Parkinson's disease, cystoid macular edema, uveitis associated cystoid macular edema, retinopathy, diabetic retinopathy and retinopathy of prematurity.

15. A pharmaceutical formulation comprising a compound of claim 1; and a pharmaceutically acceptable excipient.

16. The pharmaceutical composition of claim 15, further comprising an additional pharmaceutically active agent.

* * * * *

UNITED STATES PATENT AND TRADEMARK OFFICE
CERTIFICATE OF CORRECTION

PATENT NO. : 10,047,079 B2  
APPLICATION NO. : 15/514046  
DATED : August 14, 2018  
INVENTOR(S) : Inder Bhamra et al.

Page 1 of 1

It is certified that error appears in the above-identified patent and that said Letters Patent is hereby corrected as shown below:

In the Claims

In Claim 11, at Column 145, Line numbers 25-42, delete the following two structures:

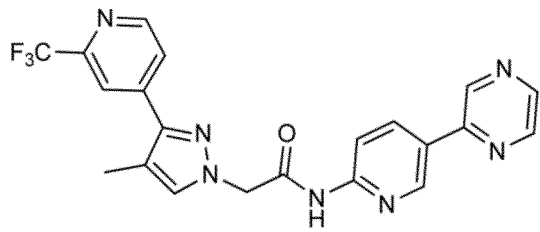

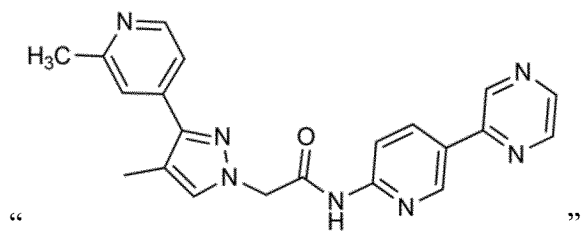

Signed and Sealed this  
Sixteenth Day of June, 2020

Andrei Iancu  
*Director of the United States Patent and Trademark Office*